United States Patent
Van Der Linde et al.

(10) Patent No.: US 12,419,235 B2
(45) Date of Patent: Sep. 23, 2025

(54) MODIFIED CULLIN1 GENE

(71) Applicant: RIJK ZWAAN ZAADTEELT EN ZAADHANDEL B.V., De Lier (NL)

(72) Inventors: Lilian Van Der Linde, De Lier (NL); Sara Movahedi, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 164 days.

(21) Appl. No.: 16/813,919

(22) Filed: Mar. 10, 2020

(65) Prior Publication Data
US 2020/0196547 A1    Jun. 25, 2020

Related U.S. Application Data

(63) Continuation of application No. 15/892,500, filed on Feb. 9, 2018, now Pat. No. 10,856,482, which is a continuation-in-part of application No. PCT/EP2016/071177, filed on Sep. 8, 2016.

(30) Foreign Application Priority Data

Sep. 8, 2015    (NL) ..................................... 2015409

(51) Int. Cl.
| | | |
|---|---|---|
| *A01H 1/00* | (2006.01) | |
| *C07K 14/415* | (2006.01) | |
| *C12N 15/82* | (2006.01) | |
| *C12Q 1/6895* | (2018.01) | |

(52) U.S. Cl.
CPC ........... *A01H 1/121* (2021.01); *C07K 14/415* (2013.01); *C12N 15/8261* (2013.01); *C12Q 1/6895* (2013.01); *Y02A 40/146* (2018.01)

(58) Field of Classification Search
None
See application file for complete search history.

(56) References Cited

FOREIGN PATENT DOCUMENTS

| | | |
|---|---|---|
| WO | WO2011/061656 A1 | 5/2011 |
| WO | WO2022018030 A1 | 1/2022 |

OTHER PUBLICATIONS

Rajeskar, Influence of weather and growing environment on vegetable growth and yield, Journal of Horticulture and Forestry, Nov. 2013 (Year: 2013).*
Chomicki, Guillaume, Hanno Schaefer, and Susanne S. Renner. "Origin and domestication of Cucurbitaceae crops: insights from phylogenies, genomics and archaeology." New Phytologist 226.5 (2020): 1240-1255 (Year: 2020).*
Wehner, Watermelon vs. Melon: Watermelon Crop Information, North Carolina State University, 2023 (Year: 2023).*
Zhang et al., Fine Mapping of Cla015407 Controlling Plant Height in Watermelon, J. Amer. Soc. Hort. Sci. 146(3):196-205 (2021). ( Year: 2021) (Year: 2021).*
Zhang et al., Fine Mapping of Cla015407 Controlling Plant Height in Watermelon, J. Amer. Soc. Hort. Sci. 146(3):196-205 (2021). ( Year: 2021).*
Genbank, Database Accession No. XM_004143037, Mar. 23. 2015.
Genbank, Database Accession No. XM_004229178, Nov. 19, 2014.
Hernandez, et al., Growth and morphological response of cucumber seedlings to supplemental red and blue photon flux ratios under varied solar daily light integrals, Scientia Horticulturae (Jun. 2014) 173:92-99.
ISR and Written Opinion dated Nov. 9, 2016, in International Application No. PCT/EP2016/071177.
Bowie et al. Deciphering the Message in Protein Sequences: Tolerance to Amino Acid Substitutions, Science (1990) 247:1306-1310.
Kano-Murakami et al., A Rice Homeotic Gene, OSH1, Causes Unusual Phenotypes in Transgenic Tobacco, FEBS (1993) 334:365-368.
McConnell et al, Radial Patterning of Arabidopsis Shoots By Class III HD-ZIP and KANADI Genes, Nature (2001) 411 (6838):709-713.

* cited by examiner

*Primary Examiner* — Weihua Fan
*Assistant Examiner* — Brian James Sullivan
(74) *Attorney, Agent, or Firm* — Duane Morris LLP; Thomas J. Kowalski

(57) ABSTRACT

The present invention relates to a modified Cullin1 gene which leads to a plant type that enables efficient cultivation and/or is suitable for situations that require smaller portions, or reduces the labour, time and expenses involved with storing, handling and transporting of redundant plant leaves. The invention also relates to plants comprising the modified Cullin1 gene. The modified Cullin1 gene provides plants with a compact growth phenotype, i.e. comprising shorter internode length and/or a smaller leaf area when compared to plants not comprising the modified Cullin1 gene. The invention further relates to the use of the modified Cullin1 gene for the identification and development of a plant showing a compact growth phenotype, i.e. comprising shorter internodes and/or a smaller leaf area.

21 Claims, 77 Drawing Sheets

Specification includes a Sequence Listing.

Fig. 1

```
ATGACAATGGGCGAGCGGAAGACTATTGACTTGGAGCAGGGATGGGAGTTTATGCAGAAGGGTATC
ACAAAGTTGAAGAACATTCTCGAGGGCTTGCCTGAGCCTCAGTTCAGCTCCGAGGACTACATGATG
CTTTACACTACCAT[A]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCACGATGAGTTCATGTTGAGAGAACTAGTAAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAATAGTAAAGTGAGGGATG
CAGTAATTTCATTGATTGATCAAGAACGTGAAGGAGAACAGATTGACAGAGCTCTACTGAAGAATG
TACTAGATATATTTGTGGAAATTGGTATGGGGCAAATGGATTACTATGAAATGACTTTGAAGCTG
CCATGCTTAAAGATACTGCTGCTTATTACTCTAGGAAGGCTTCCAATTGGATCCTAGAAGATTCTT
GTCCCGATTATATGCTTAAAGCAGAGGAGTGCTTGAAACGAGAAAAGGATAGGGTTTCCCACTATT
TGCACTCTAGTAGCGAGCCAAAGTTGTTGGAGAAAGTTCAACATGAACTATTATCTGTTTATGCTA
CTCAACTGCTGGAAAAAGAGCATTCAGGATGCCATGCATTGCTTAGAGATGACAAGGTGGAAGATT
TGTCAAGGATGTTCCGTCTATTCTCCAAAATACCGAAGGGACTGGATCCAGTTTCCAACATATTTA
AGCAGCATGTAACTGCTGAAGGAACAGCACTGGTCAAACAGGCAGAAGATGCTGCAAGTAACAAGA
AGGCTGAGAAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTATTTTGCAATAAGGGTGTTGCTGGAAGTTCTAGTGCAGAATTGCTTGCTA
CCTTTTGTGATAACATCCTTAAGAAAGGTGGGAGTGAGAAGTTGAGTGATGAAGCAATCGAGGAGA
CACTTGAGAAGGTTGTGAAGTTGTTGGCATACATTTGCGACAAAGATCTGTTTGCTGAATTCTATA
GAAAAAAACTTGCCCGAAGGCTTCTCTTTGACAAGAGCGCGAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTTGAGGAGTATCTGAGCAATAATCCACAAGCGAGTC
CTGGCATCGACCTGACTGTTACTGTTTTAACTACTGGATTTTGGCCAAGCTACAAGTCTTTTGACC
TCAACCTGCCGGCAGAGATGGTAAAGTGTGTTGAAGTTTTCAGAGAGTTTTATCAAACAAAAACCA
AGCATCGAAAACTTACATGGATTTACTCATTGGGTACTTGTAACATCAGTGGAAAATTTGAACCGA
AAACGATGGAGCTGATTGTGACAACTTATCAGGCTTCTGCCCTGTTGCTATTCAATTCTTCGGATA
GACTAAGTTACTCGGAAATCATGACACAATTAAATTTGAGTGACGATGATGTAGTTAGACTACTCC
ACTCGTTGTCATGTGCCAAGTATAAAATTCTTAATAAGGAACCAAATACGAAAACCATCTCTCCGA
ACGATCATTTTGAGTTCAATGCAAAATTCTCCGACAAAATGAGGAGAATAAAGATCCCTCTTCCGC
CTGTGGATGAGAAAAAGAAAGTCATTGAAGATGTTGACAAGGATCGAAGGTATGCTATTGACGCCT
CAATCGTGCGTATCATGAAGAGTCGGAAAGTTCTTGGTCATCAGCAACTAGTGATGGAGTGCGTCG
AGCAATTGGGCCGTATGTTCAAGCCCGATTTCAAGGCGATAAAGAAGAGAATTGAAGACCTGATCA
CTCGGGATTATCTAGAGAGAGACAAAGACAACCCCCACTTGTTTAGGTACTTGGCTTGA
```

Fig. 2

```
ATGACAATGGGCGAGCGGAAGACTATTGACTTGGAACAGGGATGGGAGTTTATGCAGAAGGGTATC
ACAAAGTTGAAGAACATTCTTGAGGGCTTGCCTGAGCCCCAGTTCAGCTCCGAGGACTACATGATG
CTTTACACTACCAT[A]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCATGACGAGTTCATGTTGAGAGAACTAGTCAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAACAGTAAAGTGAGGGATG
CAGTAATCTCATTGATTGATCAAGAACGTGAAGGAGAACAGATTGACAGAGCTCTACTGAAGAATG
TATTAGATATATTTGTGGAAATTGGTATGGGGCAAATGGATTACTATGAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAGCGAGAAAAGGATAGGGTTTCCCACTATT
TGCACTCTAGTAGCGAGCCAAAGTTGTTGGAGAAAGTTCAACACGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGTCTCTTCTCCAAAATACCGAAGGGATTGGACCCAGTTTCCAACATATTTA
AGCAGCATGTAACTGCTGAAGGAACAGCACTGGTCAAACAGGCAGAAGATGCTGCAAGTAACAAGA
AGGCCGAGAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTCTTTTGCAATAAGGGTGTTGCTGGAAGTTCTAGTGCAGAATTGCTTGCTA
CCTTCTGCGATAACATCCTTAAGAAAGGTGGGAGTGAGAAGTTGAGTGATGAAGCAATCGAAGAGA
CACTTGAGAAGGTTGTGAAGTTGTTGGCATACATCTGCGACAAAGATCTGTTTGCTGAATTCTATA
GAAAAAAaCTTGCCCGAAGGCTTCTCTTTGATAAGAGCGCCAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTCGAAGAGTATCTGAGCAATAATCCACAAGCTAGTC
CTGGAATCGACCTAACTGTTACTGTTTTGACTACTGGATTTTGGCCAAGCTACAAGTCTTTTGACC
TCAACCTGCCGGCGGAGATGGTAAAGTGTGTTGAAGTTTTCAGAGAGTTTTATCAAACAAAAACCA
AGCATAGAAAACTTACATGGATTTACTCATTGGGTACTTGTAACATCAGTGGAAAATTTGAACCGA
AGACGATGGAGCTGATTGTGACAACATATCAGGCTTCTGCCCTGTTGCTATTCAATTCTTCGGACA
GACTAAGTTACTCCGAAATCATGACACAATTAAATTTGAGTGATGATGATGTTGTTAGACTGCTCC
ACTCATTGTCGTGTGCCAAGTATAAAATTCTTAATAAGGAGCCAAATACGAAAACCATCTCACCGA
ACGATCATTTTGAGTTCAATGCAAAATTCTCCGACAAAATGAGGAGAATAAAGATCCCTCTTCCGC
CTGTGGATGAGAAAaGAAAGTCATTGAAGATGTTGACAAGGATCGAAGGTATGCTATTGACGCCT
CAATCGTGCGTATCATGAAGAGTCGAAAAGTTCTTGGTCATCAGCAACTAGTGATGGAGTGCGTCG
AGCAATTGGGTCGTATGTTCAAGCCCGATTTCAAGGCGATAAAGAAGAGAATTGAAGACCTGATCA
CTCGGGACTATCTAGAGAGAGACAAAGACAACCCCCACTTGTTTAGGTACTTGGCTTGA
```

Fig. 3

```
ATGACAATGGGTGAGCGGAAGACTATTGACTTGGAGCAAGGATGGGAGTTTATGCAGAAGGGAATC
ACAAAATTGAAGAACATTCTGGAAGGATTGCCTGAGCCACAGTTCAGCTCCGAGGACTACATGATG
CTTTACACTACAAT[A]TATAACATGTGTACCCAGAAGCCACCGCATGATTACTCCCAGCAGCTGT
ATGATAAATACCGCGAATCGTTTGAGGAGTACATCAGTTCTATGGTTTTACCATCCTTGAGGGAGA
AGCATGACGAATTTATGTTGAGAGAACTGGTCAAAAGGTGGACCAACCATAAAGTCATGGTGAGGT
GGCTTTCTCGCTTCTTCCACTATCTTGATCGATACTTCATTGCTCGAAGGTCACTTCCACCTCTCA
ATGAAGTTGGCCTCACTTGCTTCCGTGAATTGGTGTACAAAGAGCTAAACAGTAAAGTGAGGGATG
CAGTAATTTCATTGATCGATCAAGAACGTGAAGGAGAGCAGATTGACAGAGCTCTGTTGAAGAACG
TGTTGGATATATTTGTGGAGATTGGGATGGGCAAATGGATTATTATGAAAATGACTTTGAAGCTG
CCATGCTTAAAGATACTGCTGCTTACTACTCTAGGAAGGCATCAAATTGGATCTTAGAAGATTCTT
GTCCTGATTATATGCTAAAAGCAGAGGAGTGCTTGAGACGAGAAAAGGACCGAGTTTCTCACTATC
TGCACTCTAGTAGCGAGCCAAAGTTATTGGAGAAAGTTCAACATGAACTATTGTCTGTTTATGCTA
CTCAACTGCTGGAGAAAGAGCATTCAGGATGCCATGCATTGCTTAGAGATGACAAGGTGGAAGATT
TGTCAAGGATGTTCCGTCTCTTCTCCAAAATACCCAAGGGATTGGACCCAGTTTCCAACATATTTA
AGCAGCATGTCACTGCTGAAGGAACAGCATTAGTCAAACAGGCAGAAGACGCTGCAAGTAACAAGA
AGGCCGAGAAAAAGGACATCGTTGGTCTGCAAGAACAGGTTTTTGTTAGAAAAGTGATTGAGCTTC
ACGACAAGTACTTGGCATATGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGTGAGAAGTTGAGTGATGAAGCAATTGAGGAAA
CACTCGAGAAGGTCGTGAAATTGCTGGCGTATATCTGCGACAAAGATCTGTTTGCTGAATTCTATA
GAAAAAAACTCGCCCGAAGGCTTCTCTTCGACAAGAGTGCGAATGATGACCACGAGAGAAGTATAC
TGACGAAATTGAAGCAACAATGTGGTGGTCAGTTTACCTCTAAGATGGAGGGAATGGTCACGGATT
TGACACTGGCAAGGGAGAACCAAACTAGTTTTGAGGAATATCTGAGCAATAATCCACAAGCTAGTC
CTGGAATCGACTTGACCGTTACCGTTTTGACCACTGGTTTTTGGCCAAGCTACAAGTCTTTTGACC
TCAACCTGCCGGCGGAGATGGTAAAGTGTGTTGAAGTTTTCAGGGAATTTTATCAAACAAAAACCA
AGCACAGAAAACTTACGTGGATTTACTCGTTGGGTACCTGTAACATCAGCGGAAAATTCGAACCGA
AAACGATGGAGCTGATCGTGACAACCTATCAGGCTTCTGCCCTGCTGCTTTTCAATTCCTCGGATA
AACTAAGTTACTCCGAGATCATGACTCAATTAAACTTGAGTGACGATGATGTTGTTAGACTGCTCC
ACTCGTTGTCGTGTGCGAAGTATAAAATTCTTAACAAGGAGCCAAATACGAAAACCATCTCTCCGA
ACGATCATTTTGAGTTCAACGCAAAATTCTCCGACAAAATGAGGAGAATAAAGATCCCTCTTCCGC
CTGTGGATGAGAAAAGAAAGTAATAGAAGATGTTGACAAGGATCGAAGATATGCTATCGATGCCT
CGATCGTGCGTATCATGAAGAGTAGGAAAGTTCTGGGTCACCAGCAGTTAGTGATGGAGTGCGTCG
AGCAACTGGGTCGTATGTTCAAGCCTGATTTCAAGGCGATAAAGAAGAGAATCGAAGATCTGATCA
CTCGTGACTATTTAGAGAGAGACAAAGACAACCCCCACTTGTTTAGGTACTTGGCTTGA
```

Fig. 4

```
ATGACAATGGGCGAGCGGAAGACTATTGACTTGGAACAAGGATGGGAGTTTATGCAGAAGGGAATC
ACAAAGTTGAAGAACATTCTTGAGGGCTTGCCTGAGCCTCAGTTCAGCTCCGAGGACTACATGATG
CTTTATACCACCAT[A]TACAACATGTGCACACAAAAGCCGCCACATGATTACTCCCAGCAGCTAT
ACGATAAATACCGTGAATCTTTTGAGGAGTATATCACTTCTATGGTCTTACCATCCTTGAGGGAGA
AGCATGACGAGTTCATGTTGAGAGAACTGGTCAAAAGGTGGACGAACCATAAAGTCATGGTGAGGT
GGCTTTCTCGCTTCTTCCACTATCTTGACCGATACTTCATTGCTCGAAGATCACTTCCACCTCTCA
ACGAAGTTGGCCTCACATGCTTCCGTGAATTGGTGTACAAAGAGCTAAACAGTAAAGTGAGGGATG
CAGTAATTTCATTGATTGATCAAGAACGTGAAGGAGAGCAGATTGACAGAGCTCTACTGAAGAATG
TATTAGATATATTTGTGGAAATTGGGATGGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAACGAGAAAAGGATAGAGTTTCTCACTATT
TGCACTCTAGTAGCGAGCCAAAGTTATTAGAGAAAGTTCAACATGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGCCTCTTCTCCAAAATACCCAAGGGATTGGACCCAGTTTCCAACATATTTA
AGCAGCATGTCACTGCTGAAGGAACAGCATTGGTCAAACAGGCAGAAGATGCTGCAAGTAACAAGA
AGGCCGAGAAAAGGACATAGTTGGTCTGCAGGAACAGGTTTTTGTAAGAAAAGTGATTGAGCTTC
ACGACAAGTACTTGGCTTACGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGCGAGAAGTTGAGTGATGAAGCAATTGAGGAGA
CACTTGAGAAGGTCGTGAAGTTGCTGGCATACATCTGCGACAAAGATCTGTTTGCTGAATTCTATA
GAAAAAAACTTGCCCGAAGGCTTCTCTTTGACAAGAGTGCCAACGATGACCATGAGAGAAGTATAT
TGACCAAATTGAAGCAACAATGTGGTGGCCAGTTCACCTCTAAGATGGAGGGGATGGTCACTGATT
TGACTTTGGCAAGGGAGAACCAAACTAGTTTCGAGGAGTATCTGAGCAATAATCCACAAGCTAGTC
CTGGAATCGACTTGACTGTCACTGTTTTGACTACTGGCTTTTGGCCAAGCTACAAGTCTTTTGACC
TCAACCTGCCGGCAGAGATGGTAAAGTGTGTTGAAGTTTTCAGAGAGTTCTATCAAACAAAAACAA
AGCATAGAAAACTTACATGGATTTACTCATTGGGTACCTGTAACATCAGCGGAAAATTTGAACCGA
AAACGATGGAGCTGATTGTAACAACTTATCAGGCTTCTGCCCTGCTGCTATTCAATTCCTCAGATA
GATTAAGTTATTCCGAGATCATGACACAATTAAATTTGAGTGACGATGATGTTGTTAGACTGCTCC
ACTCATTGTCATGTGCCAAGTATAAAATTCTTAATAAGGAGCCGAACACGAAAACCATCTCTCCGA
ATGATCATTTTGAGTTCAATGCAAAATTCTCCGACAAAATGAGGAGAATAAAGATCCCTCTTCCGC
CTGTGGATGAGAAAAGAAAGTCATTGAAGATGTTGACAAGGATCGAAGGTATGCTATTGATGCCT
CAATCGTGCGTATCATGAAGAGTCGGAAAGTTCTGGGTCATCAGCAGCTAGTGATGGAGTGCGTCG
AGCAATTGGGTCGTATGTTCAAGCCCGACTTCAAAGCGATAAAGAAGAGAATCGAAGATCTGATCA
CTCGGGACTATTTAGAGAGAGACAAAGACAACCCCCACTTGTTTAGGTACTTGGCTTGA
```

Fig. 5

ATGAACCAACGCAGCACAATCGATCTGGAACATGGATGGGATTTCATGCAAAAGGGCATCACAAAG
CTGAAGAACATTCTAGAAGGGCTGCCTGAGCCTCAGTTCAGCTCAGAGGACTATATGATGCTGTAT
ACGACAAT[T]TACAACATGTGTACTCAGAAGCCCCCACATGATTATTCTCAACAGCTGTATGACA
AATATCGTGAAGCTTTTGAAGAATATATCACAACGACGGTATTACCTTCTTTGAGAGAAAAACATG
ACGAGTTCATGTTGCGAGAGTTGGTAAAAGGTGGTCAAACCATAAGGTCATGGTTAGATGGTTAT
CGCGATTCTTCCATTATCTTGACCGTTATTTCATTGCTCGGAGATCACTGCCAGGGCTTAATGAAG
TTGGACTAACTTGCTTCCGCGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCAATGGATTATTATGAGAATGATTTTGAAGCTGCAATGC
TCAAGGACACTGCGGCTTATTATTCTCGCAAAGCTTCTAACTGGATCCTCGAAGATTCATGTCCAG
ATTATATGCTGAAAGCTGAGGAGTGCTTGAAACGGGAGAAGGATAGGGTCTCCCATTATCTCCATT
CTAGCAGTGAGACAAAGTTGCTTGAGAAAGTGCAACATGAGTTGTTATCTGTGTATGCCAATCAAC
TTCTTGAGAAGGAGCACTCTGGATGCCATGCATTACTTAGAGATGATAAGGTCGATGATTTATCAA
GGATGTATAGACTCTTTTCTAAGATTCCTCGAGGCTTAGAGCCTGTGGCTAATATATTTAAGCAGC
ATGTTACTGCTGAAGGTACAGCTTTGGTGAAACAGGCTGAAGATGCTGCTAGCAACAAAAAGGCAG
AGAAGAGAGATGTGGTTGGTTTGCAGGAACAGGTTTTTGTTCGGAAAGTGATTGAGCTTCATGATA
AATATTTGGCGTATGTGAATAACTGTTTCCAAAACCACACTTTTTCACAAGGCACTTAAAGAAG
CTTTCGAACTTTTCTGCAACAAGGGTGTTGCTGGTAGCTCAAATGCTGAACTTCTTGCCACATTCT
GCGACAACATTCTCAAAAAAGGCGGGAGTGAAAAATTGAGTGATGAAGCCATTGAAGAGACGCTGG
AGAAGGTGGTAAAGCTGCTGGCTTATATTAGTGATAAGGACTTGTTTGCAGAATTCTATAGGAAAA
AGCTCGCCCGGCGGTTGTTATTTGATAAGAGTGCCAATGATGAACATGAGAGAAGTATCCTAACAA
AGTTGAAGCAGCAGTGTGGAGGTCAGTTCACATCAAAGATGGAGGGAATGGTCACAGATTTGACAT
TGGCAAGGGAAAATCAAGCCAGCTTTGAGGAGTATTTGAGCAATAATCCAACAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGTGTTGAAGTATTCAAGGAGTTTTATCAAACAAAAACGAAGCACA
GGAAACTTACATGGATATACTCTTTGGGAACTTGCAACATAAATGGAAAATTTGAGGCAAAGACTA
TTGAGCTCGTTGTCACTACTTATCAGGCTTCTGCTCTGCTTCTCTTTAATGCATCAGATAGATTGA
GTTATCAGGAAATCATGACGCAATTAAACCTATCAGATGATGATGTTGTTCGGCTTCTTCATTCCC
TTTCATGTGCGAAATACAAGATTCTCAACAAGGAGCCAAGCACCAAAACAATTTCTCCGACTGATG
TCTTTGAGTTCAACTCAAAGTTCACTGACAAAATGAGGAGGATCAAGATACCTCTCCCACCAGTTG
ATGAAAAGAAAAAGGTAATTGAAGACGTTGACAAGGATAGGCGGTATGCTATAGATGCCTCAATTG
TGCGTATTATGAAGAGTCGTAAAGTATTGGGCTACCAGCAACTGGTCATGGAGTGCGTTGAGCAGT
TGGGACGCATGTTCAAGCCTGATGTCAAAGCTATCAAGAAGAGAATTGAAGATCTGATAACTAGAG
ATTACCTAGAGAGGGACAAAGATAACCCAAACTTGTTCAAGTACTTGGCATGA

Fig. 6

```
ATGAACCAACGAAGCACAATCGATCTGGAACATGGATGGGACTTCATGCAAAGGGGCATTACAAAG
CTGAAGAACATTCTAGAAGGGCTGCCTGAGCCTCAATTCAGCTCAGAGGACTATATGATGCTATAT
ACGACAAT[T]TACAACATGTGTACTCAAAAGCCCCCACATGATTATTCTAACAGCTGTATGACA
AATATCGTGAAGCTTTTGAAGAATATATCACAACAACGGTATTGCCTTCTTTGAGAGAAAAACATG
ACGAGTTTATGTTGCGAGAGTTGGTAAAAGGTGGTCAAATCATAAAGTCATGGTCAGATGGTTGT
CAAGATTCTTCCATTACCTTGACCGTATTTCATTGCCCGGAGATCTCTGCCGGGGCTTAATGAAG
TTGGACTAACTTGCTTCCGCGATCAGGTCTACCAAGAGTTGAATGGAAAAGTCAGGGATGCTGTTA
TATCTCTGATTGATCAAGAGCGTGAGGGAGAGCAAATTGACAGAGCTCTACTTAAGAATGTGCTTG
ATATATTTGTCGAAATTGGAATGGGGTTAATGGATTATTATGAGAATGATTTTGAAGCTGCAATGC
TCAAGGACACAGCGGCTTATTATTCTCGCAAAGCTTCTAATTGGATCCTCGAAGATTCATGTCCGG
ATTATATGCTGAAAGCCGAGGAGTGCTTGAAACGGGAGAAGGATAGGGTCTCTCATTATCTCCATT
CAAGCAGCGAGACGAAGTTGCTTGAGAAAGTGCAACATGAGTTGTTGTCTGTGTATGCCACTCAAC
TTCTTGAGAAGGAGCACTCTGGATGCCATGCGTTACTGAGAGATGATAAGGTTGAAGATTTATCAA
GGATGTATAGGCTCTTTTCTAAGATTTCTCGAGGCTTAGACCCTGTGGCCAATATTTTTAAGCAGC
ATGTTACTGCTGAAGGTACAGCTTTGGTAAAACAGGCTGAAGATGCTGCTAGCAATAAAAAGGCAG
AGAAGAGAGATGTGGTTGGTTTGCAGGAACAGGTTTTTGTTCGGAAAGTGATTGAACTTCATGATA
AATATTTGGCTTATGTGAATAACTGTTTCCAAAACCACACACTTTTTCACAAGGCGCTTAAAGAAG
CTTTTGAGCTTTTCTGCAACAAGGGTGTTGCTGGTAGCTCAAGCGCTGAACTTCTTGCCACCTTCT
GTGACAACATTCTCAAAAAAGGCGGGAGTGAGAAATTGAGTGATGAAGCTATTGAAGAAACGTTGG
AAAAGGTGGTAAAGCTACTAGCTTATATTAGTGATAAGGACTTGTTTGCAGAATTCTATAGGAAAA
AGCTAGCCCGGCGGTTGTTATTTGATAAGAGTGCCAATGATGAACATGAAAGAAGTATCCTAACAA
AGTTGAAGCAGCAGTGTGGGGGGCAGTTCACATCAAAGATGGAGGGAATGGTCACAGATTTGACAT
TGGCAAGGGAAAATCAAGCCAGCTTCGAGGAGTATTTGAGCAATAATCCAATAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTTAAGGAGTTCTATCAAACAAAAACAAAGCACA
GGAAACTTACGTGGATATACTCTTTGGGAACTTGCAACATAAATGGAAAATTTGAGCCAAAAACTA
TTGAGCTCGTTGTCACTACTTATCAGGCTTCTGCTCTGCTGCTCTTTAATGCATCAGATAGATTGA
GTTATCAGGAAATCATGACGCAATTAAACCTATCAGATGATGATGTTGTTCGGCTTCTTCATTCCC
TTTCATGTGCGAAGTACAAGATACTCAACAAGGAGCCAAGCACCAAAACAATTTCTCCGACTGATG
TCTTTGAGTTCAACTCAAAGTTCACTGACAAAATGAGGAGGATCAAGATACCTCTCCCTCCTGTTG
ATGAGAAGAAAAAGGTAATTGAAGACGTTGACAAGGATAGGCGGTATGCTATAGATGCTTCAATTG
TGCGTATTATGAAGAGCCGTAAAGTATTGGGCTACCAGCAACTAGTCATGGAGTGCGTTGAGCAGT
TGGGGCGCATGTTCAAGCCTGATGTCAAAGCTATCAAGAAGAGAATCGAAGATTTGATAACTAGAG
ATTACCTAGAGAGGGACAAAGATAATCCAAACCTGTTCAAGTACTTGGCATGA
```

Fig. 7

ATGAACCAGCGTTCCACAATCAATCTAGAACATGGATGGGACTTCATGCAAAGGGGCATTACAAAG
CTGAAGAACATTCTAGAAGGGCTGCCCGAGCCTCAGTTCAGCTCAGAGGACTATATGATGCTGTAT
ACGACAAT[T]TACAACATGTGTACTCAGAAGCCCCCACATGATTATTCTCAACAGCTGTATGACA
AATATCGTGAAGCTTTTGAAGAATATATCACAACAACGGTATTGCCTTCTTTGAGAGAAAAACATG
ACGAGTTCATGTTGCGAGAGCTGGTAAAAGGTGGTCAAACCATAAGGTCATGGTCAGATGGTTAT
CGCGATTCTTCCATTATCTTGATCGCTATTTCATTGCCCGGAGATCTCTACCGGGGCTTAATGAAG
TTGGACTAACTTGCTTCCGAGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCGATGGATTATTATGAGAATGATTTTGAAGCTGCAATGC
TCAAGGACACCGCAGCTTATTATTCTCGCAAAGCTTCTAACTGGATACTTGAAGATTCATGTCCAG
ATTATATGCTGAAAGCCGAGGAGTGCTTGAAACGGGAGAAAGATAGGGTCTCTCACTATCTTCATT
TAAGCAGTGAGACAAAGTTGCTTGAGAAAGTGCAACATGAGTTGTTGTCTGTGTATGCCACTCAAC
TTCTTGAGAAGGAGCACTCTGGGTGCCATGCGTTACTAAGAGATGATAAGGTTGAAGATTTATCAA
GGATGTATAGGCTCTTTTCTAAGATTCCTCGAGGCTTAGACCCTGTGGCTAATATATTTAAGCAGC
ATGTTACTGCTGAAGGTACAGCTTTGGTCAAACAGGCTGAAGATGCTGCTAGCAACAAAAAGGCAG
AGAAAAGAGATGTGGTTGGTTTGCAGGAACAGATTTTTGTTCGGAAAGTGATTGAGCTTCATGATA
AGTATATGGCATATGTGAATAACTGTTTCCAAAACCACACACTTTTTCACAAGGCGCTTAAAGAAG
CTTTCGAACTTTTCTGCAACAAGGGTGTTGCTGGTAGCTCAAGTGCTGAACTTCTTGCCACATTCT
GCGACAATATTCTCAAGAAAGGCGGGAGTGAGAAATTGAGTGATGAAGCCATTGAAGAGACGCTGG
AGAAGGTTGTAAAGCTGCTAGCATATATTAGTGACAAGGACTTGTTTGCAGAATTCTATAGGAAAA
AGCTAGCCCGGCGGTTGTTATTTGATAAGAGTGCCAATGATGAACACGAGAGAAGTATCCTTACAA
AGTTGAAGCAGCAGTGTGGGGGCCAGTTCACATCAAAGATGGAGGGAATGGTGACAGATTTGACAT
TGGCAAGGGAAAATCAAGCCAGCTTTGAGGAGTATTTGAGCAACAATCCAGCAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTCAAGGAGTTTTATCAAACAAAAACGAAGCACA
GGAAACTTACGTGGATATACTCTTTGGGAACTTGCAATATAAATGGAAAATTTGAGCCAAAGACTA
TTGAGCTCGTTGTCACTACTTATCAGGCTTCTGCTCTGCTGCTCTTTAATGCATCGGATAGATTGA
GTTATCAGGAAATCATGACGCAACTAAACCTATCAGATGATGATGTTGTCGGCTTCTTCATTCCC
TTTCATGTGCGAAGTACAAGATTCTCAACAAGGAGCCAAGCACCAAAACAATTTCTCCGACTGATG
TCTTTGAGTTCAATTTTAAGTTCACTGACAAAATGAGGAGGATCAAGATACCTCTCCCTCCTGTTG
ATGAGAAGAAAAGGTAATTGAAGATGTTGACAAAGATAGGCGGTACGCTATAGATGCTTCAATTG
TGCGTATTATGAAGAGTCGTAAAGTATTGGGCTACCAGCAACTGGTCATGGAGTGTGTTGAGCAGT
TGGGACGTATGTTCAAGCCTGATGTCAAAGCTATCAAGAAGAGAATTGAAGATTTGATAACTAGAG
ATTACCTAGAGAGGGACAAAGATAATCCGAACTTGTTCAAGTACTTGGCATGA

Fig. 8

```
ATGGAGCGCAAGACGATTGACTTGGACCAAGGATGGGACTATATGCAGACTGGTATCACTAAGCTG
AAACGGATTCTTGAGGGGCTGCCTGAGCCGCAGTTTGACTCTGAGCAATACATGATGCTCTATACG
ACTAT[C]TACAACATGTGCACTCAGAAACCTCCTCATGATTACTCACAGCAGCTTTATGACAAGT
ATCGTGAAGCATTTGAGGAGTATATTCACTCAACTGTTTTGCCTGCTCTAAGGGAGAAGCATGATG
AGTACATGCTGAGGGAGCTGGTTAAGAGATGGTCTAACCATAAAGTTATGGTTCGATGGCTATCCC
GCTTCTTCTACTATCTTGACCGTTACTTCATTGCTCGGAGGTCACTTCCACCCCTGAATGAAGTTG
GCCTGACTTGCTTCCGTGACCTGGTTTATAACGAGTTGCATTCCAAGGTCAAAGATGCTGTAATAG
CACTTGTTGATAAGAACGGGAGGGTGAGCAGATTGACAGGGCTCTATTGAAAACGTATTAGACA
TTTATGTAGAGATTGGAATGGGACAGATGGAAAGATACGAGGAGGATTTTGAAAGCTTCATGCTTT
TAGATTCAGCATCTTACTATTCTCGCAAGGCGTCAAGCTGGATCCAAGAAGATTCTTGCCCTGATT
ACATGCTGAAGTCTGAAGAATGTCTTAAGAAGGAGAGGGAGAGAGTGGCTCACTACCTTCACTCAA
GCAGCGAGCCAAAGCTGGTTGAGAAAGTACAACATGAGCTGTTGGTAGTGTATGCAAATCAGCTTC
TAGAAAAAGAGCATTCAGGGTGCCGTGCATTGCTGAGAGATGACAAGGTTGATGACCTCTCCAGGA
TGTACAGGCTTTATCATAAAATTGTGAAAGGTTTGGAACCTGTTGCAAACATATTTAAGCAGCATG
TCACAGCAGAGGGTAACGCACTTGTCCAACAGGCCGAAGACACGGCCACTAATCATGCTGCAAATA
CTGCTAGCGTGCAGGAACAGGTTCTTATCAGAAAGTGATTGAACTACATGATAAATACATGGTCT
ATGTTGTTGAGTGTTTCCAGAACCACACCCTCTTCCACAAGGCATTGAAAGAGGCATTTGAGATAT
TCTGTAACAAAACAGTCGCTGGAAGTTCTAGTGCTGAATTGCTTGCAACATTTTGCGACAATATTC
TCAAGAAGGGGGGAAGTGAAAAGCTGAGCGATGAAGCTATTGAAGATACCCTTGAGAAGGTGGTCA
AATTGCTTGCTTATATAAGTGACAAGGATCTTTTCGCCGAGTTCTACAGGAAGAAGCTGGCCCGTA
GGCTCTTATTTGATCGCAGTGCTAATGATGATCATGAGAGAAGTATCCTGACAAAGCTCAAGCAAC
AATGTGGTGGGCAGTTTACTTCGAAGATGGAGGGCATGGTGACTGATTTGACATTGGCAAGGGAAA
ACCAAAACAGCTTCGAGGAGTATCTTGGCAATAACCCCGCTGCAAACCCAGGGATTGATTTGACCG
TAACTGTTCTTACCACTGGTTTTTGGCCAAGTTACAAATCATTTGACATAAATCTACCCGCTGAAA
TGGTCAAGTGTGTTGAAGTTTTCAAAGGGTTTTATGAAACAAAGACAAAACATAGGAAACTTACCT
GGATCTACTCACTAGGAACTTGCCACCTCAATGGGAAGTTTGATGTCAAGCCCATTGAGTTAGTTG
TGTCTACATACCAGGCTGCTGTGCTTCTGCTGTTCAACACAACAGACAAATTGAGCTACACTGATA
TCCTAACTCAGCTGAACCTGAGCCACGAAGATCTAGTGAGGTTGCTTCATTCCTTGTCATGTGCTA
GATACAAGATTCTTCTCAAGGAGCCAAGCACAAAGACTGTTTCCCAGTCTGATTCTTTTGAATTCA
ACTCCAAATTCACCGACAGAATGCGGAGAATAAAGATCCCTCTCCCACCTGTTGATGAGAGGAAGA
AAGTTGTGGAAGACGTGGACAAAGACAGACGCTATGCGATTGATGCTGCCATTGTGAGGATCATGA
AGAGCAGGAAAGTATTGGACATCAACAACTTGTTTCTGAGTGCGTTGAGCAACTTAGCCGAATGT
TCAAGCCTGATATCAAGGCAATCAAGAAGCGCATGGAGGATTTGATAACGAGAGATTATCTGGAGA
GGGACAAGGAGAACGCTAACATGTTTAGGTACTTGGCTTAG
```

Fig. 9

ATGATGATTGAGCGGAAAACTATAGACCTGGAGCAGGGATGGGACTTTATGCAAAAGGGAATCACA
AAGCTAAAGAATATTTTAGAAGGCTTTCCGGAGCCGCAATTCAGCTCGGAGGATTATATGATGCTT
TATACAACTAT[C]TATAACATGTGTACACAGAAACCTCCACATGATTACTCTCAGCAGCTGTATG
AAAAGTATCGTGAAGCTATTGAGGAGTACATTACTTCTACAGTATTGCCTTCATTGAGAGAGAAGC
ATGATGAATTCATGCTTAGAGAACTTGTGAAGAGATGGTCTAATCATAAGGTCATGGTCAGGTGGC
TTTCTCGATTCTTTCACTATCTTGATCGCTATTTTATTGCTCGGAGGTCACTTCCACCACTTCATG
AAGTTGGACTCACTTGCTTTCGGGACCTGGTTTACCAGGAGATAAATGGGAAAGTAAGGGATGCTG
TAATATCATTGATTAATCAAGAGCGCGAGGGAGAGCAAATTGACCGAGCTTTGTTGAAGAATGTTC
TAGATATATTTGTTGAAGTTGGAATGAGTCAAATGGATTATTATGAGAATGACTTTGAAGCAGACA
TGCTCAAAGATACAGCAGCATACTATTCTCGAAAGGCTTCCAACTGGATCTTAGAAGATTCTTGTC
CAGATTATATGCTCAAAGCGGAAGAGTGTTTGAGACGGGAAAAGGACAGGGTCTCTAACTACCTTC
ATTCTAGTAGTGAACCCAAGTTGCTTGAGAAAGTTCAACATGAGTTACTATCACACTATGCAACTC
AGCTGCTTGAGAAAGAACACTCTGGGTGTCATGCATTGCTTAGGGATGACAAGGTGGCAGATTTAT
CAAGGATGTATAGGCTCTTCTCTAAAATACCTCGAGGCCTAGATCCCGTGTCTAATATTTTCAAGC
AGCATGTTACTGCTGAAGGTACAGCTTTGGTCAAACAAGCAGAAGATGCAGCTAGCAACAAGAAGG
CAGAGAAGAGAGATGTAGTAGGTTTACAAGAACAGGTTTTTGTGAGGAAAATAATTGAATTGCATG
ACAAATACCTTACATACGTAAATGACTGTTTTACAAACCACACTCTCTTCCATAAGGCGCTTAAGG
AGGCTTTTGAAATCTTCTGCAATAAGGGTGTCTCTGGAAGCTCTAGTGCAGAATTACTTGCCACAT
TCTGTGATAATATTCTCAAGAAAGGTGGAAGCGAGAAGTTAAGTGATGAAGCCATTGAGGAAACAC
TTGAGAAGGTTGTAAGGTTGCTTGCTTATATAAGTGACAAAGACTTATTTGCTGAATTTTATAGGA
AAAAGCTTGCACGGCGTCTCTTATTCGACAAGAGTGCCAATGATGAGCATGAGAGAAGTATATTGA
CTAAGCTGAAGCAACAATGTGGGGGTCAATTTACATCAAAGATGGAAGGAATGGTCACTGACTTGA
CGTTGGCAAAGGAAAATCAGTCCAACTTCGAGGAGTACCTCAATAATAATTCAAACGTAAATCCTG
GAATTGACTTGACAGTTACTGTTCTAACCACTGGGTTTTGGCCAAGTTACAAATCTTTCGATCTCA
ACCTCCCAGCAGAGATGGTCAAATGTGTTGAAGTTTTTAGAGAATTCTACCAAACAAAAACAAAGC
ACAGAAAACTGACATGGATATACTCTTTGGGTACTTGTAACATCATTGGAAAATTTGATCCAAAAA
CCATGGAGCTTATTGTGACAACATACCAGGCCTCTGCTCTGCTGCTATTTAACTCTTCTGATAGAC
TTAGTTATAATGAAATAATGACTCAGTTGAACTTGTCGGATGATGATGTTGTCAGACTACTTCATT
CTCTTTCGTGTGCAAAGTACAAGATTCTATCTAAAGAGCCGAACACCAAAACTATATCTCCAACTG
ATTGCTTTCAGTTCAATTCCAAATTTACTGATAAAATGAGGAGGATTAAGATTCCACTTCCCCCAG
TGGATGAGAAGAAAAGGTAATTGAAGATGTTGATAAAGACAGGCGATATGCTATAGATGCTTCAA
TTGTCCGTATCATGAAGAGCCGCAAAGTTTTGGGTTATCAGCAGCTAGTAATGGAGTGCGTTGAAC
AATTGGGTCGCATGTTTAAGCCTGATGTCAAAGCAATCAAGAAGAGAATCGAAGATTTAATAACTC
GGGATTATCTGGAAAGAGACAAGGACAATGCCAACTTGTTCAGGTATCTGGCATGA

Fig. 10

```
ATGAACGAGCGGAAGACTATCGATTTGGATAATGGATGGGAATTTATGCAGAAAGGGATCACTAAG
TTGAAGAAGATTCTCGAAGGTCAACCTGAGCCTCAGTTTAGCTCCGAGGACTATATGATGCTTTAC
ACAACTAT[C]TATAATATGTGTACGCAGAAGCCTCCACATGATTATTCTCAACAGCTGTATGACA
AGTACCGTGAGGCCTTTGAGGAGTACATAACTTCAACTGTCCTGCCTTCTTTACGAGAGAAGCATG
ATGAGTTTATGTTGAGAGAGCTCGTGAATAGATGGACAAACCATAAAGTCATGGTCAGGTGGCTTT
CTCGATTCTTTCACTATCTTGATCGGTACTTCATTGCGAGGAGGTCACTTCCTGCACTTCATGAAG
TTGGACTCACGTGCTTCCGGGATCTGGTCTATCAGGAGCTGAAAGTTAAAGTGAGGGATGCTGTAA
TATCTCTGATCGATCAAGAGCGTGAGGGGGAACAGATTGACCGAGCTTTATTAAAGAACGTGTTAG
ATATATTTGTTGAAATCGGAATGAGTCAAATGGATCAATATGAGAATGACTTTGAAGAAGCCATGC
TCACTGATACTGCTGCTTACTATTCTCGAAAAGCTTCAAACTGGATCCTTGAAGATTCTTGTCCTG
ATTATATGTTAAAGGCAGAAGAATGTTTGCGACGAGAGAAGGACAGGGTTTCCCACTACCTACATT
TTAGTAGCGAGCCAAAGTTGCTTGAGAAAGTGCAACATGAGCTGCTATCTGTGTATGCAACCCAAT
TACTCGAGAAGGAACATTCTGGTTGTCATGCATTGCTTAGGGATGACAAGGTGGATGATTTGTCTA
GGATGTACAGACTCTTCTCGAAAATACCTAAAGGCCTGGATCCAGTTTCTTATATTTTTAAGCAGC
ATGTTACAAATGAAGGGATGGCATTGGTTAAACAAGCAGAAGATGCAGCAAGCAACAAGAAGGCAG
AAAAGAGAGACGTGGTTAGTTTACAGGAGCAGGTTTTTGTTAGAAAAATTATTGAATTACATGACA
AATACCTCGCCTATGTGAATGACTGCTTTACAAACCATACTCTTTTCCATAAGGCTCTCAAGGAGG
CTTTTGAAATCTTTTGCAACAAGGGTGTTGCTGGAAGCTCTAATGCTGAACTACTTGCTACTTTCT
GTGATAACATCCTCAAAAAGGGTGGGAGTGAGAAATTAAGTGATGAGGCTATTGAAGAAACACTTG
AGAAGGTAGTAAAATTGTTAGCTTACATTAGCGATAAAGACTTGTTCGCTGAATTTTACAGAAAAA
AGCTTGCACGGAGACTTCTCTTTGATAAGAGTGCAAATGACGAGCATGAACGAAGTATTTTGACTA
AACTAAAGCAACAGTGCGGTGGTCAGTTCACATCGAAAATGGAGGGGATGGTCACAGATTTGACTT
TGGCTAAAGAAAATCAATCCAGCTTTGAGGAGTATCTGGGAAATAATGCCAATGTGAATCCTGGCA
TTGACTTGACGGTTACTGTTCTGACCACTGGCTTCTGGCCTAGTTATAAATCCTTTGATCTCAACC
TTCCTGCTGAGATGGTCAAGTGCGTTGAAGTATTTAGAGAATTTTATCAAACAAAAACGAAGCATA
GAAAGCTCACATGGATATATTCTCTGGGTACTTGTAATATCAATGGAAAATTTGAACCCAAAACCA
TTGAGCTGATTGTGACAACCTACCAGGCCTCTGCTCTCCTGTTATTTAATACTTCTGATAGGTTGA
GTTATCAAGAAATCATGACTCAGTTAAATTTGTCGGATGATGATGTTGTTCGCCTGCTTCATTCCC
TTTCATGTGCCAAGTATAAAATTCTTACTAAAGAGCCGAACAACAAAACAATTTCCCCTACGGATT
ACTTTGAGTTCAACTCCAAGTTCACTGACAAAATGAGGAGAATTAAGATTCCACTACCTCCAGTTG
ATGAGAAGAAAAGGTAATTGAAGATGTTGACAAGGACCGGCGATATGCCATTGATGCATCTATTG
TCCGCATTATGAAGAGCCGTAAAGTTTTGGGCTACCAACAATTGGTTATGGAATGTGTTGAGCAAT
TGGGACGCATGTTTAAGCCTGATGTCAAAGCAATTAAGAAGAGAATCGAAGATTTAATAACGCGTG
ATTATCTGGAAAGAGACAAGGATAATGCCAACCTTTTCAGATATTTGGCATGA
```

Fig. 11

```
ATGAATGAAAGAAAAACAATAGACTTAGAACAAGGATGGGACTTCATGCAGAAAGGCATAACAAAG
TTGAAGAACATTCTAGAAGGTCTTCCCGAGCCACAATTCAGCTCGGAAGATTACATGATGCTCTAC
ACAACCAT[C]TACAATATGTGCACACAAAAACCGCCACATGATTACTCTCAACAATTGTATGACA
AATACCGCGAGTCTTTTGAAGAGTACATTACTTCAACGGTGTTACCTTCTTTAAGAGAAGCATG
ATGAGTTTATGCTTAGAGAGCTTGTTAGAAGATGGTCAAATCATAAAGTGATGGTTAGGTGGCTTT
CTAGATTCTTCCATTATCTTGATCGATACTTCATTGCCCGAAGATCTCTTCCACCATTAAATGAAG
TTGGACTTGCGTGTTTTCGTGATCTGGTATACCAAGAGGTGAATGGGAAGTGAGAGATGCTGTAA
TATCTTTGATTGATCAAGAGCGTGAAGGCGAGCAAATTGACCGAGCATTACTCAAGAATGTTCTAG
ATATATTTGTTGAAATAGGAATGGGACAAATGGAATATTATGAGAATGATTTTGAAGCATCCATGC
TTAATGATACAGCAGCATATTATTCACGCAAAGCTTCCAATTGGATTCTAGAAGATTCTTGTCCAG
ATTATATGCTCAAAGCTGAGGAGTGCTTAAAAGAGAAAAGGACAGAGTTTCTCATTATCTTCATT
CCAGCAGTGAACCAAAGCTTCTTGAGAAAGTTCAAACAGAGTTATTATCTGTTTATGCAACTCAAT
TGCTTGAAAAGGAGCACTCCGGTTGTCATGCATTACTTAGGGATGACAAGGTTGATGATTTATCAA
GAATGTACAGACTCTTTTCAAAGATACAAAAGGGCTGGATCCTGTTTCTAGTATGTTTAAGCAGC
ATGTCACTGCTGAAGGCACAACATTGGTTAAACAGGCAGAAGATGCAGCAAGTACTAAGAAGGCTG
AAAAGAGAGACGTGGTTGGCTTACAAGAACAGGTTTTTGTTAGAAAAGTTATCGAGCTTCATGACA
AGTACCTTGCATATGTAAATGACTGTTTTATGAATCATACCCTGTTTCACAAGGCTCTTAAAGAGG
CATTTGAAATATTCTGCAACAAGGGCGTTGCTGGAAGTTCAAGTGCAGAATTACTTGCTACATTTT
GTGATAATATTCTTAAAAAAGGTGGAAGTGAAAAATTGAGTGATGAAGCCATTGAGGACACACTTG
AGAAGGTGGTAAAGTTGCTTGCTTACATCAGCGATAAAGATCTATTTGCAGAGTTTTATAGGAAAA
AACTGGCTAGACGGCTTTTATTTGACAAAAGTGCAAATGATGAGCACGAAAGAAGTATTTTGACAA
AATTGAAACAACAATGTGGCGGTCAATTTACATCAAAAATGGAAGGAATGGTTACAGATTTGACAT
TGGCAAAAGAAAATCAATCACATTTTGAGGAGTATTTGAATAATAATCCCAATGTTAGCCCTGGCA
TTGACTTGACCGTGACTGTGTTGACCACTGGTTTTTGGCCTAGTTACAAATCTTTTGACCTAAATC
TCCCTGCAGAAATGGTCAAATGCGTTGAAGTTTTCAGAGAATTTTATCAAACAAAAACAAAACACA
GAAAACTCACATGGATATATTCATTGGGCACCTGCAATATAAACGGAAAATTCGAACCAAAAACCA
TGGAGCTAATCGTTACAACTTACCAGGCATCTGCTTTATTACTGTTCAACTCATCAGATCGATTGA
GTTATCAAGAAATCATGACTCAATTAAACTTATCAGATGATGATGTTGTTAGACTACTCCATTCAT
TATCATGTGCAAAATATAAAATTTTATTAAAAGAACCAAATACAAAAACAATCTCTCCAACTGATT
TCTTTGAATTCAACTCAAAGTTTACAGATAAAATGAGAAGGATCAAGATTCCTCTACCTCCTGTTG
ATGAAAAGAAAAAGTAATTGAAGATGTTGACAAAGACCGACGTTATGCAATTGATGCTTCAATTG
TACGGATAATGAAAGCAGAAAAGTTCTTGGATACCAACAATTGGTCATGGAATGTGTTGAACAAT
TAGGCCGTATGTTTAAGCCTGATGTAAAAGCAATCAAGAAACGTATTGAAGATCTCATAACTCGTG
ATTATCTTGAAAGAGACAAAGAAAATCCAAATTTGTTTCGGTACTTGGCATGA
```

Fig. 12

```
ATGAATGAAAGAAAAACAATAGACTTAGAACAAGGATGGGACTTCATGCAAAAAGGCATAACAAAG
TTGAAGAACATTCTAGAAGGTCTTCCCGAGCCACAATTCAGCTCAGAGGATTACATGATGCTCTAC
ACAACCAT[C]TACAATATGTGCACACAAAAACCGCCACATGATTACTCTCAACAATTATATGACA
AATACCGCGAGTCTTTTGAAGAGTACATAACTTCAACGGTGTTACCTTCTTTAAGAGAGAAGCATG
ATGAGTTTATGCTTAGAGAGCTTGTTAGAAGGTGGTCAAATCATAAAGTGATGGTTAGGTGGCTTT
CTAGATTCTTCCATTATCTTGATCGATACTTTATTGCAAGAAGATCTCTTCCACCATTAAATGAAG
TTGGACTTGCGTGTTTTCGTGATCTGGTATACCAAGAGGTGAATGGAAAGTGAGAGATGCTGTAA
TATCTTTGATTGATCAAGAGCGTGAAGGCGAGCAAATTGACCGAGCATTACTGAAGAATGTTCTAG
ATATATTTGTTGAAATAGGAATGGGACAAATGGAATATTATGAGAATGATTTTGAAGCATCTATGC
TTAATGATACAGCAGCATATTATTCACGCAAAGCTTCCAACTGGATTCTAGAAGATTCTTGTCCAG
ATTATATGCTCAAAGCTGAGGAGTGCTTAAAAGAGAAAAGGACAGAGTTTCTCATTATCTTCATT
CAAGTAGTGAACCAAAGCTTCTTGAGAAAGTTCAAACAGAGTTATTATCTGTTTATGCAACTCAAT
TGCTCGAAAAGGAACACTCAGGTTGTCATGCATTACTTAGAGATGACAAGGTTGATGATTTATCAA
GAATGTACAGACTCTTTTCAAAGATACAAAAAGGACTGGATCCTGTTTCCAGTATGTTTAAGCAGC
ATGTCACTGCTGAAGGCACAACATTAGTAAAACAAGCAGAAGATGCAGCAAGTACTAAGAAGGCTG
AAAAGAGAGACGTGGTTGGCTTACAGGAACAGGTTTTTGTTAGAAAAGTAATCGAGCTTCATGACA
AGTACCTCGCATATGTAAACGACTGTTTTATGAATCACACATTGTTCCACAAGGCTCTTAAAGAGG
CATTTGAAATATTCTGCAACAAGGGCGTTGCTGGAAGTTCAAGTGCAGAATTACTTGCCACATTTT
GTGATAATATTCTTAAAAAAGGTGGAAGTGAAAAATTGAGTGATGAAGCCATTGAAGACACACTTG
AGAAGGTAGTAAAGTTGCTTGCTTACATCAGCGATAAAGATCTATTTGCAGAGTTTTATAGGAAAA
AACTGGCTAGAAGGCTTTTATTTGACAAAAGTGCAAATGATGAGCATGAAAGAAGTATTTTAACAA
AGTTGAAGCAACAATGTGGTGGTCAGTTTACATCAAAGATGGAAGGAATGGTTACAGATTTAACAC
TGGCAAAAGAAAATCAATCACATTTTGAGGAGTATTTGAATAATAATCCCAATGTTAGCCCTGGCA
TTGACTTGACCGTGACTGTGTTGACCACGGGATTTTGGCCTAGTTACAAATCTTTTGACCTAAATC
TTCCTGCAGAAATGGTCAAATGCGTTGAAGTTTTCAGAGAATTTTATCAAACAAAAACAAAACACA
GAAAACTCACATGGATTTATTCATTGGGCACCTGCAATATTAACGGAAAATTCGAACCAAAAACCA
TGGAGCTAATCGTTACAACTTACCAGGCATCTGCTTTATTGTTATTCAACTCATCAGATCGATTAA
GTTATCAAGAAATCATGACTCAATTAAATTTATCAGATGATGATGTTGTTAGACTACTACATTCAT
TATCATGTGCAAAATATAAAATTTTATTAAAAGAACCAAATACCAAAACAATATCTCCAACCGATT
TCTTTGAATTCAACTCAAAGTTTACAGATAAAATGAGAAGGATCAAGATTCCTCTACCTCCTGTTG
ATGAAAAGAAAAAGTAATTGAAGATGTTGACAAAGATAGAAGGTATGCAATTGATGCTTCAATTG
TACGAATAATGAAAGCAGAAAAGTTCTTGGATACCAACAATTGGTTATGGAGTGTGTTGAACAAT
TAGGCCGTATGTTTAAGCCTGATGTAAAAGCAATCAAGAAGCGTATTGAAGATTTGATAACGCGTG
ATTATCTTGAAAGAGACAAAGAAAATCCAAATTTGTTTCGGTACTTGGCATGA
```

Fig. 13

ATGTCGTTGCACGAAAGGAAAACCATTGATTTGGAGCAGGGATGGGCTTTTATGCAGAAAGGGATC
ACCAAACTGAAGAATATTCTTGATGAGTTGAATGAACCTCAGTTCAGCTCAGAGGATTACATGATG
CTCTATACGACTAT[C]TATAATATGTGTACTCAGAAGCCGCCACATGATTATTCTCAGGAGTTGT
ATGATAAGTACCGAGAGTCCTTTGAAGAGTATATCACTACCACTGTGCTTCCTTCATTGAGAGAAA
AGCATGATGAATACATGTTAAGGGAGCTCGTGAGAAGGTGGTCAAATCATAAAATAATGGTTAGAT
GGCTTTCACGCTTTTTCCATTATCTTGATCGCTACTTTATAGCACGAAGATCATTGCCTGCTCTTA
ATGAAGTCGGTCTCACTTGTTTCCGTGATCTGGTGTACAACGAAGTCCATGGGAAAGTTAAAGATG
CCGTGATCTCATTGATTGACCAAGAGAGGGAAGGGGAGCAAATTGACAGAGCTTTATTAAAGAATG
TTTTGGGTATTTTTGTAGAGATTGGTTTGGGAAGCATGGAATGTTATGAGAATGATTTTGAAACAT
CAATGCTTAATGCTACAGCAGCCTATTATTCACGAAAAGCTTCAAATTGGATTCTAGAAGATTCAT
GTCCAGATTATATGCTAAAAGCCGAGGAGTGCTTAAAACATGAGAAAGATAGAGTTGCTCATTATT
TGCATTCAAGCAGTGAACAGAAGCTGTTAGAGAAAGTGCAACATGAGTTACTTTTCGTATATGCAA
GTCAACTTCTCGAGAAAGAACATTCCGGATGTCATGCATTGCTTCGCGATGACAAGGTGGGAGATC
TTTCACGCATGTATCGGCTGTTCTGTAGAATTACACGTGGTTTGGACCCTGTGTCTCAAATATTTA
AGCAGCATGTGACTGCAGAAGGTACTGCTTTGGTCAAACATGCCGAAGATGCTGCAAGTAACAAGA
AGGCCGAGAAAAAAGACATTGTTGGTTTGCAAGAGCAGGTCTTCGTTAGGAAAGTAATTGAGCTGC
ATGATAAATACTTGGCCTATGTGACTGACTGCTTTCAAAATCACTCTCTATTTCACAAGGCACTTA
AAGAGGCATTCGAGGTATTCTGCAATAAAGGTGTTGCAGGTAGCTCAAGCGCTGAACTTCTGGCTG
CTTTTTGTGACAATATATTGAAGAAGGGTGGAAGCGAGAAACTAAGCGATGAGGCCATAGAGGATA
CTCTTGAGAAGGTTGTAAAACTATTGGCATATATTAGCGATAAAGATCTGTTTGCTGAATTTTACA
GGAAGAAGCTTGCACGAAGATTACTCTTTGACAAAAGTGCTAATGATGACCATGAGAGGAGCATCC
TTACAAAGCTGAAACAGCAATGTGGAGGGCAGTTCACCTCTAAAATGGAAGGCATGGTAACCGATC
TGACACTTGCACGAGAAAATCAATCAAGTTTTGACGATTACCTTAGCAGCAATCCTAAAGCAAATT
CTGGAATTGACTTGACTGTTACAGTCTTAACAACTGGCTTCTGGCCCAGTTACAAGTCTTTTGATC
TCAATCTTCCTGATGAGATGGTAAAATGCGTTGAAATTTTTAAAGAGTTTTACGAGACAAAAACCA
AACACAGAAAACTTACATGGATTTATTCGTTGGGCACTTGCAACATCAATGGCAAGTTCGAAACCA
AGACAATAGAGTTGGTTGTTACAACCTATCAGGCTGCAGTGTTGCTTCTATTCAACTCTGCAGATA
AATTAAGTTATTCTGAGATTGTGCAGCAGCTAAACTTATCTGATGATGATGTAATCAGATTACTTC
ACTCTCTTTCATGCGCTAAATACAAAATTCTCAATAAAGAACCCGCTACCAAGACTATTACCCCGA
ATGATCATTTTGAGTTCAATTCTAAATTCACTGATAGAATGAGAAGGATCAAGATTCCCCTGCCTC
CTGTGGATGAGAAGAAAAAGTAATTGAAGATGTTGACAAAGACAGAAGATATGCAATTGACGCAT
CCATAGTTCGAATAATGAAAAGTAGAAAAGTTCTTGGTCATCAGCAGCTTGTTTTGGAATGTGTTG
AGCAATTAGGCCGCATGTTTAAGCCTGACTTTAAGGCCATCAAGAAAAGGATTGAAGATCTGATCG
CTAGAGATTATTTGGAGAGGGACAAGGACAATCCAAACCTCTTTAAATATTTGGCCTAA

Fig. 14

```
ATGAACGAAAGAAAAACAATAGACTTAGAGCAAGGATGGGACTTCATGCAGAAAGGAATAACAAAG
TTGAAGAATATTCTAGAAGGTCTTCCCGAGCCACAATTCAGCTCGGAGGATTACATGATGCTCTAC
ACAACCAT[C]TACAACATGTGTACACAGAAACCACCACATGATTACTCCCAACAGTTGTATGACA
AATATCGTGAGTCTTTTGAAGAGTATATTACTTCAACTGTGTTACCTTCTTTAAGAGAGAAGCATG
ATGAGTTCATGCTGAGAGAGCTTGTTAGAAGGTGGTCAAATCATAAAGTCATGGTGCGGTGGCTTT
CTAGATTCTTCCATTATCTTGACCGATATTTCATTGCCCGAAGATCTCTTCCGCCACTAAATGAAG
TTGGACTTGCCTGTTTTCGTGATCTGGTATACCAAGAGGTGAATGGTAAAGTGAGAGATGCTGTAA
TATCTTTGATTGATCAAGAGCGTGAAGGGGAGCAGATTGATCGAGCTTTACTGAAGAATGTTCTAG
ATATATTTGTTGAGATAGGAATGGGACAAATGGAGTATTATGAGAATGATTTTGAAGCATCCATGC
TTAATGATACAGCAGCATATTATTCACGCAAGGCTTCCAACTGGATTCTAGAAGATTCTTGTCCAG
ATTATATGCTCAAAGCAGAGGAGTGCTTAAAAAGAGAAAAGGACAGAGTGTCTCATTATCTTCATT
CCAGCAGTGAGCCAAAGCTTCTTGAGAAAGTTCAAAATGAGTTATTGTCTGTTTATGCAACTCAAT
TGCTTGAGAAAGAGCACTCAGGTTGTCATGCATTGCTCAGGGATGACAAGGTTGATGATTTATCAA
GAATGTACAGACTCTTTTCAAAGATACCAAAAGGATTGGATCCTGTTTCTAGTATGTTTAAGCAGC
ATGTCACTGCTGAAGGCACAACATTGGTTAAACAAGCAGAAGATGCAGCAAGTACCAAGAAGGCTG
AAAAGAGAGATGTGGTTGGGTTGCAGGAACAGGTTTTTGTTAGAAAAGTTATTGAGCTCCATGACA
AGTACCTGGCATATGTAAATGACTGTTTCATGAACCATACTCTTTTCCACAAGGCTCTTAAAGAGG
CATTTGAAATATTCTGCAACAAGGGTGTTGCTGGAAGTTCAAGTGCAGAGTTACTTGCCACATTTT
GTGATAATATTCTTAAAAAAGGTGGAAGTGAGAAACTGAGCGATGAAGCCATTGAGGACACCCTTG
AGAAGGTAGTAAAGTTGCTTGCCTACATCAGTGATAAAGATCTATTTGCTGAATTTTACAGGAAAA
AACTTGCTAGGAGGCTTTTGTTTGACAAGAGTGCAAACGATGAGCATGAGAGAAGTATTCTCACAA
AGCTGAAGCAACAGTGTGGTGGTCAGTTCACATCAAAGATGGAAGGGATGGTTACAGATTTGACAT
TGGCAAAGGAAAACCAATCCCATTTTGAAGAGTATTTGAACAATAATCCCAATGTCAGCCCTGGAA
TTGACTTGACTGTCACTGTGTTGACTACCGGCTTCTGGCCCAGCTACAAATCTTTTGACCTAAATC
TCCCTGCCGAAATGGTTAAATGCGTTGAAGTTTTCAGAGAATTTTATCAAACAAAAACAAAGCACA
GGAAGCTTACATGGATATATTCATTGGGTACCTGCAATATAAACGGGAAATTTGAACCCAAAACAA
TGGAGCTCATAGTCACAACCTACCAGGCATCTGCTTTATTACTGTTCAACTTATCGGATCGATTGA
GTTATCAAGAAATCATGACTCAGTTGAACTTGTCAGATGATGATGTTGTTAGGCTGCTCCATTCTT
TGTCATGTGCAAAATACAAAATTCTTTTAAAGGAGCCTAATACCAAAACAATCTCTCCAACCGATT
ACTTCGAATTCAACTCCAAGTTTACAGATAAAATGAGGAGGATCAAGATTCCTCTACCTCCTGTGG
ATGAGAAGAAAAGGTGATTGAGGATGTTGACAAGACAGACGTTATGCCATTGATGCTTCCATTG
TAAGGATAATGAAGAGCAGAAAGGTGCTTGGATACCAGCAGTTGGTTATGGAGTGTGTTGAACAGT
TGGGACGCATGTTTAAGCCTGATGTAAAAGCAATCAAGAAGCGGATTGAAGATCTGATAACTCGTG
ATTATCTTGAAAGAGACAAAGAGAACCCCAACTTGTTCCGATACTTGGCATGA
```

Fig. 15

```
ATGGAGCGGAAGACGATTGATCTGGAACAAGGATGGGACTATATGCAGACTGGGATCACTAAGCTG
AAACGGATTCTTGAAGGATTGCCTGAGCCGCAATTCGACTCTGAGCAGTACATGATGCTTTATACG
ACTAT[C]TACAACATGTGCACCCAGAAACCTCCTCATGATTACTCTCAGCAGCTTTATGACAAGT
ATCGCGAAGCTTTTGAGGAGTACATTGACTCTACTGTTTTGCCTGCTTTGAAGGAGAAGCATGATG
AATACATGCTACGGGAGCTGGTTAAGAGATGGTCTAACCATAAAGTTATGGTTAGATGGCTATCCC
GATTCTTCTACTATCTTGACCGTTACTTCATTGCTCGGAGATCGCTGCCACCGCTTAATGAAGTTG
GGCTCACATGCTTCCGTGACCGGGTGTATAAGGAGTTGCATTCCAAGGTCAAAGATGCTGTAATAG
CACTTGTTGATAAGAACGGGAAGGCGAGCAGATTGACAGGGCTCTTCTGAAAAACGTATTAGATA
TCTATGTAGAGATTGGAATGGGACAGATGGAAAGATACGAAGTGGATTTTGAAAGCTTCATGCTTT
TGGATTCAGCATCTTACTATTCTCGCAAAGCATCAAACTGGATCCAGGAAGATTCTTGCCCTGATT
ACATGCTGAAGTCTGAAGAATGCCTTAAGAAGGAGAGGGAGAGGGTTGCTCACTACCTTCATTCAA
GCAGCGAGCCAAAGCTGGTTGAGAAAGTACAACATGAGCTGTTGGTTGTCTATGCAAATCAGCTTC
TTGAAAAGGAGCACTCAGGGTGCCGTGCATTGCTGAGAGACGACAAGGTTGACGATCTCTCCAGGA
TGTACAGGCTCTATCATAAAATTGCTAAAGGTTTAGAACCTGTTGCAAACATATTTAAGCAGCATG
TCACAGCCGAGGGTAACGCACTTGTCCAACAGGCCGAAGACACAGCCACTAATCAGGCTGCAAATA
CTGCTAGCGTGCAGGAACAGGTTCTCATCAGAAAGTGATTGAGCTACATGATAAGTACATGGTCT
ATGTCGTGGAGTGCTTCCAGAACCACACCCTCTTCCACAAGGCTCTGAAAGAGGCATTTGAGATAT
TCTGTAACAAAACAGTCGCTGGAAGTTCAAGTGCAGAACTGCTTGCAACATTCTGCGACAACATCC
TCAAGAAGGGGGGTAGTGAGAAGCTGAGTGACGAAGCTATTGAAGATACGCTTGAGAAGGTTGTCA
AATTGCTTGCTTATATAAGCGACAAGGATCTTTTCGCCGAGTTCTACAGGAAGAAGCTGGCACGTA
GGCTCTTATTTGATCGCAGTGCGAATGATGATCATGAGAGAAGCATCCTTACAAAGCTCAAGCAAC
AATGTGGTGGGCAGTTCACTTCTAAGATGGAGGGCATGGTAACGGACTTGACATTGGCAAGAGAGA
ACCAAACCAGTTTCGAGGAGTATCTAGGCAATAACCCCGCTGCAAACCCAGGGATTGATTTGACCG
TCACTGTTCTTACCACTGGTTTCTGGCCAAGTTACAAATCATTCGACATAAATCTACCAAGTGAAA
TGGTCAAGTGTGTTGAAGTTTTCAAAGGGTTTTATGAGACGAAAACTAAACATAGGAAACTTACAT
GGATCTACTCACTAGGAACTTGTCACCTCAACGGAAAGTTTGATCACAAGCCCATTGAGTTAGTTG
TGTCTACTTACCAGGCTGCTGTGCTTCTGCTGTTCAACACAACAGACAAATTGAGCTACAACGATA
TCCTAACTCAACTGAACCTAAGCCACGAAGATTTAGTGAGGTTGCTTCATTCCCTGTCATGTGCTA
GGTACAAGATCCTTCTCAAGGAGCCAAGCACGAAGACTGTTACACAGACTGATTCATTTGAATTCA
ATGCCAAATTCACGGACAGAATGCGCAGAATCAAGATCCCTCTCCCTCCTGTTGATGAAAGGAAGA
AGGTTGTGGAAGATGTGGACAAAGACAGACGCTATGCGATTGATGCTGCCATTGTTAGGATCATGA
AGAGCAGGAAAGTGTTGGGACATCAACAACTCGTCTCTGAGTGCGTTGAGCAACTTAGCCGAATGT
TCAAGCCTGATATCAAAGCGATCAAGAAGCGTATGGAGGATCTAATTACGAGGGATTATTTGGAGA
GGGACAAGGAGAACCCTAACATGTTTAGGTACTTGGCTTAG
```

Fig. 16

```
ATGAACGATCGTAAAGTTATCGAACTAGAGCAAGGATGGGAGTTCATGGGGAAGGGGATTACGAAG
TTGAAAAGGATTTTGGAAGGATTACCAGAGCCGCCTTTTAATTCGGAAGACTACATGATGCTGTAC
ACGACAAT[A]TACAACATGTGTACACAGAAACCCCCTCATGATTACTCTCAACAACTCTATGACA
ATTACAAAGAGGCATTTGTGGATTACATACATTCAACGGTTTTACCTTCTTTGGGGGACAAACATG
ATGAGTTTATGCTGAGAGAGCTTGTGAAGAGATGGTCAAATCATAAAGTAATGGTGAGGTGGTTGT
CTCGCTTCTTCCATTATCTGGATCGGTACTTCATCGCTCGGAGATCGCTTCCTTCTTTGAATGATG
TTGGATTGACGTGCTTCCGTGATCTGGTTTATCAAGAAATATCTGGCAAAGCCAAGGATGCTGTTA
TTGCTCTGATTGATGAAGAAGAGAGGGTGGGCAAATTGACAGAGCCTTATTGAAGAATGTACTTG
ATATATACGTTGAAATTGGAATGACACAAATGGATTACTACGAAAAGGACTTTGAAGCTCATATGC
TGGATGATACTGCTGCTTATTACTCACGCAAGGCCTCAAGCTGGATTCTGGAGGACTCATGTCCGG
AATACATGTTGAAGTCGGAGGAGTGTTTGAAGAAAGAGAAAGATAGAGTGGCTCATTATCTACATT
CCAGCAGTGAGCCAAAGCTTCTGGAGAAAGTACAAAATGAGTTGCTACTGGTTTACGAAAATCAGT
TGCTTGAGAAGGAGAATTCTGGATGTCGTGCATTGTTGAAAGATGACAAGGTGGAAGATCTTTCCA
GGATGTACAGGCTTTATAGCAAGGTTACCAAAGGGTTGGAACCCATTGGCAGTATCTTCAAACAGC
ATATAACCGATGAAGGAACAGCCCTGGTGCAGCAGGCCGAAGACGCTGCAATTAGCAAGGCTGAAA
ATGCTGGCGGTGGTTCACATGAGCAGGTCTTCGTCAGGAAAGTGATTGAGTTGCATGACAAATTTA
TGACCTATGTTACAGATTGCTTCAACAGCCATACCATCTTTCACAAGGCTCTCAAGGAAGCTTTTG
AGGTATTCTTAAACAAGGGTGTTGCTGGTAGTTCAAGTGCTGAACTTCTAGCTTCATTTTGTGATA
ATATTCTCAAGAAAGGTGGTAGTGAAAAATTAAGTGATGAGGCTATTGAGGATTCACTGGAGAAGG
TGGTGAAGCTTCTCGCATATGTCAGTGATAAAGACCTGTTTGCTGAATTTTACAGAAAGAAGCTCT
CTCGCCGGCTACTCTTTGACAAAAGTGCTAATGATGATCATGAGAGGAGTATTTTAACAAAATTGA
AGCAGCAGTGTGGGGGACAGTTCACATCAAAGATGGAGGGGATGGTGACAGACTTGACATTGGCGA
GGGAGAATCAAACTAATTTTGAGGAATATCTTGGACAAAATACAGATGCCAGTCCTGGTCTTGATT
TGACTGTGACAGTTTTGACCACTGGGTTCTGGCCAAGTTACAAATCTTCTGATCTTAACCTTCCTG
CTGAGATGGTGAGGTGTGTTGAAGTTTTTAAGCAATTTTATCAAACAAAGACAAAACACAGGAAGC
TCACCTGGGTATATTCGTTGGGAAGTTGTAACATTAATGGCAAGTTTGGTCCGAAAACAATTGAAT
TGGTTGTTGGAACTTATCAGGCTGCTGCGCTGATGCTCTTTAACACATCAGATCGACTGAGTTATT
CAGAAATAACGACCCAACTAAATCTAGCTGACGAAGACTTGGTTAGAGTGCTTCAATCTCTATCTT
GCGCAAAGTATAAGATTCTTCTAAAAGAGCCAAGCACAAGAAACGTGATCTCAACTGATTGTTTTT
CATTCAACTCTAATTTTACTGACAGAATGAGGAGGATTAGGATTCCTCTTCCTCCAATGGATGAGA
GGAAAAAGGTTGTTGAAGATGTTGACAAAGATAGAAGATATGCTATTGATGCCTCAATTGTACGCA
TAATGAAAAGTAGGAAGGCTTTGGGATATCAACAATTAATCACGGAGTGTGTGGAGCAGCTAAGCC
GCATGTTCAAGCCTGATTTCAAAGCAATTAAGAAGAGGATCGAGGACTTGATAACCAGAGATTATA
TTGAAAGAGACAAGGAAAACCCTCAGCTATTCCGGTACTTGGCTTGA
```

Fig. 17

ATGAATGATCGTAAAGTTATTGAACTAGAGCAAGGATGGGAGTTCATGGGGAAGGGGATTACAAAG
TTGAAGAGGATTCTGGAAGGATTGCCAGAGCCACCATTTAATTCTGAAGACTACATGATGTTGTAC
ACGACGAT[A]TACAATATGTGTACTCAGAAACCCCCACATGATTACTCTCAACAGCTCTATGACA
ATTACAAACAGGCTTTTGTGGATTACATCAACTCGACGGTTTTACCTTCTTTGCGGGAGAAGCATG
ATGAGTTTATGTTAAGAGAACTTGTGAAAGATGGGCAAATCATAAAGTAATGGTCAGGTGGTTGT
CTCGTTTCTTCCATTATCTGGACCGGTATTTCATTGCTCGGAGGTCGCTTCCTTCTTTGAATGAAG
TTGGACTGACTTGTTTCCGTGATCTGGTTTATCAAGAAATATCTGGCAAAGCCAAGGATGCTGTTA
TAGCCCTGATTGATATAGAAAGAGAAGGTGGGCAGATTGACAGATCATTATTGAAAAATGTACTTG
ATATATATGTTGAAATTGGAATGGGACAAATGGATCACTATGAAAAGACTTTGAAGCTCATATGC
TGGATGATACTGCTGCTTACTACTCGCGCAAAGCGTCTAGCTGGATTCTTGAGGACTCTTGTCCGG
AATACATGTTAAAGTCTGAGGAGTGTTTGAAGAAGGAGAAAGAGAGTGGCTAATTATTTACATT
CCAGCAGTGAGCCAAAGCTTCTGGAGAAAGTGCAAAACGAGTTGCTATTGGTTTATGAAAGCCAAT
TGCTTGAGAAGGAGAATTCGGGATGTCGTGCATTACTGAAAGATGACAAGGTGGATGATCTTTCCA
GGATGTACAGGCTTTACAGTAAGGTTACCAAAGGATTGGAACCCATTGGCAGTATCTTCAAACAGC
ATATAACTGATGAAGGAACAGCCTTAGTGCAGCAGGCCGAAGATGCTGCTATCAGCAAGGCTGAAA
ATACTGGTGGTTCACATGAGCAGGTCTTCGTCAGGAAAGTAATAGAGTTGCATGACAAATTCATGA
CTTATGTCACCGATTGCTTCAACAGCCATACCATATTTCACAAGGCTCTTAAGGAGGCTTTTGAGG
TATTTTTGAACAAGGGTGTTGCTGGTAGCTCAAGTGCTGAGTTGCTAGCTACATTCTGTGATAACA
TTCTCAAGAAAGGTGGGAGCGAAAAACTAAGCGATGAGGCTATTGAGGATTCACTTGAGAAGGTGG
TGAAGCTTCTGGCCTATGTCAGTGATAAAGACCTGTTTGCTGAATTTTACAGAAAGAAGCTCTCTC
GCCGGCTACTCTTTGACAAGAGTGCTAATGATGATCATGAAAGAAGTATTTTAACCAAATTGAAGC
AGCAGTGTGGCGGACAATTCACATCAAAGATGGAGGGGATGGTGACAGACTTGACCTTGGCGAGGG
AGAATCAAACTAATTTTGAGGAATATCTTAGTCAGAATCCAGATGCCAGTCCTGGTCTTGATTTGA
CTGTGACTGTTCTGACAACTGGGTTCTGGCCAAGTTACAAATCTTCCGATCTTAACCTTCCCGCTG
AGATGGTGAGGTGTGTTGAAGTTTTTAAGCAGTTCTATTCAACTAAAACAAAGCACAGGAAGCTGA
CCTGGGTTTACTCATTGGGAAGCTGTAATATTAATGGCAAGTTTGGTCCAAAAACTATTGAATTGG
TTGTCGGAACTTATCAGGCTGCTGCTTTGATGCTCTTTAACACATCAGACCGACTGAGTTATTCAG
AGATAGCAACTCAACTAAATTTAGCTGATGAAGATCTGGTTAGAGTGCTTCAATCTTTATCCTGCG
CAAAGTATAAGATTCTTTTAAAGGAGCCAAACACGAAAACCGTGTCCCGACTGATTGTTTTTCAT
TTAACTCTAGTTTCACTGACAGGATGAGGAGGATAAGAATTCCTCTTCCTCCGATGGATGAGAGGA
AAAAGGTTGTTGAGGATGTTGACAAAGATAGAAGATATGCTATTGATGCCTCAATTGTACGCATAA
TGAAAAGTAGGAAGGTTTTGGGGTACCAGCAATTAATCACAGAGTGTGTGGAGCAGCTAAGCCGCA
TGTTCAAGCCTGATTTCAAGGCAATTAAGAAGAGGATCGAGGACTTAATAACCCGAGATTATATTG
AAAGAGACAAGGAGAACCCGCAGCTATTCCGATACTTGGCTTGA

Fig. 18

MTMGERKTIDLEQGWEFMQKGITKLKNILEGLPEPQFSSEDYMMLYTT[I]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 19

MTMGERKTIDLEQGWEFMQKGITKLKNILEGLPEPQFSSEDYMMLYTT[I]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 20

MTMGERKTIDLEQGWEFMQKGITKLKNILEGLPEPQFSSEDYMMLYTT[I]YNMCTQKPPHDYSQQ
LYDKYRESFEEYISSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLRREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DKLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig.21

MTMGERKTIDLEQGWEFMQKGITKLKNILEGLPEPQFSSEDYMMLYTT[I]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLRKEKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 22

MNQRSTIDLEHGWDFMQKGITKLKNILEGLPEPQFSSEDYMMLYTT[I]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHSSSETKLLEKVQHELLSVYAN
QLLEKEHSGCHALLRDDKVDDLSRMYRLFSKIPRGLEPVANIFKQHVTAEGTALVKQAEDAASNKK
AEKRDVVGLQEQVFVRKVIELHDKYLAYVNNCFQNHTLFHKALKEAFELFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPTANPGIDLTVTVLTTGFWPSYKSFDL
NLPAEMVRCVEVFKEFYQTKTKHRKLTWIYSLGTCNINGKFEAKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 23

MNQRSTIDLEHGWDFMQRGITKLKNILEGLPEPQFSSEDYMMLYTT[I]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDQVYQELNGKVRDAVISLIDQEREGEQIDRALLKNVLDIFVEIGMGLMDYYENDFEAA
MLKDTAAYYSRKASNWILEDSCPDYMLKAEECLKREKDRVSHYLHSSSETKLLEKVQHELLSVYAT
QLLEKEHSGCHALLRDDKVEDLSRMYRLFSKISRGLDPVANIFKQHVTAEGTALVKQAEDAASNKK
AEKRDVVGLQEQVFVRKVIELHDKYLAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPIANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 24

MNQRSTINLEHGWDFMQRGITKLKNILEGLPEPQFSSEDYMMLYTT[I]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHLSSETKLLEKVQHELLSVYAT
QLLEKEHSGCHALLRDDKVEDLSRMYRLFSKIPRGLDPVANIFKQHVTAEGTALVKQAEDAASNKK
AEKRDVVGLQEQIFVRKVIELHDKYMAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPAANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNFKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 25

MERKTIDLDQGWDYMQTGITKLKRILEGLPEPQFDSEQYMMLYTT[I]YNMCTQKPPHDYSQQLYD
KYREAFEEYIHSTVLPALREKHDEYMLRELVKRWSNHKVMVRWLSRFFYYLDRYFIARRSLPPLNE
VGLTCFRDLVYNELHSKVKDAVIALVDKEREGEQIDRALLKNVLDIYVEIGMGQMERYEEDFESFM
LLDSASYYSRKASSWIQEDSCPDYMLKSEECLKKERERVAHYLHSSSEPKLVEKVQHELLVVYANQ
LLEKEHSGCRALLRDDKVDDLSRMYRLYHKIVKGLEPVANIFKQHVTAEGNALVQQAEDTATNHAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQNSFEEYLGNNPAANPGIDLTVTVLTTGFWPSYKSFDINLPA
EMVKCVEVFKGFYETKTKHRKLTWIYSLGTCHLNGKFDVKPIELVVSTYQAAVLLLFNTTDKLSYT
DILTQLNLSHEDLVRLLHSLSCARYKILLKEPSTKTVSQSDSFEFNSKFTDRMRRIKIPLPPVDER
KKVVEDVDKDRRYAIDAAIVRIMKSRKVLGHQQLVSECVEQLSRMFKPDIKAIKKRMEDLITRDYL
ERDKENANMFRYLA

Fig. 26

MMIERKTIDLEQGWDFMQKGITKLKNILEGFPEPQFSSEDYMMLYTT[I]YNMCTQKPPHDYSQQL
YEKYREAIEEYITSTVLPSLREKHDEFMLRELVKRWSNHKVMVRWLSRFFHYLDRYFIARRSLPPL
HEVGLTCFRDLVYQEINGKVRDAVISLINQEREGEQIDRALLKNVLDIFVEVGMSQMDYYENDFEA
DMLKDTAAYYSRKASNWILEDSCPDYMLKAEECLRREKDRVSNYLHSSSEPKLLEKVQHELLSHYA
TQLLEKEHSGCHALLRDDKVADLSRMYRLFSKIPRGLDPVSNIFKQHVTAEGTALVKQAEDAASNK
KAEKRDVVGLQEQVFVRKIIELHDKYLTYVNDCFTNHTLFHKALKEAFEIFCNKGVSGSSSAELLA
TFCDNILKKGGSEKLSDEAIEETLEKVVRLLAYISDKDLFAEFYRKKLARRLLFDKSANDEHERSI
LTKLKQQCGGQFTSKMEGMVTDLTLAKENQSNFEEYLNNNSNVNPGIDLTVTVLTTGFWPSYKSFD
LNLPAEMVKCVEVFREFYQTKTKHRKLTWIYSLGTCNIIGKFDPKTMELIVTTYQASALLLFNSSD
RLSYNEIMTQLNLSDDDVVRLLHSLSCAKYKILSKEPNTKTISPTDCFQFNSKFTDKMRRIKIPLP
PVDEKKKVIEDVDKDRRYAIDASIVRIMKSRKVLGYQQLVMECVEQLGRMFKPDVKAIKKRIEDLI
TRDYLERDKDNANLFRYLA

Fig. 27

MNERKTIDLDNGWEFMQKGITKLKKILEGQPEPQFSSEDYMMLYTT[I]YNMCTQKPPHDYSQQLY
DKYREAFEEYITSTVLPSLREKHDEFMLRELVNRWTNHKVMVRWLSRFFHYLDRYFIARRSLPALH
EVGLTCFRDLVYQELKVKVRDAVISLIDQEREGEQIDRALLKNVLDIFVEIGMSQMDYENDFEEA
MLTDTAAYYSRKASNWILEDSCPDYMLKAEECLRREKDRVSHYLHFSSEPKLLEKVQHELLSVYAT
QLLEKEHSGCHALLRDDKVDDLSRMYRLFSKIPKGLDPVSYIFKQHVTNEGMALVKQAEDAASNKK
AEKRDVVSLQEQVFVRKIIELHDKYLAYVNDCFTNHTLFHKALKEAFEIFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLAKENQSSFEEYLGNNANVNPGIDLTVTVLTTGFWPSYKSFDL
NLPAEMVKCVEVFREFYQTKTKHRKLTWIYSLGTCNINGKFEPKTIELIVTTYQASALLLFNTSDR
LSYQEIMTQLNLSDDDVVRLLHSLSCAKYKILTKEPNNKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNANLFRYLA

Fig. 28

MNERKTIDLEQGWDFMQKGITKLKNILEGLPEPQFSSEDYMMLYTT[I]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 29

MNERKTIDLEQGWDFMQKGITKLKNILEGLPEPQFSSEDYMMLYTT[I]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 30

MSLHERKTIDLEQGWAFMQKGITKLKNILDELNEPQFSSEDYMMLYTT[I]YNMCTQKPPHDYSQE
LYDKYRESFEEYITTTVLPSLREKHDEYMLRELVRRWSNHKIMVRWLSRFFHYLDRYFIARRSLPA
LNEVGLTCFRDLVYNEVHGKVKDAVISLIDQEREGEQIDRALLKNVLGIFVEIGLGSMECYENDFE
TSMLNATAAYYSRKASNWILEDSCPDYMLKAEECLKHEKDRVAHYLHSSSEQKLLEKVQHELLFVY
ASQLLEKEHSGCHALLRDDKVGDLSRMYRLFCRITRGLDPVSQIFKQHVTAEGTALVKHAEDAASN
KKAEKKDIVGLQEQVFVRKVIELHDKYLAYVTDCFQNHSLFHKALKEAFEVFCNKGVAGSSSAELL
AAFCDNILKKGGSEKLSDEAIEDTLEKVVKLLAYISDKDLFAEFYRKKLARRLLFDKSANDDHERS
ILTKLKQQCGGQFTSKMEGMVTDLTLARENQSSFDDYLSSNPKANSGIDLTVTVLTTGFWPSYKSF
DLNLPDEMVKCVEIFKEFYETKTKHRKLTWIYSLGTCNINGKFETKTIELVVTTYQAAVLLLFNSA
DKLSYSEIVQQLNLSDDDVIRLLHSLSCAKYKILNKEPATKTITPNDHFEFNSKFTDRMRRIKIPL
PPVDEKKKVIEDVDKDRRYAIDASIVRIMKSRKVLGHQQLVLECVEQLGRMFKPDFKAIKKRIEDL
IARDYLERDKDNPNLFKYLA

Fig. 31

MNERKTIDLEQGWDFMQKGITKLKNILEGLPEPQFSSEDYMMLYTT[I]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQNELLSVYAT
QLLEKEHSGCHALLRDDKVDDLSRMYRLFSKIPKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNLSDR
LSYQEIMTQLNLSDDDVVRLLHSLSCAKYKILLKEPNTKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 32

MERKTIDLEQGWDYMQTGITKLKRILEGLPEPQFDSEQYMMLYTT[I]YNMCTQKPPHDYSQQLYD
KYREAFEEYIDSTVLPALKEKHDEYMLRELVKRWSNHKVMVRWLSRFFYYLDRYFIARRSLPPLNE
VGLTCFRDRVYKELHSKVKDAVIALVDKEREGEQIDRALLKNVLDIYVEIGMGQMERYEVDFESFM
LLDSASYYSRKASNWIQEDSCPDYMLKSEECLKKERERVAHYLHSSSEPKLVEKVQHELLVVYANQ
LLEKEHSGCRALLRDDKVDDLSRMYRLYHKIAKGLEPVANIFKQHVTAEGNALVQQAEDTATNQAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQTSFEEYLGNNPAANPGIDLTVTVLTTGFWPSYKSFDINLPS
EMVKCVEVFKGFYETKTKHRKLTWIYSLGTCHLNGKFDHKPIELVVSTYQAAVLLLFNTTDKLSYN
DILTQLNLSHEDLVRLLHSLSCARYKILLKEPSTKTVTQTDSFEFNAKFTDRMRRIKIPLPPVDER
KKVVEDVDKDRRYAIDAAIVRIMKSRKVLGHQQLVSECVEQLSRMFKPDIKAIKKRMEDLITRDYL
ERDKENPNMFRYLA

Fig. 33

MNDRKVIELEQGWEFMGKGITKLKRILEGLPEPPFNSEDYMMLYTT[I]YNMCTQKPPHDYSQQLY
DNYKEAFVDYIHSTVLPSLGDKHDEFMLRELVKRWSNHKVMVRWLSRFFHYLDRYFIARRSLPSLN
DVGLTCFRDLVYQEISGKAKDAVIALIDEEREGGQIDRALLKNVLDIYVEIGMTQMDYYEKDFEAH
MLDDTAAYYSRKASSWILEDSCPEYMLKSEECLKKEKDRVAHYLHSSSEPKLLEKVQNELLLVYEN
QLLEKENSGCRALLKDDKVEDLSRMYRLYSKVTKGLEPIGSIFKQHITDEGTALVQQAEDAAISKA
ENAGGGSHEQVFVRKVIELHDKFMTYVTDCFNSHTIFHKALKEAFEVFLNKGVAGSSSAELLASFC
DNILKKGGSEKLSDEAIEDSLEKVVKLLAYVSDKDLFAEFYRKKLSRRLLFDKSANDDHERSILTK
LKQQCGGQFTSKMEGMVTDLTLARENQTNFEEYLGQNTDASPGLDLTVTVLTTGFWPSYKSSDLNL
PAEMVRCVEVFKQFYQTKTKHRKLTWVYSLGSCNINGKFGPKTIELVVGTYQAAALMLFNTSDRLS
YSEITTQLNLADEDLVRVLQSLSCAKYKILLKEPSTRNVISTDCFSFNSNFTDRMRRIRIPLPPMD
ERKKVVEDVDKDRRYAIDASIVRIMKSRKALGYQQLITECVEQLSRMFKPDFKAIKKRIEDLITRD
YIERDKENPQLFRYLA

Fig. 34

MNDRKVIELEQGWEFMGKGITKLKRILEGLPEPPFNSEDYMMLYTT[I]YNMCTQKPPHDYSQQLY
DNYKQAFVDYINSTVLPSLREKHDEFMLRELVKRWANHKVMVRWLSRFFHYLDRYFIARRSLPSLN
EVGLTCFRDLVYQEISGKAKDAVIALIDIEREGGQIDRSLLKNVLDIYVEIGMGQMDHYEKDFEAH
MLDDTAAYYSRKASSWILEDSCPEYMLKSEECLKKEKERVANYLHSSSEPKLLEKVQNELLLVYES
QLLEKENSGCRALLKDDKVDDLSRMYRLYSKVTKGLEPIGSIFKQHITDEGTALVQQAEDAAISKA
ENTGGSHEQVFVRKVIELHDKFMTYVTDCFNSHTIFHKALKEAFEVFLNKGVAGSSSAELLATFCD
NILKKGGSEKLSDEAIEDSLEKVVKLLAYVSDKDLFAEFYRKKLSRRLLFDKSANDDHERSILTKL
KQQCGGQFTSKMEGMVTDLTLARENQTNFEEYLSQNPDASPGLDLTVTVLTTGFWPSYKSSDLNLP
AEMVRCVEVFKQFYSTKTKHRKLTWVYSLGSCNINGKFGPKTIELVVGTYQAAALMLFNTSDRLSY
SEIATQLNLADEDLVRVLQSLSCAKYKILLKEPNTKTVSPTDCFSFNSSFTDRMRRIRIPLPPMDE
RKKVVEDVDKDRRYAIDASIVRIMKSRKVLGYQQLITECVEQLSRMFKPDFKAIKKRIEDLITRDY
IERDKENPQLFRYLA

Fig. 35

```
ATGACAATGGGCGAGCGGAAGACTATTGACTTGGAGCAGGGATGGGAGTTTATGCAGAAGGGTATC
ACAAAGTTGAAGAACATTCTCGAGGGCTTGCCTGAGCCTCAGTTCAGCTCCGAGGACTACATGATG
CTTTACACTACCAT[G]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCACGATGAGTTCATGTTGAGAGAACTAGTAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAATAGTAAAGTGAGGGATG
CAGTAATTTCATTGATTGATCAAGAACGTGAAGGAGAACAGATTGACAGAGCTCTACTGAAGAATG
TACTAGATATATTTGTGGAAATTGGTATGGGGCAAATGGATTACTATGAAATGACTTTGAAGCTG
CCATGCTTAAAGATACTGCTGCTTATTACTCTAGGAAGGCTTCCAATTGGATCCTAGAAGATTCTT
GTCCCGATTATATGCTTAAAGCAGAGGAGTGCTTGAAACGAGAAAGGATAGGGTTTCCCACTATT
TGCACTCTAGTAGCGAGCCAAAGTTGTTGGAGAAAGTTCAACATGAACTATTATCTGTTTATGCTA
CTCAACTGCTGGAAAAAGAGCATTCAGGATGCCATGCATTGCTTAGAGATGACAAGGTGGAAGATT
TGTCAAGGATGTTCCGTCTATTCTCCAAAATACCGAAGGGACTGGATCCAGTTTCCAACATATTTA
AGCAGCATGTAACTGCTGAAGGAACAGCACTGGTCAAACAGGCAGAAGATGCTGCAAGTAACAAGA
AGGCTGAGAAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTATTTTGCAATAAGGGTGTTGCTGGAAGTTCTAGTGCAGAATTGCTTGCTA
CCTTTTGTGATAACATCCTTAAGAAAGGTGGGAGTGAGAAGTTGAGTGATGAAGCAATCGAGGAGA
CACTTGAGAAGGTTGTGAAGTTGTTGGCATACATTTGCGACAAAGATCTGTTTGCTGAATTCTATA
GAAAAAAACTTGCCCGAAGGCTTCTCTTTGACAAGAGCGCGAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTTGAGGAGTATCTGAGCAATAATCCACAAGCGAGTC
CTGGCATCGACCTGACTGTTACTGTTTTAACTACTGGATTTTGGCCAAGCTACAAGTCTTTTGACC
TCAACCTGCCGGCAGAGATGGTAAAGTGTGTTGAAGTTTTCAGAGAGTTTTATCAAACAAAAACCA
AGCATCGAAAACTTACATGGATTTACTCATTGGGTACTTGTAACATCAGTGGAAAATTTGAACCGA
AAACGATGGAGCTGATTGTGACAACTTATCAGGCTTCTGCCCTGTTGCTATTCAATTCTTCGGATA
GACTAAGTTACTCGGAAATCATGACACAATTAAATTTGAGTGACGATGATGTAGTTAGACTACTCC
ACTCGTTGTCATGTGCCAAGTATAAAATTCTTAATAAGGAACCAAATACGAAAACCATCTCTCCGA
ACGATCATTTTGAGTTCAATGCAAAATTCTCCGACAAAATGAGGAGAATAAAGATCCCTCTTCCGC
CTGTGGATGAGAAAAAGAAAGTCATTGAAGATGTTGACAAGGATCGAAGGTATGCTATTGACGCCT
CAATCGTGCGTATCATGAAGAGTCGGAAAGTTCTTGGTCATCAGCAACTAGTGATGGAGTGCGTCG
AGCAATTGGGCCGTATGTTCAAGCCCGATTTCAAGGCGATAAAGAAGAGAATTGAAGACCTGATCA
CTCGGGATTATCTAGAGAGAGACAAAGACAACCCCCACTTGTTTAGGTACTTGGCTTGA
```

Fig. 36

```
ATGACAATGGGCGAGCGGAAGACTATTGACTTGGAACAGGGATGGGAGTTTATGCAGAAGGGTATC
ACAAAGTTGAAGAACATTCTTGAGGGCTTGCCTGAGCCCCAGTTCAGCTCCGAGGACTACATGATG
CTTTACACTACCAT[G]TATAACATGTGCACCCAAAAGCCGCCGCATGATTACTCCCAGCAGCTGT
ATGATAAATATCGTGAATCTTTTGAAGAGTACATCACTTCTATGGTCTTACCATCCTTGAGGGAGA
AGCATGACGAGTTCATGTTGAGAGAACTAGTCAAAAGGTGGACAAACCATAAAGTCATGGTGAGGT
GGCTTTCTCGCTTCTTCCACTATCTTGATCGGTACTTCATCGCTCGAAGGTCACTTCCACCTCTAA
ATGAAGTTGGCCTCACATGCTTCCGCGAATTGGTGTACAAAGAGCTAAACAGTAAAGTGAGGGATG
CAGTAATCTCATTGATTGATCAAGAACGTGAAGGAGAACAGATTGACAGAGCTCTACTGAAGAATG
TATTAGATATATTTGTGGAAATTGGTATGGGGCAAATGGATTACTATGAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAGCGAGAAAAGGATAGGGTTTCCCACTATT
TGCACTCTAGTAGCGAGCCAAAGTTGTTGGAGAAAGTTCAACACGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGTCTCTTCTCCAAAATACCGAAGGGATTGGACCCAGTTTCCAACATATTTA
AGCAGCATGTAACTGCTGAAGGAACAGCACTGGTCAAACAGGCAGAAGATGCTGCAAGTAACAAGA
AGGCCGAGAAAAGGACATAGTTGGTCTGCAGGAACAGGTTTTTGTAAGAAAAGTGATTGAGCTTC
ACGACAAGTACTTGGCTTATGTGAATGATTGTTTCCAAAACCACACACTTTTCCATAAGGCTCTCA
AGGAAGCTTTTGAAGTCTTTTGCAATAAGGGTGTTGCTGGAAGTTCTAGTGCAGAATTGCTTGCTA
CCTTCTGCGATAACATCCTTAAGAAAGGTGGGAGTGAGAAGTTGAGTGATGAAGCAATCGAAGAGA
CACTTGAGAAGGTTGTGAAGTTGTTGGCATACATCTGCGACAAAGATCTGTTTGCTGAATTCTATA
GAAAAAAaCTTGCCCGAAGGCTTCTCTTTGATAAGAGCGCCAACGATGACCACGAGAGAAGTATAT
TGACCAAATTGAAGCAACAATGTGGTGGTCAGTTCACTTCTAAGATGGAGGGAATGGTTACTGATT
TGACTTTGGCAAGGGAGAACCAAACTAGTTTCGAAGAGTATCTGAGCAATAATCCACAAGCTAGTC
CTGGAATCGACCTAACTGTTACTGTTTTGACTACTGGATTTTGGCCAAGCTACAAGTCTTTTGACC
TCAACCTGCCGGCGGAGATGGTAAAGTGTGTTGAAGTTTTCAGAGAGTTTTATCAAACAAAAACCA
AGCATAGAAAACTTACATGGATTTACTCATTGGGTACTTGTAACATCAGTGGAAAATTTGAACCGA
AGACGATGGAGCTGATTGTGACAACATATCAGGCTTCTGCCCTGTTGCTATTCAATTCTTCGGACA
GACTAAGTTACTCCGAAATCATGACACAATTAAATTTGAGTGATGATGATGTTGTTAGACTGCTCC
ACTCATTGTCGTGTGCCAAGTATAAAATTCTTAATAAGGAGCCAAATACGAAAACCATCTCACCGA
ACGATCATTTTGAGTTCAATGCAAAATTCTCCGACAAAATGAGGAGAATAAAGATCCCTCTTCCGC
CTGTGGATGAGAAAaGAAAGTCATTGAAGATGTTGACAAGGATCGAAGGTATGCTATTGACGCCT
CAATCGTGCGTATCATGAAGAGTCGAAAAGTTCTTGGTCATCAGCAACTAGTGATGGAGTGCGTCG
AGCAATTGGGTCGTATGTTCAAGCCCGATTTCAAGGCGATAAAGAAGAGAATTGAAGACCTGATCA
CTCGGGACTATCTAGAGAGAGACAAAGACAACCCCCACTTGTTTAGGTACTTGGCTTGA
```

Fig. 37

```
ATGACAATGGGTGAGCGGAAGACTATTGACTTGGAGCAAGGATGGGAGTTTATGCAGAAGGGAATC
ACAAAATTGAAGAACATTCTGGAAGGATTGCCTGAGCCACAGTTCAGCTCCGAGGACTACATGATG
CTTTACACTACAAT[G]TATAACATGTGTACCCAGAAGCCACCGCATGATTACTCCCAGCAGCTGT
ATGATAAATACCGCGAATCGTTTGAGGAGTACATCAGTTCTATGGTTTTACCATCCTTGAGGGAGA
AGCATGACGAATTTATGTTGAGAGAACTGGTCAAAAGGTGGACCAACCATAAAGTCATGGTGAGGT
GGCTTTCTCGCTTCTTCCACTATCTTGATCGATACTTCATTGCTCGAAGGTCACTTCCACCTCTCA
ATGAAGTTGGCCTCACTTGCTTCCGTGAATTGGTGTACAAAGAGCTAAACAGTAAAGTGAGGGATG
CAGTAATTTCATTGATCGATCAAGAACGTGAAGGAGAGCAGATTGACAGAGCTCTGTTGAAGAACG
TGTTGGATATATTTGTGGAGATTGGGATGGGCAAATGGATTATTATGAAAATGACTTTGAAGCTG
CCATGCTTAAAGATACTGCTGCTTACTACTCTAGGAAGGCATCAAATTGGATCTTAGAAGATTCTT
GTCCTGATTATATGCTAAAAGCAGAGGAGTGCTTGAGACGAGAAAAGGACCGAGTTTCTCACTATC
TGCACTCTAGTAGCGAGCCAAAGTTATTGGAGAAAGTTCAACATGAACTATTGTCTGTTTATGCTA
CTCAACTGCTGGAGAAAGAGCATTCAGGATGCCATGCATTGCTTAGAGATGACAAGGTGGAAGATT
TGTCAAGGATGTTCCGTCTCTTCTCCAAAATACCCAAGGGATTGGACCCAGTTTCCAACATATTTA
AGCAGCATGTCACTGCTGAAGGAACAGCATTAGTCAAACAGGCAGAAGACGCTGCAAGTAACAAGA
AGGCCGAGAAAAAGGACATCGTTGGTCTGCAAGAACAGGTTTTTGTTAGAAAAGTGATTGAGCTTC
ACGACAAGTACTTGGCATATGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGTGAGAAGTTGAGTGATGAAGCAATTGAGGAAA
CACTCGAGAAGGTCGTGAAATTGCTGGCGTATATCTGCGACAAAGATCTGTTTGCTGAATTCTATA
GAAAAAAACTCGCCCGAAGGCTTCTCTTCGACAAGAGTGCGAATGATGACCACGAGAGAAGTATAC
TGACGAAATTGAAGCAACAATGTGGTGGTCAGTTTACCTCTAAGATGGAGGGAATGGTCACGGATT
TGACACTGGCAAGGGAGAACCAAACTAGTTTTGAGGAATATCTGAGCAATAATCCACAAGCTAGTC
CTGGAATCGACTTGACCGTTACCGTTTTGACCACTGGTTTTTGGCCAAGCTACAAGTCTTTTGACC
TCAACCTGCCGGCGGAGATGGTAAAGTGTGTTGAAGTTTTCAGGGAATTTTATCAAACAAAAACCA
AGCACAGAAAACTTACGTGGATTTACTCGTTGGGTACCTGTAACATCAGCGGAAAATTCGAACCGA
AAACGATGGAGCTGATCGTGACAACCTATCAGGCTTCTGCCCTGCTGCTTTTCAATTCCTCGGATA
AACTAAGTTACTCCGAGATCATGACTCAATTAAACTTGAGTGACGATGATGTTGTTAGACTGCTCC
ACTCGTTGTCGTGTGCGAAGTATAAAATTCTTAACAAGGAGCCAAATACGAAAACCATCTCTCCGA
ACGATCATTTTGAGTTCAACGCAAAATTCTCCGACAAAATGAGGAGAATAAAGATCCCTCTTCCGC
CTGTGGATGAGAAAAGAAAGTAATAGAAGATGTTGACAAGGATCGAAGATATGCTATCGATGCCT
CGATCGTGCGTATCATGAAGAGTAGGAAAGTTCTGGGTCACCAGCAGTTAGTGATGGAGTGCGTCG
AGCAACTGGGTCGTATGTTCAAGCCTGATTTCAAGGCGATAAAGAAGAGAATCGAAGATCTGATCA
CTCGTGACTATTTAGAGAGAGACAAAGACAACCCCCACTTGTTTAGGTACTTGGCTTGA
```

Fig. 38

```
ATGACAATGGGCGAGCGGAAGACTATTGACTTGGAACAAGGATGGGAGTTTATGCAGAAGGGAATC
ACAAAGTTGAAGAACATTCTTGAGGGCTTGCCTGAGCCTCAGTTCAGCTCCGAGGACTACATGATG
CTTTATACCACCAT[G]TACAACATGTGCACACAAAAGCCGCCACATGATTACTCCCAGCAGCTAT
ACGATAAATACCGTGAATCTTTTGAGGAGTATATCACTTCTATGGTCTTACCATCCTTGAGGGAGA
AGCATGACGAGTTCATGTTGAGAGAACTGGTCAAAAGGTGGACGAACCATAAAGTCATGGTGAGGT
GGCTTTCTCGCTTCTTCCACTATCTTGACCGATACTTCATTGCTCGAAGATCACTTCCACCTCTCA
ACGAAGTTGGCCTCACATGCTTCCGTGAATTGGTGTACAAAGAGCTAAACAGTAAAGTGAGGGATG
CAGTAATTTCATTGATTGATCAAGAACGTGAAGGAGAGCAGATTGACAGAGCTCTACTGAAGAATG
TATTAGATATATTTGTGGAAATTGGGATGGGCAAATGGATTACTATGAAAATGACTTTGAAGCTG
CCATGCTTAAAGATACTGCTGCTTATTACTCTAGGAAGGCTTCCAATTGGATCCTAGAAGATTCTT
GTCCCGATTATATGCTAAAAGCAGAGGAGTGCTTGAAACGAGAAAAGGATAGAGTTTCTCACTATT
TGCACTCTAGTAGCGAGCCAAAGTTATTAGAGAAAGTTCAACATGAACTGTTATCTGTGTATGCTA
CTCAACTGCTGGAAAAAGAGCATTCAGGATGCCATGCATTGCTTAGAGATGACAAGGTGGAAGATT
TGTCAAGGATGTTCCGCCTCTTCTCCAAAATACCCAAGGGATTGGACCCAGTTTCCAACATATTTA
AGCAGCATGTCACTGCTGAAGGAACAGCATTGGTCAAACAGGCAGAAGATGCTGCAAGTAACAAGA
AGGCCGAGAAAAGGACATAGTTGGTCTGCAGGAACAGGTTTTTGTAAGAAAAGTGATTGAGCTTC
ACGACAAGTACTTGGCTTACGTGAATGATTGTTTCCAAAACCACACACTTTTTCACAAGGCTCTCA
AGGAAGCTTTTGAAGTCTTTTGCAATAAGGGTGTTGCTGGAAGTTCTAGTGCAGAATTACTTGCTA
CCTTTTGTGATAACATCCTTAAGAAAGGTGGGAGCGAGAAGTTGAGTGATGAAGCAATTGAGGAGA
CACTTGAGAAGGTCGTGAAGTTGCTGGCATACATCTGCGACAAAGATCTGTTTGCTGAATTCTATA
GAAAAAAACTTGCCCGAAGGCTTCTCTTTGACAAGAGTGCCAACGATGACCATGAGAGAAGTATAT
TGACCAAATTGAAGCAACAATGTGGTGGCCAGTTCACCTCTAAGATGGAGGGGATGGTCACTGATT
TGACTTTGGCAAGGGAGAACCAAACTAGTTTCGAGGAGTATCTGAGCAATAATCCACAAGCTAGTC
CTGGAATCGACTTGACTGTCACTGTTTTGACTACTGGCTTTTGGCCAAGCTACAAGTCTTTTGACC
TCAACCTGCCGGCAGAGATGGTAAAGTGTGTTGAAGTTTTCAGAGAGTTCTATCAAACAAAAACAA
AGCATAGAAAACTTACATGGATTTACTCATTGGGTACCTGTAACATCAGCGGAAAATTTGAACCGA
AAACGATGGAGCTGATTGTAACAACTTATCAGGCTTCTGCCCTGCTGCTATTCAATTCCTCAGATA
GATTAAGTTATTCCGAGATCATGACACAATTAAATTTGAGTGACGATGATGTTGTTAGACTGCTCC
ACTCATTGTCATGTGCCAAGTATAAAATTCTTAATAAGGAGCCGAACACGAAAACCATCTCTCCGA
ATGATCATTTTGAGTTCAATGCAAAATTCTCCGACAAAATGAGGAGAATAAAGATCCCTCTTCCGC
CTGTGGATGAGAAAAGAAAGTCATTGAAGATGTTGACAAGGATCGAAGGTATGCTATTGATGCCT
CAATCGTGCGTATCATGAAGAGTCGGAAAGTTCTGGGTCATCAGCAGCTAGTGATGGAGTGCGTCG
AGCAATTGGGTCGTATGTTCAAGCCCGACTTCAAAGCGATAAAGAAGAGAATCGAAGATCTGATCA
CTCGGGACTATTTAGAGAGAGACAAAGACAACCCCCACTTGTTTAGGTACTTGGCTTGA
```

Fig. 39

```
ATGAACCAACGCAGCACAATCGATCTGGAACATGGATGGGATTTCATGCAAAAGGGCATCACAAAG
CTGAAGAACATTCTAGAAGGGCTGCCTGAGCCTCAGTTCAGCTCAGAGGACTATATGATGCTGTAT
ACGACAAT[G]TACAACATGTGTACTCAGAAGCCCCCACATGATTATTCTCAACAGCTGTATGACA
AATATCGTGAAGCTTTTGAAGAATATATCACAACGACGGTATTACCTTCTTTGAGAGAAAACATG
ACGAGTTCATGTTGCGAGAGTTGGTAAAAGGTGGTCAAACCATAAGGTCATGGTTAGATGGTTAT
CGCGATTCTTCCATTATCTTGACCGTTATTTCATTGCTCGGAGATCACTGCCAGGGCTTAATGAAG
TTGGACTAACTTGCTTCCGCGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCAATGGATTATTATGAGAATGATTTTGAAGCTGCAATGC
TCAAGGACACTGCGGCTTATTATTCTCGCAAAGCTTCTAACTGGATCCTCGAAGATTCATGTCCAG
ATTATATGCTGAAAGCTGAGGAGTGCTTGAAACGGGAGAAGGATAGGGTCTCCCATTATCTCCATT
CTAGCAGTGAGACAAAGTTGCTTGAGAAAGTGCAACATGAGTTGTTATCTGTGTATGCCAATCAAC
TTCTTGAGAAGGAGCACTCTGGATGCCATGCATTACTTAGAGATGATAAGGTCGATGATTTATCAA
GGATGTATAGACTCTTTTCTAAGATTCCTCGAGGCTTAGAGCCTGTGGCTAATATATTTAAGCAGC
ATGTTACTGCTGAAGGTACAGCTTTGGTGAAACAGGCTGAAGATGCTGCTAGCAACAAAAAGGCAG
AGAAGAGAGATGTGGTTGGTTTGCAGGAACAGGTTTTTGTTCGGAAAGTGATTGAGCTTCATGATA
AATATTTGGCGTATGTGAATAACTGTTTCCAAAACCACACTTTTTCACAAGGCACTTAAAGAAG
CTTTCGAACTTTTCTGCAACAAGGGTGTTGCTGGTAGCTCAAATGCTGAACTTCTTGCCACATTCT
GCGACAACATTCTCAAAAAAGGCGGGAGTGAAAAATTGAGTGATGAAGCCATTGAAGAGACGCTGG
AGAAGGTGGTAAAGCTGCTGGCTTATATTAGTGATAAGGACTTGTTTGCAGAATTCTATAGGAAAA
AGCTCGCCCGGCGGTTGTTATTTGATAAGAGTGCCAATGATGAACATGAGAGAAGTATCCTAACAA
AGTTGAAGCAGCAGTGTGGAGGTCAGTTCACATCAAAGATGGAGGGAATGGTCACAGATTTGACAT
TGGCAAGGGAAAATCAAGCCAGCTTTGAGGAGTATTTGAGCAATAATCCAACAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGTGTTGAAGTATTCAAGGAGTTTTATCAAACAAAAACGAAGCACA
GGAAACTTACATGGATATACTCTTTGGGAACTTGCAACATAAATGGAAAATTTGAGGCAAAGACTA
TTGAGCTCGTTGTCACTACTTATCAGGCTTCTGCTCTGCTTCTCTTTAATGCATCAGATAGATTGA
GTTATCAGGAAATCATGACGCAATTAAACCTATCAGATGATGATGTTGTCGGCTTCTTCATTCCC
TTTCATGTGCGAAATACAAGATTCTCAACAAGGAGCCAAGCACCAAAACAATTTCTCCGACTGATG
TCTTTGAGTTCAACTCAAAGTTCACTGACAAAATGAGGAGGATCAAGATACCTCTCCCACCAGTTG
ATGAAAAGAAAAGGTAATTGAAGACGTTGACAAGGATAGGCGGTATGCTATAGATGCCTCAATTG
TGCGTATTATGAAGAGTCGTAAAGTATTGGGCTACCAGCAACTGGTCATGGAGTGCGTTGAGCAGT
TGGGACGCATGTTCAAGCCTGATGTCAAAGCTATCAAGAAGAGAATTGAAGATCTGATAACTAGAG
ATTACCTAGAGAGGGACAAAGATAACCCAAACTTGTTCAAGTACTTGGCATGA
```

Fig. 40

```
ATGAACCAACGAAGCACAATCGATCTGGAACATGGATGGGACTTCATGCAAAGGGGCATTACAAAG
CTGAAGAACATTCTAGAAGGGCTGCCTGAGCCTCAATTCAGCTCAGAGGACTATATGATGCTATAT
ACGACAAT[G]TACAACATGTGTACTCAAAAGCCCCCACATGATTATTCTCAACAGCTGTATGACA
AATATCGTGAAGCTTTTGAAGAATATATCACAACAACGGTATTGCCTTCTTTGAGAGAAAAACATG
ACGAGTTTATGTTGCGAGAGTTGGTAAAAGGTGGTCAAATCATAAAGTCATGGTCAGATGGTTGT
CAAGATTCTTCCATTACCTTGACCGGTATTTCATTGCCCGGAGATCTCTGCCGGGGCTTAATGAAG
TTGGACTAACTTGCTTCCGCGATCAGGTCTACCAAGAGTTGAATGGAAAAGTCAGGGATGCTGTTA
TATCTCTGATTGATCAAGAGCGTGAGGGAGAGCAAATTGACAGAGCTCTACTTAAGAATGTGCTTG
ATATATTTGTCGAAATTGGAATGGGGTTAATGGATTATTATGAGAATGATTTTGAAGCTGCAATGC
TCAAGGACACAGCGGCTTATTATTCTCGCAAAGCTTCTAATTGGATCCTCGAAGATTCATGTCCGG
ATTATATGCTGAAAGCCGAGGAGTGCTTGAAACGGGAGAAGGATAGGGTCTCTCATTATCTCCATT
CAAGCAGCGAGACGAAGTTGCTTGAGAAAGTGCAACATGAGTTGTTGTCTGTGTATGCCACTCAAC
TTCTTGAGAAGGAGCACTCTGGATGCCATGCGTTACTGAGAGATGATAAGGTTGAAGATTTATCAA
GGATGTATAGGCTCTTTTCTAAGATTTCTCGAGGCTTAGACCCTGTGGCCAATATTTTTAAGCAGC
ATGTTACTGCTGAAGGTACAGCTTTGGTAAAACAGGCTGAAGATGCTGCTAGCAATAAAAAGGCAG
AGAAGAGAGATGTGGTTGGTTTGCAGGAACAGGTTTTTGTTCGGAAAGTGATTGAACTTCATGATA
AATATTTGGCTTATGTGAATAACTGTTTCCAAAACCACACTTTTTCACAAGGCGCTTAAAGAAG
CTTTTGAGCTTTTCTGCAACAAGGGTGTTGCTGGTAGCTCAAGCGCTGAACTTCTTGCCACCTTCT
GTGACAACATTCTCAAAAAAGGCGGGAGTGAGAAATTGAGTGATGAAGCTATTGAAGAAACGTTGG
AAAAGGTGGTAAAGCTACTAGCTTATATTAGTGATAAGGACTTGTTTGCAGAATTCTATAGGAAAA
AGCTAGCCCGGCGGTTGTTATTTGATAAGAGTGCCAATGATGAACATGAAAGAAGTATCCTAACAA
AGTTGAAGCAGCAGTGTGGGGGGCAGTTCACATCAAAGATGGAGGGAATGGTCACAGATTTGACAT
TGGCAAGGGAAAATCAAGCCAGCTTCGAGGAGTATTTGAGCAATAATCCAATAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTTAAGGAGTTCTATCAAACAAAAACAAAGCACA
GGAAACTTACGTGGATATACTCTTTGGGAACTTGCAACATAAATGGAAAATTTGAGCCAAAAACTA
TTGAGCTCGTTGTCACTACTTATCAGGCTTCTGCTCTGCTGCTCTTTAATGCATCAGATAGATTGA
GTTATCAGGAAATCATGACGCAATTAAACCTATCAGATGATGATGTTGTTCGGCTTCTTCATTCCC
TTTCATGTGCGAAGTACAAGATACTCAACAAGGAGCCAAGCACCAAAACAATTTCTCCGACTGATG
TCTTTGAGTTCAACTCAAAGTTCACTGACAAAATGAGGAGGATCAAGATACCTCTCCCTCCTGTTG
ATGAGAAGAAAAGGTAATTGAAGACGTTGACAAGGATAGGCGGTATGCTATAGATGCTTCAATTG
TGCGTATTATGAAGAGCCGTAAAGTATTGGGCTACCAGCAACTAGTCATGGAGTGCGTTGAGCAGT
TGGGGCGCATGTTCAAGCCTGATGTCAAAGCTATCAAGAAGAGAATCGAAGATTTGATAACTAGAG
ATTACCTAGAGAGGGACAAAGATAATCCAAACCTGTTCAAGTACTTGGCATGA
```

Fig. 41

ATGAACCAGCGTTCCACAATCAATCTAGAACATGGATGGGACTTCATGCAAAGGGGCATTACAAAG
CTGAAGAACATTCTAGAAGGGCTGCCCGAGCCTCAGTTCAGCTCAGAGGACTATATGATGCTGTAT
ACGACAAT[G]TACAACATGTGTACTCAGAAGCCCCCACATGATTATTCTCAACAGCTGTATGACA
AATATCGTGAAGCTTTTGAAGAATATATCACAACAACGGTATTGCCTTCTTTGAGAGAAAAACATG
ACGAGTTCATGTTGCGAGAGCTGGTAAAAGGTGGTCAAACCATAAGGTCATGGTCAGATGGTTAT
CGCGATTCTTCCATTATCTTGATCGCTATTTCATTGCCCGGAGATCTCTACCGGGGCTTAATGAAG
TTGGACTAACTTGCTTCCGAGATCTGGTCTACCAAGAGTTGAATGGAAAAGTCAGGGATGCTGTTA
TATCTCTGATTGATCAAGAGCGTGAGGGAGAGCAAATTGACAGAGCTCTACTGAAGAATGTGCTAG
ATATATTTGTTGAAATTGGAATGGGGTCGATGGATTATTATGAGAATGATTTTGAAGCTGCAATGC
TCAAGGACACCGCAGCTTATTATTCTCGCAAAGCTTCTAACTGGATACTTGAAGATTCATGTCCAG
ATTATATGCTGAAAGCCGAGGAGTGCTTGAAACGGGAGAAAGATAGGGTCTCTCACTATCTTCATT
TAAGCAGTGAGACAAAGTTGCTTGAGAAAGTGCAACATGAGTTGTTGTCTGTGTATGCCACTCAAC
TTCTTGAGAAGGAGCACTCTGGGTGCCATGCGTTACTAAGAGATGATAAGGTTGAAGATTTATCAA
GGATGTATAGGCTCTTTTCTAAGATTCCTCGAGGCTTAGACCCTGTGGCTAATATATTTAAGCAGC
ATGTTACTGCTGAAGGTACAGCTTTGGTCAAACAGGCTGAAGATGCTGCTAGCAACAAAAAGGCAG
AGAAAAGAGATGTGGTTGGTTTGCAGGAACAGATTTTTGTTCGGAAAGTGATTGAGCTTCATGATA
AGTATATGGCATATGTGAATAACTGTTTCCAAAACCACACACTTTTTCACAAGGCGCTTAAAGAAG
CTTTCGAACTTTTCTGCAACAAGGGTGTTGCTGGTAGCTCAAGTGCTGAACTTCTTGCCACATTCT
GCGACAATATTCTCAAGAAAGGCGGGAGTGAGAAATTGAGTGATGAAGCCATTGAAGAGACGCTGG
AGAAGGTTGTAAAGCTGCTAGCATATATTAGTGACAAGGACTTGTTTGCAGAATTCTATAGGAAAA
AGCTAGCCCGGCGGTTGTTATTTGATAAGAGTGCCAATGATGAACACGAGAGAAGTATCCTTACAA
AGTTGAAGCAGCAGTGTGGGGGCCAGTTCACATCAAAGATGGAGGGAATGGTGACAGATTTGACAT
TGGCAAGGGAAAATCAAGCCAGCTTTGAGGAGTATTTGAGCAACAATCCAGCAGCAAATCCAGGAA
TTGACTTGACGGTGACTGTCTTGACTACTGGCTTCTGGCCTAGCTACAAGTCTTTTGATCTCAACC
TCCCAGCAGAAATGGTTAGGTGCGTTGAAGTATTCAAGGAGTTTTATCAAACAAAAACGAAGCACA
GGAAACTTACGTGGATATACTCTTTGGGAACTTGCAATATAAATGGAAAATTTGAGCCAAAGACTA
TTGAGCTCGTTGTCACTACTTATCAGGCTTCTGCTCTGCTGCTCTTTAATGCATCGGATAGATTGA
GTTATCAGGAAATCATGACGCAACTAAACCTATCAGATGATGATGTTGTCGGCTTCTTCATTCCC
TTTCATGTGCGAAGTACAAGATTCTCAACAAGGAGCCAAGCACCAAAACAATTTCTCCGACTGATG
TCTTTGAGTTCAATTTTAAGTTCACTGACAAAATGAGGAGGATCAAGATACCTCTCCCTCCTGTTG
ATGAGAAGAAAAGGTAATTGAAGATGTTGACAAAGATAGGCGGTACGCTATAGATGCTTCAATTG
TGCGTATTATGAAGAGTCGTAAAGTATTGGCTACCAGCAACTGGTCATGGAGTGTGTTGAGCAGT
TGGGACGTATGTTCAAGCCTGATGTCAAAGCTATCAAGAAGAGAATTGAAGATTTGATAACTAGAG
ATTACCTAGAGAGGGACAAAGATAATCCGAACTTGTTCAAGTACTTGGCATGA

Fig. 42

ATGGAGCGCAAGACGATTGACTTGGACCAAGGATGGGACTATATGCAGACTGGTATCACTAAGCTG
AAACGGATTCTTGAGGGGCTGCCTGAGCCGCAGTTTGACTCTGAGCAATACATGATGCTCTATACG
ACTAT[G]TACAACATGTGCACTCAGAAACCTCCTCATGATTACTCACAGCAGCTTTATGACAAGT
ATCGTGAAGCATTTGAGGAGTATATTCACTCAACTGTTTTGCCTGCTCTAAGGGAGAAGCATGATG
AGTACATGCTGAGGGAGCTGGTTAAGAGATGGTCTAACCATAAAGTTATGGTTCGATGGCTATCCC
GCTTCTTCTACTATCTTGACCGTTACTTCATTGCTCGGAGGTCACTTCCACCCCTGAATGAAGTTG
GCCTGACTTGCTTCCGTGACCTGGTTTATAACGAGTTGCATTCCAAGGTCAAAGATGCTGTAATAG
CACTTGTTGATAAGAACGGGAGGGTGAGCAGATTGACAGGGCTCTATTGAAAACGTATTAGACA
TTTATGTAGAGATTGGAATGGGACAGATGGAAAGATACGAGGAGGATTTTGAAAGCTTCATGCTTT
TAGATTCAGCATCTTACTATTCTCGCAAGGCGTCAAGCTGGATCCAAGAAGATTCTTGCCCTGATT
ACATGCTGAAGTCTGAAGAATGTCTTAAGAAGGAGAGGGAGAGAGTGGCTCACTACCTTCACTCAA
GCAGCGAGCCAAAGCTGGTTGAGAAAGTACAACATGAGCTGTTGGTAGTGTATGCAAATCAGCTTC
TAGAAAAAGAGCATTCAGGGTGCCGTGCATTGCTGAGAGATGACAAGGTTGATGACCTCTCCAGGA
TGTACAGGCTTTATCATAAAATTGTGAAAGGTTTGGAACCTGTTGCAAACATATTTAAGCAGCATG
TCACAGCAGAGGGTAACGCACTTGTCCAACAGGCCGAAGACACGGCCACTAATCATGCTGCAAATA
CTGCTAGCGTGCAGGAACAGGTTCTTATCAGAAAGTGATTGAACTACATGATAAATACATGGTCT
ATGTTGTTGAGTGTTTCCAGAACCACACCCTCTTCCACAAGGCATTGAAAGAGGCATTTGAGATAT
TCTGTAACAAAACAGTCGCTGGAAGTTCTAGTGCTGAATTGCTTGCAACATTTTGCGACAATATTC
TCAAGAAGGGGGGAAGTGAAAAGCTGAGCGATGAAGCTATTGAAGATACCCTTGAGAAGGTGGTCA
AATTGCTTGCTTATATAAGTGACAAGGATCTTTTCGCCGAGTTCTACAGGAAGAAGCTGGCCCGTA
GGCTCTTATTTGATCGCAGTGCTAATGATGATCATGAGAGAAGTATCCTGACAAAGCTCAAGCAAC
AATGTGGTGGGCAGTTTACTTCGAAGATGGAGGGCATGGTGACTGATTTGACATTGGCAAGGGAAA
ACCAAAACAGCTTCGAGGAGTATCTTGGCAATAACCCCGCTGCAAACCCAGGGATTGATTTGACCG
TAACTGTTCTTACCACTGGTTTTTGGCCAAGTTACAAATCATTTGACATAAATCTACCCGCTGAAA
TGGTCAAGTGTGTTGAAGTTTTCAAAGGGTTTTATGAAACAAAGACAAAACATAGGAAACTTACCT
GGATCTACTCACTAGGAACTTGCCACCTCAATGGGAAGTTTGATGTCAAGCCCATTGAGTTAGTTG
TGTCTACATACCAGGCTGCTGTGCTTCTGCTGTTCAACACAACAGACAAATTGAGCTACACTGATA
TCCTAACTCAGCTGAACCTGAGCCACGAAGATCTAGTGAGGTTGCTTCATTCCTTGTCATGTGCTA
GATACAAGATTCTTCTCAAGGAGCCAAGCACAAAGACTGTTTCCCAGTCTGATTCTTTTGAATTCA
ACTCCAAATTCACCGACAGAATGCGGAGAATAAAGATCCCTCTCCCACCTGTTGATGAGAGGAAGA
AAGTTGTGGAAGACGTGGACAAAGACAGACGCTATGCGATTGATGCTGCCATTGTGAGGATCATGA
AGAGCAGGAAAGTATTGGGACATCAACAACTTGTTTCTGAGTGCGTTGAGCAACTTAGCCGAATGT
TCAAGCCTGATATCAAGGCAATCAAGAAGCGCATGGAGGATTTGATAACGAGAGATTATCTGGAGA
GGGACAAGGAGAACGCTAACATGTTTAGGTACTTGGCTTAG

Fig. 43

ATGATGATTGAGCGGAAAACTATAGACCTGGAGCAGGGATGGGACTTTATGCAAAAGGGAATCACA
AAGCTAAAGAATATTTTAGAAGGCTTTCCGGAGCCGCAATTCAGCTCGGAGGATTATATGATGCTT
TATACAACTAT[G]TATAACATGTGTACACAGAAACCTCCACATGATTACTCTCAGCAGCTGTATG
AAAAGTATCGTGAAGCTATTGAGGAGTACATTACTTCTACAGTATTGCCTTCATTGAGAGAGAAGC
ATGATGAATTCATGCTTAGAGAACTTGTGAAGAGATGGTCTAATCATAAGGTCATGGTCAGGTGGC
TTTCTCGATTCTTTCACTATCTTGATCGCTATTTTATTGCTCGGAGGTCACTTCCACCACTTCATG
AAGTTGGACTCACTTGCTTTCGGGACCTGGTTTACCAGGAGATAAATGGGAAAGTAAGGGATGCTG
TAATATCATTGATTAATCAAGAGCGCGAGGGAGAGCAAATTGACCGAGCTTTGTTGAAGAATGTTC
TAGATATATTTGTTGAAGTTGGAATGAGTCAAATGGATTATTATGAGAATGACTTTGAAGCAGACA
TGCTCAAAGATACAGCAGCATACTATTCTCGAAAGGCTTCCAACTGGATCTTAGAAGATTCTTGTC
CAGATTATATGCTCAAAGCGGAAGAGTGTTTGAGACGGGAAAAGGACAGGGTCTCTAACTACCTTC
ATTCTAGTAGTGAACCCAAGTTGCTTGAGAAAGTTCAACATGAGTTACTATCACACTATGCAACTC
AGCTGCTTGAGAAAGAACACTCTGGGTGTCATGCATTGCTTAGGGATGACAAGGTGGCAGATTTAT
CAAGGATGTATAGGCTCTTCTCTAAAATACCTCGAGGCCTAGATCCCGTGTCTAATATTTTCAAGC
AGCATGTTACTGCTGAAGGTACAGCTTTGGTCAAACAAGCAGAAGATGCAGCTAGCAACAAGAAGG
CAGAGAAGAGAGATGTAGTAGGTTTACAAGAACAGGTTTTTGTGAGGAAAATAATTGAATTGCATG
ACAAATACCTTACATACGTAAATGACTGTTTTACAAACCACACTCTCTTCCATAAGGCGCTTAAGG
AGGCTTTTGAAATCTTCTGCAATAAGGGTGTCTCTGGAAGCTCTAGTGCAGAATTACTTGCCACAT
TCTGTGATAATATTCTCAAGAAAGGTGGAAGCGAGAAGTTAAGTGATGAAGCCATTGAGGAAACAC
TTGAGAAGGTTGTAAGGTTGCTTGCTTATATAAGTGACAAAGACTTATTTGCTGAATTTTATAGGA
AAAAGCTTGCACGGCGTCTCTTATTCGACAAGAGTGCCAATGATGAGCATGAGAGAAGTATATTGA
CTAAGCTGAAGCAACAATGTGGGGGTCAATTTACATCAAAGATGGAAGGAATGGTCACTGACTTGA
CGTTGGCAAAGGAAAATCAGTCCAACTTCGAGGAGTACCTCAATAATAATTCAAACGTAAATCCTG
GAATTGACTTGACAGTTACTGTTCTAACCACTGGGTTTTGGCCAAGTTACAAATCTTTCGATCTCA
ACCTCCCAGCAGAGATGGTCAAATGTGTTGAAGTTTTTAGAGAATTCTACCAAACAAAAACAAAGC
ACAGAAAACTGACATGGATATACTCTTTGGGTACTTGTAACATCATTGGAAAATTTGATCCAAAAA
CCATGGAGCTTATTGTGACAACATACCAGGCCTCTGCTCTGCTGCTATTTAACTCTTCTGATAGAC
TTAGTTATAATGAAATAATGACTCAGTTGAACTTGTCGGATGATGATGTTGTCAGACTACTTCATT
CTCTTTCGTGTGCAAAGTACAAGATTCTATCTAAAGAGCCGAACACCAAAACTATATCTCCAACTG
ATTGCTTTCAGTTCAATTCCAAATTTACTGATAAAATGAGGAGGATTAAGATTCCACTTCCCCCAG
TGGATGAGAAGAAAAAGGTAATTGAAGATGTTGATAAAGACAGGCGATATGCTATAGATGCTTCAA
TTGTCCGTATCATGAAGAGCCGCAAAGTTTTGGGTTATCAGCAGCTAGTAATGGAGTGCGTTGAAC
AATTGGGTCGCATGTTTAAGCCTGATGTCAAAGCAATCAAGAAGAGAATCGAAGATTTAATAACTC
GGGATTATCTGGAAAGAGACAAGGACAATGCCAACTTGTTCAGGTATCTGGCATGA

Fig. 44

```
ATGAACGAGCGGAAGACTATCGATTTGGATAATGGATGGGAATTTATGCAGAAAGGGATCACTAAG
TTGAAGAAGATTCTCGAAGGTCAACCTGAGCCTCAGTTTAGCTCCGAGGACTATATGATGCTTTAC
ACAACTAT[G]TATAATATGTGTACGCAGAAGCCTCCACATGATTATTCTCAACAGCTGTATGACA
AGTACCGTGAGGCCTTTGAGGAGTACATAACTTCAACTGTCCTGCCTTCTTTACGAGAGAAGCATG
ATGAGTTTATGTTGAGAGAGCTCGTGAATAGATGGACAAACCATAAAGTCATGGTCAGGTGGCTTT
CTCGATTCTTTCACTATCTTGATCGGTACTTCATTGCGAGGAGGTCACTTCCTGCACTTCATGAAG
TTGGACTCACGTGCTTCCGGGATCTGGTCTATCAGGAGCTGAAAGTTAAAGTGAGGGATGCTGTAA
TATCTCTGATCGATCAAGAGCGTGAGGGGGAACAGATTGACCGAGCTTTATTAAAGAACGTGTTAG
ATATATTTGTTGAAATCGGAATGAGTCAAATGGATCAATATGAGAATGACTTTGAAGAAGCCATGC
TCACTGATACTGCTGCTTACTATTCTCGAAAAGCTTCAAACTGGATCCTTGAAGATTCTTGTCCTG
ATTATATGTTAAAGGCAGAAGAATGTTTGCGACGAGAGAAGGACAGGGTTTCCCACTACCTACATT
TTAGTAGCGAGCCAAAGTTGCTTGAGAAAGTGCAACATGAGCTGCTATCTGTGTATGCAACCCAAT
TACTCGAGAAGGAACATTCTGGTTGTCATGCATTGCTTAGGGATGACAAGGTGGATGATTTGTCTA
GGATGTACAGACTCTTCTCGAAAATACCTAAAGGCCTGGATCCAGTTTCTTATATTTTTAAGCAGC
ATGTTACAAATGAAGGGATGGCATTGGTTAAACAAGCAGAAGATGCAGCAAGCAACAAGAAGGCAG
AAAAGAGAGACGTGGTTAGTTTACAGGAGCAGGTTTTTGTTAGAAAAATTATTGAATTACATGACA
AATACCTCGCCTATGTGAATGACTGCTTTACAAACCATACTCTTTTCCATAAGGCTCTCAAGGAGG
CTTTTGAAATCTTTTGCAACAAGGGTGTTGCTGGAAGCTCTAATGCTGAACTACTTGCTACTTTCT
GTGATAACATCCTCAAAAAGGGTGGGAGTGAGAAATTAAGTGATGAGGCTATTGAAGAAACACTTG
AGAAGGTAGTAAAATTGTTAGCTTACATTAGCGATAAAGACTTGTTCGCTGAATTTTACAGAAAAA
AGCTTGCACGGAGACTTCTCTTTGATAAGAGTGCAAATGACGAGCATGAACGAAGTATTTTGACTA
AACTAAAGCAACAGTGCGGTGGTCAGTTCACATCGAAAATGGAGGGGATGGTCACAGATTTGACTT
TGGCTAAAGAAAATCAATCCAGCTTTGAGGAGTATCTGGGAAATAATGCCAATGTGAATCCTGGCA
TTGACTTGACGGTTACTGTTCTGACCACTGGCTTCTGGCCTAGTTATAAATCCTTTGATCTCAACC
TTCCTGCTGAGATGGTCAAGTGCGTTGAAGTATTTAGAGAATTTTATCAAACAAAAACGAAGCATA
GAAAGCTCACATGGATATATTCTCTGGGTACTTGTAATATCAATGGAAAATTTGAACCCAAAACCA
TTGAGCTGATTGTGACAACCTACCAGGCCTCTGCTCTCCTGTTATTTAATACTTCTGATAGGTTGA
GTTATCAAGAAATCATGACTCAGTTAAATTTGTCGGATGATGATGTTGTTCGCCTGCTTCATTCCC
TTTCATGTGCCAAGTATAAAATTCTTACTAAAGAGCCGAACAACAAAACAATTTCCCCTACGGATT
ACTTTGAGTTCAACTCCAAGTTCACTGACAAAATGAGGAGAATTAAGATTCCACTACCTCCAGTTG
ATGAGAAGAAAAAGGTAATTGAAGATGTTGACAAGGACCGGCGATATGCCATTGATGCATCTATTG
TCCGCATTATGAAGAGCCGTAAAGTTTTGGGCTACCAACAATTGGTTATGGAATGTGTTGAGCAAT
TGGGACGCATGTTTAAGCCTGATGTCAAAGCAATTAAGAAGAGAATCGAAGATTTAATAACGCGTG
ATTATCTGGAAAGAGACAAGGATAATGCCAACCTTTTCAGATATTTGGCATGA
```

Fig. 45

```
ATGAATGAAAGAAAAACAATAGACTTAGAACAAGGATGGGACTTCATGCAGAAAGGCATAACAAAG
TTGAAGAACATTCTAGAAGGTCTTCCCGAGCCACAATTCAGCTCGGAAGATTACATGATGCTCTAC
ACAACCAT[G]TACAATATGTGCACACAAAAACCGCCACATGATTACTCTCAACAATTGTATGACA
AATACCGCGAGTCTTTTGAAGAGTACATTACTTCAACGGTGTTACCTTCTTTAAGAGAGAAGCATG
ATGAGTTTATGCTTAGAGAGCTTGTTAGAAGATGGTCAAATCATAAAGTGATGGTTAGGTGGCTTT
CTAGATTCTTCCATTATCTTGATCGATACTTCATTGCCCGAAGATCTCTTCCACCATTAAATGAAG
TTGGACTTGCGTGTTTTCGTGATCTGGTATACCAAGAGGTGAATGGGAAAGTGAGAGATGCTGTAA
TATCTTTGATTGATCAAGAGCGTGAAGGCGAGCAAATTGACCGAGCATTACTCAAGAATGTTCTAG
ATATATTTGTTGAAATAGGAATGGGACAAATGGAATATTATGAGAATGATTTTGAAGCATCCATGC
TTAATGATACAGCAGCATATTATTCACGCAAAGCTTCCAATTGGATTCTAGAAGATTCTTGTCCAG
ATTATATGCTCAAAGCTGAGGAGTGCTTAAAAGAGAAAAGGACAGAGTTTCTCATTATCTTCATT
CCAGCAGTGAACCAAAGCTTCTTGAGAAAGTTCAAACAGAGTTATTATCTGTTTATGCAACTCAAT
TGCTTGAAAAGGAGCACTCCGGTTGTCATGCATTACTTAGGGATGACAAGGTTGATGATTTATCAA
GAATGTACAGACTCTTTTCAAAGATACAAAAAGGGCTGGATCCTGTTTCTAGTATGTTTAAGCAGC
ATGTCACTGCTGAAGGCACAACATTGGTTAAACAGGCAGAAGATGCAGCAAGTACTAAGAAGGCTG
AAAAGAGAGACGTGGTTGGCTTACAAGAACAGGTTTTTGTTAGAAAAGTTATCGAGCTTCATGACA
AGTACCTTGCATATGTAAATGACTGTTTTATGAATCATACCCTGTTTCACAAGGCTCTTAAAGAGG
CATTTGAAATATTCTGCAACAAGGGCGTTGCTGGAAGTTCAAGTGCAGAATTACTTGCTACATTTT
GTGATAATATTCTTAAAAAAGGTGGAAGTGAAAAATTGAGTGATGAAGCCATTGAGGACACACTTG
AGAAGGTGGTAAAGTTGCTTGCTTACATCAGCGATAAAGATCTATTTGCAGAGTTTTATAGGAAAA
AACTGGCTAGACGGCTTTTATTTGACAAAAGTGCAAATGATGAGCACGAAAGAAGTATTTTGACAA
AATTGAAACAACAATGTGGCGGTCAATTTACATCAAAAATGGAAGGAATGGTTACAGATTTGACAT
TGGCAAAAGAAAATCAATCACATTTTGAGGAGTATTTGAATAATAATCCCAATGTTAGCCCTGGCA
TTGACTTGACCGTGACTGTGTTGACCACTGGTTTTTGGCCTAGTTACAAATCTTTTGACCTAAATC
TCCCTGCAGAAATGGTCAAATGCGTTGAAGTTTTCAGAGAATTTTATCAAACAAAAACAAAACACA
GAAAACTCACATGGATATATTCATTGGGCACCTGCAATATAAACGGAAAATTCGAACCAAAAACCA
TGGAGCTAATCGTTACAACTTACCAGGCATCTGCTTTATTACTGTTCAACTCATCAGATCGATTGA
GTTATCAAGAAATCATGACTCAATTAAACTTATCAGATGATGATGTTGTTAGACTACTCCATTCAT
TATCATGTGCAAAATATAAAATTTTATTAAAAGAACCAAATACAAAAACAATCTCTCCAACTGATT
TCTTTGAATTCAACTCAAAGTTTACAGATAAAATGAGAAGGATCAAGATTCCTCTACCTCCTGTTG
ATGAAAAGAAAAAGTAATTGAAGATGTTGACAAAGACCGACGTTATGCAATTGATGCTTCAATTG
TACGGATAATGAAAGCAGAAAAGTTCTTGGATACCAACAATTGGTCATGGAATGTGTTGAACAAT
TAGGCCGTATGTTTAAGCCTGATGTAAAAGCAATCAAGAAACGTATTGAAGATCTCATAACTCGTG
ATTATCTTGAAAGAGACAAAGAAAATCCAAATTTGTTTCGGTACTTGGCATGA
```

Fig. 46

```
ATGAATGAAAGAAAAACAATAGACTTAGAACAAGGATGGGACTTCATGCAAAAAGGCATAACAAAG
TTGAAGAACATTCTAGAAGGTCTTCCCGAGCCACAATTCAGCTCAGAGGATTACATGATGCTCTAC
ACAACCAT[G]TACAATATGTGCACACAAAAACCGCCACATGATTACTCTCAACAATTATATGACA
AATACCGCGAGTCTTTTGAAGAGTACATAACTTCAACGGTGTTACCTTCTTTAAGAGAGAAGCATG
ATGAGTTTATGCTTAGAGAGCTTGTTAGAAGGTGGTCAAATCATAAAGTGATGGTTAGGTGGCTTT
CTAGATTCTTCCATTATCTTGATCGATACTTTATTGCAAGAAGATCTCTTCCACCATTAAATGAAG
TTGGACTTGCGTGTTTTCGTGATCTGGTATACCAAGAGGTGAATGGAAAAGTGAGAGATGCTGTAA
TATCTTTGATTGATCAAGAGCGTGAAGGCGAGCAAATTGACCGAGCATTACTGAAGAATGTTCTAG
ATATATTTGTTGAAATAGGAATGGGACAAATGGAATATTATGAGAATGATTTTGAAGCATCTATGC
TTAATGATACAGCAGCATATTATTCACGCAAAGCTTCCAACTGGATTCTAGAAGATTCTTGTCCAG
ATTATATGCTCAAAGCTGAGGAGTGCTTAAAAAGAGAAAAGGACAGAGTTTCTCATTATCTTCATT
CAAGTAGTGAACCAAAGCTTCTTGAGAAAGTTCAAACAGAGTTATTATCTGTTTATGCAACTCAAT
TGCTCGAAAAGGAACACTCAGGTTGTCATGCATTACTTAGAGATGACAAGGTTGATGATTTATCAA
GAATGTACAGACTCTTTTCAAAGATACAAAAAGGACTGGATCCTGTTTCCAGTATGTTTAAGCAGC
ATGTCACTGCTGAAGGCACAACATTAGTAAAACAAGCAGAAGATGCAGCAAGTACTAAGAAGGCTG
AAAAGAGAGACGTGGTTGGCTTACAGGAACAGGTTTTTGTTAGAAAAGTAATCGAGCTTCATGACA
AGTACCTCGCATATGTAAACGACTGTTTTATGAATCACACATTGTTCCACAAGGCTCTTAAAGAGG
CATTTGAAATATTCTGCAACAAGGGCGTTGCTGGAAGTTCAAGTGCAGAATTACTTGCCACATTTT
GTGATAATATTCTTAAAAAAGGTGGAAGTGAAAAATTGAGTGATGAAGCCATTGAAGACACACTTG
AGAAGGTAGTAAAGTTGCTTGCTTACATCAGCGATAAAGATCTATTTGCAGAGTTTTATAGGAAAA
AACTGGCTAGAAGGCTTTTATTTGACAAAAGTGCAAATGATGAGCATGAAAGAAGTATTTTAACAA
AGTTGAAGCAACAATGTGGTGGTCAGTTTACATCAAAGATGGAAGGAATGGTTACAGATTTAACAC
TGGCAAAAGAAAATCAATCACATTTTGAGGAGTATTTGAATAATAATCCCAATGTTAGCCCTGGCA
TTGACTTGACCGTGACTGTGTTGACCACGGGATTTTGGCCTAGTTACAAATCTTTTGACCTAAATC
TTCCTGCAGAAATGGTCAAATGCGTTGAAGTTTTCAGAGAATTTTATCAAACAAAAACAAAACACA
GAAAACTCACATGGATTTATTCATTGGGCACCTGCAATATTAACGGAAAATTCGAACCAAAAACCA
TGGAGCTAATCGTTACAACTTACCAGGCATCTGCTTTATTGTTATTCAACTCATCAGATCGATTAA
GTTATCAAGAAATCATGACTCAATTAAATTTATCAGATGATGATGTTGTTAGACTACTACATTCAT
TATCATGTGCAAAATATAAAATTTTATTAAAAGAACCAAATACCAAAACAATATCTCCAACCGATT
TCTTTGAATTCAACTCAAAGTTTACAGATAAAATGAGAAGGATCAAGATTCCTCTACCTCCTGTTG
ATGAAAAGAAAAAGTAATTGAAGATGTTGACAAAGATAGAAGGTATGCAATTGATGCTTCAATTG
TACGAATAATGAAAGCAGAAAAGTTCTTGGATACCAACAATTGGTTATGGAGTGTGTTGAACAAT
TAGGCCGTATGTTTAAGCCTGATGTAAAAGCAATCAAGAAGCGTATTGAAGATTTGATAACGCGTG
ATTATCTTGAAAGAGACAAAGAAAATCCAAATTTGTTTCGGTACTTGGCATGA
```

Fig. 47

```
ATGTCGTTGCACGAAAGGAAAACCATTGATTTGGAGCAGGGATGGGCTTTTATGCAGAAAGGGATC
ACCAAACTGAAGAATATTCTTGATGAGTTGAATGAACCTCAGTTCAGCTCAGAGGATTACATGATG
CTCTATACGACTAT[G]TATAATATGTGTACTCAGAAGCCGCCACATGATTATTCTCAGGAGTTGT
ATGATAAGTACCGAGAGTCCTTTGAAGAGTATATCACTACCACTGTGCTTCCTTCATTGAGAGAAA
AGCATGATGAATACATGTTAAGGGAGCTCGTGAGAAGGTGGTCAAATCATAAAATAATGGTTAGAT
GGCTTTCACGCTTTTTCCATTATCTTGATCGCTACTTTATAGCACGAAGATCATTGCCTGCTCTTA
ATGAAGTCGGTCTCACTTGTTTCCGTGATCTGGTGTACAACGAAGTCCATGGGAAAGTTAAAGATG
CCGTGATCTCATTGATTGACCAAGAGAGGGAAGGGGAGCAAATTGACAGAGCTTTATTAAAGAATG
TTTTGGGTATTTTTGTAGAGATTGGTTTGGGAAGCATGGAATGTTATGAGAATGATTTTGAAACAT
CAATGCTTAATGCTACAGCAGCCTATTATTCACGAAAAGCTTCAAATTGGATTCTAGAAGATTCAT
GTCCAGATTATATGCTAAAAGCCGAGGAGTGCTTAAAACATGAGAAAGATAGAGTTGCTCATTATT
TGCATTCAAGCAGTGAACAGAAGCTGTTAGAGAAAGTGCAACATGAGTTACTTTTCGTATATGCAA
GTCAACTTCTCGAGAAAGAACATTCCGGATGTCATGCATTGCTTCGCGATGACAAGGTGGGAGATC
TTTCACGCATGTATCGGCTGTTCTGTAGAATTACACGTGGTTTGGACCCTGTGTCTCAAATATTTA
AGCAGCATGTGACTGCAGAAGGTACTGCTTTGGTCAAACATGCCGAAGATGCTGCAAGTAACAAGA
AGGCCGAGAAAAAAGACATTGTTGGTTTGCAAGAGCAGGTCTTCGTTAGGAAAGTAATTGAGCTGC
ATGATAAATACTTGGCCTATGTGACTGACTGCTTTCAAAATCACTCTCTATTTCACAAGGCACTTA
AAGAGGCATTCGAGGTATTCTGCAATAAAGGTGTTGCAGGTAGCTCAAGCGCTGAACTTCTGGCTG
CTTTTTGTGACAATATATTGAAGAAGGGTGGAAGCGAGAAACTAAGCGATGAGGCCATAGAGGATA
CTCTTGAGAAGGTTGTAAAACTATTGGCATATATTAGCGATAAAGATCTGTTTGCTGAATTTTACA
GGAAGAAGCTTGCACGAAGATTACTCTTTGACAAAAGTGCTAATGATGACCATGAGAGGAGCATCC
TTACAAAGCTGAAACAGCAATGTGGAGGGCAGTTCACCTCTAAAATGGAAGGCATGGTAACCGATC
TGACACTTGCACGAGAAAATCAATCAAGTTTTGACGATTACCTTAGCAGCAATCCTAAAGCAAATT
CTGGAATTGACTTGACTGTTACAGTCTTAACAACTGGCTTCTGGCCCAGTTACAAGTCTTTTGATC
TCAATCTTCCTGATGAGATGGTAAAATGCGTTGAAATTTTTAAAGAGTTTTACGAGACAAAAACCA
AACACAGAAAACTTACATGGATTTATTCGTTGGGCACTTGCAACATCAATGGCAAGTTCGAAACCA
AGACAATAGAGTTGGTTGTTACAACCTATCAGGCTGCAGTGTTGCTTCTATTCAACTCTGCAGATA
AATTAAGTTATTCTGAGATTGTGCAGCAGCTAAACTTATCTGATGATGATGTAATCAGATTACTTC
ACTCTCTTTCATGCGCTAAATACAAAATTCTCAATAAAGAACCCGCTACCAAGACTATTACCCCGA
ATGATCATTTTGAGTTCAATTCTAAATTCACTGATAGAATGAGAAGGATCAAGATTCCCCTGCCTC
CTGTGGATGAGAAGAAAAAGTAATTGAAGATGTTGACAAAGACAGAAGATATGCAATTGACGCAT
CCATAGTTCGAATAATGAAAGTAGAAAAGTTCTTGGTCATCAGCAGCTTGTTTTGGAATGTGTTG
AGCAATTAGGCCGCATGTTTAAGCCTGACTTTAAGGCCATCAAGAAAAGGATTGAAGATCTGATCG
CTAGAGATTATTTGGAGAGGGACAAGGACAATCCAAACCTCTTTAAATATTTGGCCTAA
```

Fig. 48

ATGAACGAAAGAAAAACAATAGACTTAGAGCAAGGATGGGACTTCATGCAGAAAGGAATAACAAAG
TTGAAGAATATTCTAGAAGGTCTTCCCGAGCCACAATTCAGCTCGGAGGATTACATGATGCTCTAC
ACAACCAT[G]TACAACATGTGTACACAGAAACCACCACATGATTACTCCCAACAGTTGTATGACA
AATATCGTGAGTCTTTTGAAGAGTATATTACTTCAACTGTGTTACCTTCTTTAAGAGAGAAGCATG
ATGAGTTCATGCTGAGAGAGCTTGTTAGAAGGTGGTCAAATCATAAAGTCATGGTGCGGTGGCTTT
CTAGATTCTTCCATTATCTTGACCGATATTTCATTGCCCGAAGATCTCTTCCGCCACTAAATGAAG
TTGGACTTGCCTGTTTTCGTGATCTGGTATACCAAGAGGTGAATGGTAAAGTGAGAGATGCTGTAA
TATCTTTGATTGATCAAGAGCGTGAAGGGGAGCAGATTGATCGAGCTTTACTGAAGAATGTTCTAG
ATATATTTGTTGAGATAGGAATGGGACAAATGGAGTATTATGAGAATGATTTTGAAGCATCCATGC
TTAATGATACAGCAGCATATTATTCACGCAAGGCTTCCAACTGGATTCTAGAAGATTCTTGTCCAG
ATTATATGCTCAAAGCAGAGGAGTGCTTAAAAAGAGAAAAGGACAGAGTGTCTCATTATCTTCATT
CCAGCAGTGAGCCAAAGCTTCTTGAGAAAGTTCAAAATGAGTTATTGTCTGTTTATGCAACTCAAT
TGCTTGAGAAAGAGCACTCAGGTTGTCATGCATTGCTCAGGGATGACAAGGTTGATGATTTATCAA
GAATGTACAGACTCTTTTCAAAGATACCAAAAGGATTGGATCCTGTTTCTAGTATGTTTAAGCAGC
ATGTCACTGCTGAAGGCACAACATTGGTTAAACAAGCAGAAGATGCAGCAAGTACCAAGAAGGCTG
AAAAGAGAGATGTGGTTGGGTTGCAGGAACAGGTTTTTGTTAGAAAAGTTATTGAGCTCCATGACA
AGTACCTGGCATATGTAAATGACTGTTTCATGAACCATACTCTTTTCCACAAGGCTCTTAAAGAGG
CATTTGAAATATTCTGCAACAAGGGTGTTGCTGGAAGTTCAAGTGCAGAGTTACTTGCCACATTTT
GTGATAATATTCTTAAAAAAGGTGGAAGTGAGAAACTGAGCGATGAAGCCATTGAGGACACCCTTG
AGAAGGTAGTAAAGTTGCTTGCCTACATCAGTGATAAAGATCTATTTGCTGAATTTTACAGGAAAA
AACTTGCTAGGAGGCTTTTGTTTGACAAGAGTGCAAACGATGAGCATGAGAGAAGTATTCTCACAA
AGCTGAAGCAACAGTGTGGTGGTCAGTTCACATCAAAGATGGAAGGGATGGTTACAGATTTGACAT
TGGCAAAGGAAAACCAATCCCATTTTGAAGAGTATTTGAACAATAATCCCAATGTCAGCCCTGGAA
TTGACTTGACTGTCACTGTGTTGACTACCGGCTTCTGGCCCAGCTACAAATCTTTTGACCTAAATC
TCCCTGCCGAAATGGTTAAATGCGTTGAAGTTTTCAGAGAATTTTATCAAACAAAAACAAAGCACA
GGAAGCTTACATGGATATATTCATTGGGTACCTGCAATATAAACGGGAAATTTGAACCCAAAACAA
TGGAGCTCATAGTCACAACCTACCAGGCATCTGCTTTATTACTGTTCAACTTATCGGATCGATTGA
GTTATCAAGAAATCATGACTCAGTTGAACTTGTCAGATGATGATGTTGTTAGGCTGCTCCATTCTT
TGTCATGTGCAAAATACAAAATTCTTTTAAAGGAGCCTAATACCAAAACAATCTCTCCAACCGATT
ACTTCGAATTCAACTCCAAGTTTACAGATAAAATGAGGAGGATCAAGATTCCTCTACCTCCTGTGG
ATGAGAAGAAAAGGTGATTGAGGATGTTGACAAGACAGACGTTATGCCATTGATGCTTCCATTG
TAAGGATAATGAAGAGCAGAAAGGTGCTTGGATACCAGCAGTTGGTTATGGAGTGTGTTGAACAGT
TGGGACGCATGTTTAAGCCTGATGTAAAAGCAATCAAGAAGCGGATTGAAGATCTGATAACTCGTG
ATTATCTTGAAAGAGACAAAGAGAACCCCAACTTGTTCCGATACTTGGCATGA

Fig. 49

```
ATGGAGCGGAAGACGATTGATCTGGAACAAGGATGGGACTATATGCAGACTGGGATCACTAAGCTG
AAACGGATTCTTGAAGGATTGCCTGAGCCGCAATTCGACTCTGAGCAGTACATGATGCTTTATACG
ACTAT[G]TACAACATGTGCACCCAGAAACCTCCTCATGATTACTCTCAGCAGCTTTATGACAAGT
ATCGCGAAGCTTTTGAGGAGTACATTGACTCTACTGTTTTGCCTGCTTTGAAGGAGAAGCATGATG
AATACATGCTACGGGAGCTGGTTAAGAGATGGTCTAACCATAAAGTTATGGTTAGATGGCTATCCC
GATTCTTCTACTATCTTGACCGTTACTTCATTGCTCGGAGATCGCTGCCACCGCTTAATGAAGTTG
GGCTCACATGCTTCCGTGACCGGGTGTATAAGGAGTTGCATTCCAAGGTCAAAGATGCTGTAATAG
CACTTGTTGATAAAGAACGGGAAGGCGAGCAGATTGACAGGGCTCTTCTGAAAAACGTATTAGATA
TCTATGTAGAGATTGGAATGGGACAGATGGAAAGATACGAAGTGGATTTTGAAAGCTTCATGCTTT
TGGATTCAGCATCTTACTATTCTCGCAAAGCATCAAACTGGATCCAGGAAGATTCTTGCCCTGATT
ACATGCTGAAGTCTGAAGAATGCCTTAAGAAGGAGAGGGAGAGGGTTGCTCACTACCTTCATTCAA
GCAGCGAGCCAAAGCTGGTTGAGAAAGTACAACATGAGCTGTTGGTTGTCTATGCAAATCAGCTTC
TTGAAAAGGAGCACTCAGGGTGCCGTGCATTGCTGAGAGACGACAAGGTTGACGATCTCTCCAGGA
TGTACAGGCTCTATCATAAAATTGCTAAAGGTTTAGAACCTGTTGCAAACATATTTAAGCAGCATG
TCACAGCCGAGGGTAACGCACTTGTCCAACAGGCCGAAGACACAGCCACTAATCAGGCTGCAAATA
CTGCTAGCGTGCAGGAACAGGTTCTCATCAGAAAGTGATTGAGCTACATGATAAGTACATGGTCT
ATGTCGTGGAGTGCTTCCAGAACCACACCCTCTTCCACAAGGCTCTGAAAGAGGCATTTGAGATAT
TCTGTAACAAAACAGTCGCTGGAAGTTCAAGTGCAGAACTGCTTGCAACATTCTGCGACAACATCC
TCAAGAAGGGGGGTAGTGAGAAGCTGAGTGACGAAGCTATTGAAGATACGCTTGAGAAGGTTGTCA
AATTGCTTGCTTATATAAGCGACAAGGATCTTTTCGCCGAGTTCTACAGGAAGAAGCTGGCACGTA
GGCTCTTATTTGATCGCAGTGCGAATGATGATCATGAGAGAAGCATCCTTACAAAGCTCAAGCAAC
AATGTGGTGGGCAGTTCACTTCTAAGATGGAGGGCATGGTAACGGACTTGACATTGGCAAGAGAGA
ACCAAACCAGTTTCGAGGAGTATCTAGGCAATAACCCCGCTGCAAACCCAGGGATTGATTTGACCG
TCACTGTTCTTACCACTGGTTTCTGGCCAAGTTACAAATCATTCGACATAAATCTACCAAGTGAAA
TGGTCAAGTGTGTTGAAGTTTTCAAAGGGTTTTATGAGACGAAAACTAAACATAGGAAACTTACAT
GGATCTACTCACTAGGAACTTGTCACCTCAACGGAAAGTTTGATCACAAGCCCATTGAGTTAGTTG
TGTCTACTTACCAGGCTGCTGTGCTTCTGCTGTTCAACACAACAGACAAATTGAGCTACAACGATA
TCCTAACTCAACTGAACCTAAGCCACGAAGATTTAGTGAGGTTGCTTCATTCCCTGTCATGTGCTA
GGTACAAGATCCTTCTCAAGGAGCCAAGCACGAAGACTGTTACACAGACTGATTCATTTGAATTCA
ATGCCAAATTCACGGACAGAATGCGCAGAATCAAGATCCCTCTCCCTCCTGTTGATGAAAGGAAGA
AGGTTGTGGAAGATGTGGACAAAGACAGACGCTATGCGATTGATGCTGCCATTGTTAGGATCATGA
AGAGCAGGAAAGTGTTGGGACATCAACAACTCGTCTCTGAGTGCGTTGAGCAACTTAGCCGAATGT
TCAAGCCTGATATCAAAGCGATCAAGAAGCGTATGGAGGATCTAATTACGAGGGATTATTTGGAGA
GGGACAAGGAGAACCCTAACATGTTTAGGTACTTGGCTTAG
```

Fig. 50

```
ATGAACGATCGTAAAGTTATCGAACTAGAGCAAGGATGGGAGTTCATGGGGAAGGGGATTACGAAG
TTGAAAAGGATTTTGGAAGGATTACCAGAGCCGCCTTTTAATTCGGAAGACTACATGATGCTGTAC
ACGACAAT[G]TACAACATGTGTACACAGAAACCCCCTCATGATTACTCTCAACAACTCTATGACA
ATTACAAAGAGGCATTTGTGGATTACATACATTCAACGGTTTTACCTTCTTTGGGGGACAAACATG
ATGAGTTTATGCTGAGAGAGCTTGTGAAGAGATGGTCAAATCATAAAGTAATGGTGAGGTGGTTGT
CTCGCTTCTTCCATTATCTGGATCGGTACTTCATCGCTCGGAGATCGCTTCCTTCTTTGAATGATG
TTGGATTGACGTGCTTCCGTGATCTGGTTTATCAAGAAATATCTGGCAAAGCCAAGGATGCTGTTA
TTGCTCTGATTGATGAAGAAGAGAGGGTGGGCAAATTGACAGAGCCTTATTGAAGAATGTACTTG
ATATATACGTTGAAATTGGAATGACACAAATGGATTACTACGAAAAGGACTTTGAAGCTCATATGC
TGGATGATACTGCTGCTTATTACTCACGCAAGGCCTCAAGCTGGATTCTGGAGGACTCATGTCCGG
AATACATGTTGAAGTCGGAGGAGTGTTTGAAGAAAGAGAAAGATAGAGTGGCTCATTATCTACATT
CCAGCAGTGAGCCAAAGCTTCTGGAGAAAGTACAAAATGAGTTGCTACTGGTTTACGAAAATCAGT
TGCTTGAGAAGGAGAATTCTGGATGTCGTGCATTGTTGAAAGATGACAAGGTGGAAGATCTTTCCA
GGATGTACAGGCTTTATAGCAAGGTTACCAAAGGGTTGGAACCCATTGGCAGTATCTTCAAACAGC
ATATAACCGATGAAGGAACAGCCCTGGTGCAGCAGGCCGAAGACGCTGCAATTAGCAAGGCTGAAA
ATGCTGGCGGTGGTTCACATGAGCAGGTCTTCGTCAGGAAAGTGATTGAGTTGCATGACAAATTTA
TGACCTATGTTACAGATTGCTTCAACAGCCATACCATCTTTCACAAGGCTCTCAAGGAAGCTTTTG
AGGTATTCTTAAACAAGGGTGTTGCTGGTAGTTCAAGTGCTGAACTTCTAGCTTCATTTTGTGATA
ATATTCTCAAGAAAGGTGGTAGTGAAAAATTAAGTGATGAGGCTATTGAGGATTCACTGGAGAAGG
TGGTGAAGCTTCTCGCATATGTCAGTGATAAAGACCTGTTTGCTGAATTTTACAGAAAGAAGCTCT
CTCGCCGGCTACTCTTTGACAAAAGTGCTAATGATGATCATGAGAGGAGTATTTTAACAAAATTGA
AGCAGCAGTGTGGGGGACAGTTCACATCAAAGATGGAGGGGATGGTGACAGACTTGACATTGGCGA
GGGAGAATCAAACTAATTTTGAGGAATATCTTGGACAAAATACAGATGCCAGTCCTGGTCTTGATT
TGACTGTGACAGTTTTGACCACTGGGTTCTGGCCAAGTTACAAATCTTCTGATCTTAACCTTCCTG
CTGAGATGGTGAGGTGTGTTGAAGTTTTTAAGCAATTTTATCAAACAAAGACAAAACACAGGAAGC
TCACCTGGGTATATTCGTTGGGAAGTTGTAACATTAATGGCAAGTTTGGTCCGAAAACAATTGAAT
TGGTTGTTGGAACTTATCAGGCTGCTGCGCTGATGCTCTTTAACACATCAGATCGACTGAGTTATT
CAGAAATAACGACCCAACTAAATCTAGCTGACGAAGACTTGGTTAGAGTGCTTCAATCTCTATCTT
GCGCAAAGTATAAGATTCTTCTAAAAGAGCCAAGCACAAGAAACGTGATCTCAACTGATTGTTTTT
CATTCAACTCTAATTTTACTGACAGAATGAGGAGGATTAGGATTCCTCTTCCTCCAATGGATGAGA
GGAAAAAGGTTGTTGAAGATGTTGACAAAGATAGAAGATATGCTATTGATGCCTCAATTGTACGCA
TAATGAAAAGTAGGAAGGCTTTGGGATATCAACAATTAATCACGGAGTGTGTGGAGCAGCTAAGCC
GCATGTTCAAGCCTGATTTCAAAGCAATTAAGAAGAGGATCGAGGACTTGATAACCAGAGATTATA
TTGAAAGAGACAAGGAAAACCCTCAGCTATTCCGGTACTTGGCTTGA
```

Fig. 51

```
ATGAATGATCGTAAAGTTATTGAACTAGAGCAAGGATGGGAGTTCATGGGGAAGGGGATTACAAAG
TTGAAGAGGATTCTGGAAGGATTGCCAGAGCCACCATTTAATTCTGAAGACTACATGATGTTGTAC
ACGACGAT[G]TACAATATGTGTACTCAGAAACCCCCACATGATTACTCTCAACAGCTCTATGACA
ATTACAAACAGGCTTTTGTGGATTACATCAACTCGACGGTTTTACCTTCTTTGCGGGAGAAGCATG
ATGAGTTTATGTTAAGAGAACTTGTGAAAAGATGGGCAAATCATAAAGTAATGGTCAGGTGGTTGT
CTCGTTTCTTCCATTATCTGGACCGGTATTTCATTGCTCGGAGGTCGCTTCCTTCTTTGAATGAAG
TTGGACTGACTTGTTTCCGTGATCTGGTTTATCAAGAAATATCTGGCAAAGCCAAGGATGCTGTTA
TAGCCCTGATTGATATAGAAAGAGAAGGTGGGCAGATTGACAGATCATTATTGAAAAATGTACTTG
ATATATATGTTGAAATTGGAATGGGACAAATGGATCACTATGAAAAGACTTTGAAGCTCATATGC
TGGATGATACTGCTGCTTACTACTCGCGCAAAGCGTCTAGCTGGATTCTTGAGGACTCTTGTCCGG
AATACATGTTAAAGTCTGAGGAGTGTTTGAAGAAGGAGAAAGAGAGAGTGGCTAATTATTTACATT
CCAGCAGTGAGCCAAAGCTTCTGGAGAAAGTGCAAAACGAGTTGCTATTGGTTTATGAAAGCCAAT
TGCTTGAGAAGGAGAATTCGGGATGTCGTGCATTACTGAAAGATGACAAGGTGGATGATCTTTCCA
GGATGTACAGGCTTTACAGTAAGGTTACCAAAGGATTGGAACCCATTGGCAGTATCTTCAAACAGC
ATATAACTGATGAAGGAACAGCCTTAGTGCAGCAGGCCGAAGATGCTGCTATCAGCAAGGCTGAAA
ATACTGGTGGTTCACATGAGCAGGTCTTCGTCAGGAAAGTAATAGAGTTGCATGACAAATTCATGA
CTTATGTCACCGATTGCTTCAACAGCCATACCATATTTCACAAGGCTCTTAAGGAGGCTTTTGAGG
TATTTTTGAACAAGGGTGTTGCTGGTAGCTCAAGTGCTGAGTTGCTAGCTACATTCTGTGATAACA
TTCTCAAGAAAGGTGGGAGCGAAAAACTAAGCGATGAGGCTATTGAGGATTCACTTGAGAAGGTGG
TGAAGCTTCTGGCCTATGTCAGTGATAAAGACCTGTTTGCTGAATTTTACAGAAAGAAGCTCTCTC
GCCGGCTACTCTTTGACAAGAGTGCTAATGATGATCATGAAAGAAGTATTTTAACCAAATTGAAGC
AGCAGTGTGGCGGACAATTCACATCAAAGATGGAGGGGATGGTGACAGACTTGACCTTGGCGAGGG
AGAATCAAACTAATTTTGAGGAATATCTTAGTCAGAATCCAGATGCCAGTCCTGGTCTTGATTTGA
CTGTGACTGTTCTGACAACTGGGTTCTGGCCAAGTTACAAATCTTCCGATCTTAACCTTCCCGCTG
AGATGGTGAGGTGTGTTGAAGTTTTTAAGCAGTTCTATTCAACTAAAACAAAGCACAGGAAGCTGA
CCTGGGTTTACTCATTGGGAAGCTGTAATATTAATGGCAAGTTTGGTCCAAAAACTATTGAATTGG
TTGTCGGAACTTATCAGGCTGCTGCTTTGATGCTCTTTAACACATCAGACCGACTGAGTTATTCAG
AGATAGCAACTCAACTAAATTTAGCTGATGAAGATCTGGTTAGAGTGCTTCAATCTTTATCCTGCG
CAAAGTATAAGATTCTTTTAAAGGAGCCAAACACGAAAACCGTGTCCCGACTGATTGTTTTTCAT
TTAACTCTAGTTTCACTGACAGGATGAGGAGGATAAGAATTCCTCTTCCTCCGATGGATGAGAGGA
AAAAGGTTGTTGAGGATGTTGACAAAGATAGAAGATATGCTATTGATGCCTCAATTGTACGCATAA
TGAAAAGTAGGAAGGTTTTGGGGTACCAGCAATTAATCACAGAGTGTGTGGAGCAGCTAAGCCGCA
TGTTCAAGCCTGATTTCAAGGCAATTAAGAAGAGGATCGAGGACTTAATAACCCGAGATTATATTG
AAAGAGACAAGGAGAACCCGCAGCTATTCCGATACTTGGCTTGA
```

Fig. 52

MTMGERKTIDLEQGWEFMQKGITKLKNILEGLPEPQFSSEDYMMLYTT[M]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 53

MTMGERKTIDLEQGWEFMQKGITKLKNILEGLPEPQFSSEDYMMLYTT[M]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLKREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 54

MTMGERKTIDLEQGWEFMQKGITKLKNILEGLPEPQFSSEDYMMLYTT[M]YNMCTQKPPHDYSQQ
LYDKYRESFEEYISSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLRREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DKLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 55

MTMGERKTIDLEQGWEFMQKGITKLKNILEGLPEPQFSSEDYMMLYTT[M]YNMCTQKPPHDYSQQ
LYDKYRESFEEYITSMVLPSLREKHDEFMLRELVKRWTNHKVMVRWLSRFFHYLDRYFIARRSLPP
LNEVGLTCFRELVYKELNSKVRDAVISLIDQEREGEQIDRALLKNVLDIFVEIGMGQMDYYENDFE
AAMLKDTAAYYSRKASNWILEDSCPDYMLKAEECLREKDRVSHYLHSSSEPKLLEKVQHELLSVY
ATQLLEKEHSGCHALLRDDKVEDLSRMFRLFSKIPKGLDPVSNIFKQHVTAEGTALVKQAEDAASN
KKAEKKDIVGLQEQVFVRKVIELHDKYLAYVNDCFQNHTLFHKALKEAFEVFCNKGVAGSSSAELL
ATFCDNILKKGGSEKLSDEAIEETLEKVVKLLAYICDKDLFAEFYRKKLARRLLFDKSANDDHERS
ILTKLKQQCGGQFTSKMEGMVTDLTLARENQTSFEEYLSNNPQASPGIDLTVTVLTTGFWPSYKSF
DLNLPAEMVKCVEVFREFYQTKTKHRKLTWIYSLGTCNISGKFEPKTMELIVTTYQASALLLFNSS
DRLSYSEIMTQLNLSDDDVVRLLHSLSCAKYKILNKEPNTKTISPNDHFEFNAKFSDKMRRIKIPL
PPVDEKKKVIEDVDKDRRYAIDASIVRIMKSRKVLGHQQLVMECVEQLGRMFKPDFKAIKKRIEDL
ITRDYLERDKDNPHLFRYLA

Fig. 56

MNQRSTIDLEHGWDFMQKGITKLKNILEGLPEPQFSSEDYMMLYTT[M]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHSSSETKLLEKVQHELLSVYAN
QLLEKEHSGCHALLRDDKVDDLSRMYRLFSKIPRGLEPVANIFKQHVTAEGTALVKQAEDAASNKK
AEKRDVVGLQEQVFVRKVIELHDKYLAYVNNCFQNHTLFHKALKEAFELFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPTANPGIDLTVTVLTTGFWPSYKSFDL
NLPAEMVRCVEVFKEFYQTKTKHRKLTWIYSLGTCNINGKFEAKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 57

MNQRSTIDLEHGWDFMQRGITKLKNILEGLPEPQFSSEDYMMLYTT[M]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDQVYQELNGKVRDAVISLIDQEREGEQIDRALLKNVLDIFVEIGMGLMDYYENDFEAA
MLKDTAAYYSRKASNWILEDSCPDYMLKAEECLKREKDRVSHYLHSSSETKLLEKVQHELLSVYAT
QLLEKEHSGCHALLRDDKVEDLSRMYRLFSKISRGLDPVANIFKQHVTAEGTALVKQAEDAASNKK
AEKRDVVGLQEQVFVRKVIELHDKYLAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPIANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 58

MNQRSTINLEHGWDFMQRGITKLKNILEGLPEPQFSSEDYMMLYTT[M]YNMCTQKPPHDYSQQLY
DKYREAFEEYITTTVLPSLREKHDEFMLRELVKRWSNHKVMVRWLSRFFHYLDRYFIARRSLPGLN
EVGLTCFRDLVYQELNGKVRDAVISLIDQEREGEQIDRALLKNVLDIFVEIGMGSMDYYENDFEAA
MLKDTAAYYSRKASNWILEDSCPDYMLKAEECLKREKDRVSHYLHLSSETKLLEKVQHELLSVYAT
QLLEKEHSGCHALLRDDKVEDLSRMYRLFSKIPRGLDPVANIFKQHVTAEGTALVKQAEDAASNKK
AEKRDVVGLQEQIFVRKVIELHDKYMAYVNNCFQNHTLFHKALKEAFELFCNKGVAGSSSAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLARENQASFEEYLSNNPAANPGIDLTVTVLTTGFWPSYKSFDL
NLPAEMVRCVEVFKEFYQTKTKHRKLTWIYSLGTCNINGKFEPKTIELVVTTYQASALLLFNASDR
LSYQEIMTQLNLSDDDVVRLLHSLSCAKYKILNKEPSTKTISPTDVFEFNFKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNPNLFKYLA

Fig. 59

MERKTIDLDQGWDYMQTGITKLKRILEGLPEPQFDSEQYMMLYTT[M]YNMCTQKPPHDYSQQLYD
KYREAFEEYIHSTVLPALREKHDEYMLRELVKRWSNHKVMVRWLSRFFYYLDRYFIARRSLPPLNE
VGLTCFRDLVYNELHSKVKDAVIALVDKEREGEQIDRALLKNVLDIYVEIGMGQMERYEEDFESFM
LLDSASYYSRKASSWIQEDSCPDYMLKSEECLKKERERVAHYLHSSSEPKLVEKVQHELLVVYANQ
LLEKEHSGCRALLRDDKVDDLSRMYRLYHKIVKGLEPVANIFKQHVTAEGNALVQQAEDTATNHAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQNSFEEYLGNNPAANPGIDLTVTVLTTGFWPSYKSFDINLPA
EMVKCVEVFKGFYETKTKHRKLTWIYSLGTCHLNGKFDVKPIELVVSTYQAAVLLLFNTTDKLSYT
DILTQLNLSHEDLVRLLHSLSCARYKILLKEPSTKTVSQSDSFEFNSKFTDRMRRIKIPLPPVDER
KKVVEDVDKDRRYAIDAAIVRIMKSRKVLGHQQLVSECVEQLSRMFKPDIKAIKKRMEDLITRDYL
ERDKENANMFRYLA

Fig. 60

MMIERKTIDLEQGWDFMQKGITKLKNILEGFPEPQFSSEDYMMLYTT[M]YNMCTQKPPHDYSQQL
YEKYREAIEEYITSTVLPSLREKHDEFMLRELVKRWSNHKVMVRWLSRFFHYLDRYFIARRSLPPL
HEVGLTCFRDLVYQEINGKVRDAVISLINQEREGEQIDRALLKNVLDIFVEVGMSQMDYYENDFEA
DMLKDTAAYYSRKASNWILEDSCPDYMLKAEECLRREKDRVSNYLHSSSEPKLLEKVQHELLSHYA
TQLLEKEHSGCHALLRDDKVADLSRMYRLFSKIPRGLDPVSNIFKQHVTAEGTALVKQAEDAASNK
KAEKRDVVGLQEQVFVRKIIELHDKYLTYVNDCFTNHTLFHKALKEAFEIFCNKGVSGSSSAELLA
TFCDNILKKGGSEKLSDEAIEETLEKVVRLLAYISDKDLFAEFYRKKLARRLLFDKSANDEHERSI
LTKLKQQCGGQFTSKMEGMVTDLTLAKENQSNFEEYLNNNSNVNPGIDLTVTVLTTGFWPSYKSFD
LNLPAEMVKCVEVFREFYQTKTKHRKLTWIYSLGTCNIIGKFDPKTMELIVTTYQASALLLFNSSD
RLSYNEIMTQLNLSDDDVVRLLHSLSCAKYKILSKEPNTKTISPTDCFQFNSKFTDKMRRIKIPLP
PVDEKKKVIEDVDKDRRYAIDASIVRIMKSRKVLGYQQLVMECVEQLGRMFKPDVKAIKKRIEDLI
TRDYLERDKDNANLFRYLA

Fig. 61

MNERKTIDLDNGWEFMQKGITKLKKILEGQPEPQFSSEDYMMLYTT[M]YNMCTQKPPHDYSQQLY
DKYREAFEEYITSTVLPSLREKHDEFMLRELVNRWTNHKVMVRWLSRFFHYLDRYFIARRSLPALH
EVGLTCFRDLVYQELKVKVRDAVISLIDQEREGEQIDRALLKNVLDIFVEIGMSQMDYENDFEEA
MLTDTAAYYSRKASNWILEDSCPDYMLKAEECLRREKDRVSHYLHFSSEPKLLEKVQHELLSVYAT
QLLEKEHSGCHALLRDDKVDDLSRMYRLFSKIPKGLDPVSYIFKQHVTNEGMALVKQAEDAASNKK
AEKRDVVSLQEQVFVRKIIELHDKYLAYVNDCFTNHTLFHKALKEAFEIFCNKGVAGSSNAELLAT
FCDNILKKGGSEKLSDEAIEETLEKVVKLLAYISDKDLFAEFYRKKLARRLLFDKSANDEHERSIL
TKLKQQCGGQFTSKMEGMVTDLTLAKENQSSFEEYLGNNANVNPGIDLTVTVLTTGFWPSYKSFDL
NLPAEMVKCVEVFREFYQTKTKHRKLTWIYSLGTCNINGKFEPKTIELIVTTYQASALLLFNTSDR
LSYQEIMTQLNLSDDDVVRLLHSLSCAKYKILTKEPNNKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKDNANLFRYLA

Fig. 62

MNERKTIDLEQGWDFMQKGITKLKNILEGLPEPQFSSEDYMMLYTT[M]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 63

MNERKTIDLEQGWDFMQKGITKLKNILEGLPEPQFSSEDYMMLYTT[M]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQTELLSVYAT
QLLEKEHSGCHALLRDDKVDDLSRMYRLFSKIQKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNSSDR
LSYQEIMTQLNLSDDDVVRLLHSLSCAKYKILLKEPNTKTISPTDFFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 64

MSLHERKTIDLEQGWAFMQKGITKLKNILDELNEPQFSSEDYMMLYTT[M]YNMCTQKPPHDYSQE
LYDKYRESFEEYITTTVLPSLREKHDEYMLRELVRRWSNHKIMVRWLSRFFHYLDRYFIARRSLPA
LNEVGLTCFRDLVYNEVHGKVKDAVISLIDQEREGEQIDRALLKNVLGIFVEIGLGSMECYENDFE
TSMLNATAAYYSRKASNWILEDSCPDYMLKAEECLKHEKDRVAHYLHSSSEQKLLEKVQHELLFVY
ASQLLEKEHSGCHALLRDDKVGDLSRMYRLFCRITRGLDPVSQIFKQHVTAEGTALVKHAEDAASN
KKAEKKDIVGLQEQVFVRKVIELHDKYLAYVTDCFQNHSLFHKALKEAFEVFCNKGVAGSSSAELL
AAFCDNILKKGGSEKLSDEAIEDTLEKVVKLLAYISDKDLFAEFYRKKLARRLLFDKSANDDHERS
ILTKLKQQCGGQFTSKMEGMVTDLTLARENQSSFDDYLSSNPKANSGIDLTVTVLTTGFWPSYKSF
DLNLPDEMVKCVEIFKEFYETKTKHRKLTWIYSLGTCNINGKFETKTIELVVTTYQAAVLLLFNSA
DKLSYSEIVQQLNLSDDDVIRLLHSLSCAKYKILNKEPATKTITPNDHFEFNSKFTDRMRRIKIPL
PPVDEKKKVIEDVDKDRRYAIDASIVRIMKSRKVLGHQQLVLECVEQLGRMFKPDFKAIKKRIEDL
IARDYLERDKDNPNLFKYLA

Fig. 65

MNERKTIDLEQGWDFMQKGITKLKNILEGLPEPQFSSEDYMMLYTT[M]YNMCTQKPPHDYSQQLY
DKYRESFEEYITSTVLPSLREKHDEFMLRELVRRWSNHKVMVRWLSRFFHYLDRYFIARRSLPPLN
EVGLACFRDLVYQEVNGKVRDAVISLIDQEREGEQIDRALLKNVLDIFVEIGMGQMEYYENDFEAS
MLNDTAAYYSRKASNWILEDSCPDYMLKAEECLKREKDRVSHYLHSSSEPKLLEKVQNELLSVYAT
QLLEKEHSGCHALLRDDKVDDLSRMYRLFSKIPKGLDPVSSMFKQHVTAEGTTLVKQAEDAASTKK
AEKRDVVGLQEQVFVRKVIELHDKYLAYVNDCFMNHTLFHKALKEAFEIFCNKGVAGSSSAELLAT
FCDNILKKGGSEKLSDEAIEDTLEKVVKLLAYISDKDLFAEFYRKKLARRLLFDKSANDEHERSIL
TKLKQQCGGQFTSKMEGMVTDLTLAKENQSHFEEYLNNNPNVSPGIDLTVTVLTTGFWPSYKSFDL
NLPAEMVKCVEVFREFYQTKTKHRKLTWIYSLGTCNINGKFEPKTMELIVTTYQASALLLFNLSDR
LSYQEIMTQLNLSDDDVVRLLHSLSCAKYKILLKEPNTKTISPTDYFEFNSKFTDKMRRIKIPLPP
VDEKKKVIEDVDKDRRYAIDASIVRIMKSRKVLGYQQLVMECVEQLGRMFKPDVKAIKKRIEDLIT
RDYLERDKENPNLFRYLA

Fig. 66

MERKTIDLEQGWDYMQTGITKLKRILEGLPEPQFDSEQYMMLYTT[M]YNMCTQKPPHDYSQQLYD
KYREAFEEYIDSTVLPALKEKHDEYMLRELVKRWSNHKVMVRWLSRFFYYLDRYFIARRSLPPLNE
VGLTCFRDRVYKELHSKVKDAVIALVDKEREGEQIDRALLKNVLDIYVEIGMGQMERYEVDFESFM
LLDSASYYSRKASNWIQEDSCPDYMLKSEECLKKERERVAHYLHSSSEPKLVEKVQHELLVVYANQ
LLEKEHSGCRALLRDDKVDDLSRMYRLYHKIAKGLEPVANIFKQHVTAEGNALVQQAEDTATNQAA
NTASVQEQVLIRKVIELHDKYMVYVVECFQNHTLFHKALKEAFEIFCNKTVAGSSSAELLATFCDN
ILKKGGSEKLSDEAIEDTLEKVVKLLAYISDKDLFAEFYRKKLARRLLFDRSANDDHERSILTKLK
QQCGGQFTSKMEGMVTDLTLARENQTSFEEYLGNNPAANPGIDLTVTVLTTGFWPSYKSFDINLPS
EMVKCVEVFKGFYETKTKHRKLTWIYSLGTCHLNGKFDHKPIELVVSTYQAAVLLLFNTTDKLSYN
DILTQLNLSHEDLVRLLHSLSCARYKILLKEPSTKTVTQTDSFEFNAKFTDRMRRIKIPLPPVDER
KKVVEDVDKDRRYAIDAAIVRIMKSRKVLGHQQLVSECVEQLSRMFKPDIKAIKKRMEDLITRDYL
ERDKENPNMFRYLA

Fig. 67

MNDRKVIELEQGWEFMGKGITKLKRILEGLPEPPFNSEDYMMLYTT[M]YNMCTQKPPHDYSQQLY
DNYKEAFVDYIHSTVLPSLGDKHDEFMLRELVKRWSNHKVMVRWLSRFFHYLDRYFIARRSLPSLN
DVGLTCFRDLVYQEISGKAKDAVIALIDEEREGGQIDRALLKNVLDIYVEIGMTQMDYYEKDFEAH
MLDDTAAYYSRKASSWILEDSCPEYMLKSEECLKKEKDRVAHYLHSSSEPKLLEKVQNELLLVYEN
QLLEKENSGCRALLKDDKVEDLSRMYRLYSKVTKGLEPIGSIFKQHITDEGTALVQQAEDAAISKA
ENAGGGSHEQVFVRKVIELHDKFMTYVTDCFNSHTIFHKALKEAFEVFLNKGVAGSSSAELLASFC
DNILKKGGSEKLSDEAIEDSLEKVVKLLAYVSDKDLFAEFYRKKLSRRLLFDKSANDDHERSILTK
LKQQCGGQFTSKMEGMVTDLTLARENQTNFEEYLGQNTDASPGLDLTVTVLTTGFWPSYKSSDLNL
PAEMVRCVEVFKQFYQTKTKHRKLTWVYSLGSCNINGKFGPKTIELVVGTYQAAALMLFNTSDRLS
YSEITTQLNLADEDLVRVLQSLSCAKYKILLKEPSTRNVISTDCFSFNSNFTDRMRRIRIPLPPMD
ERKKVVEDVDKDRRYAIDASIVRIMKSRKALGYQQLITECVEQLSRMFKPDFKAIKKRIEDLITRD
YIERDKENPQLFRYLA

Fig. 68

MNDRKVIELEQGWEFMGKGITKLKRILEGLPEPPFNSEDYMMLYTT[M]YNMCTQKPPHDYSQQLY
DNYKQAFVDYINSTVLPSLREKHDEFMLRELVKRWANHKVMVRWLSRFFHYLDRYFIARRSLPSLN
EVGLTCFRDLVYQEISGKAKDAVIALIDIEREGGQIDRSLLKNVLDIYVEIGMGQMDHYEKDFEAH
MLDDTAAYYSRKASSWILEDSCPEYMLKSEECLKKEKERVANYLHSSSEPKLLEKVQNELLLVYES
QLLEKENSGCRALLKDDKVDDLSRMYRLYSKVTKGLEPIGSIFKQHITDEGTALVQQAEDAAISKA
ENTGGSHEQVFVRKVIELHDKFMTYVTDCFNSHTIFHKALKEAFEVFLNKGVAGSSSAELLATFCD
NILKKGGSEKLSDEAIEDSLEKVVKLLAYVSDKDLFAEFYRKKLSRRLLFDKSANDDHERSILTKL
KQQCGGQFTSKMEGMVTDLTLARENQTNFEEYLSQNPDASPGLDLTVTVLTTGFWPSYKSSDLNLP
AEMVRCVEVFKQFYSTKTKHRKLTWVYSLGSCNINGKFGPKTIELVVGTYQAAALMLFNTSDRLSY
SEIATQLNLADEDLVRVLQSLSCAKYKILLKEPNTKTVSPTDCFSFNSSFTDRMRRIRIPLPPMDE
RKKVVEDVDKDRRYAIDASIVRIMKSRKVLGYQQLITECVEQLSRMFKPDFKAIKKRIEDLITRDY
IERDKENPQLFRYLA

Fig. 69A

| | |
|---|---|
| Brassica_Cul1_Cds | -------ATGGAGCGCAAGACGATTGACTTGGACCAAGGATGGGACTATATGCAGACT |
| Radish_Cul1_Cds | -------ATGGAGCGGAAGACGATTGATCTGGAACAAGGATGGGACTATATGCAGACT |
| Beet_Cul1_Cds | ----ATGAATGATCGTAAAGTTATTGAACTAGAGCAAGGATGGGAGTTCATGGGGAAG |
| Spinach_Cul1_Cds | ----ATGAACGATCGTAAAGTTATCGAACTAGAGCAAGGATGGGAGTTCATGGGGAAG |
| Leek_Cul1_Cds | ATGTCGTTGCACGAAAGGAAAACCATTGATTTGGAGCAGGGATGGCTTTTATGCAGAAA |
| Squash_Cul1_Cds | ATGACAATGGGTGAGCGGAAGACTATTGACTTGGAGCAAGGATGGGAGTTTATGCAGAAG |
| WaterMelon_Cul1_Cds | ATGACAATGGGCGAGCGGAAGACTATTGACTTGGAACAAGGATGGGAGTTTATGCAGAAG |
| Cucumber_Cul1_Cds | ATGACAATGGGCGAGCGGAAGACTATTGACTTGGAGCAGGGATGGGAGTTTATGCAGAAG |
| Melon_Cul1_Cds | ATGACAATGGGCGAGCGGAAGACTATTGACTTGGAACAGGGATGGGAGTTTATGCAGAAG |
| Tomato_Cul1_Cds | ----ATGAACCAACGAAGCACAATCGATCTGGAACATGGATGGGACTTCATGCAAAGG |
| Eggplant_Cul1_Cds | ----ATGAACCAACGCAGCACAATCGATCTGGAACATGGATGGGATTTCATGCAAAAG |
| Pepper_Cul1_Cds | ----ATGAACCAGCGTTCCACAATCAATCTAGAACATGGATGGGACTTCATGCAAAGG |
| Lettuce_Cul1_Cds | ----ATGAACGAAAGAAAAACAATAGACTTAGAGCAAGGATGGGACTTCATGCAGAAA |
| Chicory_Cul1_Cds | ----ATGAATGAAAGAAAAACAATAGACTTAGAACAAGGATGGGACTTCATGCAGAAA |
| Endive_Cul1_Cds | ----ATGAATGAAAGAAAAACAATAGACTTAGAACAAGGATGGGACTTCATGCAAAAA |
| Carrot_Cul1_Cds | -ATGATGATTGAGCGGAAAACTATAGACCTGGAGCAGGGATGGGACTTTATGCAAAAG |
| Celery_Cul1_Cds | ----ATGAACGAGCGGAAGACTATCGATTTGGATAATGGATGGGAATTTATGCAGAAA |
| | |
| Brassica_Cul1_Cds | GGTATCACTAAGCTGAAACGGATTCTTGAGGGGCTGCCTGAGCCGCAGTTTGACTCTGAG |
| Radish_Cul1_Cds | GGGATCACTAAGCTGAAACGGATTCTTGAAGGATTGCCTGAGCCGCAATTCGACTCTGAG |
| Beet_Cul1_Cds | GGGATTACAAAGTTGAAGAGGATTCTGGAAGGATTGCCAGAGCCCACCATTTAATTCTGAA |
| Spinach_Cul1_Cds | GGGATTACGAAGTTGAAAAGGATTTTGGAAGGATTACCAGAGCCGCCTTTTAATTCGGAA |
| Leek_Cul1_Cds | GGGATCACCAAACTGAAGAATATTCTTGATGAGTTGAATGAACCTCAGTTCAGCTCAGAG |
| Squash_Cul1_Cds | GGAATCACAAAATTGAAGAACATTCTGGAAGGATTGCCTGAGCCACAGTTCAGCTCCGAG |
| WaterMelon_Cul1_Cds | GGAATCACAAAGTTGAAGAACATTCTTGAGGGCTTGCCTGAGCCTCAGTTCAGCTCCGAG |
| CuCumber_Cul1_Cds | GGTATCACAAAGTTGAAGAACATTCTCGAGGGCTTGCCTGAGCCTCAGTTCAGCTCCGAG |
| Melon_Cul1_Cds | GGTATCACAAAGTTGAAGAACATTCTTGAGGGCTTGCCTGAGCCCCAGTTCAGCTCCGAG |
| Tomato_Cul1_Cds | GGCATTACAAAGCTGAAGAACATTCTAGAAGGGCTGCCTGAGCCTCAATTCAGCTCAGAG |
| Eggplant_Cul1_Cds | GGCATCACAAAGCTGAAGAACATTCTAGAAGGGCTGCCTGAGCCTCAGTTCAGCTCAGAG |
| Pepper_Cul1_Cds | GGCATTACAAAGCTGAAGAACATTCTAGAAGGGCTGCCCGAGCCTCAGTTCAGCTCAGAG |
| Lettuce_Cul1_Cds | GGAATAACAAAGTTGAAGAATATTCTAGAAGGTCTTCCCGAGCCACAATTCAGCTCGGAG |
| Chicory_Cul1_Cds | GGCATAACAAAGTTGAAGAACATTCTAGAAGGTCTTCCCGAGCCACAATTCAGCTCGGAA |
| Endive_Cul1_Cds | GGCATAACAAAGTTGAAGAACATTCTAGAAGGTCTTCCCGAGCCACAATTCAGCTCAGAG |
| Carrot_Cul1_Cds | GGAATCACAAAGCTAAAGAATATTTTAGAAGGCTTTCCGGAGCCGCAATTCAGCTCGGAG |
| Celery_Cul1_Cds | GGGATCACTAAGTTGAAGAAGATTCTCGAAGGTCAACCTGAGCCTCAGTTTAGCTCCGAG |

Fig. 69B

```
Brassica_Cul1_Cds      CAATACATGATGCTCTATACGACTAT [C] TACAACATGTGCACTCAGAAACCTCCTCATGAT
Radish_Cul1_Cds        CAGTACATGATGCTTTATACGACTAT [C] TACAACATGTGCACCCAGAAACCTCCTCATGAT
Beet_Cul1_Cds          GACTACATGATGTTGTACACGACGAT [A] TACAATATGTGTACTCAGAAACCCCCACATGAT
Spinach_Cul1_Cds       GACTACATGATGCTGTACACGACAAT [A] TACAACATGTGTACACAGAAACCCCCTCATGAT
Leek_Cul1_Cds          GATTACATGATGCTCTATACGACTAT [C] TATAATATGTGTACTCAGAAGCCGCCACATGAT
Squash_Cul1_Cds        GACTACATGATGCTTTACACTACAAT [A] TATAACATGTGTACCCAGAAGCCACCGCATGAT
WaterMelon_Cul1_Cds    GACTACATGATGCTTTATACCACCAT [A] TACAACATGTGCACACAAAAGCCGCCACATGAT
CuCumber_Cul1_Cds      GACTACATGATGCTTTACACTACCAT [A] TATAACATGTGCACCCAAAAGCCGCCGCATGAT
Melon_Cul1_Cds         GACTACATGATGCTTTACACTACCAT [A] TATAACATGTGCACCCAAAAGCCGCCGCATGAT
Tomato_Cul1_Cds        GACTATATGATGCTATATACGACAAT [T] TACAACATGTGTACTCAAAAGCCCCCACATGAT
Eggplant_Cul1_Cds      GACTATATGATGCTGTATACGACAAT [T] TACAACATGTGTACTCAGAAGCCCCCACATGAT
Pepper_Cul1_Cds        GACTATATGATGCTGTATACGACAAT [T] TACAACATGTGTACTCAGAAGCCCCCACATGAT
Lettuce_Cul1_Cds       GATTACATGATGCTCTACACAACCAT [C] TACAACATGTGTACACAGAAACCACCACATGAT
Chicory_Cul1_Cds       GATTACATGATGCTCTACACAACCAT [C] TACAATATGTGCACACAAAAACCGCCACATGAT
Endive_Cul1_Cds        GATTACATGATGCTCTACACAACCAT [C] TACAATATGTGCACACAAAAACCGCCACATGAT
Carrot_Cul1_Cds        GATTATATGATGCTTTATACAACTAT [C] TATAACATGTGTACACAGAAACCTCCACATGAT
Celery_Cul1_Cds        GACTATATGATGCTTTACACAACTAT [C] TATAATATGTGTACGCAGAAGCCTCCACATGAT Brassica_Cul1_Cds         TACTCACAGCAGCTTTATGACAAGTATCGTGAAGCATTTGAGGAGTATATTCACTCAACT
Radish_Cul1_Cds           TACTCTCAGCAGCTTTATGACAAGTATCGCGAAGCTTTTGAGGAGTACATTGACTCTACT
Beet_Cul1_Cds             TACTCTCAACAGCTCTATGACAATTACAAACAGGCTTTTGTGGATTACATCAACTCGACG
Spinach_Cul1_Cds          TACTCTCAACAACTCTATGACAATTACAAAGAGGCATTTGTGGATTACATACATTCAACG
Leek_Cul1_Cds             TATTCTCAGGAGTTGTATGATAAGTACCGAGAGTCCTTTGAAGAGTATATCACTACCACT
Squash_Cul1_Cds           TACTCCCAGCAGCTGTATGATAAATACCGCGAATCGTTTGAGGAGTACATCAGTTCTATG
WaterMelon_Cul1_Cds       TACTCCCAGCAGCTATACGATAAATACCGTGAATCTTTTGAGGAGTATATCACTTCTATG
CuCumber_Cul1_Cds         TACTCCCAGCAGCTGTATGATAAATATCGTGAATCTTTTGAAGAGTACATCACTTCTATG
Melon_Cul1_Cds            TACTCCCAGCAGCTGTATGATAAATATCGTGAATCTTTTGAAGAGTACATCACTTCTATG
Tomato_Cul1_Cds           TATTCTCAACAGCTGTATGACAAATATCGTGAAGCTTTTGAAGAATATATCACAACAACG
Eggplant_Cul1_Cds         TATTCTCAACAGCTGTATGACAAATATCGTGAAGCTTTTGAAGAATATATCACAACGACG
Pepper_Cul1_Cds           TATTCTCAACAGCTGTATGACAAATATCGTGAAGCTTTTGAAGAATATATCACAACAACG
Lettuce_Cul1_Cds          TACTCCCAACAGTTGTATGACAAATATCGTGAGTCTTTTGAAGAGTATATTACTTCAACT
Chicory_Cul1_Cds          TACTCTCAACAATTGTATGACAAATACCGCGAGTCTTTTGAAGAGTACATTACTTCAACG
Endive_Cul1_Cds           TACTCTCAACAATTATATGACAAATACCGCGAGTCTTTTGAAGAGTACATAACTTCAACG
Carrot_Cul1_Cds           TACTCTCAGCAGCTGTATGAAAAGTATCGTGAAGCTATTGAGGAGTACATTACTTCTACA
Celery_Cul1_Cds           TATTCTCAACAGCTGTATGACAAGTACCGTGAGGCCTTTGAGGAGTACATAACTTCAACT
```

Fig. 69C

| | |
|---|---|
| Brassica_Cul1_Cds | GTTTTGCCTGCTCTAAGGGAGAAGCATGATGAGTACATGCTGAGGGAGCTGGTTAAGAGA |
| Radish_Cul1_Cds | GTTTTGCCTGCTTTGAAGGAGAAGCATGATGAATACATGCTACGGGAGCTGGTTAAGAGA |
| Beet_Cul1_Cds | GTTTTACCTTCTTTGCGGGAGAAGCATGATGAGTTTATGTTAAGAGAACTTGTGAAAAGA |
| Spinach_Cul1_Cds | GTTTTACCTTCTTTGGGGGACAAACATGATGAGTTTATGCTGAGAGAGCTTGTGAAGAGA |
| Leek_Cul1_Cds | GTGCTTCCTTCATTGAGAGAAAAGCATGATGAATACATGTTAAGGGAGCTCGTGAGAAGG |
| Squash_Cul1_Cds | GTTTTACCATCCTTGAGGGAGAAGCATGACGAATTTATGTTGAGAGAACTGGTCAAAAGG |
| WaterMelon_Cul1_Cds | GTCTTACCATCCTTGAGGGAGAAGCATGACGAGTTCATGTTGAGAGAACTGGTCAAAAGG |
| CuCumber_Cul1_Cds | GTCTTACCATCCTTGAGGGAGAAGCACGATGAGTTCATGTTGAGAGAACTAGTAAAAAGG |
| Melon_Cul1_Cds | GTCTTACCATCCTTGAGGGAGAAGCATGACGAGTTCATGTTGAGAGAACTAGTCAAAAGG |
| Tomato_Cul1_Cds | GTATTGCCTTCTTTGAGAGAAAAACATGACGAGTTTATGTTGCGAGAGTTGGTAAAAAGG |
| Eggplant_Cul1_Cds | GTATTACCTTCTTTGAGAGAAAAACATGACGAGTTCATGTTGCGAGAGTTGGTAAAAAGG |
| Pepper_Cul1_Cds | GTATTGCCTTCTTTGAGAGAAAAACATGACGAGTTCATGTTGCGAGAGCTGGTAAAAAGG |
| Lettuce_Cul1_Cds | GTGTTACCTTCTTTAAGAGAGAAGCATGATGAGTTCATGCTGAGAGAGCTTGTTAGAAGG |
| Chicory_Cul1_Cds | GTGTTACCTTCTTTAAGAGAAGCATGATGAGTTTATGCTTAGAGAGCTTGTTAGAAGA |
| Endive_Cul1_Cds | GTGTTACCTTCTTTAAGAGAAGCATGATGAGTTTATGCTTAGAGAGCTTGTTAGAAGG |
| Carrot_Cul1_Cds | GTATTGCCTTCATTGAGAGAGAAGCATGATGAATTCATGCTTAGAGAACTTGTGAAGAGA |
| Celery_Cul1_Cds | GTCCTGCCTTCTTTACGAGAGAAGCATGATGAGTTTATGTTGAGAGAGCTCGTGAATAGA |

| | |
|---|---|
| Brassica_Cul1_Cds | TGGTCTAACCATAAAGTTATGGTTCGATGGCTATCCCGCTTCTTCTACTATCTTGACCGT |
| Radish_Cul1_Cds | TGGTCTAACCATAAAGTTATGGTTAGATGGCTATCCCGATTCTTCTACTATCTTGACCGT |
| Beet_Cul1_Cds | TGGGCAAATCATAAAGTAATGGTCAGGTGGTTGTCTCGTTTCTTCCATTATCTGGACCGG |
| Spinach_Cul1_Cds | TGGTCAAATCATAAAGTAATGGTGAGGTGGTTGTCTCGCTTCTTCCATTATCTGGATCGG |
| Leek_Cul1_Cds | TGGTCAAATCATAAAATAATGGTTAGATGGCTTTCACGCTTTTTCCATTATCTTGATCGC |
| Squash_Cul1_Cds | TGGACCAACCATAAAGTCATGGTGAGGTGGCTTTCTCGCTTCTTCCACTATCTTGATCGA |
| WaterMelon_Cul1_Cds | TGGACGAACCATAAAGTCATGGTGAGGTGGCTTTCTCGCTTCTTCCACTATCTTGACCGA |
| CuCumber_Cul1_Cds | TGGACAAACCATAAAGTCATGGTGAGGTGGCTTTCTCGCTTCTTCCACTATCTTGATCGG |
| Melon_Cul1_Cds | TGGACAAACCATAAAGTCATGGTGAGGTGGCTTTCTCGCTTCTTCCACTATCTTGATCGG |
| Tomato_Cul1_Cds | TGGTCAAATCATAAAGTCATGGTCAGATGGTTGTCAAGATTCTTCCATTACCTTGACCGG |
| Eggplant_Cul1_Cds | TGGTCAAACCATAAGGTCATGGTTAGATGGTTATCGCGATTCTTCCATTATCTTGACCGT |
| Pepper_Cul1_Cds | TGGTCAAACCATAAGGTCATGGTCAGATGGTTATCGCGATTCTTCCATTATCTTGATCGC |
| Lettuce_Cul1_Cds | TGGTCAAATCATAAAGTCATGGTGCGGTGGCTTTCTAGATTCTTCCATTATCTTGACCGA |
| Chicory_Cul1_Cds | TGGTCAAATCATAAAGTGATGGTTAGGTGGCTTTCTAGATTCTTCCATTATCTTGATCGA |
| Endive_Cul1_Cds | TGGTCAAATCATAAAGTGATGGTTAGGTGGCTTTCTAGATTCTTCCATTATCTTGATCGA |
| Carrot_Cul1_Cds | TGGTCTAATCATAAGGTCATGGTCAGGTGGCTTTCTCGATTCTTTCACTATCTTGATCGC |
| Celery_Cul1_Cds | TGGACAAACCATAAAGTCATGGTCAGGTGGCTTTCTCGATTCTTTCACTATCTTGATCGG |

Fig. 69D

```
Brassica_Cul1_Cds      TACTTCATTGCTCGGAGGTCACTTCCACCCCTGAATGAAGTTGGCCTGACTTGCTTCCGT
Radish_Cul1_Cds        TACTTCATTGCTCGGAGATCGCTGCCACCGCTTAATGAAGTTGGGCTCACATGCTTCCGT
Beet_Cul1_Cds          TATTTCATTGCTCGGAGGTCGCTTCCTTCTTTGAATGAAGTTGGACTGACTTGTTTCCGT
Spinach_Cul1_Cds       TACTTCATCGCTCGGAGATCGCTTCCTTCTTTGAATGATGTTGGATTGACGTGCTTCCGT
Leek_Cul1_Cds          TACTTTATAGCACGAAGATCATTGCCTGCTCTTAATGAAGTCGGTCTCACTTGTTTCCGT
Squash_Cul1_Cds        TACTTCATTGCTCGAAGGTCACTTCCACCTCTCAATGAAGTTGGCCTCACTTGCTTCCGT
WaterMelon_Cul1_Cds    TACTTCATTGCTCGAAGATCACTTCCACCTCTCAACGAAGTTGGCCTCACATGCTTCCGT
CuCumber_Cul1_Cds      TACTTCATCGCTCGAAGGTCACTTCCACCTCTAAATGAAGTTGGCCTCACATGCTTCCGC
Melon_Cul1_Cds         TACTTCATCGCTCGAAGGTCACTTCCACCTCTAAATGAAGTTGGCCTCACATGCTTCCGC
Tomato_Cul1_Cds        TATTTCATTGCCCGGAGATCTCTGCCGGGGCTTAATGAAGTTGGACTAACTTGCTTCCGC
Eggplant_Cul1_Cds      TATTTCATTGCTCGGAGATCACTGCCAGGGCTTAATGAAGTTGGACTAACTTGCTTCCGC
Pepper_Cul1_Cds        TATTTCATTGCCCGGAGATCTCTACCGGGGCTTAATGAAGTTGGACTAACTTGCTTCCGA
Lettuce_Cul1_Cds       TATTTCATTGCCCGAAGATCTCTTCCGCCACTAAATGAAGTTGGACTTGCCTGTTTTCGT
Chicory_Cul1_Cds       TACTTCATTGCCCGAAGATCTCTTCCACCATTAAATGAAGTTGGACTTGCGTGTTTTCGT
Endive_Cul1_Cds        TACTTTATTGCAAGAAGATCTCTTCCACCATTAAATGAAGTTGGACTTGCGTGTTTTCGT
Carrot_Cul1_Cds        TATTTTATTGCTCGGAGGTCACTTCCACCACTTCATGAAGTGGACTCACTTGCTTTCGG
Celery_Cul1_Cds        TACTTCATTGCGAGGAGGTCACTTCCTGCACTTCATGAAGTTGGACTCACGTGCTTCCGG Brassica_Cul1_Cds      GACCTGGTTTATAACGAGTTGCATTCCAAGGTCAAAGATGCTGTAATAGCACTTGTTGAT
Radish_Cul1_Cds        GACCGGGTGTATAAGGAGTTGCATTCCAAGGTCAAAGATGCTGTAATAGCACTTGTTGAT
Beet_Cul1_Cds          GATCTGGTTTATCAAGAAATATCTGGCAAAGCCAAGGATGCTGTTATAGCCCTGATTGAT
Spinach_Cul1_Cds       GATCTGGTTTATCAAGAAATATCTGGCAAAGCCAAGGATGCTGTTATTGCTCTGATTGAT
Leek_Cul1_Cds          GATCTGGTGTACAACGAAGTCCATGGGAAAGTTAAAGATGCCGTGATCTCATTGATTGAC
Squash_Cul1_Cds        GAATTGGTGTACAAAGAGCTAAACAGTAAAGTGAGGGATGCAGTAATTTCATTGATCGAT
WaterMelon_Cul1_Cds    GAATTGGTGTACAAAGAGCTAAACAGTAAAGTGAGGGATGCAGTAATTTCATTGATTGAT
CuCumber_Cul1_Cds      GAATTGGTGTACAAAGAGCTAAATAGTAAAGTGAGGGATGCAGTAATTTCATTGATTGAT
Melon_Cul1_Cds         GAATTGGTGTACAAAGAGCTAAACAGTAAAGTGAGGGATGCAGTAATCTCATTGATTGAT
Tomato_Cul1_Cds        GATCAGGTCTACCAAGAGTTGAATGGAAAGTCAGGGATGCTGTTATATCTCTGATTGAT
Eggplant_Cul1_Cds      GATCTGGTCTACCAAGAGTTGAATGGAAAGTCAGGGATGCTGTTATATCTCTGATTGAT
Pepper_Cul1_Cds        GATCTGGTCTACCAAGAGTTGAATGGAAAGTCAGGGATGCTGTTATATCTCTGATTGAT
Lettuce_Cul1_Cds       GATCTGGTATACCAAGAGGTGAATGGTAAAGTGAGAGATGCTGTAATATCTTTGATTGAT
Chicory_Cul1_Cds       GATCTGGTATACCAAGAGGTGAATGGGAAAGTGAGAGATGCTGTAATATCTTTGATTGAT
Endive_Cul1_Cds        GATCTGGTATACCAAGAGGTGAATGGAAAAGTGAGAGATGCTGTAATATCTTTGATTGAT
Carrot_Cul1_Cds        GACCTGGTTTACCAGGAGATAAATGGGAAAGTAAGGGATGCTGTAATATCATTGATTAAT
Celery_Cul1_Cds        GATCTGGTCTATCAGGAGCTGAAAGTTAAAGTGAGGGATGCTGTAATATCTCTGATCGAT
```

Fig. 69E

```
Brassica_Cul1_Cds      AAAGAACGGGAGGGTGAGCAGATTGACAGGGCTCTATTGAAAAACGTATTAGACATTTAT
Radish_Cul1_Cds        AAAGAACGGGAAGGCGAGCAGATTGACAGGGCTCTTCTGAAAAACGTATTAGATATCTAT
Beet_Cul1_Cds          ATAGAAAGAGAAGGTGGGCAGATTGACAGATCATTATTGAAAAATGTACTTGATATATAT
Spinach_Cul1_Cds       GAAGAAAGAGAGGGTGGGCAAATTGACAGAGCCTTATTGAAGAATGTACTTGATATATAC
Leek_Cul1_Cds          CAAGAGAGGGAAGGGGAGCAAATTGACAGAGCTTTATTAAAGAATGTTTTGGGTATTTTT
Squash_Cul1_Cds        CAAGAACGTGAAGGAGAGCAGATTGACAGAGCTCTGTTGAAGAACGTGTTGGATATATTT
WaterMelon_Cul1_Cds    CAAGAACGTGAAGGAGAGCAGATTGACAGAGCTCTACTGAAGAATGTATTAGATATATTT
CuCumber_Cul1_Cds      CAAGAACGTGAAGGAGAACAGATTGACAGAGCTCTACTGAAGAATGTACTAGATATATTT
Melon_Cul1_Cds         CAAGAACGTGAAGGAGAACAGATTGACAGAGCTCTACTGAAGAATGTATTAGATATATTT
Tomato_Cul1_Cds        CAAGAGCGTGAGGGAGAGCAAATTGACAGAGCTCTACTTAAGAATGTGCTTGATATATTT
Eggplant_Cul1_Cds      CAAGAGCGTGAGGGAGAGCAAATTGACAGAGCTCTACTGAAGAATGTGCTAGATATATTT
Pepper_Cul1_Cds        CAAGAGCGTGAGGGAGAGCAAATTGACAGAGCTCTACTGAAGAATGTGCTAGATATATTT
Lettuce_Cul1_Cds       CAAGAGCGTGAAGGGAGCAGATTGATCGAGCTTTACTGAAGAATGTTCTAGATATATTT
Chicory_Cul1_Cds       CAAGAGCGTGAAGGCGAGCAAATTGACCGAGCATTACTCAAGAATGTTCTAGATATATTT
Endive_Cul1_Cds        CAAGAGCGTGAAGGCGAGCAAATTGACCGAGCATTACTGAAGAATGTTCTAGATATATTT
Carrot_Cul1_Cds        CAAGAGCGCGAGGGAGAGCAAATTGACCGAGCTTTGTTGAAGAATGTTCTAGATATATTT
Celery_Cul1_Cds        CAAGAGCGTGAGGGGAACAGATTGACCGAGCTTTATTAAAGAACGTGTTAGATATATTT Brassica_Cul1_Cds      GTAGAGATTGGAATGGGACAGATGGAAAGATACGAGGAGGATTTTGAAAGCTTCATGCTT
Radish_Cul1_Cds        GTAGAGATTGGAATGGGACAGATGGAAAGATACGAAGTGGATTTTGAAAGCTTCATGCTT
Beet_Cul1_Cds          GTTGAAATTGGAATGGGACAAATGGATCACTATGAAAAAGACTTTGAAGCTCATATGCTG
Spinach_Cul1_Cds       GTTGAAATTGGAATGACACAAATGGATTACTACGAAAAGGACTTTGAAGCTCATATGCTG
Leek_Cul1_Cds          GTAGAGATTGGTTTGGGAAGCATGGAATGTTATGAGAATGATTTTGAAACATCAATGCTT
Squash_Cul1_Cds        GTGGAGATTGGGATGGGCAAATGGATTATTATGAAAATGACTTTGAAGCTGCCATGCTT
WaterMelon_Cul1_Cds    GTGGAAATTGGGATGGGCAAATGGATTACTATGAAAATGACTTTGAAGCTGCCATGCTT
CuCumber_Cul1_Cds      GTGGAAATTGGTATGGGCAAATGGATTACTATGAAAATGACTTTGAAGCTGCCATGCTT
Melon_Cul1_Cds         GTGGAAATTGGTATGGGCAAATGGATTACTATGAAAATGACTTTGAAGCTGCCATGCTT
Tomato_Cul1_Cds        GTCGAAATTGGAATGGGGTTAATGGATTATTATGAGAATGATTTTGAAGCTGCAATGCTC
Eggplant_Cul1_Cds      GTTGAAATTGGAATGGGGTCAATGGATTATTATGAGAATGATTTTGAAGCTGCAATGCTC
Pepper_Cul1_Cds        GTTGAAATTGGAATGGGGTCGATGGATTATTATGAGAATGATTTTGAAGCTGCAATGCTC
Lettuce_Cul1_Cds       GTTGAGATAGGAATGGGACAAATGGAGTATTATGAGAATGATTTTGAAGCATCCATGCTT
Chicory_Cul1_Cds       GTTGAAATAGGAATGGGACAAATGGAATATTATGAGAATGATTTTGAAGCATCCATGCTT
Endive_Cul1_Cds        GTTGAAATAGGAATGGGACAAATGGAATATTATGAGAATGATTTTGAAGCATCTATGCTT
Carrot_Cul1_Cds        GTTGAAGTTGGAATGAGTCAAATGGATTATTATGAGAATGACTTTGAAGCAGACATGCTC
Celery_Cul1_Cds        GTTGAAATCGGAATGAGTCAAATGGATCAATATGAGAATGACTTTGAAGAAGCCATGCTC
```

Fig. 69F

```
Brassica_Cul1_Cds      TTAGATTCAGCATCTTACTATTCTCGCAAGGCGTCAAGCTGGATCCAAGAAGATTCTTGC
Radish_Cul1_Cds        TTGGATTCAGCATCTTACTATTCTCGCAAAGCATCAAACTGGATCCAGGAAGATTCTTGC
Beet_Cul1_Cds          GATGATACTGCTGCTTACTACTCGCGCAAAGCGTCTAGCTGGATTCTTGAGGACTCTTGT
Spinach_Cul1_Cds       GATGATACTGCTGCTTATTACTCACGCAAGGCCTCAAGCTGGATTCTGGAGGACTCATGT
Leek_Cul1_Cds          AATGCTACAGCAGCCTATTATTCACGAAAAGCTTCAAATTGGATTCTAGAAGATTCATGT
Squash_Cul1_Cds        AAAGATACTGCTGCTTACTACTCTAGGAAGGCATCAAATTGGATCTTAGAAGATTCTTGT
WaterMelon_Cul1_Cds    AAAGATACTGCTGCTTATTACTCTAGGAAGGCTTCCAATTGGATCCTAGAAGATTCTTGT
CuCumber_Cul1_Cds      AAAGATACTGCTGCTTATTACTCTAGGAAGGCTTCCAATTGGATCCTAGAAGATTCTTGT
Melon_Cul1_Cds         AAAGATACTGCTGCTTATTACTCTAGGAAGCTTCCAATTGGATCCTAGAAGATTCTTGT
Tomato_Cul1_Cds        AAGGACACAGCGGCTTATTATTCTCGCAAAGCTTCTAATTGGATCCTCGAAGATTCATGT
Eggplant_Cul1_Cds      AAGGACACTGCGGCTTATTATTCTCGCAAAGCTTCTAACTGGATCCTCGAAGATTCATGT
Pepper_Cul1_Cds        AAGGACACCGCAGCTTATTATTCTCGCAAAGCTTCTAACTGGATACTTGAAGATTCATGT
Lettuce_Cul1_Cds       AATGATACAGCAGCATATTATTCACGCAAGGCTTCCAACTGGATTCTAGAAGATTCTTGT
Chicory_Cul1_Cds       AATGATACAGCAGCATATTATTCACGCAAAGCTTCCAATTGGATTCTAGAAGATTCTTGT
Endive_Cul1_Cds        AATGATACAGCAGCATATTATTCACGCAAAGCTTCCAACTGGATTCTAGAAGATTCTTGT
Carrot_Cul1_Cds        AAAGATACAGCAGCATACTATTCTCGAAAGGCTTCCAACTGGATCTTAGAAGATTCTTGT
Celery_Cul1_Cds        ACTGATACTGCTGCTTACTATTCTCGAAAAGCTTCAAACTGGATCCTTGAAGATTCTTGT Brassica_Cul1_Cds      CCTGATTACATGCTGAAGTCTGAAGAATGTCTTAAGAAGGAGAGGGAGAGAGTGGCTCAC
Radish_Cul1_Cds        CCTGATTACATGCTGAAGTCTGAAGAATGCCTTAAGAAGGAGAGGGAGAGGGTTGCTCAC
Beet_Cul1_Cds          CCGGAATACATGTTAAAGTCTGAGGAGTGTTTGAAGAAGGAGAAAGAGAGAGTGGCTAAT
Spinach_Cul1_Cds       CCGGAATACATGTTGAAGTCGGAGGAGTGTTTGAAGAAAGAGAAAGATAGAGTGGCTCAT
Leek_Cul1_Cds          CCAGATTATATGCTAAAAGCCGAGGAGTGCTTAAAACATGAGAAAGATAGAGTTGCTCAT
Squash_Cul1_Cds        CCTGATTATATGCTAAAAGCAGAGGAGTGCTTGAGACGAGAAAAGGACCGAGTTTCTCAC
WaterMelon_Cul1_Cds    CCCGATTATATGCTAAAAGCAGAGGAGTGCTTGAAACGAGAAAAGGATAGAGTTTCTCAC
CuCumber_Cul1_Cds      CCCGATTATATGCTTAAAGCAGAGGAGTGCTTGAAACGAGAAAAGGATAGGGTTTCCCAC
Melon_Cul1_Cds         CCCGATTATATGCTAAAAGCAGAGGAGTGCTTGAAGCGAGAAAAGGATAGGGTTTCCCAC
Tomato_Cul1_Cds        CCGGATTATATGCTGAAAGCCGAGGAGTGCTTGAAACGGGAGAAGGATAGGGTCTCTCAT
Eggplant_Cul1_Cds      CCAGATTATATGCTGAAAGCTGAGGAGTGCTTGAAACGGGAGAAGGATAGGGTCTCCCAT
Pepper_Cul1_Cds        CCAGATTATATGCTGAAAGCCGAGGAGTGCTTGAAACGGGAGAAAGATAGGGTCTCTCAC
Lettuce_Cul1_Cds       CCAGATTATATGCTCAAAGCAGAGGAGTGCTTAAAAAGAGAAAAGGACAGAGTGTCTCAT
Chicory_Cul1_Cds       CCAGATTATATGCTCAAAGCTGAGGAGTGCTTAAAAAGAGAAAAGGACAGAGTTTCTCAT
Endive_Cul1_Cds        CCAGATTATATGCTCAAAGCTGAGGAGTGCTTAAAAAGAGAAAAGGACAGAGTTTCTCAT
Carrot_Cul1_Cds        CCAGATTATATGCTCAAAGCGGAAGAGTGTTTGAGACGGGAAAAGGACAGGGTCTCTAAC
Celery_Cul1_Cds        CCTGATTATATGTTAAAGGCAGAAGAATGTTTGCGACGAGAGAAGGACAGGGTTTCCCAC
```

Fig. 69G

```
Brassica_Cul1_Cds      TACCTTCACTCAAGCAGCGAGCCAAAGCTGGTTGAGAAAGTACAACATGAGCTGTTGGTA
Radish_Cul1_Cds        TACCTTCATTCAAGCAGCGAGCCAAAGCTGGTTGAGAAAGTACAACATGAGCTGTTGGTT
Beet_Cul1_Cds          TATTTACATTCCAGCAGTGAGCCAAAGCTTCTGGAGAAAGTGCAAAACGAGTTGCTATTG
Spinach_Cul1_Cds       TATCTACATTCCAGCAGTGAGCCAAAGCTTCTGGAGAAAGTACAAAATGAGTTGCTACTG
Leek_Cul1_Cds          TATTTGCATTCAAGCAGTGAACAGAAGCTGTTAGAGAAAGTGCAACATGAGTTACTTTTC
Squash_Cul1_Cds        TATCTGCACTCTAGTAGCGAGCCAAAGTTATTGGAGAAAGTTCAACATGAACTATTGTCT
WaterMelon_Cul1_Cds    TATTTGCACTCTAGTAGCGAGCCAAAGTTATTAGAGAAAGTTCAACATGAACTGTTATCT
CuCumber_Cul1_Cds      TATTTGCACTCTAGTAGCGAGCCAAAGTTGTTGGAGAAAGTTCAACATGAACTATTATCT
Melon_Cul1_Cds         TATTTGCACTCTAGTAGCGAGCCAAAGTTGTTGGAGAAAGTTCAACACGAACTGTTATCT
Tomato_Cul1_Cds        TATCTCCATTCAAGCAGCGAGACGAAGTTGCTTGAGAAAGTGCAACATGAGTTGTTGTCT
Eggplant_Cul1_Cds      TATCTCCATTCTAGCAGTGAGACAAAGTTGCTTGAGAAAGTGCAACATGAGTTGTTATCT
Pepper_Cul1_Cds        TATCTTCATTTAAGCAGTGAGACAAAGTTGCTTGAGAAAGTGCAACATGAGTTGTTGTCT
Lettuce_Cul1_Cds       TATCTTCATTCCAGCAGTGAGCCAAAGCTTCTTGAGAAAGTTCAAAATGAGTTATTGTCT
Chicory_Cul1_Cds       TATCTTCATTCCAGCAGTGAACCAAAGCTTCTTGAGAAAGTTCAAACAGAGTTATTATCT
Endive_Cul1_Cds        TATCTTCATTCAAGTAGTGAACCAAAGCTTCTTGAGAAAGTTCAAACAGAGTTATTATCT
Carrot_Cul1_Cds        TACCTTCATTCTAGTAGTGAACCCAAGTTGCTTGAGAAAGTTCAACATGAGTTACTATCA
Celery_Cul1_Cds        TACCTACATTTTAGTAGCGAGCCAAAGTTGCTTGAGAAAGTGCAACATGAGCTGCTATCT Brassica_Cul1_Cds      GTGTATGCAAATCAGCTTCTAGAAAAAGAGCATTCAGGGTGCCGTGCATTGCTGAGAGAT
Radish_Cul1_Cds        GTCTATGCAAATCAGCTTCTTGAAAAGGAGCACTCAGGGTGCCGTGCATTGCTGAGAGAC
Beet_Cul1_Cds          GTTTATGAAAGCCAATTGCTTGAGAAGGAGAATTCGGGATGTCGTGCATTACTGAAAGAT
Spinach_Cul1_Cds       GTTTACGAAATCAGTTGCTTGAGAAGGAGAATTCTGGATGTCGTGCATTGTTGAAAGAT
Leek_Cul1_Cds          GTATATGCAAGTCAACTTCTCGAGAAAGAACATTCCGGATGTCATGCATTGCTTCGCGAT
Squash_Cul1_Cds        GTTTATGCTACTCAACTGCTGGAGAAAGAGCATTCAGGATGCCATGCATTGCTTAGAGAT
WaterMelon_Cul1_Cds    GTGTATGCTACTCAACTGCTGGAAAAAGAGCATTCAGGATGCCATGCATTGCTTAGAGAT
CuCumber_Cul1_Cds      GTTTATGCTACTCAACTGCTGGAAAAAGAGCATTCAGGATGCCATGCATTGCTTAGAGAT
Melon_Cul1_Cds         GTGTATGCTACTCAACTGCTGGAAAAAGAGCATTCAGGATGCCATGCATTGCTTAGAGAT
Tomato_Cul1_Cds        GTGTATGCCACTCAACTTCTTGAGAAGGAGCACTCTGGATGCCATGCGTTACTGAGAGAT
Eggplant_Cul1_Cds      GTGTATGCCAATCAACTTCTTGAGAAGGAGCACTCTGGATGCCATGCATTACTTAGAGAT
Pepper_Cul1_Cds        GTGTATGCCACTCAACTTCTTGAGAAGGAGCACTCTGGGTGCCATGCGTTACTAAGAGAT
Lettuce_Cul1_Cds       GTTTATGCAACTCAATTGCTTGAGAAAGAGCACTCAGGTTGTCATGCATTGCTCAGGGAT
Chicory_Cul1_Cds       GTTTATGCAACTCAATTGCTTGAAAAGGAGCACTCCGGTTGTCATGCATTACTTAGGGAT
Endive_Cul1_Cds        GTTTATGCAACTCAATTGCTCGAAAAGGAACACTCAGGTTGTCATGCATTACTTAGAGAT
Carrot_Cul1_Cds        CACTATGCAACTCAGCTGCTTGAGAAAGAACACTCTGGGTGTCATGCATTGCTTAGGGAT
Celery_Cul1_Cds        GTGTATGCAACCCAATTACTCGAGAAGGAACATTCTGGTTGTCATGCATTGCTTAGGGAT
```

Fig. 69H

```
Brassica_Cul1_Cds      GACAAGGTTGATGACCTCTCCAGGATGTACAGGCTTTATCATAAAATTGTGAAAGGTTTG
Radish_Cul1_Cds        GACAAGGTTGACGATCTCTCCAGGATGTACAGGCTCTATCATAAAATTGCTAAAGGTTTA
Beet_Cul1_Cds          GACAAGGTGGATGATCTTTCCAGGATGTACAGGCTTTACAGTAAGGTTACCAAAGGATTG
Spinach_Cul1_Cds       GACAAGGTGGAAGATCTTTCCAGGATGTACAGGCTTTATAGCAAGGTTACCAAAGGGTTG
Leek_Cul1_Cds          GACAAGGTGGGAGATCTTTCACGCATGTATCGGCTGTTCTGTAGAATTACACGTGGTTTG
Squash_Cul1_Cds        GACAAGGTGGAAGATTTGTCAAGGATGTTCCGTCTCTTCTCCAAAATACCCAAGGGATTG
WaterMelon_Cul1_Cds    GACAAGGTGGAAGATTTGTCAAGGATGTTCCGCCTCTTCTCCAAAATACCCAAGGGATTG
CuCumber_Cul1_Cds      GACAAGGTGGAAGATTTGTCAAGGATGTTCCGTCTATTCTCCAAAATACCGAAGGGACTG
Melon_Cul1_Cds         GACAAGGTGGAAGATTTGTCAAGGATGTTCCGTCTCTTCTCCAAAATACCGAAGGGATTG
Tomato_Cul1_Cds        GATAAGGTTGAAGATTTATCAAGGATGTATAGGCTCTTTTCTAAGATTTCTCGAGGCTTA
Eggplant_Cul1_Cds      GATAAGGTCGATGATTTATCAAGGATGTATAGACTCTTTTCTAAGATTCCTCGAGGCTTA
Pepper_Cul1_Cds        GATAAGGTTGAAGATTTATCAAGGATGTATAGGCTCTTTTCTAAGATTCCTCGAGGCTTA
Lettuce_Cul1_Cds       GACAAGGTTGATGATTTATCAAGAATGTACAGACTCTTTTCAAAGATACCAAAAGGATTG
Chicory_Cul1_Cds       GACAAGGTTGATGATTTATCAAGAATGTACAGACTCTTTTCAAAGATACAAAAAGGGCTG
Endive_Cul1_Cds        GACAAGGTTGATGATTTATCAAGAATGTACAGACTCTTTTCAAAGATACAAAAAGGACTG
Carrot_Cul1_Cds        GACAAGGTGGCAGATTTATCAAGGATGTATAGGCTCTTCTCTAAAATACCTCGAGGCCTA
Celery_Cul1_Cds        GACAAGGTGGATGATTTGTCTAGGATGTACAGACTCTTCTCGAAAATACCTAAAGGCCTG Brassica_Cul1_Cds      GAACCTGTTGCAAACATATTTAAGCAGCATGTCACAGCAGAGGGTAACGCACTTGTCCAA
Radish_Cul1_Cds        GAACCTGTTGCAAACATATTTAAGCAGCATGTCACAGCCGAGGGTAACGCACTTGTCCAA
Beet_Cul1_Cds          GAACCCATTGGCAGTATCTTCAAACAGCATATAACTGATGAAGGAACAGCCTTAGTGCAG
Spinach_Cul1_Cds       GAACCCATTGGCAGTATCTTCAAACAGCATATAACCGATGAAGGAACAGCCCTGGTGCAG
Leek_Cul1_Cds          GACCCTGTGTCTCAAATATTTAAGCAGCATGTGACTGCAGAAGGTACTGCTTTGGTCAAA
Squash_Cul1_Cds        GACCCAGTTTCCAACATATTTAAGCAGCATGTCACTGCTGAAGGAACAGCATTAGTCAAA
WaterMelon_Cul1_Cds    GACCCAGTTTCCAACATATTTAAGCAGCATGTCACTGCTGAAGGAACAGCATTGGTCAAA
CuCumber_Cul1_Cds      GATCCAGTTTCCAACATATTTAAGCAGCATGTAACTGCTGAAGGAACAGCACTGGTCAAA
Melon_Cul1_Cds         GACCCAGTTTCCAACATATTTAAGCAGCATGTAACTGCTGAAGGAACAGCACTGGTCAAA
Tomato_Cul1_Cds        GACCCTGTGGCCAATATTTTTAAGCAGCATGTTACTGCTGAAGGTACAGCTTTGGTAAAA
Eggplant_Cul1_Cds      GAGCCTGTGGCTAATATATTTAAGCAGCATGTTACTGCTGAAGGTACAGCTTTGGTGAAA
Pepper_Cul1_Cds        GACCCTGTGGCTAATATATTTAAGCAGCATGTTACTGCTGAAGGTACAGCTTTGGTCAAA
Lettuce_Cul1_Cds       GATCCTGTTTCTAGTATGTTTAAGCAGCATGTCACTGCTGAAGGCACAACATTGGTTAAA
Chicory_Cul1_Cds       GATCCTGTTTCTAGTATGTTTAAGCAGCATGTCACTGCTGAAGGCACAACATTGGTTAAA
Endive_Cul1_Cds        GATCCTGTTTCCAGTATGTTTAAGCAGCATGTCACTGCTGAAGGCACAACATTAGTAAAA
Carrot_Cul1_Cds        GATCCCGTGTCTAATATTTTCAAGCAGCATGTTACTGCTGAAGGTACAGCTTTGGTCAAA
Celery_Cul1_Cds        GATCCAGTTTCTTATATTTTTAAGCAGCATGTTACAAATGAAGGGATGGCATTGGTTAAA
```

Fig. 69I

```
Brassica_Cul1_Cds        CAGGCCGAAGACACGGCCACTAATCATGCTGCA-------AATACTGCTAGCGTGCAG
Radish_Cul1_Cds          CAGGCCGAAGACACAGCCACTAATCAGGCTGCA-------AATACTGCTAGCGTGCAG
Beet_Cul1_Cds            CAGGCCGAAGATGCTGCTATCAGCAAGGCTGAA------AATACT-GGTGGTTCACAT
Spinach_Cul1_Cds         CAGGCCGAAGACGCTGCAATTAGCAAGGCTGAA----AATGCTGGCGGTGGTTCACAT
Leek_Cul1_Cds            CATGCCGAAGATGCTGCAAGTAACAAGAAGGCCGAGAAAAAAGACATTGTTGGTTTGCAA
Squash_Cul1_Cds          CAGGCAGAAGACGCTGCAAGTAACAAGAAGGCCGAGAAAAAGGACATCGTTGGTCTGCAA
WaterMelon_Cul1_Cds      CAGGCAGAAGATGCTGCAAGTAACAAGAAGGCCGAGAAAAAGGACATAGTTGGTCTGCAG
CuCumber_Cul1_Cds        CAGGCAGAAGATGCTGCAAGTAACAAGAAGGCTGAGAAAAAGGACATAGTTGGTCTGCAG
Melon_Cul1_Cds           CAGGCAGAAGATGCTGCAAGTAACAAGAAGGCCGAGAAAAAGGACATAGTTGGTCTGCAG
Tomato_Cul1_Cds          CAGGCTGAAGATGCTGCTAGCAATAAAAAGGCAGAGAAGAGAGATGTGGTTGGTTTGCAG
Eggplant_Cul1_Cds        CAGGCTGAAGATGCTGCTAGCAACAAAAAGGCAGAGAAGAGAGATGTGGTTGGTTTGCAG
Pepper_Cul1_Cds          CAGGCTGAAGATGCTGCTAGCAACAAAAAGGCAGAGAAAAGAGATGTGGTTGGTTTGCAG
Lettuce_Cul1_Cds         CAAGCAGAAGATGCAGCAAGTACCAAGAAGGCTGAAAAGAGAGATGTGGTTGGGTTGCAG
Chicory_Cul1_Cds         CAGGCAGAAGATGCAGCAAGTACTAAGAAGGCTGAAAAGAGAGACGTGGTTGGCTTACAA
Endive_Cul1_Cds          CAAGCAGAAGATGCAGCAAGTACTAAGAAGGCTGAAAAGAGAGACGTGGTTGGCTTACAG
Carrot_Cul1_Cds          CAAGCAGAAGATGCAGCTAGCAACAAGAAGGCAGAGAAGAGAGATGTAGTAGGTTTACAA
Celery_Cul1_Cds          CAAGCAGAAGATGCAGCAAGCAACAAGAAGGCAGAAAAGAGAGACGTGGTTAGTTTACAG Brassica_Cul1_Cds        GAACAGGTTCTTATCAGAAAAGTGATTGAACTACATGATAAATACATGGTCTATGTTGTT
Radish_Cul1_Cds          GAACAGGTTCTCATCAGAAAAGTGATTGAGCTACATGATAAGTACATGGTCTATGTCGTG
Beet_Cul1_Cds            GAGCAGGTCTTCGTCAGGAAAGTAATAGAGTTGCATGACAAATTCATGACTTATGTCACC
Spinach_Cul1_Cds         GAGCAGGTCTTCGTCAGGAAAGTGATTGAGTTGCATGACAAATTTATGACCTATGTTACA
Leek_Cul1_Cds            GAGCAGGTCTTCGTTAGGAAAGTAATTGAGCTGCATGATAAATACTTGGCCTATGTGACT
Squash_Cul1_Cds          GAACAGGTTTTTGTTAGAAAAGTGATTGAGCTTCACGACAAGTACTTGGCATATGTGAAT
WaterMelon_Cul1_Cds      GAACAGGTTTTTGTAAGAAAAGTGATTGAGCTTCACGACAAGTACTTGGCTTACGTGAAT
CuCumber_Cul1_Cds        GAACAGGTTTTTGTAAGAAAAGTGATTGAGCTTCACGACAAGTACTTGGCTTATGTGAAT
Melon_Cul1_Cds           GAACAGGTTTTTGTAAGAAAAGTGATTGAGCTTCACGACAAGTACTTGGCTTATGTGAAT
Tomato_Cul1_Cds          GAACAGGTTTTTGTTCGGAAAGTGATTGAACTTCATGATAAATATTTGGCTTATGTGAAT
Eggplant_Cul1_Cds        GAACAGGTTTTTGTTCGGAAAGTGATTGAGCTTCATGATAAATATTTGGCGTATGTGAAT
Pepper_Cul1_Cds          GAACAGATTTTTGTTCGGAAAGTGATTGAGCTTCATGATAAGTATATGGCATATGTGAAT
Lettuce_Cul1_Cds         GAACAGGTTTTTGTTAGAAAAGTTATTGAGCTCCATGACAAGTACCTGGCATATGTAAAT
Chicory_Cul1_Cds         GAACAGGTTTTTGTTAGAAAAGTTATCGAGCTTCATGACAAGTACCTTGCATATGTAAAT
Endive_Cul1_Cds          GAACAGGTTTTTGTTAGAAAAGTAATCGAGCTTCATGACAAGTACCTCGCATATGTAAAC
Carrot_Cul1_Cds          GAACAGGTTTTTGTGAGGAAAATAATTGAATTGCATGACAAATACCTTACATACGTAAAT
Celery_Cul1_Cds          GAGCAGGTTTTTGTTAGAAAAATTATTGAATTACATGACAAATACCTCGCCTATGTGAAT
```

Fig. 69J

| | |
|---|---|
| Brassica_Cul1_Cds | GAGTGTTTCCAGAACCACACCCTCTTCCACAAGGCATTGAAAGAGGCATTTGAGATATTC |
| Radish_Cul1_Cds | GAGTGCTTCCAGAACCACACCCTCTTCCACAAGGCTCTGAAAGAGGCATTTGAGATATTC |
| Beet_Cul1_Cds | GATTGCTTCAACAGCCATACCATATTTCACAAGGCTCTTAAGGAGGCTTTTGAGGTATTT |
| Spinach_Cul1_Cds | GATTGCTTCAACAGCCATACCATCTTTCACAAGGCTCTCAAGGAAGCTTTTGAGGTATTC |
| Leek_Cul1_Cds | GACTGCTTTCAAAATCACTCTCTATTTCACAAGGCACTTAAAGAGGCATTCGAGGTATTC |
| Squash_Cul1_Cds | GATTGTTTCCAAAACCACACACTTTTTCACAAGGCTCTCAAGGAAGCTTTTGAAGTCTTT |
| WaterMelon_Cul1_Cds | GATTGTTTCCAAAACCACACACTTTTTCACAAGGCTCTCAAGGAAGCTTTTGAAGTCTTT |
| CuCumber_Cul1_Cds | GATTGTTTCCAAAACCACACACTTTTCCATAAGGCTCTCAAGGAAGCTTTTGAAGTATTT |
| Melon_Cul1_Cds | GATTGTTTCCAAAACCACACACTTTTCCATAAGGCTCTCAAGGAAGCTTTTGAAGTCTTT |
| Tomato_Cul1_Cds | AACTGTTTCCAAAACCACACACTTTTTCACAAGGCGCTTAAAGAAGCTTTTGAGCTTTTC |
| Eggplant_Cul1_Cds | AACTGTTTCCAAAACCACACACTTTTTCACAAGGCACTTAAAGAAGCTTTCGAACTTTTC |
| Pepper_Cul1_Cds | AACTGTTTCCAAAACCACACACTTTTTCACAAGGCGCTTAAAGAAGCTTTCGAACTTTTC |
| Lettuce_Cul1_Cds | GACTGTTTCATGAACCATACTCTTTTCCACAAGGCTCTTAAAGAGGCATTTGAAATATTC |
| Chicory_Cul1_Cds | GACTGTTTTATGAATCATACCCTGTTTCACAAGGCTCTTAAAGAGGCATTTGAAATATTC |
| Endive_Cul1_Cds | GACTGTTTTATGAATCACACATTGTTCCACAAGGCTCTTAAAGAGGCATTTGAAATATTC |
| Carrot_Cul1_Cds | GACTGTTTTACAAACCACACTCTCTTCCATAAGGCGCTTAAGGAGGCTTTTGAAATCTTC |
| Celery_Cul1_Cds | GACTGCTTTACAAACCATACTCTTTTCCATAAGGCTCTCAAGGAGGCTTTTGAAATCTTT |

| | |
|---|---|
| Brassica_Cul1_Cds | TGTAACAAAACAGTCGCTGGAAGTTCTAGTGCTGAATTGCTTGCAACATTTTGCGACAAT |
| Radish_Cul1_Cds | TGTAACAAAACAGTCGCTGGAAGTTCAAGTGCAGAACTGCTTGCAACATTCTGCGACAAC |
| Beet_Cul1_Cds | TTGAACAAGGGTGTTGCTGGTAGCTCAAGTGCTGAGTTGCTAGCTACATTCTGTGATAAC |
| Spinach_Cul1_Cds | TTAAACAAGGGTGTTGCTGGTAGTTCAAGTGCTGAACTTCTAGCTTCATTTTGTGATAAT |
| Leek_Cul1_Cds | TGCAATAAGGTGTTGCAGGTAGCTCAAGCGCTGAACTTCTGGCTGCTTTTTGTGACAAT |
| Squash_Cul1_Cds | TGCAATAAGGGTGTTGCTGGAAGTTCTAGTGCAGAATTACTTGCTACCTTTTGTGATAAC |
| WaterMelon_Cul1_Cds | TGCAATAAGGGTGTTGCTGGAAGTTCTAGTGCAGAATTACTTGCTACCTTTTGTGATAAC |
| CuCumber_Cul1_Cds | TGCAATAAGGGTGTTGCTGGAAGTTCTAGTGCAGAATTGCTTGCTACCTTTTGTGATAAC |
| Melon_Cul1_Cds | TGCAATAAGGGTGTTGCTGGAAGTTCTAGTGCAGAATTGCTTGCTACCTTCTGCGATAAC |
| Tomato_Cul1_Cds | TGCAACAAGGGTGTTGCTGGTAGCTCAAGCGCTGACTTCTTGCCACCTTCTGTGACAAC |
| Eggplant_Cul1_Cds | TGCAACAAGGGTGTTGCTGGTAGCTCAAATGCTGAACTTCTTGCCACATTCTGCGACAAC |
| Pepper_Cul1_Cds | TGCAACAAGGGTGTTGCTGGTAGCTCAAGTGCTGAACTTCTTGCCACATTCTGCGACAAT |
| Lettuce_Cul1_Cds | TGCAACAAGGGTGTTGCTGGAAGTTCAAGTGCAGAGTTACTTGCCACATTTTGTGATAAT |
| Chicory_Cul1_Cds | TGCAACAAGGGCGTTGCTGGAAGTTCAAGTGCAGAATTACTTGCTACATTTTGTGATAAT |
| Endive_Cul1_Cds | TGCAACAAGGGCGTTGCTGGAAGTTCAAGTGCAGAATTACTTGCCACATTTTGTGATAAT |
| Carrot_Cul1_Cds | TGCAATAAGGGTGTCTCTGGAAGCTCTAGTGCAGAATTACTTGCCACATTCTGTGATAAT |
| Celery_Cul1_Cds | TGCAACAAGGGTGTTGCTGGAAGCTCTAATGCTGAACTACTTGCTACTTTCTGTGATAAC |

Fig. 69K

```
Brassica_Cul1_Cds      ATTCTCAAGAAGGGGGAAGTGAAAAGCTGAGCGATGAAGCTATTGAAGATACCCTTGAG
Radish_Cul1_Cds        ATCCTCAAGAAGGGGGTAGTGAGAAGCTGAGTGACGAAGCTATTGAAGATACGCTTGAG
Beet_Cul1_Cds          ATTCTCAAGAAAGGTGGGAGCGAAAAACTAAGCGATGAGGCTATTGAGGATTCACTTGAG
Spinach_Cul1_Cds       ATTCTCAAGAAAGGTGGTAGTGAAAAATTAAGTGATGAGGCTATTGAGGATTCACTGGAG
Leek_Cul1_Cds          ATATTGAAGAAGGTGGAAGCGAGAAACTAAGCGATGAGGCCATAGAGGATACTCTTGAG
Squash_Cul1_Cds        ATCCTTAAGAAAGTGGGAGTGAGAAGTTGAGTGATGAAGCAATTGAGGAAACACTCGAG
WaterMelon_Cul1_Cds    ATCCTTAAGAAAGGTGGGAGCGAGAAGTTGAGTGATGAAGCAATTGAGGAGACACTTGAG
CuCumber_Cul1_Cds      ATCCTTAAGAAAGGTGGGAGTGAGAAGTTGAGTGATGAAGCAATCGAGGAGACACTTGAG
Melon_Cul1_Cds         ATCCTTAAGAAAGGTGGGAGTGAGAAGTTGAGTGATGAAGCAATCGAAGAGACACTTGAG
Tomato_Cul1_Cds        ATTCTCAAAAAGGCGGGAGTGAGAAATTGAGTGATGAAGCTATTGAAGAAACGTTGGAA
Eggplant_Cul1_Cds      ATTCTCAAAAAAGGCGGGAGTGAAAAATTGAGTGATGAAGCCATTGAAGAGACGCTGGAG
Pepper_Cul1_Cds        ATTCTCAAGAAAGGCGGGAGTGAGAAATTGAGTGATGAAGCCATTGAAGAGACGCTGGAG
Lettuce_Cul1_Cds       ATTCTTAAAAAAGGTGGAAGTGAGAAACTGAGCGATGAAGCCATTGAGGACACCCTTGAG
Chicory_Cul1_Cds       ATTCTTAAAAAAGGTGGAAGTGAAAAATTGAGTGATGAAGCCATTGAGGACACACTTGAG
Endive_Cul1_Cds        ATTCTTAAAAAAGGTGGAAGTGAAAAATTGAGTGATGAAGCCATTGAAGACACACTTGAG
Carrot_Cul1_Cds        ATTCTCAAGAAAGGTGGAAGCGAGAAGTTAAGTGATGAAGCCATTGAGGAAACACTTGAG
Celery_Cul1_Cds        ATCCTCAAAAAGGGTGGGAGTGAGAAATTAAGTGATGAGGCTATTGAAGAAACACTTGAG Brassica_Cul1_Cds      AAGGTGGTCAAATTGCTTGCTTATATAAGTGACAAGGATCTTTTCGCCGAGTTCTACAGG
Radish_Cul1_Cds        AAGGTTGTCAAATTGCTTGCTTATATAAGCGACAAGGATCTTTTCGCCGAGTTCTACAGG
Beet_Cul1_Cds          AAGGTGGTGAAGCTTCTGGCCTATGTCAGTGATAAAGACCTGTTTGCTGAATTTTACAGA
Spinach_Cul1_Cds       AAGGTGGTGAAGCTTCTCGCATATGTCAGTGATAAAGACCTGTTTGCTGAATTTTACAGA
Leek_Cul1_Cds          AAGGTTGTAAAACTATTGGCATATATTAGCGATAAAGATCTGTTTGCTGAATTTTACAGG
Squash_Cul1_Cds        AAGGTCGTGAAATTGCTGGCGTATATCTGCGACAAAGATCTGTTTGCTGAATTCTATAGA
WaterMelon_Cul1_Cds    AAGGTCGTGAAGTTGCTGGCATACATCTGCGACAAAGATCTGTTTGCTGAATTCTATAGA
CuCumber_Cul1_Cds      AAGGTTGTGAAGTTGTTGGCATACATTTGCGACAAAGATCTGTTTGCTGAATTCTATAGA
Melon_Cul1_Cds         AAGGTTGTGAAGTTGTTGGCATACATCTGCGACAAAGATCTGTTTGCTGAATTCTATAGA
Tomato_Cul1_Cds        AAGGTGGTAAAGCTACTAGCTTATATTAGTGATAAGGACTTGTTTGCAGAATTCTATAGG
Eggplant_Cul1_Cds      AAGGTGGTAAAGCTGCTGGCTTATATTAGTGATAAGGACTTGTTTGCAGAATTCTATAGG
Pepper_Cul1_Cds        AAGGTTGTAAAGCTGCTAGCATATATTAGTGACAAGGACTTGTTTGCAGAATTCTATAGG
Lettuce_Cul1_Cds       AAGGTAGTAAAGTTGCTTGCCTACATCAGTGATAAAGATCTATTTGCTGAATTTTACAGG
Chicory_Cul1_Cds       AAGGTGGTAAAGTTGCTTGCTTACATCAGCGATAAAGATCTATTTGCAGAGTTTTATAGG
Endive_Cul1_Cds        AAGGTAGTAAAGTTGCTTGCTTACATCAGCGATAAAGATCTATTTGCAGAGTTTTATAGG
Carrot_Cul1_Cds        AAGGTTGTAAGGTTGCTTGCTTATATAAGTGACAAAGACTTATTTGCTGAATTTTATAGG
Celery_Cul1_Cds        AAGGTAGTAAAATTGTTAGCTTACATTAGCGATAAAGACTTGTTCGCTGAATTTTACAGA
```

Fig. 69L

```
Brassica_Cul1_Cds      AAGAAGCTGGCCCGTAGGCTCTTATTTGATCGCAGTGCTAATGATGATCATGAGAGAAGT
Radish_Cul1_Cds        AAGAAGCTGGCACGTAGGCTCTTATTTGATCGCAGTGCGAATGATGATCATGAGAGAAGC
Beet_Cul1_Cds          AAGAAGCTCTCTCGCCGGCTACTCTTTGACAAGAGTGCTAATGATGATCATGAAAGAAGT
Spinach_Cul1_Cds       AAGAAGCTCTCTCGCCGGCTACTCTTTGACAAAAGTGCTAATGATGATCATGAGAGGAGT
Leek_Cul1_Cds          AAGAAGCTTGCACGAAGATTACTCTTTGACAAAAGTGCTAATGATGACCATGAGAGGAGC
Squash_Cul1_Cds        AAAAAACTCGCCCGAAGGCTTCTCTTCGACAAGAGTGCGAATGATGACCACGAGAGAAGT
WaterMelon_Cul1_Cds    AAAAAACTTGCCCGAAGGCTTCTCTTTGACAAGAGTGCCAACGATGACCATGAGAGAAGT
CuCumber_Cul1_Cds      AAAAAACTTGCCCGAAGGCTTCTCTTTGACAAGAGCGCGAACGATGACCACGAGAGAAGT
Melon_Cul1_Cds         AAAAAACTTGCCCGAAGGCTTCTCTTTGATAAGAGCGCCAACGATGACCACGAGAGAAGT
Tomato_Cul1_Cds        AAAAAGCTAGCCCGGCGGTTGTTATTTGATAAGAGTGCCAATGATGAACATGAAAGAAGT
Eggplant_Cul1_Cds      AAAAAGCTCGCCCGGCGGTTGTTATTTGATAAGAGTGCCAATGATGAACATGAGAGAAGT
Pepper_Cul1_Cds        AAAAAGCTAGCCCGGCGGTTGTTATTTGATAAGAGTGCCAATGATGAACACGAGAGAAGT
Lettuce_Cul1_Cds       AAAAAACTTGCTAGGAGGCTTTTGTTTGACAAGAGTGCAAACGATGAGCATGAGAGAAGT
Chicory_Cul1_Cds       AAAAAACTGGCTAGACGGCTTTTATTTGACAAAAGTGCAAATGATGAGCACGAAAGAAGT
Endive_Cul1_Cds        AAAAAACTGGCTAGAAGGCTTTTATTTGACAAAAGTGCAAATGATGAGCATGAAAGAAGT
Carrot_Cul1_Cds        AAAAAGCTTGCACGGCGTCTCTTATTCGACAAGAGTGCCAATGATGAGCATGAGAGAAGT
Celery_Cul1_Cds        AAAAAGCTTGCACGGAGACTTCTCTTTGATAAGAGTGCAAATGACGAGCATGAACGAAGT Brassica_Cul1_Cds      ATCCTGACAAAGCTCAAGCAACAATGTGGTGGGCAGTTTACTTCGAAGATGGAGGGCATG
Radish_Cul1_Cds        ATCCTTACAAAGCTCAAGCAACAATGTGGTGGGCAGTTCACTTCTAAGATGGAGGGCATG
Beet_Cul1_Cds          ATTTTAACCAAATTGAAGCAGCAGTGTGGCGGACAATTCACATCAAAGATGGAGGGGATG
Spinach_Cul1_Cds       ATTTTAACAAAATTGAAGCAGCAGTGTGGGGACAGTTCACATCAAAGATGGAGGGGATG
Leek_Cul1_Cds          ATCCTTACAAAGCTGAAACAGCAATGTGGAGGGCAGTTCACCTCTAAAATGGAAGGCATG
Squash_Cul1_Cds        ATACTGACGAAATTGAAGCAACAATGTGGTGGTCAGTTTACCTCTAAGATGGAGGGAATG
WaterMelon_Cul1_Cds    ATATTGACCAAATTGAAGCAACAATGTGGTGGCCAGTTCACCTCTAAGATGGAGGGGATG
CuCumber_Cul1_Cds      ATATTGACCAAATTGAAGCAACAATGTGGTGGTCAGTTCACTTCTAAGATGGAGGGAATG
Melon_Cul1_Cds         ATATTGACCAAATTGAAGCAACAATGTGGTGGTCAGTTCACTTCTAAGATGGAGGGAATG
Tomato_Cul1_Cds        ATCCTAACAAAGTTGAAGCAGCAGTGTGGGGGCAGTTCACATCAAAGATGGAGGGAATG
Eggplant_Cul1_Cds      ATCCTAACAAAGTTGAAGCAGCAGTGTGGAGGTCAGTTCACATCAAAGATGGAGGGAATG
Pepper_Cul1_Cds        ATCCTTACAAAGTTGAAGCAGCAGTGTGGGGGCCAGTTCACATCAAAGATGGAGGGAATG
Lettuce_Cul1_Cds       ATTCTCACAAAGCTGAAGCAACAGTGTGGTGGTCAGTTCACATCAAAGATGGAAGGGATG
Chicory_Cul1_Cds       ATTTTGACAAAATTGAACAACAATGTGGCGGTCAATTTACATCAAAAATGGAAGGAATG
Endive_Cul1_Cds        ATTTTAACAAAGTTGAAGCAACAATGTGGTGGTCAGTTTACATCAAAGATGGAAGGAATG
Carrot_Cul1_Cds        ATATTGACTAAGCTGAAGCAACAATGTGGGGGTCAATTTACATCAAAGATGGAAGGAATG
Celery_Cul1_Cds        ATTTTGACTAAACTAAAGCAACAGTGCGGTGGTCAGTTCACATCGAAAATGGAGGGGATG
```

Fig. 69M

| | |
|---|---|
| Brassica_Cul1_Cds | GTGACTGATTTGACATTGGCAAGGGAAAACCAAAACAGCTTCGAGGAGTATCTTGGCAAT |
| Radish_Cul1_Cds | GTAACGGACTTGACATTGGCAAGAGAGAACCAAACCAGTTTCGAGGAGTATCTAGGCAAT |
| Beet_Cul1_Cds | GTGACAGACTTGACCTTGGCGAGGGAGAATCAAACTAATTTTGAGGAATATCTTAGTCAG |
| Spinach_Cul1_Cds | GTGACAGACTTGACATTGGCGAGGGAGAATCAAACTAATTTTGAGGAATATCTTGGACAA |
| Leek_Cul1_Cds | GTAACCGATCTGACACTTGCACGAGAAAATCAATCAAGTTTTGACGATTACCTTAGCAGC |
| Squash_Cul1_Cds | GTCACGGATTTGACACTGGCAAGGGAGAACCAAACTAGTTTTGAGGAATATCTGAGCAAT |
| WaterMelon_Cul1_Cds | GTCACTGATTTGACTTTGGCAAGGGAGAACCAAACTAGTTTCGAGGAGTATCTGAGCAAT |
| CuCumber_Cul1_Cds | GTTACTGATTTGACTTTGGCAAGGGAGAACCAAACTAGTTTTGAGGAGTATCTGAGCAAT |
| Melon_Cul1_Cds | GTTACTGATTTGACTTTGGCAAGGGAGAACCAAACTAGTTTCGAAGAGTATCTGAGCAAT |
| Tomato_Cul1_Cds | GTCACAGATTTGACATTGGCAAGGGAAAATCAAGCCAGCTTCGAGGAGTATTTGAGCAAT |
| Eggplant_Cul1_Cds | GTCACAGATTTGACATTGGCAAGGGAAAATCAAGCCAGCTTTGAGGAGTATTTGAGCAAT |
| Pepper_Cul1_Cds | GTGACAGATTTGACATTGGCAAGGGAAAATCAAGCCAGCTTTGAGGAGTATTTGAGCAAC |
| Lettuce_Cul1_Cds | GTTACAGATTTGACATTGGCAAAGGAAAACCAATCCCATTTTGAAGAGTATTTGAACAAT |
| Chicory_Cul1_Cds | GTTACAGATTTGACATTGGCAAAAGAAAATCAATCACATTTTGAGGAGTATTTGAATAAT |
| Endive_Cul1_Cds | GTTACAGATTTAACACTGGCAAAAGAAAATCAATCACATTTTGAGGAGTATTTGAATAAT |
| Carrot_Cul1_Cds | GTCACTGACTTGACGTTGGCAAAGGAAAATCAGTCCAACTTCGAGGAGTACCTCAATAAT |
| Celery_Cul1_Cds | GTCACAGATTTGACTTTGGCTAAAGAAAATCAATCCAGCTTTGAGGAGTATCTGGGAAAT |

| | |
|---|---|
| Brassica_Cul1_Cds | AACCCCGCTGCAAACCCAGGGATTGATTTGACCGTAACTGTTCTTACCACTGGTTTTTGG |
| Radish_Cul1_Cds | AACCCCGCTGCAAACCCAGGGATTGATTTGACCGTCACTGTTCTTACCACTGGTTTCTGG |
| Beet_Cul1_Cds | AATCCAGATGCCAGTCCTGGTCTTGATTTGACTGTGACTGTTCTGACAACTGGGTTCTGG |
| Spinach_Cul1_Cds | AATACAGATGCCAGTCCTGGTCTTGATTTGACTGTGACAGTTTTGACCACTGGGTTCTGG |
| Leek_Cul1_Cds | AATCCTAAAGCAAATTCTGGAATTGACTTGACTGTTACAGTCTTAACAACTGGCTTCTGG |
| Squash_Cul1_Cds | AATCCACAAGCTAGTCCTGGAATCGACTTGACCGTTACCGTTTTGACCACTGGTTTTTGG |
| WaterMelon_Cul1_Cds | AATCCACAAGCTAGTCCTGGAATCGACTTGACTGTCACTGTTTTGACTACTGGCTTTTGG |
| CuCumber_Cul1_Cds | AATCCACAAGCGAGTCCTGGCATCGACCTGACTGTTACTGTTTTAACTACTGGATTTTGG |
| Melon_Cul1_Cds | AATCCACAAGCTAGTCCTGGAATCGACCTAACTGTTACTGTTTTGACTACTGGATTTTGG |
| Tomato_Cul1_Cds | AATCCAATAGCAAATCCAGGAATTGACTTGACGGTGACTGTCTTGACTACTGGCTTCTGG |
| Eggplant_Cul1_Cds | AATCCAACAGCAAATCCAGGAATTGACTTGACGGTGACTGTCTTGACTACTGGCTTCTGG |
| Pepper_Cul1_Cds | AATCCAGCAGCAAATCCAGGAATTGACTTGACGGTGACTGTCTTGACTACTGGCTTCTGG |
| Lettuce_Cul1_Cds | AATCCCAATGTCAGCCCTGGAATTGACTTGACTGTCACTGTGTTGACTACCGGCTTCTGG |
| Chicory_Cul1_Cds | AATCCCAATGTTAGCCCTGGCATTGACTTGACCGTGACTGTGTTGACCACTGGTTTTTGG |
| Endive_Cul1_Cds | AATCCCAATGTTAGCCCTGGCATTGACTTGACCGTGACTGTGTTGACCACGGGATTTTGG |
| Carrot_Cul1_Cds | AATTCAAACGTAAATCCTGGAATTGACTTGACAGTTACTGTTCTAACCACTGGGTTTTGG |
| Celery_Cul1_Cds | AATGCCAATGTGAATCCTGGCATTGACTTGACGGTTACTGTTCTGACCACTGGCTTCTGG |

Fig. 69N

```
Brassica_Cul1_Cds      CCAAGTTACAAATCATTTGACATAAATCTACCCGCTGAAATGGTCAAGTGTGTTGAAGTT
Radish_Cul1_Cds        CCAAGTTACAAATCATTCGACATAAATCTACCAAGTGAAATGGTCAAGTGTGTTGAAGTT
Beet_Cul1_Cds          CCAAGTTACAAATCTTCCGATCTTAACCTTCCCGCTGAGATGGTGAGGTGTGTTGAAGTT
Spinach_Cul1_Cds       CCAAGTTACAAATCTTCTGATCTTAACCTTCCTGCTGAGATGGTGAGGTGTGTTGAAGTT
Leek_Cul1_Cds          CCCAGTTACAAGTCTTTTGATCTCAATCTTCCTGATGAGATGGTAAAATGCGTTGAAATT
Squash_Cul1_Cds        CCAAGCTACAAGTCTTTTGACCTCAACCTGCCGGCGGAGATGGTAAAGTGTGTTGAAGTT
WaterMelon_Cul1_Cds    CCAAGCTACAAGTCTTTTGACCTCAACCTGCCGGCAGAGATGGTAAAGTGTGTTGAAGTT
CuCumber_Cul1_Cds      CCAAGCTACAAGTCTTTTGACCTCAACCTGCCGGCAGAGATGGTAAAGTGTGTTGAAGTT
Melon_Cul1_Cds         CCAAGCTACAAGTCTTTTGACCTCAACCTGCCGGCGGAGATGGTAAAGTGTGTTGAAGTT
Tomato_Cul1_Cds        CCTAGCTACAAGTCTTTTGATCTCAACCTCCCAGCAGAAATGGTTAGGTGCGTTGAAGTA
Eggplant_Cul1_Cds      CCTAGCTACAAGTCTTTTGATCTCAACCTCCCAGCAGAAATGGTTAGGTGTGTTGAAGTA
Pepper_Cul1_Cds        CCTAGCTACAAGTCTTTTGATCTCAACCTCCCAGCAGAAATGGTTAGGTGCGTTGAAGTA
Lettuce_Cul1_Cds       CCCAGCTACAAATCTTTTGACCTAAATCTCCCTGCCGAAATGGTTAAATGCGTTGAAGTT
Chicory_Cul1_Cds       CCTAGTTACAAATCTTTTGACCTAAATCTCCCTGCAGAAATGGTCAAATGCGTTGAAGTT
Endive_Cul1_Cds        CCTAGTTACAAATCTTTTGACCTAAATCTTCCTGCAGAAATGGTCAAATGCGTTGAAGTT
Carrot_Cul1_Cds        CCAAGTTACAAATCTTTCGATCTCAACCTCCCAGCAGAGATGGTCAAATGTGTTGAAGTT
Celery_Cul1_Cds        CCTAGTTATAAATCCTTTGATCTCAACCTTCCTGCTGAGATGGTCAAGTGCGTTGAAGTA Brassica_Cul1_Cds      TTCAAAGGGTTTTATGAAACAAAGACAAAACATAGGAAACTTACCTGGATCTACTCACTA
Radish_Cul1_Cds        TTCAAAGGGTTTTATGAGACGAAAACTAAACATAGGAAACTTACATGGATCTACTCACTA
Beet_Cul1_Cds          TTTAAGCAGTTCTATTCAACTAAAACAAAGCACAGGAAGCTGACCTGGGTTTACTCATTG
Spinach_Cul1_Cds       TTTAAGCAATTTTATCAAACAAAGACAAAACACAGGAAGCTCACCTGGGTATATTCGTTG
Leek_Cul1_Cds          TTTAAAGAGTTTTACGAGACAAAAACCAAACACAGAAAACTTACATGGATTTATTCGTTG
Squash_Cul1_Cds        TTCAGGGAATTTTATCAAACAAAAACCAAGCACAGAAAACTTACGTGGATTTACTCGTTG
WaterMelon_Cul1_Cds    TTCAGAGAGTTCTATCAAACAAAAACAAAGCATAGAAAACTTACATGGATTTACTCATTG
CuCumber_Cul1_Cds      TTCAGAGAGTTTTATCAAACAAAAACCAAGCATCGAAAACTTACATGGATTTACTCATTG
Melon_Cul1_Cds         TTCAGAGAGTTTTATCAAACAAAAACCAAGCATAGAAAACTTACATGGATTTACTCATTG
Tomato_Cul1_Cds        TTTAAGGAGTTCTATCAAACAAAAACAAAGCACAGGAAACTTACGTGGATATACTCTTTG
Eggplant_Cul1_Cds      TTCAAGGAGTTTTATCAAACAAAAACGAAGCACAGGAAACTTACATGGATATACTCTTTG
Pepper_Cul1_Cds        TTCAAGGAGTTTTATCAAACAAAAACGAAGCACAGGAAACTTACGTGGATATACTCTTTG
Lettuce_Cul1_Cds       TTCAGAGAATTTTATCAAACAAAAACAAAGCACAGGAAGCTTACATGGATATATTCATTG
Chicory_Cul1_Cds       TTCAGAGAATTTTATCAAACAAAAACAAACACAGAAAACTCACATGGATATATTCATTG
Endive_Cul1_Cds        TTCAGAGAATTTTATCAAACAAAAACAAACACAGAAAACTCACATGGATTTATTCATTG
Carrot_Cul1_Cds        TTTAGAGAATTCTACCAAACAAAAACAAAGCACAGAAAACTGACATGGATATACTCTTTG
Celery_Cul1_Cds        TTTAGAGAATTTTATCAAACAAAAACGAAGCATAGAAAGCTCACATGGATATATTCTCTG
```

Fig. 690

| | |
|---|---|
| Brassica_Cul1_Cds | GGAACTTGCCACCTCAATGGGAAGTTTGATGTCAAGCCCATTGAGTTAGTTGTGTCTACA |
| Radish_Cul1_Cds | GGAACTTGTCACCTCAACGGAAAGTTTGATCACAAGCCCATTGAGTTAGTTGTGTCTACT |
| Beet_Cul1_Cds | GGAAGCTGTAATATTAATGGCAAGTTTGGTCCAAAAACTATTGAATTGGTTGTCGGAACT |
| Spinach_Cul1_Cds | GGAAGTTGTAACATTAATGGCAAGTTTGGTCCGAAAACAATTGAATTGGTTGTTGGAACT |
| Leek_Cul1_Cds | GGCACTTGCAACATCAATGGCAAGTTCGAAACCAAGACAATAGAGTTGGTTGTTACAACC |
| Squash_Cul1_Cds | GGTACCTGTAACATCAGCGGAAAATTCGAACCGAAAACGATGGAGCTGATCGTGACAACC |
| WaterMelon_Cul1_Cds | GGTACCTGTAACATCAGCGGAAAATTTGAACCGAAAACGATGGAGCTGATTGTAACAACT |
| CuCumber_Cul1_Cds | GGTACTTGTAACATCAGTGGAAAATTTGAACCGAAAACGATGGAGCTGATTGTGACAACT |
| Melon_Cul1_Cds | GGTACTTGTAACATCAGTGGAAAATTTGAACCGAAGACGATGGAGCTGATTGTGACAACA |
| Tomato_Cul1_Cds | GGAACTTGCAACATAAATGGAAAATTTGAGCCAAAAACTATTGAGCTCGTTGTCACTACT |
| Eggplant_Cul1_Cds | GGAACTTGCAACATAAATGGAAAATTTGAGGCAAAGACTATTGAGCTCGTTGTCACTACT |
| Pepper_Cul1_Cds | GGAACTTGCAATATAAATGGAAAATTTGAGCCAAAGACTATTGAGCTCGTTGTCACTACT |
| Lettuce_Cul1_Cds | GGTACCTGCAATATAAACGGGAAATTTGAACCCAAAACAATGGAGCTCATAGTCACAACC |
| Chicory_Cul1_Cds | GGCACCTGCAATATAAACGGAAAATTCGAACCAAAAACCATGGAGCTAATCGTTACAACT |
| Endive_Cul1_Cds | GGCACCTGCAATATTAACGGAAAATTCGAACCAAAAACCATGGAGCTAATCGTTACAACT |
| Carrot_Cul1_Cds | GGTACTTGTAACATCATTGGAAAATTTGATCCAAAAACCATGGAGCTTATTGTGACAACA |
| Celery_Cul1_Cds | GGTACTTGTAATATCAATGGAAAATTTGAACCCAAAACCATTGAGCTGATTGTGACAACC |

| | |
|---|---|
| Brassica_Cul1_Cds | TACCAGGCTGCTGTGCTTCTGCTGTTCAACACAACAGACAAATTGAGCTACACTGATATC |
| Radish_Cul1_Cds | TACCAGGCTGCTGTGCTTCTGCTGTTCAACACAACAGACAAATTGAGCTACAACGATATC |
| Beet_Cul1_Cds | TATCAGGCTGCTGCTTTGATGCTCTTTAACACATCAGACCGACTGAGTTATTCAGAGATA |
| Spinach_Cul1_Cds | TATCAGGCTGCTGCGCTGATGCTCTTTAACACATCAGATCGACTGAGTTATTCAGAAATA |
| Leek_Cul1_Cds | TATCAGGCTGCAGTGTTGCTTCTATTCAACTCTGCAGATAAATTAAGTTATTCTGAGATT |
| Squash_Cul1_Cds | TATCAGGCTTCTGCCCTGCTGCTTTTCAATTCCTCGGATAAACTAAGTTACTCCGAGATC |
| WaterMelon_Cul1_Cds | TATCAGGCTTCTGCCCTGCTGCTATTCAATTCCTCAGATAGATTAAGTTATTCCGAGATC |
| CuCumber_Cul1_Cds | TATCAGGCTTCTGCCCTGTTGCTATTCAATTCTTCGGATAGACTAAGTTACTCGGAAATC |
| Melon_Cul1_Cds | TATCAGGCTTCTGCCCTGTTGCTATTCAATTCTTCGGACAGACTAAGTTACTCCGAAATC |
| Tomato_Cul1_Cds | TATCAGGCTTCTGCTCTGCTGCTCTTTAATGCATCAGATAGATTGAGTTATCAGGAAATC |
| Eggplant_Cul1_Cds | TATCAGGCTTCTGCTCTGCTTCTCTTTAATGCATCAGATAGATTGAGTTATCAGGAAATC |
| Pepper_Cul1_Cds | TATCAGGCTTCTGCTCTGCTGCTCTTTAATGCATCGGATAGATTGAGTTATCAGGAAATC |
| Lettuce_Cul1_Cds | TACCAGGCATCTGCTTTATTACTGTTCAACTTATCGGATCGATTGAGTTATCAAGAAATC |
| Chicory_Cul1_Cds | TACCAGGCATCTGCTTTATTACTGTTCAACTCATCAGATCGATTGAGTTATCAAGAAATC |
| Endive_Cul1_Cds | TACCAGGCATCTGCTTTATTGTTATTCAACTCATCAGATCGATTAAGTTATCAAGAAATC |
| Carrot_Cul1_Cds | TACCAGGCCTCTGCTCTGCTGCTATTTAACTCTTCTGATAGACTTAGTTATAATGAAATA |
| Celery_Cul1_Cds | TACCAGGCCTCTGCTCTCCTGTTATTTAATACTTCTGATAGGTTGAGTTATCAAGAAATC |

Fig. 69P

| | |
|---|---|
| Brassica_Cul1_Cds | CTAACTCAGCTGAACCTGAGCCACGAAGATCTAGTGAGGTTGCTTCATTCCTTGTCATGT |
| Radish_Cul1_Cds | CTAACTCAACTGAACCTAAGCCACGAAGATTTAGTGAGGTTGCTTCATTCCCTGTCATGT |
| Beet_Cul1_Cds | GCAACTCAACTAAATTTAGCTGATGAAGATCTGGTTAGAGTGCTTCAATCTTTATCCTGC |
| Spinach_Cul1_Cds | ACGACCCAACTAAATCTAGCTGACGAAGACTTGGTTAGAGTGCTTCAATCTCTATCTTGC |
| Leek_Cul1_Cds | GTGCAGCAGCTAAACTTATCTGATGATGATGTAATCAGATTACTTCACTCTCTTTCATGC |
| Squash_Cul1_Cds | ATGACTCAATTAAACTTGAGTGACGATGATGTTGTTAGACTGCTCCACTCGTTGTCGTGT |
| WaterMelon_Cul1_Cds | ATGACACAATTAAATTTGAGTGACGATGATGTTGTTAGACTGCTCCACTCATTGTCATGT |
| CuCumber_Cul1_Cds | ATGACACAATTAAATTTGAGTGACGATGATGTAGTTAGACTACTCCACTCGTTGTCATGT |
| Melon_Cul1_Cds | ATGACACAATTAAATTTGAGTGATGATGATGTTGTTAGACTGCTCCACTCATTGTCGTGT |
| Tomato_Cul1_Cds | ATGACGCAATTAAACCTATCAGATGATGATGTTGTTCGGCTTCTTCATTCCCTTTCATGT |
| Eggplant_Cul1_Cds | ATGACGCAATTAAACCTATCAGATGATGATGTTGTTCGGCTTCTTCATTCCCTTTCATGT |
| Pepper_Cul1_Cds | ATGACGCAACTAAACCTATCAGATGATGATGTTGTTCGGCTTCTTCATTCCCTTTCATGT |
| Lettuce_Cul1_Cds | ATGACTCAGTTGAACTTGTCAGATGATGATGTTGTTAGGCTGCTCCATTCTTTGTCATGT |
| Chicory_Cul1_Cds | ATGACTCAATTAAACTTATCAGATGATGATGTTGTTAGACTACTCCATTCATTATCATGT |
| Endive_Cul1_Cds | ATGACTCAATTAAATTTATCAGATGATGATGTTGTTAGACTACTACATTCATTATCATGT |
| Carrot_Cul1_Cds | ATGACTCAGTTGAACTTGTCGGATGATGATGTTGTCAGACTACTTCATTCTCTTTCGTGT |
| Celery_Cul1_Cds | ATGACTCAGTTAAATTTGTCGGATGATGATGTTGTTCGCCTGCTTCATTCCCTTTCATGT |

| | |
|---|---|
| Brassica_Cul1_Cds | GCTAGATACAAGATTCTTCTCAAGGAGCCAAGCACAAAGACTGTTTCCCAGTCTGATTCT |
| Radish_Cul1_Cds | GCTAGGTACAAGATCCTTCTCAAGGAGCCAAGCACGAAGACTGTTACACAGACTGATTCA |
| Beet_Cul1_Cds | GCAAAGTATAAGATTCTTTTAAAGGAGCCAAACACGAAAACCGTGTCCCCGACTGATTGT |
| Spinach_Cul1_Cds | GCAAAGTATAAGATTCTTCTAAAAGAGCCAAGCACAAGAAACGTGATCTCAACTGATTGT |
| Leek_Cul1_Cds | GCTAAATACAAAATTCTCAATAAAGAACCCGCTACCAAGACTATTACCCCGAATGATCAT |
| Squash_Cul1_Cds | GCGAAGTATAAAATTCTTAACAAGGAGCCAAATACGAAAACCATCTCTCCGAACGATCAT |
| WaterMelon_Cul1_Cds | GCCAAGTATAAAATTCTTAATAAGGAGCCGAACACGAAAACCATCTCTCCGAATGATCAT |
| CuCumber_Cul1_Cds | GCCAAGTATAAAATTCTTAATAAGGAACCAAATACGAAAACCATCTCTCCGAACGATCAT |
| Melon_Cul1_Cds | GCCAAGTATAAAATTCTTAATAAGGAGCCAAATACGAAAACCATCTCACCGAACGATCAT |
| Tomato_Cul1_Cds | GCGAAGTACAAGATACTCAACAAGGAGCCAAGCACCAAAACAATTTCTCCGACTGATGTC |
| Eggplant_Cul1_Cds | GCGAAATACAAGATTCTCAACAAGGAGCCAAGCACCAAAACAATTTCTCCGACTGATGTC |
| Pepper_Cul1_Cds | GCGAAGTACAAGATTCTCAACAAGGAGCCAAGCACCAAAACAATTTCTCCGACTGATGTC |
| Lettuce_Cul1_Cds | GCAAAATACAAAATTCTTTTAAAGGAGCCTAATACCAAAACAATCTCTCCAACCGATTAC |
| Chicory_Cul1_Cds | GCAAAATATAAAATTTATTAAAAGAACCAAATACAAAAACAATCTCTCCAACTGATTTC |
| Endive_Cul1_Cds | GCAAAATATAAAATTTATTAAAAGAACCAAATACCAAAACAATATCTCCAACCGATTTC |
| Carrot_Cul1_Cds | GCAAAGTACAAGATTCTATCTAAAGAGCCGAACACCAAAACTATATCTCCAACTGATTGC |
| Celery_Cul1_Cds | GCCAAGTATAAAATTCTTACTAAAGAGCCGAACAACAAAACAATTTCCCCTACGGATTAC |

Fig. 69Q

| | |
|---|---|
| Brassica_Cul1_Cds | TTTGAATTCAACTCCAAATTCACCGACAGAATGCGGAGAATAAAGATCCCTCTCCCACCT |
| Radish_Cul1_Cds | TTTGAATTCAATGCCAAATTCACGGACAGAATGCGCAGAATCAAGATCCCTCTCCCTCCT |
| Beet_Cul1_Cds | TTTTCATTTAACTCTAGTTTCACTGACAGGATGAGGAGGATAAGAATTCCTCTTCCTCCG |
| Spinach_Cul1_Cds | TTTTCATTCAACTCTAATTTTACTGACAGAATGAGGAGGATTAGGATTCCTCTTCCTCCA |
| Leek_Cul1_Cds | TTTGAGTTCAATTCTAAATTCACTGATAGAATGAGAAGGATCAAGATTCCCCTGCCTCCT |
| Squash_Cul1_Cds | TTTGAGTTCAACGCAAAATTCTCCGACAAAATGAGGAGAATAAAGATCCCTCTTCCGCCT |
| WaterMelon_Cul1_Cds | TTTGAGTTCAATGCAAAATTCTCCGACAAAATGAGGAGAATAAAGATCCCTCTTCCGCCT |
| CuCumber_Cul1_Cds | TTTGAGTTCAATGCAAAATTCTCCGACAAAATGAGGAGAATAAAGATCCCTCTTCCGCCT |
| Melon_Cul1_Cds | TTTGAGTTCAATGCAAAATTCTCCGACAAAATGAGGAGAATAAAGATCCCTCTTCCGCCT |
| Tomato_Cul1_Cds | TTTGAGTTCAACTCAAAGTTCACTGACAAAATGAGGAGGATCAAGATACCTCTCCCTCCT |
| Eggplant_Cul1_Cds | TTTGAGTTCAACTCAAAGTTCACTGACAAAATGAGGAGGATCAAGATACCTCTCCCACCA |
| Pepper_Cul1_Cds | TTTGAGTTCAATTTTAAGTTCACTGACAAAATGAGGAGGATCAAGATACCTCTCCCTCCT |
| Lettuce_Cul1_Cds | TTCGAATTCAACTCCAAGTTTACAGATAAAATGAGGAGGATCAAGATTCCTCTACCTCCT |
| Chicory_Cul1_Cds | TTTGAATTCAACTCAAAGTTTACAGATAAAATGAGAAGGATCAAGATTCCTCTACCTCCT |
| Endive_Cul1_Cds | TTTGAATTCAACTCAAAGTTTACAGATAAAATGAGAAGGATCAAGATTCCTCTACCTCCT |
| Carrot_Cul1_Cds | TTTCAGTTCAATTCCAAATTTACTGATAAAATGAGGAGGATTAAGATTCCACTTCCCCCA |
| Celery_Cul1_Cds | TTTGAGTTCAACTCCAAGTTCACTGACAAAATGAGGAGAATTAAGATTCCACTACCTCCA |

| | |
|---|---|
| Brassica_Cul1_Cds | GTTGATGAGAGGAAGAAAGTTGTGGAAGACGTGGACAAAGACAGACGCTATGCGATTGAT |
| Radish_Cul1_Cds | GTTGATGAAAGGAAGAAGGTTGTGGAAGATGTGGACAAAGACAGACGCTATGCGATTGAT |
| Beet_Cul1_Cds | ATGGATGAGAGGAAAAAGGTTGTTGAGGATGTTGACAAAGATAGAAGATATGCTATTGAT |
| Spinach_Cul1_Cds | ATGGATGAGAGGAAAAAGGTTGTTGAAGATGTTGACAAAGATAGAAGATATGCTATTGAT |
| Leek_Cul1_Cds | GTGGATGAGAAGAAAAAGTAATTGAAGATGTTGACAAAGACAGAAGATATGCAATTGAC |
| Squash_Cul1_Cds | GTGGATGAGAAAAGAAAGTAATAGAAGATGTTGACAAGGATCGAAGATATGCTATCGAT |
| WaterMelon_Cul1_Cds | GTGGATGAGAAAAAGAAAGTCATTGAAGATGTTGACAAGGATCGAAGGTATGCTATTGAT |
| CuCumber_Cul1_Cds | GTGGATGAGAAAAAGAAAGTCATTGAAGATGTTGACAAGGATCGAAGGTATGCTATTGAC |
| Melon_Cul1_Cds | GTGGATGAGAAAAAGAAAGTCATTGAAGATGTTGACAAGGATCGAAGGTATGCTATTGAC |
| Tomato_Cul1_Cds | GTTGATGAGAAGAAAAAGGTAATTGAAGACGTTGACAAGGATAGGCGGTATGCTATAGAT |
| Eggplant_Cul1_Cds | GTTGATGAAAGAAAAAGGTAATTGAAGACGTTGACAAGGATAGGCGGTATGCTATAGAT |
| Pepper_Cul1_Cds | GTTGATGAGAAGAAAAAGGTAATTGAAGATGTTGACAAAGATAGGCGGTACGCTATAGAT |
| Lettuce_Cul1_Cds | GTGGATGAGAAGAAAAGGTGATTGAGGATGTTGACAAAGACAGACGTTATGCCATTGAT |
| Chicory_Cul1_Cds | GTTGATGAAAGAAAAAAGTAATTGAAGATGTTGACAAAGACCGACGTTATGCAATTGAT |
| Endive_Cul1_Cds | GTTGATGAAAGAAAAAAGTAATTGAAGATGTTGACAAAGATAGAAGGTATGCAATTGAT |
| Carrot_Cul1_Cds | GTGGATGAGAAGAAAAAGGTAATTGAAGATGTTGATAAAGACAGGCGATATGCTATAGAT |
| Celery_Cul1_Cds | GTTGATGAGAAGAAAAAGGTAATTGAAGATGTTGACAAGGACCGGCGATATGCCATTGAT |

Fig. 69R

| | |
|---|---|
| Brassica_Cul1_Cds | GCTGCCATTGTGAGGATCATGAAGAGCAGGAAAGTATTGGGACATCAACAACTTGTTTCT |
| Radish_Cul1_Cds | GCTGCCATTGTTAGGATCATGAAGAGCAGGAAAGTGTTGGGACATCAACAACTCGTCTCT |
| Beet_Cul1_Cds | GCCTCAATTGTACGCATAATGAAAAGTAGGAAGGTTTTGGGGTACCAGCAATTAATCACA |
| Spinach_Cul1_Cds | GCCTCAATTGTACGCATAATGAAAAGTAGGAAGGCTTTGGGATATCAACAATTAATCACG |
| Leek_Cul1_Cds | GCATCCATAGTTCGAATAATGAAAAGTAGAAAAGTTCTTGGTCATCAGCAGCTTGTTTTG |
| Squash_Cul1_Cds | GCCTCGATCGTGCGTATCATGAAGAGTAGGAAAGTTCTGGGTCACCAGCAGTTAGTGATG |
| WaterMelon_Cul1_Cds | GCCTCAATCGTGCGTATCATGAAGAGTCGGAAAGTTCTGGGTCATCAGCAGCTAGTGATG |
| CuCumber_Cul1_Cds | GCCTCAATCGTGCGTATCATGAAGAGTCGGAAAGTTCTTGGTCATCAGCAACTAGTGATG |
| Melon_Cul1_Cds | GCCTCAATCGTGCGTATCATGAAGAGTCGAAAAGTTCTTGGTCATCAGCAACTAGTGATG |
| Tomato_Cul1_Cds | GCTTCAATTGTGCGTATTATGAAGAGCCGTAAAGTATTGGGCTACCAGCAACTAGTCATG |
| Eggplant_Cul1_Cds | GCCTCAATTGTGCGTATTATGAAGAGTCGTAAAGTATTGGGCTACCAGCAACTGGTCATG |
| Pepper_Cul1_Cds | GCTTCAATTGTGCGTATTATGAAGAGTCGTAAAGTATTGGGCTACCAGCAACTGGTCATG |
| Lettuce_Cul1_Cds | GCTTCCATTGTAAGGATAATGAAGAGCAGAAAGGTGCTTGGATACCAGCAGTTGGTTATG |
| Chicory_Cul1_Cds | GCTTCAATTGTACGGATAATGAAAAGCAGAAAAGTTCTTGGATACCAACAATTGGTCATG |
| Endive_Cul1_Cds | GCTTCAATTGTACGAATAATGAAAAGCAGAAAAGTTCTTGGATACCAACAATTGGTTATG |
| Carrot_Cul1_Cds | GCTTCAATTGTCCGTATCATGAAGAGCCGCAAAGTTTTGGGTTATCAGCAGCTAGTAATG |
| Celery_Cul1_Cds | GCATCTATTGTCCGCATTATGAAGAGCCGTAAAGTTTTGGGCTACCAACAATTGGTTATG |

| | |
|---|---|
| Brassica_Cul1_Cds | GAGTGCGTTGAGCAACTTAGCCGAATGTTCAAGCCTGATATCAAGGCAATCAAGAAGCGC |
| Radish_Cul1_Cds | GAGTGCGTTGAGCAACTTAGCCGAATGTTCAAGCCTGATATCAAAGCGATCAAGAAGCGT |
| Beet_Cul1_Cds | GAGTGTGTGGAGCAGCTAAGCCGCATGTTCAAGCCTGATTTCAAGGCAATTAAGAAGAGG |
| Spinach_Cul1_Cds | GAGTGTGTGGAGCAGCTAAGCCGCATGTTCAAGCCTGATTTCAAAGCAATTAAGAAGAGG |
| Leek_Cul1_Cds | GAATGTGTTGAGCAATTAGGCCGCATGTTTAAGCCTGACTTTAAGGCCATCAAGAAAAGG |
| Squash_Cul1_Cds | GAGTGCGTCGAGCAACTGGGTCGTATGTTCAAGCCTGATTTCAAGGCGATAAAGAAGAGA |
| WaterMelon_Cul1_Cds | GAGTGCGTCGAGCAATTGGGTCGTATGTTCAAGCCCGACTTCAAAGCGATAAAGAAGAGA |
| CuCumber_Cul1_Cds | GAGTGCGTCGAGCAATTGGGCCGTATGTTCAAGCCCGATTTCAAGGCGATAAAGAAGAGA |
| Melon_Cul1_Cds | GAGTGCGTCGAGCAATTGGGTCGTATGTTCAAGCCCGATTTCAAGGCGATAAAGAAGAGA |
| Tomato_Cul1_Cds | GAGTGCGTTGAGCAGTTGGGGCGCATGTTCAAGCCTGATGTCAAAGCTATCAAGAAGAGA |
| Eggplant_Cul1_Cds | GAGTGCGTTGAGCAGTTGGGACGCATGTTCAAGCCTGATGTCAAAGCTATCAAGAAGAGA |
| Pepper_Cul1_Cds | GAGTGTGTTGAGCAGTTGGGACGTATGTTCAAGCCTGATGTCAAAGCTATCAAGAAGAGA |
| Lettuce_Cul1_Cds | GAGTGTGTTGAACAGTTGGGACGCATGTTTAAGCCTGATGTAAAAGCAATCAAGAAGCGG |
| Chicory_Cul1_Cds | GAATGTGTTGAACAATTAGGCCGTATGTTTAAGCCTGATGTAAAAGCAATCAAGAAACGT |
| Endive_Cul1_Cds | GAGTGTGTTGAACAATTAGGCCGTATGTTTAAGCCTGATGTAAAAGCAATCAAGAAGCGT |
| Carrot_Cul1_Cds | GAGTGCGTTGAACAATTGGGTCGCATGTTTAAGCCTGATGTCAAAGCAATCAAGAAGAGA |
| Celery_Cul1_Cds | GAATGTGTTGAGCAATTGGGACGCATGTTTAAGCCTGATGTCAAAGCAATTAAGAAGAGA |

Fig. 69S

```
Brassica_Cul1_Cds        ATGGAGGATTTGATAACGAGAGATTATCTGGAGAGGGACAAGGAGAACGCTAACATGTTT
Radish_Cul1_Cds          ATGGAGGATCTAATTACGAGGGATTATTTGGAGAGGGACAAGGAGAACCCTAACATGTTT
Beet_Cul1_Cds            ATCGAGGACTTAATAACCCGAGATTATATTGAAAGAGACAAGGAGAACCCGCAGCTATTC
Spinach_Cul1_Cds         ATCGAGGACTTGATAACCAGAGATTATATTGAAAGAGACAAGGAAAACCCTCAGCTATTC
Leek_Cul1_Cds            ATTGAAGATCTGATCGCTAGAGATTATTTGGAGAGGGACAAGGACAATCCAAACCTCTTT
Squash_Cul1_Cds          ATCGAAGATCTGATCACTCGTGACTATTTAGAGAGAGACAAAGACAACCCCCACTTGTTT
WaterMelon_Cul1_Cds      ATCGAAGATCTGATCACTCGGGACTATTTAGAGAGAGACAAAGACAACCCCCACTTGTTT
CuCumber_Cul1_Cds        ATTGAAGACCTGATCACTCGGGATTATCTAGAGAGAGACAAAGACAACCCCCACTTGTTT
Melon_Cul1_Cds           ATTGAAGACCTGATCACTCGGGACTATCTAGAGAGAGACAAAGACAACCCCCACTTGTTT
Tomato_Cul1_Cds          ATCGAAGATTTGATAACTAGAGATTACCTAGAGAGGGACAAAGATAATCCAAACCTGTTC
Eggplant_Cul1_Cds        ATTGAAGATCTGATAACTAGAGATTACCTAGAGAGGGACAAAGATAACCCAAACTTGTTC
Pepper_Cul1_Cds          ATTGAAGATTTGATAACTAGAGATTACCTAGAGAGGGACAAAGATAATCCGAACTTGTTC
Lettuce_Cul1_Cds         ATTGAAGATCTGATAACTCGTGATTATCTTGAAAGAGACAAAGAGAACCCCACTTGTTC
Chicory_Cul1_Cds         ATTGAAGATCTCATAACTCGTGATTATCTTGAAAGAGACAAAGAAAATCCAAATTTGTTT
Endive_Cul1_Cds          ATTGAAGATTTGATAACGCGTGATTATCTTGAAAGAGACAAAGAAAATCCAAATTTGTTT
Carrot_Cul1_Cds          ATCGAAGATTTAATAACTCGGGATTATCTGGAAAGAGACAAGGACAATGCCAACTTGTTC
Celery_Cul1_Cds          ATCGAAGATTTAATAACGCGTGATTATCTGGAAAGAGACAAGGATAATGCCAACCTTTTC Brassica_Cul1_Cds            AGGTACTTGGCTTAG
Radish_Cul1_Cds              AGGTACTTGGCTTAG
Beet_Cul1_Cds                CGATACTTGGCTTGA
Spinach_Cul1_Cds             CGGTACTTGGCTTGA
Leek_Cul1_Cds                AAATATTTGGCCTAA
Squash_Cul1_Cds              AGGTACTTGGCTTGA
WaterMelon_Cul1_Cds          AGGTACTTGGCTTGA
CuCumber_Cul1_Cds            AGGTACTTGGCTTGA
Melon_Cul1_Cds               AGGTACTTGGCTTGA
Tomato_Cul1_Cds              AAGTACTTGGCATGA
Eggplant_Cul1_Cds            AAGTACTTGGCATGA
Pepper_Cul1_Cds              AAGTACTTGGCATGA
Lettuce_Cul1_Cds             CGATACTTGGCATGA
Chicory_Cul1_Cds             CGGTACTTGGCATGA
Endive_Cul1_Cds              CGGTACTTGGCATGA
Carrot_Cul1_Cds              AGGTATCTGGCATGA
Celery_Cul1_Cds              AGATATTTGGCATGA
Endive_Cul1_Cds              CGGTACTTGGCATGA
Carrot_Cul1_Cds              AGGTATCTGGCATGA
Celery_Cul1_Cds              AGATATTTGGCATGA
```

Fig. 70A

```
beet_cul1          --MNDRKVIELEQGWEFMGKGITKLKRILEGLPEPPFNSEDYMMLYTT[I]YNMCTQKPPHD
spinach_cul1       --MNDRKVIELEQGWEFMGKGITKLKRILEGLPEPPFNSEDYMMLYTT[I]YNMCTQKPPHD
arabidopsis_cul1   ---MERKTIDLEQGWDYMQTGITKLKRILEGLNEPAFDSEQYMMLYTT[I]YNMCTQKPPHD
brassica_cul1      ---MERKTIDLDQGWDYMQTGITKLKRILEGLPEPQFDSEQYMMLYTT[I]YNMCTQKPPHD
radish_cul1        ---MERKTIDLEQGWDYMQTGITKLKRILEGLPEPQFDSEQYMMLYTT[I]YNMCTQKPPHD
leek_cul1          MSLHERKTIDLEQGWAFMQKGITKLKNILDELNEPQFSSEDYMMLYTT[I]YNMCTQKPPHD
eggplant_cul1      --MNQRSTIDLEHGWDFMQKGITKLKNILEGLPEPQFSSEDYMMLYTT[I]YNMCTQKPPHD
tomato_cul1        --MNQRSTIDLEHGWDFMQRGITKLKNILEGLPEPQFSSEDYMMLYTT[I]YNMCTQKPPHD
pepper_cul1        --MNQRSTINLEHGWDFMQRGITKLKNILEGLPEPQFSSEDYMMLYTT[I]YNMCTQKPPHD
cucumber_cul1      MTMGERKTIDLEQGWEFMQKGITKLKNILEGLPEPQFSSEDYMMLYTT[I]YNMCTQKPPHD
melon_cul1         MTMGERKTIDLEQGWEFMQKGITKLKNILEGLPEPQFSSEDYMMLYTT[I]YNMCTQKPPHD
watermelon_cul1    MTMGERKTIDLEQGWEFMQKGITKLKNILEGLPEPQFSSEDYMMLYTT[I]YNMCTQKPPHD
squash_cul1        MTMGERKTIDLEQGWEFMQKGITKLKNILEGLPEPQFSSEDYMMLYTT[I]YNMCTQKPPHD
celery_cul1        --MNERKTIDLDNGWEFMQKGITKLKKILEGQPEPQFSSEDYMMLYTT[I]YNMCTQKPPHD
lettuce_cul1       --MNERKTIDLEQGWDFMQKGITKLKNILEGLPEPQFSSEDYMMLYTT[I]YNMCTQKPPHD
endive_cul1        --MNERKTIDLEQGWDFMQKGITKLKNILEGLPEPQFSSEDYMMLYTT[I]YNMCTQKPPHD
chicory_cul1       --MNERKTIDLEQGWDFMQKGITKLKNILEGLPEPQFSSEDYMMLYTT[I]YNMCTQKPPHD
carrot_cul1        -MMIERKTIDLEQGWDFMQKGITKLKNILEGFPEPQFSSEDYMMLYTT[I]YNMCTQKPPHD beet_cul1          YSQQLYDNYKQAFVDYINSTVLPSLREKHDEFMLRELVKRWANHKVMVRWLSRFFHYLDR
spinach_cul1       YSQQLYDNYKEAFVDYIHSTVLPSLGDKHDEFMLRELVKRWSNHKVMVRWLSRFFHYLDR
arabidopsis_cul1   YSQQLYDKYREAFEEYINSTVLPALREKHDEFMLRELFKRWSNHKVMVRWLSRFFYYLDR
brassica_cul1      YSQQLYDKYREAFEEYIHSTVLPALREKHDEYMLRELVKRWSNHKVMVRWLSRFFYYLDR
radish_cul1        YSQQLYDKYREAFEEYIDSTVLPALKEKHDEYMLRELVKRWSNHKVMVRWLSRFFYYLDR
leek_cul1          YSQELYDKYRESFEEYITTTVLPSLREKHDEYMLRELVRRWSNHKIMVRWLSRFFHYLDR
eggplant_cul1      YSQQLYDKYREAFEEYITTTVLPSLREKHDEFMLRELVKRWSNHKVMVRWLSRFFHYLDR
tomato_cul1        YSQQLYDKYREAFEEYITTTVLPSLREKHDEFMLRELVKRWSNHKVMVRWLSRFFHYLDR
pepper_cul1        YSQQLYDKYREAFEEYITTTVLPSLREKHDEFMLRELVKRWSNHKVMVRWLSRFFHYLDR
cucumber_cul1      YSQQLYDKYRESFEEYITSMVLPSLREKHDEFMLRELVKRWTNHKVMVRWLSRFFHYLDR
melon_cul1         YSQQLYDKYRESFEEYITSMVLPSLREKHDEFMLRELVKRWTNHKVMVRWLSRFFHYLDR
watermelon_cul1    YSQQLYDKYRESFEEYITSMVLPSLREKHDEFMLRELVKRWTNHKVMVRWLSRFFHYLDR
squash_cul1        YSQQLYDKYRESFEEYISSMVLPSLREKHDEFMLRELVKRWTNHKVMVRWLSRFFHYLDR
celery_cul1        YSQQLYDKYREAFEEYITSTVLPSLREKHDEFMLRELVNRWTNHKVMVRWLSRFFHYLDR
lettuce_cul1       YSQQLYDKYRESFEEYITSTVLPSLREKHDEFMLRELVRRWSNHKVMVRWLSRFFHYLDR
endive_cul1        YSQQLYDKYRESFEEYITSTVLPSLREKHDEFMLRELVRRWSNHKVMVRWLSRFFHYLDR
chicory_cul1       YSQQLYDKYRESFEEYITSTVLPSLREKHDEFMLRELVRRWSNHKVMVRWLSRFFHYLDR
carrot_cul1        YSQQLYEKYREAIEEYITSTVLPSLREKHDEFMLRELVKRWSNHKVMVRWLSRFFHYLDR beet_cul1          YFIARRSLPSLNEVGLTCFRDLVYQEISGKAKDAVIALIDIEREGGQIDRSLLKNVLDIY
spinach_cul1       YFIARRSLPSLNDVGLTCFRDLVYQEISGKAKDAVIALIDEEREGGQIDRALLKNVLDIY
arabidopsis_cul1   YFIARRSLPPLNEVGLTCFRDLVYNELHSKVKQAVIALVDKEREGEQIDRALLKNVLDIY
brassica_cul1      YFIARRSLPPLNEVGLTCFRDLVYNELHSKVKDAVIALVDKEREGEQIDRALLKNVLDIY
radish_cul1        YFIARRSLPPLNEVGLTCFRDRVYKELHSKVKDAVIALVDKEREGEQIDRALLKNVLDIY
leek_cul1          YFIARRSLPALNEVGLTCFRDLVYNEVHGKVKDAVISLIDQEREGEQIDRALLKNVLGIF
eggplant_cul1      YFIARRSLPGLNEVGLTCFRDLVYQELNGKVRDAVISLIDQEREGEQIDRALLKNVLDIF
tomato_cul1        YFIARRSLPGLNEVGLTCFRDQVYQELNGKVRDAVISLIDQEREGEQIDRALLKNVLDIF
```

Fig. 70B

```
pepper_cul1        YFIARRSLPGLNEVGLTCFRDLVYQELNGKVRDAVISLIDQEREGEQIDRALLKNVLDIF
cucumber_cul1      YFIARRSLPPLNEVGLTCFRELVYKELNSKVRDAVISLIDQEREGEQIDRALLKNVLDIF
melon_cul1         YFIARRSLPPLNEVGLTCFRELVYKELNSKVRDAVISLIDQEREGEQIDRALLKNVLDIF
watermelon_cul1    YFIARRSLPPLNEVGLTCFRELVYKELNSKVRDAVISLIDQEREGEQIDRALLKNVLDIF
squash_cul1        YFIARRSLPPLNEVGLTCFRELVYKELNSKVRDAVISLIDQEREGEQIDRALLKNVLDIF
celery_cul1        YFIARRSLPALHEVGLTCFRDLVYQELKVKVRDAVISLIDQEREGEQIDRALLKNVLDIF
lettuce_cul1       YFIARRSLPPLNEVGLACFRDLVYQEVNGKVRDAVISLIDQEREGEQIDRALLKNVLDIF
endive_cul1        YFIARRSLPPLNEVGLACFRDLVYQEVNGKVRDAVISLIDQEREGEQIDRALLKNVLDIF
chicory_cul1       YFIARRSLPPLNEVGLACFRDLVYQEVNGKVRDAVISLIDQEREGEQIDRALLKNVLDIF
carrot_cul1        YFIARRSLPPLHEVGLTCFRDLVYQEINGKVRDAVISLINQEREGEQIDRALLKNVLDIF beet_cul1          VEIGMGQMDHYEKDFEAHMLDDTAAYYSRKASSWILEDSCPEYMLKSEECLKKEKERVAN
spinach_cul1       VEIGMTQMDYYEKDFEAHMLDDTAAYYSRKASSWILEDSCPEYMLKSEECLKKEKDRVAH
arabidopsis_cul1   VEIGMGQMERYEEDFESFMLQDTSSYYSRKASSWIQEDSCPDYMLKSEECLKKERERVAH
brassica_cul1      VEIGMGQMERYEEDFESFMLLDSASYYSRKASSWIQEDSCPDYMLKSEECLKKERERVAH
radish_cul1        VEIGMGQMERYEVDFESFMLLDSASYYSRKASNWIQEDSCPDYMLKSEECLKKERERVAH
leek_cul1          VEIGLGSMECYENDFETSMLNATAAYYSRKASNWILEDSCPDYMLKAEECLKHEKDRVAH
eggplant_cul1      VEIGMGSMDYYENDFEAAMLKDTAAYYSRKASNWILEDSCPDYMLKAEECLKREKDRVSH
tomato_cul1        VEIGMGLMDYYENDFEAAMLKDTAAYYSRKASNWILEDSCPDYMLKAEECLKREKDRVSH
pepper_cul1        VEIGMGSMDYYENDFEAAMLKDTAAYYSRKASNWILEDSCPDYMLKAEECLKREKDRVSH
cucumber_cul1      VEIGMGQMDYYENDFEAAMLKDTAAYYSRKASNWILEDSCPDYMLKAEECLKREKDRVSH
melon_cul1         VEIGMGQMDYYENDFEAAMLKDTAAYYSRKASNWILEDSCPDYMLKAEECLKREKDRVSH
watermelon_cul1    VEIGMGQMDYYENDFEAAMLKDTAAYYSRKASNWILEDSCPDYMLKAEECLKREKDRVSH
squash_cul1        VEIGMGQMDYYENDFEAAMLKDTAAYYSRKASNWILEDSCPDYMLKAEECLRREKDRVSH
celery_cul1        VEIGMSQMDQYENDFEEAMLTDTAAYYSRKASNWILEDSCPDYMLKAEECLRREKDRVSH
lettuce_cul1       VEIGMGQMEYYENDFEASMLNDTAAYYSRKASNWILEDSCPDYMLKAEECLKREKDRVSH
endive_cul1        VEIGMGQMEYYENDFEASMLNDTAAYYSRKASNWILEDSCPDYMLKAEECLKREKDRVSH
chicory_cul1       VEIGMGQMEYYENDFEASMLNDTAAYYSRKASNWILEDSCPDYMLKAEECLKREKDRVSH
carrot_cul1        VEVGMSQMDYYENDFEADMLKDTAAYYSRKASNWILEDSCPDYMLKAEECLRREKDRVSN beet_cul1          YLHSSSEPKLLEKVQNELLLVYESQLLEKENSGCRALLKDDKVDDLSRMYRLYSKVTKGL
spinach_cul1       YLHSSSEPKLLEKVQNELLLVYENQLLEKENSGCRALLKDDKVEDLSRMYRLYSKVTKGL
arabidopsis_cul1   YLHSSSEPKLVEKVQHELLVVFASQLLEKEHSGCRALLRDDKVDDLSRMYRLYHKILRGL
brassica_cul1      YLHSSSEPKLVEKVQHELLVVYANQLLEKEHSGCRALLRDDKVDDLSRMYRLYHKIVKGL
radish_cul1        YLHSSSEPKLVEKVQHELLVVYANQLLEKEHSGCRALLRDDKVDDLSRMYRLYHKIAKGL
leek_cul1          YLHSSSEQKLLEKVQHELLFVYASQLLEKEHSGCHALLRDDKVGDLSRMYRLFCRITRGL
eggplant_cul1      YLHSSSETKLLEKVQHELLSVYANQLLEKEHSGCHALLRDDKVDDLSRMYRLFSKIPRGL
tomato_cul1        YLHSSSETKLLEKVQHELLSVYATQLLEKEHSGCHALLRDDKVEDLSRMYRLFSKISRGL
pepper_cul1        YLHLSSETKLLEKVQHELLSVYATQLLEKEHSGCHALLRDDKVEDLSRMYRLFSKIPRGL
cucumber_cul1      YLHSSSEPKLLEKVQHELLSVYATQLLEKEHSGCHALLRDDKVEDLSRMFRLFSKIPKGL
melon_cul1         YLHSSSEPKLLEKVQHELLSVYATQLLEKEHSGCHALLRDDKVEDLSRMFRLFSKIPKGL
watermelon_cul1    YLHSSSEPKLLEKVQHELLSVYATQLLEKEHSGCHALLRDDKVEDLSRMFRLFSKIPKGL
squash_cul1        YLHSSSEPKLLEKVQHELLSVYATQLLEKEHSGCHALLRDDKVEDLSRMFRLFSKIPKGL
celery_cul1        YLHFSSEPKLLEKVQHELLSVYATQLLEKEHSGCHALLRDDKVDDLSRMYRLFSKIPKGL
lettuce_cul1       YLHSSSEPKLLEKVQNELLSVYATQLLEKEHSGCHALLRDDKVDDLSRMYRLFSKIPKGL
endive_cul1        YLHSSSEPKLLEKVQTELLSVYATQLLEKEHSGCHALLRDDKVDDLSRMYRLFSKIQKGL
```

Fig. 70C

```
chicory_cul1         YLHSSSEPKLLEKVQTELLSVYATQLLEKEHSGCHALLRDDKVDDLSRMYRLFSKIQKGL
carrot_cul1          YLHSSSEPKLLEKVQHELLSHYATQLLEKEHSGCHALLRDDKVADLSRMYRLFSKIPRGL beet_cul1            EPIGSIFKQHITDEGTALVQQAEDAAISKAENT--G-GSHEQVFVRKVIELHDKFMTYVT
spinach_cul1         EPIGSIFKQHITDEGTALVQQAEDAAISKAENA--GGGSHEQVFVRKVIELHDKFMTYVT
arabidopsis_cul1     EPVANIFKQHVTAEGNALVQQAEDTATNQVAN---TASVQEQVLIRKVIELHDKYMVYVT
brassica_cul1        EPVANIFKQHVTAEGNALVQQAEDTATNHAAN---TASVQEQVLIRKVIELHDKYMVYVV
radish_cul1          EPVANIFKQHVTAEGNALVQQAEDTATNQAAN---TASVQEQVLIRKVIELHDKYMVYVV
leek_cul1            DPVSQIFKQHVTAEGTALVKHAEDAASNKKAEKKDIVGLQEQVFVRKVIELHDKYLAYVT
eggplant_cul1        EPVANIFKQHVTAEGTALVKQAEDAASNKKAEKRDVVGLQEQVFVRKVIELHDKYLAYVN
tomato_cul1          DPVANIFKQHVTAEGTALVKQAEDAASNKKAEKRDVVGLQEQVFVRKVIELHDKYLAYVN
pepper_cul1          DPVANIFKQHVTAEGTALVKQAEDAASNKKAEKRDVVGLQEQIFVRKVIELHDKYMAYVN
cucumber_cul1        DPVSNIFKQHVTAEGTALVKQAEDAASNKKAEKKDIVGLQEQVFVRKVIELHDKYLAYVN
melon_cul1           DPVSNIFKQHVTAEGTALVKQAEDAASNKKAEKKDIVGLQEQVFVRKVIELHDKYLAYVN
watermelon_cul1      DPVSNIFKQHVTAEGTALVKQAEDAASNKKAEKKDIVGLQEQVFVRKVIELHDKYLAYVN
squash_cul1          DPVSNIFKQHVTAEGTALVKQAEDAASNKKAEKKDIVGLQEQVFVRKVIELHDKYLAYVN
celery_cul1          DPVSYIFKQHVTNEGMALVKQAEDAASNKKAEKRDVVSLQEQVFVRKIIELHDKYLAYVN
lettuce_cul1         DPVSSMFKQHVTAEGTTLVKQAEDAASTKKAEKRDVVGLQEQVFVRKVIELHDKYLAYVN
endive_cul1          DPVSSMFKQHVTAEGTTLVKQAEDAASTKKAEKRDVVGLQEQVFVRKVIELHDKYLAYVN
chicory_cul1         DPVSSMFKQHVTAEGTTLVKQAEDAASTKKAEKRDVVGLQEQVFVRKVIELHDKYLAYVN
carrot_cul1          DPVSNIFKQHVTAEGTALVKQAEDAASNKKAEKRDVVGLQEQVFVRKIIELHDKYLTYVN beet_cul1            DCFNSHTIFHKALKEAFEVFLNKGVAGSSSAELLATFCDNILKKGGSEKLSDEAIEDSLE
spinach_cul1         DCFNSHTIFHKALKEAFEVFLNKGVAGSSSAELLASFCDNILKKGGSEKLSDEAIEDSLE
arabidopsis_cul1     ECFQNHTLFHKALKEAFEIFCNKTVAGSSSAELLATFCDNILKKGGSEKLSDEAIEDTLE
brassica_cul1        ECFQNHTLFHKALKEAFEIFCNKTVAGSSSAELLATFCDNILKKGGSEKLSDEAIEDTLE
radish_cul1          ECFQNHTLFHKALKEAFEIFCNKTVAGSSSAELLATFCDNILKKGGSEKLSDEAIEDTLE
leek_cul1            DCFQNHSLFHKALKEAFEVFCNKGVAGSSSAELLAAFCDNILKKGGSEKLSDEAIEDTLE
eggplant_cul1        NCFQNHTLFHKALKEAFELFCNKGVAGSSNAELLATFCDNILKKGGSEKLSDEAIEETLE
tomato_cul1          NCFQNHTLFHKALKEAFELFCNKGVAGSSSAELLATFCDNILKKGGSEKLSDEAIEETLE
pepper_cul1          NCFQNHTLFHKALKEAFELFCNKGVAGSSSAELLATFCDNILKKGGSEKLSDEAIEETLE
cucumber_cul1        DCFQNHTLFHKALKEAFEVFCNKGVAGSSSAELLATFCDNILKKGGSEKLSDEAIEETLE
melon_cul1           DCFQNHTLFHKALKEAFEVFCNKGVAGSSSAELLATFCDNILKKGGSEKLSDEAIEETLE
watermelon_cul1      DCFQNHTLFHKALKEAFEVFCNKGVAGSSSAELLATFCDNILKKGGSEKLSDEAIEETLE
squash_cul1          DCFQNHTLFHKALKEAFEVFCNKGVAGSSSAELLATFCDNILKKGGSEKLSDEAIEETLE
celery_cul1          DCFTNHTLFHKALKEAFEIFCNKGVAGSSNAELLATFCDNILKKGGSEKLSDEAIEETLE
lettuce_cul1         DCFMNHTLFHKALKEAFEIFCNKGVAGSSSAELLATFCDNILKKGGSEKLSDEAIEDTLE
endive_cul1          DCFMNHTLFHKALKEAFEIFCNKGVAGSSSAELLATFCDNILKKGGSEKLSDEAIEDTLE
chicory_cul1         DCFMNHTLFHKALKEAFEIFCNKGVAGSSSAELLATFCDNILKKGGSEKLSDEAIEDTLE
carrot_cul1          DCFTNHTLFHKALKEAFEIFCNKGVSGSSSAELLATFCDNILKKGGSEKLSDEAIEETLE beet_cul1            KVVKLLAYVSDKDLFAEFYRKKLSRRLLFDKSANDDHERSILTKLKQQCGGQFTSKMEGM
spinach_cul1         KVVKLLAYVSDKDLFAEFYRKKLSRRLLFDKSANDDHERSILTKLKQQCGGQFTSKMEGM
arabidopsis_cul1     KVVKLLAYISDKDLFAEFYRKKLARRLLFDRSANDDHERSILTKLKQQCGGQFTSKMEGM
brassica_cul1        KVVKLLAYISDKDLFAEFYRKKLARRLLFDRSANDDHERSILTKLKQQCGGQFTSKMEGM
```

Fig. 70D

```
radish_cul1        KVVKLLAYISDKDLFAEFYRKKLARRLLFDRSANDDHERSILTKLKQQCGGQFTSKMEGM
leek_cul1          KVVKLLAYISDKDLFAEFYRKKLARRLLFDKSANDDHERSILTKLKQQCGGQFTSKMEGM
eggplant_cul1      KVVKLLAYISDKDLFAEFYRKKLARRLLFDKSANDEHERSILTKLKQQCGGQFTSKMEGM
tomato_cul1        KVVKLLAYISDKDLFAEFYRKKLARRLLFDKSANDEHERSILTKLKQQCGGQFTSKMEGM
pepper_cul1        KVVKLLAYISDKDLFAEFYRKKLARRLLFDKSANDEHERSILTKLKQQCGGQFTSKMEGM
cucumber_cul1      KVVKLLAYICDKDLFAEFYRKKLARRLLFDKSANDDHERSILTKLKQQCGGQFTSKMEGM
melon_cul1         KVVKLLAYICDKDLFAEFYRKKLARRLLFDKSANDDHERSILTKLKQQCGGQFTSKMEGM
watermelon_cul1    KVVKLLAYICDKDLFAEFYRKKLARRLLFDKSANDDHERSILTKLKQQCGGQFTSKMEGM
squash_cul1        KVVKLLAYICDKDLFAEFYRKKLARRLLFDKSANDDHERSILTKLKQQCGGQFTSKMEGM
celery_cul1        KVVKLLAYISDKDLFAEFYRKKLARRLLFDKSANDEHERSILTKLKQQCGGQFTSKMEGM
lettuce_cul1       KVVKLLAYISDKDLFAEFYRKKLARRLLFDKSANDEHERSILTKLKQQCGGQFTSKMEGM
endive_cul1        KVVKLLAYISDKDLFAEFYRKKLARRLLFDKSANDEHERSILTKLKQQCGGQFTSKMEGM
chicory_cul1       KVVKLLAYISDKDLFAEFYRKKLARRLLFDKSANDEHERSILTKLKQQCGGQFTSKMEGM
carrot_cul1        KVVRLLAYISDKDLFAEFYRKKLARRLLFDKSANDEHERSILTKLKQQCGGQFTSKMEGM beet_cul1          VTDLTLARENQTNFEEYLSQNPDASPGLDLTVTVLTTGFWPSYKSSDLNLPAEMVRCVEV
spinach_cul1       VTDLTLARENQTNFEEYLGQNTDASPGLDLTVTVLTTGFWPSYKSSDLNLPAEMVRCVEV
arabidopsis_cul1   VTDLTLARENQNSFEDYLGSNPAANPGIDLTVTVLTTGFWPSYKSFDINLPSEMIKCVEV
brassica_cul1      VTDLTLARENQNSFEEYLGNNPAANPGIDLTVTVLTTGFWPSYKSFDINLPAEMVKCVEV
radish_cul1        VTDLTLARENQTSFEEYLGNNPAANPGIDLTVTVLTTGFWPSYKSFDINLPSEMVKCVEV
leek_cul1          VTDLTLARENQSSFDDYLSSNPKANSGIDLTVTVLTTGFWPSYKSFDLNLPDEMVKCVEI
eggplant_cul1      VTDLTLARENQASFEEYLSNNPTANPGIDLTVTVLTTGFWPSYKSFDLNLPAEMVRCVEV
tomato_cul1        VTDLTLARENQASFEEYLSNNPIANPGIDLTVTVLTTGFWPSYKSFDLNLPAEMVRCVEV
pepper_cul1        VTDLTLARENQASFEEYLSNNPAANPGIDLTVTVLTTGFWPSYKSFDLNLPAEMVRCVEV
cucumber_cul1      VTDLTLARENQTSFEEYLSNNPQASPGIDLTVTVLTTGFWPSYKSFDLNLPAEMVKCVEV
melon_cul1         VTDLTLARENQTSFEEYLSNNPQASPGIDLTVTVLTTGFWPSYKSFDLNLPAEMVKCVEV
watermelon_cul1    VTDLTLARENQTSFEEYLSNNPQASPGIDLTVTVLTTGFWPSYKSFDLNLPAEMVKCVEV
squash_cul1        VTDLTLARENQTSFEEYLSNNPQASPGIDLTVTVLTTGFWPSYKSFDLNLPAEMVKCVEV
celery_cul1        VTDLTLAKENQSSFEEYLGNNANVNPGIDLTVTVLTTGFWPSYKSFDLNLPAEMVKCVEV
lettuce_cul1       VTDLTLAKENQSHFEEYLNNNPNVSPGIDLTVTVLTTGFWPSYKSFDLNLPAEMVKCVEV
endive_cul1        VTDLTLAKENQSHFEEYLNNNPNVSPGIDLTVTVLTTGFWPSYKSFDLNLPAEMVKCVEV
chicory_cul1       VTDLTLAKENQSHFEEYLNNNPNVSPGIDLTVTVLTTGFWPSYKSFDLNLPAEMVKCVEV
carrot_cul1        VTDLTLAKENQSNFEEYLNNNSNVNPGIDLTVTVLTTGFWPSYKSFDLNLPAEMVKCVEV beet_cul1          FKQFYSTKTKHRKLTWVYSLGSCNINGKFGPKTIELVVGTYQAAALMLFNTSDRLSYSEI
spinach_cul1       FKQFYQTKTKHRKLTWVYSLGSCNINGKFGPKTIELVVGTYQAAALMLFNTSDRLSYSEI
arabidopsis_cul1   FKGFYETKTKHRKLTWIYSLGTCHINGKFDQKAIELIVSTYQAVLLLFNTTDKLSYTEI
brassica_cul1      FKGFYETKTKHRKLTWIYSLGTCHLNGKFDVKPIELVVSTYQAVLLLFNTTDKLSYTDI
radish_cul1        FKGFYETKTKHRKLTWIYSLGTCHLNGKFDHKPIELVVSTYQAVLLLFNTTDKLSYNDI
leek_cul1          FKEFYETKTKHRKLTWIYSLGTCNINGKFETKTIELVVTTYQAVLLLFNSADKLSYSEI
eggplant_cul1      FKEFYQTKTKHRKLTWIYSLGTCNINGKFEAKTIELVVTTYQASALLLFNASDRLSYQEI
tomato_cul1        FKEFYQTKTKHRKLTWIYSLGTCNINGKFEPKTIELVVTTYQASALLLFNASDRLSYQEI
pepper_cul1        FKEFYQTKTKHRKLTWIYSLGTCNINGKFEPKTIELVVTTYQASALLLFNASDRLSYQEI
cucumber_cul1      FREFYQTKTKHRKLTWIYSLGTCNISGKFEPKTMELIVTTYQASALLLFNSSDRLSYSEI
melon_cul1         FREFYQTKTKHRKLTWIYSLGTCNISGKFEPKTMELIVTTYQASALLLFNSSDRLSYSEI
watermelon_cul1    FREFYQTKTKHRKLTWIYSLGTCNISGKFEPKTMELIVTTYQASALLLFNSSDRLSYSEI
```

Fig. 70E

```
squash_cul1       FREFYQTKTKHRKLTWIYSLGTCNISGKFEPKTMELIVTTYQASALLLFNSSDKLSYSEI
celery_cul1       FREFYQTKTKHRKLTWIYSLGTCNINGKFEPKTIELIVTTYQASALLLFNTSDRLSYQEI
lettuce_cul1      FREFYQTKTKHRKLTWIYSLGTCNINGKFEPKTMELIVTTYQASALLLFNLSDRLSYQEI
endive_cul1       FREFYQTKTKHRKLTWIYSLGTCNINGKFEPKTMELIVTTYQASALLLFNSSDRLSYQEI
chicory_cul1      FREFYQTKTKHRKLTWIYSLGTCNINGKFEPKTMELIVTTYQASALLLFNSSDRLSYQEI
carrot_cul1       FREFYQTKTKHRKLTWIYSLGTCNIIGKFDPKTMELIVTTYQASALLLFNSSDRLSYNEI beet_cul1         ATQLNLADEDLVRVLQSLSCAKYKILLKEPNTKTVSPTDCFSFNSSFTDRMRRIRIPLPP
spinach_cul1      TTQLNLADEDLVRVLQSLSCAKYKILLKEPSTRNVISTDCFSFNSNFTDRMRRIRIPLPP
arabidopsis_cul1  LAQLNLSHEDLVRLLHSLSCAKYKILLKEPNTKTVSQNDAFEFNSKFTDRMRRIKIPLPP
brassica_cul1     LTQLNLSHEDLVRLLHSLSCARYKILLKEPSTKTVSQSDSFEFNSKFTDRMRRIKIPLPP
radish_cul1       LTQLNLSHEDLVRLLHSLSCARYKILLKEPSTKTVTQTDSFEFNAKFTDRMRRIKIPLPP
leek_cul1         VQQLNLSDDDVIRLLHSLSCAKYKILNKEPATKTITPNDHFEFNSKFTDRMRRIKIPLPP
eggplant_cul1     MTQLNLSDDDVVRLLHSLSCAKYKILNKEPSTKTISPTDVFEFNSKFTDKMRRIKIPLPP
tomato_cul1       MTQLNLSDDDVVRLLHSLSCAKYKILNKEPSTKTISPTDVFEFNSKFTDKMRRIKIPLPP
pepper_cul1       MTQLNLSDDDVVRLLHSLSCAKYKILNKEPSTKTISPTDVFEFNFKFTDKMRRIKIPLPP
cucumber_cul1     MTQLNLSDDDVVRLLHSLSCAKYKILNKEPNTKTISPNDHFEFNAKFSDKMRRIKIPLPP
melon_cul1        MTQLNLSDDDVVRLLHSLSCAKYKILNKEPNTKTISPNDHFEFNAKFSDKMRRIKIPLPP
watermelon_cul1   MTQLNLSDDDVVRLLHSLSCAKYKILNKEPNTKTISPNDHFEFNAKFSDKMRRIKIPLPP
squash_cul1       MTQLNLSDDDVVRLLHSLSCAKYKILNKEPNTKTISPNDHFEFNAKFSDKMRRIKIPLPP
celery_cul1       MTQLNLSDDDVVRLLHSLSCAKYKILTKEPNNKTISPTDYFEFNSKFTDKMRRIKIPLPP
lettuce_cul1      MTQLNLSDDDVVRLLHSLSCAKYKILLKEPNTKTISPTDYFEFNSKFTDKMRRIKIPLPP
endive_cul1       MTQLNLSDDDVVRLLHSLSCAKYKILLKEPNTKTISPTDFFEFNSKFTDKMRRIKIPLPP
chicory_cul1      MTQLNLSDDDVVRLLHSLSCAKYKILLKEPNTKTISPTDFFEFNSKFTDKMRRIKIPLPP
carrot_cul1       MTQLNLSDDDVVRLLHSLSCAKYKILSKEPNTKTISPTDCFQFNSKFTDKMRRIKIPLPP beet_cul1         MDERKKVVEDVDKDRRYAIDASIVRIMKSRKVLGYQQLITECVEQLSRMFKPDFKAIKKR
spinach_cul1      MDERKKVVEDVDKDRRYAIDASIVRIMKSRKALGYQQLITECVEQLSRMFKPDFKAIKKR
arabidopsis_cul1  VDERKKVVEDVDKDRRYAIDAAIVRIMKSRKVLGHQQLVSECVEQLSRMFKPDIKAIKKR
brassica_cul1     VDERKKVVEDVDKDRRYAIDAAIVRIMKSRKVLGHQQLVSECVEQLSRMFKPDIKAIKKR
radish_cul1       VDERKKVVEDVDKDRRYAIDAAIVRIMKSRKVLGHQQLVSECVEQLSRMFKPDIKAIKKR
leek_cul1         VDEKKKVIEDVDKDRRYAIDASIVRIMKSRKVLGHQQLVLECVEQLGRMFKPDFKAIKKR
eggplant_cul1     VDEKKKVIEDVDKDRRYAIDASIVRIMKSRKVLGYQQLVMECVEQLGRMFKPDVKAIKKR
tomato_cul1       VDEKKKVIEDVDKDRRYAIDASIVRIMKSRKVLGYQQLVMECVEQLGRMFKPDVKAIKKR
pepper_cul1       VDEKKKVIEDVDKDRRYAIDASIVRIMKSRKVLGYQQLVMECVEQLGRMFKPDVKAIKKR
cucumber_cul1     VDEKKKVIEDVDKDRRYAIDASIVRIMKSRKVLGHQQLVMECVEQLGRMFKPDFKAIKKR
melon_cul1        VDEKKKVIEDVDKDRRYAIDASIVRIMKSRKVLGHQQLVMECVEQLGRMFKPDFKAIKKR
watermelon_cul1   VDEKKKVIEDVDKDRRYAIDASIVRIMKSRKVLGHQQLVMECVEQLGRMFKPDFKAIKKR
squash_cul1       VDEKKKVIEDVDKDRRYAIDASIVRIMKSRKVLGHQQLVMECVEQLGRMFKPDFKAIKKR
celery_cul1       VDEKKKVIEDVDKDRRYAIDASIVRIMKSRKVLGYQQLVMECVEQLGRMFKPDVKAIKKR
lettuce_cul1      VDEKKKVIEDVDKDRRYAIDASIVRIMKSRKVLGYQQLVMECVEQLGRMFKPDVKAIKKR
endive_cul1       VDEKKKVIEDVDKDRRYAIDASIVRIMKSRKVLGYQQLVMECVEQLGRMFKPDVKAIKKR
chicory_cul1      VDEKKKVIEDVDKDRRYAIDASIVRIMKSRKVLGYQQLVMECVEQLGRMFKPDVKAIKKR
carrot_cul1       VDEKKKVIEDVDKDRRYAIDASIVRIMKSRKVLGYQQLVMECVEQLGRMFKPDVKAIKKR
```

Fig. 70F

```
beet_cul1          IEDLITRDYIERDKENPQLFRYLA
spinach_cul1       IEDLITRDYIERDKENPQLFRYLA
arabidopsis_cul1   MEDLITRDYLERDKENPNMFRYLA
brassica_cul1      MEDLITRDYLERDKENANMFRYLA
radish_cul1        MEDLITRDYLERDKENPNMFRYLA
leek_cul1          IEDLIARDYLERDKDNPNLFKYLA
eggplant_cul1      IEDLITRDYLERDKDNPNLFKYLA
tomato_cul1        IEDLITRDYLERDKDNPNLFKYLA
pepper_cul1        IEDLITRDYLERDKDNPNLFKYLA
cucumber_cul1      IEDLITRDYLERDKDNPHLFRYLA
melon_cul1         IEDLITRDYLERDKDNPHLFRYLA
watermelon_cul1    IEDLITRDYLERDKDNPHLFRYLA
squash_cul1        IEDLITRDYLERDKDNPHLFRYLA
celery_cul1        IEDLITRDYLERDKDNANLFRYLA
lettuce_cul1       IEDLITRDYLERDKENPNLFRYLA
endive_cul1        IEDLITRDYLERDKENPNLFRYLA
chicory_cul1       IEDLITRDYLERDKENPNLFRYLA
carrot_cul1        IEDLITRDYLERDKDNANLFRYLA
```

MODIFIED CULLIN1 GENE

RELATED APPLICATIONS AND INCORPORATION BY REFERENCE

This application is a continuation of U.S. application Ser. No. 15/892,500 filed Feb. 9, 2018, which is a continuation-in-part application of international patent application Serial No. PCT/EP2016/071177 filed 8 Sep. 2016, which published as PCT Publication No. WO 2017/042270 on 16 Mar. 2017, which claims benefit of Dutch patent application Serial No. 2015409 filed 8 Sep. 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Feb. 8, 2018, is named 43104002349_SL.txt and is 322,107 bytes in size.

FIELD OF THE INVENTION

The present invention relates to a plant type that enables efficient cultivation, and to methods for identifying and developing such a plant. The present invention also relates to a plant type suitable for situations that require smaller portions, or reduces the labour, time and expenses involved with storing, handling and transporting of redundant plant leaves, and to methods for identifying and developing such plant.

BACKGROUND OF THE INVENTION

Plant breeders are continuously looking for more efficient ways to cultivate plants. One way to increase the efficiency is by high-wire cultivation. In the high-wire cultivation, higher planting densities are used to obtain higher yields per $m^2$. In addition, high-wire cultivation allows a longer cultivation period during which the plant produces fruits. Cucumber and tomato are crops that are suitable for high-wire cultivation. However, not all varieties are fit for this type of cultivation.

More efficient cultivation can also be achieved in other crops if the plants have a compact growth phenotype. Such a compact growth phenotype may be characterized by the plants showing shorter internodes and/or a smaller leave area. Because of this compact growth phenotype, the plants can be planted in higher densities, thereby saving a lot of space.

It is one goal of the present invention to provide a plant type that enables efficient cultivation. This goal has been achieved by providing a plant type showing a compact growth phenotype.

In the research leading to the present invention, it was found that a mutation in the Cullin1 gene leads to a modification in plant type that may be expressed as a compact growth phenotype. A plant that has the mutant gene is in particular suitable for efficient cultivation. Such a plant shows a shorter internode length and/or a smaller leaf area and may also display other characteristics that lead to a compact growth phenotype.

Cullin proteins are a family of proteins present in all eukaryotes, not only plants. The Cullin proteins combine with RING proteins to form so-called Cullin-RING ubiquitine ligases (CRLs). In general, Cullin proteins play an important role in protein ubiquitination and protein degradation.

Ubiquitination (also known as ubiquitylation) is an enzymatic, post-translational modification process in which an ubiquitin protein is ligated to substrate protein.

Ubiquitine is a highly conserved, small polypeptide, ubiquitously distributed among eukaryotes. An ATP-dependent reaction cascade (involving the sequential action of ubiquitine-activating (E1s), ubiquitine-conjugating (E2s) and ubiquitine-protein ligase (E3s) enzymes) performs the ligation of ubiquitine to other proteins. Proteins that are ligated with ubiquitine are subsequently degraded and broken down, or relocated.

The Cullin1 protein, which is a member of the Cullin protein family, is one out of the four subunits that make up the SCF complex. The abbreviation SCF stands for SKP1-CUL1-F-box protein E3 ubiquitin ligase complex, which mediates the ubiquitination of proteins involved in cell cycle progression, signal transduction and transcription. In the SCF complex, Cullin1 serves as a rigid scaffold that organizes the SKP1-F-box protein and RBX1 subunits. It may contribute to catalysis through positioning of the substrate and the ubiquitin-conjugating enzyme.

Citation or identification of any document in this application is not an admission that such document is available as prior art to the present invention.

SUMMARY OF THE INVENTION

Cullin proteins are present in all eukaryotes. Through its involvement in ubiquitination and subsequent processes it is engaged in a wide range of cellular processes. Surprisingly, the mutation of the invention causes shorter internode length and/or smaller leaf area without causing a deleterious effect on the plant, which would be expected based on the state of the art knowledge available on the conserved status of Cullin1 protein and its functionality.

The characterisation of the modified Cullin1 gene in the present research was performed in cucumber (*Cucumis sativus*). This enabled the identification of further crops having a Cullin1 gene, which when modified leads to plants with a compact growth phenotype, i.e. showing shorter internode length and/or a smaller leaf area, or a reduction in other plant parts when compared to plants not having the modified Cullin1 gene. These crops include those belonging to the family of Cucurbitacea, such as for instance melon (*Cucumis melo*), watermelon (*Citrullus lanatus*), and squash (*Cucurbita pepo*); fruit crops, such as pepper (*Capsicum annuum*), tomato (*Solanum lycopersicum*), and eggplant (*Solanum melongena*); leafy vegetables, such as lettuce (*Lactuca sativa*), spinach (*Spinacia oleracea*), chicory (*Cichorium intybus*), and cabbage (*Brassica oleracea*); root vegetables, such as for instance carrot (*Daucus carota*), radish (*Raphanus sativus*), and beetroot (*Beta vulgaris*); and other crops, such as celery (*Apium graveolens*) and leek (*Allium ampeloprasum*).

It is another goal of the present invention to provide a plant type that is suitable for situations that require smaller portions, or reduces the labour, time and expenses involved with storing, handling and transporting of redundant plant leaves.

The invention thus relates to a modified Cullin1 gene which may comprise a modification in the wild type Cullin1 nucleotide sequence which leads to a modification in the wild type Cullin1 amino acid sequence.

The Cullin1 gene can be modified by different means known in the art, including mutagenesis. Mutagenesis may comprise the random introduction of at least one modification to DNA by means of one or more chemical compounds, such as ethyl methanesulphonate (EMS), nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements. Mutagenesis also may comprise the more specific, targeted introduction of at least one modification by means of homologous recombination, oligonucleotide-based mutation induction, zinc-finger nucleases (ZFNs), transcription activator-like effector nucleases (TALENs) or Clustered Regularly Interspaced Short Palindromic Repeat (CRISPR) systems.

The modified Cullin1 gene may be an exogenous Cullin1 gene introduced into a plant by a transgenic method or a cisgenic method. Use of a modified Cullin1 gene of the invention for developing a plant that shows a compact growth phenotype, i.e. may comprise shorter internodes and/or smaller leaf area, may comprise the introduction of a modified exogenous Cullin1 gene by a transgenic or a cisgenic method.

The modified Cullin1 gene may be part of a gene construct, which gene construct may comprise a selectable marker, a promoter sequence, a Cullin1 gene sequence, and a terminator sequence.

The present invention is widely applicable to all plant species that have a functional orthologue of the Cullin1 gene in their genome, i.e. an orthologue that performs the same or a similar biological function. Identification of Cullin1 orthologues, i.e. Cullin1 genes in other species, can be performed in many crops, methods of which are known in the art. The present invention can for instance be applied to a plant belonging to a species selected from the group consisting of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea,* and *Beta vulgaris*.

Accordingly, the present invention relates to a modified Cullin1 gene which may comprise a modification in the wild type Cullin1 nucleotide sequence of SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID NO: 13, SEQ ID NO: 14, SEQ ID NO: 15, SEQ ID NO: 16, SEQ ID NO: 17 which leads to a modification in the wild type Cullin1 amino acid sequence of SEQ ID No: 18, SEQ ID No: 19, SEQ ID No: 20, SEQ ID No: 21, SEQ ID No: 22, SEQ ID No: 23, SEQ ID No: 24, SEQ ID No: 25, SEQ ID No: 26, SEQ ID No: 27, SEQ ID No: 28, SEQ ID NO: 29, SEQ ID NO: 30, SEQ ID NO: 31, SEQ ID NO:32, SEQ ID NO. 33, SEQ ID NO: 34 respectively.

FIGS. 1-17 show the wild type Cullin1 nucleotide sequences SEQ ID NO. 1-17 of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea,* and *Beta vulgaris*, respectively. FIGS. 18-34 show the wild type Cullin1 amino acid sequences SEQ ID NO.18-34 of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea,* and *Beta vulgaris*, respectively.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 Cucumber Cullin1 coding sequence wildtype, SEQ ID NO. 1. The nucleotide between brackets and bold indicates the position of the SNP, 147 nucleotides from the start. The wildtype nucleotide is "A", as shown here.

FIG. 2 Melon Cullin1 coding sequence wildtype, SEQ ID NO. 2. The nucleotide between brackets and bold indicates the position of the SNP, 147 nucleotides from the start. The wildtype nucleotide is "A", as shown here.

FIG. 3 Squash Cullin1 coding sequence wildtype, SEQ ID NO. 3. The nucleotide between brackets and bold indicates the position of the SNP, 147 nucleotides from the start. The wildtype nucleotide is "A", as shown here.

FIG. 4 Watermelon Cullin1 coding sequence wildtype, SEQ ID NO. 4. The nucleotide between brackets and bold indicates the position of the SNP, 147 nucleotides from the start. The wildtype nucleotide is "A", as shown here.

FIG. 5 Eggplant Cullin1 coding sequence wildtype, SEQ ID NO. 5. The nucleotide between brackets and bold indicates the position of the SNP, 141 nucleotides from the start. The wildtype nucleotide is "T", as shown here.

FIG. 6 Tomato Cullin1 coding sequence wildtype, SEQ ID NO. 6. The nucleotide between brackets and bold indicates the position of the SNP, 141 nucleotides from the start. The wildtype nucleotide is "T", as shown here.

FIG. 7 Pepper Cullin1 coding sequence wildtype, SEQ ID NO. 7. The nucleotide between brackets and bold indicates the position of the SNP, 141 nucleotides from the start. The wildtype nucleotide is "T", as shown here.

FIG. 8 Cabbage Cullin1 coding sequence wildtype, SEQ ID NO. 8. The nucleotide between brackets and bold indicates the position of the SNP, 138 nucleotides from the start. The wildtype nucleotide is "C", as shown here.

FIG. 9 Carrot Cullin1 coding sequence wildtype, SEQ ID NO. 9. The nucleotide between brackets and bold indicates the position of the SNP, 144 nucleotides from the start. The wildtype nucleotide is "C", as shown here.

FIG. 10 Celery Cullin1 coding sequence wildtype, SEQ ID NO. 10. The nucleotide between brackets and bold indicates the position of the SNP, 141 nucleotides from the start. The wildtype nucleotide is "C", as shown here.

FIG. 11 Chicory Cullin1 coding sequence wildtype, SEQ ID NO. 11. The nucleotide between brackets and bold indicates the position of the SNP, 141 nucleotides from the start. The wildtype nucleotide is "C", as shown here.

FIG. 12 Endive Cullin1 coding sequence wildtype, SEQ ID NO. 12. The nucleotide between brackets and bold indicates the position of the SNP, 141 nucleotides from the start. The wildtype nucleotide is "C", as shown here.

FIG. 13 Leek Cullin1 coding sequence wildtype, SEQ ID NO. 13. The nucleotide between brackets and bold indicates the position of the SNP, 147 nucleotides from the start. The wildtype nucleotide is "C", as shown here.

FIG. 14 Lettuce Cullin1 coding sequence wildtype, SEQ ID NO. 14. The nucleotide between brackets and bold indicates the position of the SNP, 141 nucleotides from the start. The wildtype nucleotide is "C", as shown here.

FIG. 15 Radish Cullin1 coding sequence wildtype, SEQ ID NO. 15. The nucleotide between brackets and bold indicates the position of the SNP, 138 nucleotides from the start. The wildtype nucleotide is "C", as shown here.

FIG. 16 Spinach Cullin1 coding sequence wildtype, SEQ ID NO. 16. The nucleotide between brackets and bold indicates the position of the SNP, 141 nucleotides from the start. The wildtype nucleotide is "A", as shown here.

FIG. 17 Beetroot Cullin1 coding sequence wildtype, SEQ ID NO. 17. The nucleotide between brackets and bold indicates the position of the SNP, 141 nucleotides from the start. The wildtype nucleotide is "A", as shown here.

FIG. 18 Cucumber Cullin1 protein sequence wildtype, SEQ ID NO.18. The amino acid between brackets and bold indicates the position of the amino acid change caused by the SNP, 49 amino acids from the start. The wildtype amino acid is 'I', as shown here.

FIG. 19 Melon Cullin1 protein sequence wildtype, SEQ ID NO.19. The amino acid between brackets and bold indicates the position of the amino acid change caused by the SNP, 49 amino acids from the start. The wildtype amino acid is 'I', as shown here.

FIG. 20 Squash Cullin1 protein sequence wildtype, SEQ ID NO.20. The amino acid between brackets and bold indicates the position of the amino acid change caused by the SNP, 49 amino acids from the start. The wildtype amino acid is 'I', as shown here.

FIG. 21 Watermelon Cullin1 protein sequence wildtype, SEQ ID NO.21. The amino acid between brackets and bold indicates the position of the amino acid change caused by the SNP, 49 amino acids from the start. The wildtype amino acid is 'I', as shown here.

FIG. 22 Eggplant Cullin1 protein sequence wildtype, SEQ ID NO.22. The amino acid between brackets and bold indicates the position of the amino acid change caused by the SNP, 47 amino acids from the start. The wildtype amino acid is 'I', as shown here.

FIG. 23 Tomato Cullin1 protein sequence wildtype, SEQ ID NO.23. The amino acid between brackets and bold indicates the position of the amino acid change caused by the SNP, 47 amino acids from the start. The wildtype amino acid is 'I', as shown here.

FIG. 24 Pepper Cullin1 protein sequence wildtype, SEQ ID NO.24. The amino acid between brackets and bold indicates the position of the amino acid change caused by the SNP, 47 amino acids from the start. The wildtype amino acid is 'I', as shown here.

FIG. 25 Cabbage Cullin1 protein sequence wildtype, SEQ ID NO.25. The amino acid between brackets and bold indicates the position of the amino acid change caused by the SNP, 46 amino acids from the start. The wildtype amino acid is 'I', as shown here.

FIG. 26 Carrot Cullin1 protein sequence wildtype, SEQ ID NO.26. The amino acid between brackets and bold indicates the position of the amino acid change caused by the SNP, 48 amino acids from the start. The wildtype amino acid is 'I', as shown here.

FIG. 27 Celery Cullin1 protein sequence wildtype, SEQ ID NO.27. The amino acid between brackets and bold indicates the position of the amino acid change caused by the SNP, 47 amino acids from the start. The wildtype amino acid is 'I', as shown here.

FIG. 28 Chicory Cullin1 protein sequence wildtype, SEQ ID NO.28. The amino acid between brackets and bold indicates the position of the amino acid change caused by the SNP, 47 amino acids from the start. The wildtype amino acid is 'I', as shown here.

FIG. 29 Endive Cullin1 protein sequence wildtype, SEQ ID NO.29. The amino acid between brackets and bold indicates the position of the amino acid change caused by the SNP, 47 amino acids from the start. The wildtype amino acid is 'I', as shown here.

FIG. 30 Leek Cullin1 protein sequence wildtype, SEQ ID NO.30. The amino acid between brackets and bold indicates the position of the amino acid change caused by the SNP, 49 amino acids from the start. The wildtype amino acid is 'I', as shown here.

FIG. 31 Lettuce Cullin1 protein sequence wildtype, SEQ ID NO.31. The amino acid between brackets and bold indicates the position of the amino acid change caused by the SNP, 47 amino acids from the start. The wildtype amino acid is 'I', as shown here.

FIG. 32 Radish Cullin1 protein sequence wildtype, SEQ ID NO.32. The amino acid between brackets and bold indicates the position of the amino acid change caused by the SNP, 46 amino acids from the start. The wildtype amino acid is 'I', as shown here.

FIG. 33 Spinach Cullin1 protein sequence wildtype, SEQ ID NO.33. The amino acid between brackets and bold indicates the position of the amino acid change caused by the SNP, 47 amino acids from the start. The wildtype amino acid is 'I', as shown here.

FIG. 34 Beetroot Cullin1 protein sequence wildtype, SEQ ID NO.34. The amino acid between brackets and bold indicates the position of the amino acid change caused by the SNP, 47 amino acids from the start. The wildtype amino acid is 'I', as shown here.

FIG. 35 Cucumber Cullin1 coding sequence "modified" SEQ ID NO. 35. The nucleotide between brackets and bold and bold indicates the position of the SNP 147 bp from the start. The modified nucleotide is "G", as shown here.

FIG. 36 Melon Cullin1 coding sequence "modified" SEQ ID NO. 36. The nucleotide between brackets and bold indicates the position of the SNP 147 bp from the start. The modified nucleotide is "G", as shown here.

FIG. 37 Squash Cullin1 coding sequence "modified" SEQ ID NO. 37. The nucleotide between brackets and bold indicates the position of the SNP 147 bp from the start. The modified nucleotide is "G", as shown here.

FIG. 38 Watermelon Cullin1 coding sequence "modified" SEQ ID NO. 38. The nucleotide between brackets and bold indicates the position of the SNP 147 bp from the start. The modified nucleotide is "G", as shown here.

FIG. 39 Eggplant Cullin1 coding sequence "modified" SEQ ID NO. 39. The nucleotide between brackets and bold indicates the position of the SNP 141 bp from the start. The modified nucleotide is "G", as shown here.

FIG. 40 Tomato Cullin1 coding sequence "modified" SEQ ID NO. 40. The nucleotide between brackets and bold indicates the position of the SNP 141 bp from the start. The modified nucleotide is "G", as shown here.

FIG. 41 Pepper Cullin1 coding sequence "modified" SEQ ID NO. 41. The nucleotide between brackets and bold indicates the position of the SNP 141 bp from the start. The modified nucleotide is "G", as shown here.

FIG. 42 Cabbage Cullin1 coding sequence "modified" SEQ ID NO. 42. The nucleotide between brackets and bold indicates the position of the SNP 138 bp from the start. The modified nucleotide is "G", as shown here.

FIG. 43 Carrot Cullin1 coding sequence "modified" SEQ ID NO. 43. The nucleotide between brackets and bold indicates the position of the SNP 144 bp from the start. The modified nucleotide is "G", as shown here.

FIG. 44 Celery Cullin1 coding sequence "modified" SEQ ID NO. 44. The nucleotide between brackets and bold indicates the position of the SNP 141 bp from the start. The modified nucleotide is "G", as shown here.

FIG. 45 Chicory Cullin1 coding sequence "modified" SEQ ID NO. 45. The nucleotide between brackets and bold indicates the position of the SNP 141 bp from the start. The modified nucleotide is "G", as shown here.

FIG. 46 Endive Cullin1 coding sequence "modified" SEQ ID NO. 46. The nucleotide between brackets and bold indicates the position of the SNP 141 bp from the start. The modified nucleotide is "G", as shown here.

FIG. 47 Leek Cullin1 coding sequence "modified" SEQ ID NO. 47. The nucleotide between brackets and bold indicates the position of the SNP 147 bp from the start. The modified nucleotide is "G", as shown here.

FIG. 48 Lettuce Cullin1 coding sequence "modified" SEQ ID NO. 48. The nucleotide between brackets and bold indicates the position of the SNP 141 bp from the start. The modified nucleotide is "G", as shown here.

FIG. 49 Radish Cullin1 coding sequence "modified" SEQ ID NO. 49. The nucleotide between brackets and bold indicates the position of the SNP 138 bp from the start. The modified nucleotide is "G", as shown here.

FIG. 50 Spinach Cullin1 coding sequence "modified" SEQ ID NO. 50. The nucleotide between brackets and bold indicates the position of the SNP 141 bp from the start. The modified nucleotide is "G", as shown here.

FIG. 51 Beetroot Cullin1 coding sequence "modified" SEQ ID NO. 51. The nucleotide between brackets and bold indicates the position of the SNP 141 bp from the start. The modified nucleotide is "G", as shown here.

FIG. 52 Cucumber Cullin1 protein sequence "modified" SEQ ID NO. 52. The amino acid between brackets and bold indicates the position of the amino acid change caused by the SNP, 49 amino acids from the start. The modified amino acid is 'M', as shown here.

FIG. 53 Melon Cullin1 protein sequence "modified" SEQ ID NO. 53. The amino acid between brackets and bold indicates the position of the amino acid change caused by the SNP, 49 amino acids from the start. The modified amino acid is 'M', as shown here.

FIG. 54 Squash Cullin1 protein sequence "modified" SEQ ID NO. 54. The amino acid between brackets and bold indicates the position of the amino acid change caused by the SNP, 49 amino acids from the start. The modified amino acid is 'M', as shown here.

FIG. 55 Watermelon Cullin1 protein sequence "modified" SEQ ID NO. 55. The amino acid between brackets and bold indicates the position of the amino acid change caused by the SNP, 49 amino acids from the start. The modified amino acid is 'M', as shown here.

FIG. 56 Eggplant Cullin1 protein sequence "modified" SEQ ID NO. 56. The amino acid between brackets and bold indicates the position of the amino acid change caused by the SNP, 47 amino acids from the start. The modified amino acid is 'M', as shown here.

FIG. 57 Tomato Cullin1 protein sequence "modified" SEQ ID NO. 57. The amino acid between brackets and bold indicates the position of the amino acid change caused by the SNP, 47 amino acids from the start. The modified amino acid is 'M', as shown here.

FIG. 58 Pepper Cullin1 protein sequence "modified" SEQ ID NO. 58. The amino acid between brackets and bold indicates the position of the amino acid change caused by the SNP, 47 amino acids from the start. The modified amino acid is 'M', as shown here.

FIG. 59 Cabbage Cullin1 protein sequence "modified" SEQ ID NO. 59. The amino acid between brackets and bold indicates the position of the amino acid change caused by the SNP, 46 amino acids from the start. The modified amino acid is 'M', as shown here.

FIG. 60 Carrot Cullin1 protein sequence "modified" SEQ ID NO. 60. The amino acid between brackets and bold indicates the position of the amino acid change caused by the SNP, 48 amino acids from the start. The modified amino acid is 'M', as shown here.

FIG. 61 Celery Cullin1 protein sequence "modified" SEQ ID NO. 61. The amino acid between brackets and bold indicates the position of the amino acid change caused by the SNP, 47 amino acids from the start. The modified amino acid is 'M', as shown here.

FIG. 62 Cichory Cullin1 protein sequence "modified" SEQ ID NO. 62. The amino acid between brackets and bold indicates the position of the amino acid change caused by the SNP, 47 amino acids from the start. The modified amino acid is 'M', as shown here.

FIG. 63 Endive Cullin1 protein sequence "modified" SEQ ID NO. 63. The amino acid between brackets and bold indicates the position of the amino acid change caused by the SNP, 47 amino acids from the start. The modified amino acid is 'M', as shown here.

FIG. 64 Leek Cullin1 protein sequence "modified" SEQ ID NO. 64. The amino acid between brackets and bold indicates the position of the amino acid change caused by the SNP, 49 amino acids from the start. The modified amino acid is 'M', as shown here.

FIG. 65 Lettuce Cullin1 protein sequence "modified" SEQ ID NO. 65. The amino acid between brackets and bold indicates the position of the amino acid change caused by the SNP, 47 amino acids from the start. The modified amino acid is 'NI', as shown here.

FIG. 66 Radish Cullin1 protein sequence "modified" SEQ ID NO. 66. The amino acid between brackets and bold indicates the position of the amino acid change caused by the SNP, 46 amino acids from the start. The modified amino acid is 'NI', as shown here.

FIG. 67 Spinach Cullin1 protein sequence "modified" SEQ ID NO. 67. The amino acid between brackets and bold indicates the position of the amino acid change caused by the SNP, 47 amino acids from the start. The modified amino acid is 'NI', as shown here.

FIG. 68 Beetroot Cullin1 protein sequence "modified" SEQ ID NO. 68. The amino acid between brackets and bold indicates the position of the amino acid change caused by the SNP, 47 amino acids from the start. The modified amino acid is 'NI', as shown here.

FIGS. 69A-69S The multiple sequence alignment of the Cullin1 coding sequence orthologues (wild type) of various crops: brassica (SEQ ID NO. 8), radish (SEQ ID NO. 15), beet (SEQ ID NO. 17), spinach (SEQ ID NO. 16), leek (SEQ ID NO. 13), squash (SEQ ID NO. 3), watermelon (SEQ ID NO. 4), cucumber (SEQ ID NO. 1), melon (SEQ ID NO. 2), tomato (SEQ ID NO. 6), eggplant (SEQ ID NO. 5), pepper (SEQ ID NO. 7), lettuce (SEQ ID NO. 14), chicory (SEQ ID NO. 11), endive (SEQ ID NO. 12), carrot (SEQ ID NO. 9), celery (SEQ ID NO. 10). Between brackets and bold is indicated the SNP on position 147 in the Cucumber coding sequence and for other crops on a position corresponding to this position.

FIGS. 70A-70F The multiple sequence alignment of the Cullin1 amino acid orthologues (wild type) of various crops: beet (SEQ ID NO. 34), spinach (SEQ ID NO. 33), arabidopsis (SEQ ID NO. 69), brassica (SEQ ID NO. 25), radish (SEQ ID NO. 32), leek (SEQ ID NO. 30), eggplant (SEQ ID NO. 22), tomato (SEQ ID NO. 23), pepper (SEQ ID NO. 24), cucumber (SEQ ID NO. 18), melon (SEQ ID NO. 19), watermelon (SEQ ID NO. 21), squash (SEQ ID NO. 20), celery (SEQ ID NO. 27), lettuce (SEQ ID NO. 31), endive (SEQ ID NO. 29), chicory (SEQ ID NO. 28), carrot (SEQ ID NO. 26). Between brackets and bold is indicated the SNP on position 49 in the Cucumber amino acid sequence and for other crops on a position corresponding to this position.

DETAILED DESCRIPTION OF THE INVENTION

The term "wild type" as used herein refers in general to the form of an organism, gene, protein, or trait as it would occur in nature, as opposed to a mutated or modified form. In this application wild type refers specifically to the naturally occurring form of the Cullin1 gene, the naturally occurring form of the nucleotide sequence of Cullin1 and the naturally occurring form of the Cullin1 amino acid sequence. The naturally occurring forms of the Cullin1 gene and Cullin1 protein of several crops are shown in FIGS. 1-17 and FIGS. 18-34 respectively.

The terms "mutant", "mutation", "modification", "modified", "mutated Cullin1 gene" and "modified Cullin1 gene" as used herein refer to nucleotide changes and amino acid changes to the wild type Cullin1 gene thereof that lead to a modified version of the wild type gene. The modification can be any modification, including but not limited to a SNP.

The modified Cullin1 gene is also referred to herein as "the gene of the invention", "the modified Cullin1 gene", or "the modified Cullin1 gene of the invention". These terms are used interchangeably herein. As used herein the phrase "the modified Cullin1 gene" is intended to encompass the Cullin1 gene with any modification that leads to the compact growth phenotype.

The terms "compact gene phenotype", "compact phenotype" or "compact growth phenotype" are used interchangeably herein and refer to a phenotype of a shorter internode length and/or a smaller leaf area. Crops which may comprise the modified Cullin1 gene and which have internodes, such as for instance cucumber, may show shorter internodes or a smaller leaf area. They may also show shorter internodes and a smaller leaf area. Crops which may comprise the modified Cullin1 gene but which do not have internodes, such as for instance lettuce, may show a smaller leaf area.

The term "smaller leaf area" as used herein is the leaf area that displays a reduction in individual leaf area of, in order of increased preference, at least 10%, at least 20%, at least 30%, at least 40%, at least 50%, at least 60%, at least 70%, at least 80% as a result of the homozygous or heterozygous presence of the modified gene of the invention. To investigate the influence of the gene of the invention on the smaller leaf area, a skilled person would have to compare plants having the gene of the invention homozygously or heterozygously with plants that are isogenic to first mentioned plants but do not have the gene of the invention.

With the term "leaf" is meant the part of the plant consisting of the petiole and leaf blade. With the term "leaf area" is meant the surface of the part of the plant consisting of the leaf blade.

The term "shorter internodes" or "shorter internode length" as used herein is internode length that has a reduction in individual length of, in order of increased preference, at least 10%, at least 20%, at least 30%, at least 40%, at least 50%, at least 60%, at least 70%, at least 80% as a result of the homozygous or heterozygous presence of the gene of the invention. To investigate the influence of the gene of the invention on the shorter internode length, a skilled person would have to compare plants having the gene of the invention homozygously or heterozygously with plants that are isogenic to first mentioned plants but without the gene of the invention.

The modification leading to the modified Cullin1 gene may be selected from a modification that changes the mRNA level of the Cullin1 gene, a modification that changes the Cullin1 protein structure and/or levels, and/or a modification that changes the Cullin1 protein activity.

One aspect of the invention relates to a modified Cullin1 gene, which may comprise a mutation as compared to its wild type genomic sequence, which mutation leads to a change in the Cullin1 protein and/or protein activity, wherein the modified Cullin1 gene is capable of causing a compact growth phenotype.

In one embodiment, the mutation is a Single Nucleotide Polymorphism (SNP).

In one embodiment of the present invention, the change in the amino acid sequence is a substitution.

In a preferred embodiment of the present invention, the change in the amino acid sequence is found in the part of the Cullin1 protein between the amino acids on position 30-60, preferably in the part between the amino acids on positions 40-55 of the cucumber amino acid sequence of SEQ ID No: 18, or on a part corresponding thereto.

In a further preferred embodiment of the present invention, the change in the amino acid sequence is found in the part of the Cullin1 protein that binds SKP1 and/or ETA2.

Preferably, the physical location of the amino acid substitution in the Cullin1 protein lies in the region of the protein where the Cullin1 protein binds to SKP1 and/or ETA2. The Cullin1 protein forms a so-called SCF complex, together with SKP1, RBX1 and a F-box protein, which has important functionalities such as a role in leaf development. ETA2 is according to some theories, required to sustain the SCF complex activity, most probably by facilitating cycles of assembly and disassembly of the SCF complex.

In a specific embodiment, the modified Cullin1 gene includes, a Cullin1 gene which may comprise a SNP on position 147 of SEQ ID NO.1 of cucumber, or on a position corresponding thereto in the Cullin1 gene of other crops, wherein the modification may comprise a change in the nucleotide on that position and wherein the modification leads to an amino acid substitution in the Cullin1 protein on position 49 of the wildtype protein sequence SEQ ID NO: 18. of cucumber, or on a position corresponding thereto, in other crops. In cucumber the change is from A to G and from Isoleucine to Methionine. In other crops the change in nucleotide and amino acid may be different.

In a preferred embodiment of the present invention, the modification of the nucleotide sequence may comprise a change from Adenine, Cytosine or Thymine to Guanine.

The definition "coding sequence" as used herein is the portion of the gene's DNA composed of exons that code for the protein.

In a further embodiment of the present invention, the modification in the amino acid sequence is a substitution on position 49 of the cucumber amino acid sequence of SEQ ID No: 18, or, in case of a crop other than cucumber, on a position corresponding to position 49 of the cucumber amino acid sequence of SEQ ID No: 18.

The amino acid substitution caused by the mutation of the current invention was found to be present on position 49 of the cucumber amino acid sequence of SEQ ID No: 18, or, in case of a crop other than cucumber, on a position corresponding to position 49 of the wild type amino acid sequence SEQ ID NO. 18 of cucumber. This nucleotide mutation is considered to be non-conservative, and the amino acid change can be considered non-conservative.

Amino acid changes in a protein occur when the mutation of one or more base pairs in the coding DNA sequence result in an altered codon triplet that encodes a different amino acid. Not all point mutations in the coding DNA sequence lead to amino acid changes, due to the redundancy of the genetic code. Mutations in the coding sequence that do not lead to amino acid changes are called "silent mutations". Other mutations are called "conservative", they lead to the replacement of one amino acid by another amino acid with comparable properties, such that the mutations are unlikely to change the folding of the mature protein, or influence its function. As used herein a "non-conservative amino acid change" refers to an amino acid that is replaced by another amino acid that has different chemical properties that may lead to decreased stability, changed functionality and/or structural effects of the encoded protein.

In a further preferred embodiment of the present invention, the modification in the amino acid sequence is a substitution and consists of a change from Isoleucine to Methionine The invention further relates to a plant which may comprise the modified Cullin1 gene.

A *Cucumis sativus* plant which may comprise the modified Cullin1 gene with the nucleotide sequence of SEQ ID No: 35 is not part of this invention and is therefore disclaimed herewith.

A plant which may comprise the modified Cullin1 gene shows a compact growth phenotype, i.e. may comprise a shorter internode length and/or a smaller leaf area, compared to an isogenic plant of the same species not comprising the modified Cullin1 gene. For example, a *Cucumis sativus* plant a *Cucumis melo* plant, a *Cucurbita pepo* plant, a *Citrullus lanatus* plant, a *Solanum melongena* plant, a, *Solanum lycopersicum* plant, and a *Capsicum annuum* plant which may comprise the modified Cullin1 gene show a shorter internode length and/or a smaller leaf area. These plants are therefore particularly suitable for efficient cultivation. A *Cichorium intybus* plant, a *Cichorium endivia* plant, a *Lactuca sativa* plant, a *Brassica oleracea* plant and a *Spinacia oleracea* plant which may comprise the modified Cullin1 gene show for example a smaller leaf area. As such, the parts of these plants harvested for consumption are smaller in size. These plants are therefore particularly suitable for a situation in which smaller portions are required. A *Daucus carota* plant which may comprise the modified Cullin1 gene shows a shorter internode length and/or a smaller leaf area. As such, the plant may comprise less foliage that needs to be removed before the product is sold and/or consumed. An *Apium graveolens* plant which may comprise the modified Cullin1 gene shows a shorter internode length and/or a smaller leaf area. As such, the plant is of a more compact size suitable for a situation in which smaller portions are required and/or may comprise less foliage that needs to be removed before the product is sold and/or consumed. An *Allium ampeloprasum* plant which may comprise the modified Cullin1 gene shows a smaller leaf area. As such, the leaves that are not consumed do not need to be removed before the product is sold and/or consumed. A *Raphanus sativus* plant and a *Beta vulgaris* plant which may comprise the modified Cullin1 gene show a smaller leaf area. As such, less foliage needs to be removed before the product is sold and/or consumed.

The plant of the invention which may comprise the modified Cullin1 gene either homozygously or heterozygously may be a plant of an inbred line, a hybrid, a doubled haploid, or a plant of a segregating population.

The plant of the invention may have the modified Cullin1 gene in heterozygous state since such a plant shows the trait in an intermediate level. Furthermore such plant may be a potential source of the gene and when crossed with another plant that optionally also has the modified gene either homozygously or heterozygously can result in progeny plants that have the modified gene homozygously or heterozygously and show the trait of having a compact growth phenotype.

The invention also relates to a method for the production of a plant having the modified Cullin1 gene that leads to a compact growth phenotype by using a seed that may comprise the modified Cullin1 gene for growing the said plant.

The invention further relates to a method for the production of a plant having the modified Cullin1 gene by using tissue culture of plant material that carries the modified Cullin1 gene in its genome.

The invention furthermore relates to a method for the production of a plant having the modified Cullin1 gene which leads to a compact growth phenotype, by using vegetative reproduction of plant material that carries the modified Cullin1 gene in its genome.

The invention further provides a method for the production of a plant having the modified Cullin1 gene by using a doubled haploid generation technique to generate a doubled haploid line from a cucumber plant which may comprise the modified Cullin1 gene.

The invention further relates to a plant seed which may comprise the modified Cullin1 gene of the invention, wherein the plant that can be grown from the seed shows a compact growth phenotype.

The invention also relates to a method for seed production which may comprise growing plants from seeds of the invention, allowing the plants to produce seeds by allowing pollination to occur, and harvesting those seeds. Production of the seeds is suitably done by crossing or selfing. Seeds produced in that manner result in a compact growth phenotype of the plants grown thereof.

The invention furthermore relates to hybrid seed and to a method for producing such hybrid seed which may comprise crossing a first parent plant with a second parent plant and harvesting the resultant hybrid seed, wherein said first parent plant and/or said second parent plant has the modified Cullin1 gene of the invention. A hybrid plant resulting from growing the resulting seed that may comprise the modified Cullin1 gene of the invention, showing the compact growth phenotype of the invention is also a plant of the invention.

Another aspect of the invention relates to propagation material capable of developing into and/or being derived from a plant which may comprise a modified Cullin1 gene, wherein the plant shows a compact growth phenotype, compared to an isogenic plant of the same species not comprising the modified Cullin1 gene, wherein the propagation material may comprise the modified Cullin1 gene of the invention and wherein the propagation material is selected from the group consisting of microspores, pollen, ovaries, ovules, embryos, embryo sacs, egg cells, cuttings, roots, hypocotyls, cotyledons, stems, leaves, flowers, anthers, seeds, meristematic cells, protoplasts and cells, or tissue culture thereof.

The invention thus further relates to parts of a claimed plant that are suitable for sexual reproduction. Such parts are for example selected from the group consisting of microspores, pollen, ovaries, ovules, embryo sacs, and egg cells. In addition, the invention relates to parts of a claimed plant that are suitable for vegetative reproduction, which are in particular cuttings, roots, stems, cells, protoplasts. The parts of the plants as mentioned above are considered propagation material. The plant that is produced from the propagation material may comprise the modified Cullin1 gene that leads to a compact growth phenotype and thus enables efficient cultivation and/or is suitable for the production for market segments that require a smaller product.

According to a further aspect thereof, the invention provides a tissue culture of a plant carrying the modified Cullin1 gene of the invention, which is also propagation material. The tissue culture may comprise regenerable cells. Such tissue culture can be selected or derived from any part of the plant, in particular from leaves, pollen, embryos, cotyledon, hypocotyls, meristematic cells, roots, root tips, anthers, flowers, seeds, and stems. The tissue culture can be regenerated into a plant carrying the modified Cullin1 gene of the invention, which regenerated plant expresses the trait of the invention and is also part of the invention.

The invention further relates to the use of the modified Cullin1 gene for the development of a plant showing a compact growth phenotype. A skilled person is familiar with introducing a new trait into a plant already having other desired agricultural properties, for instance by introgression. Introgression can be done by means of standard breeding techniques, wherein selection can be done either phenotypically or with the use of markers or a combination thereof.

The invention further relates to the use of the modified Cullin1 gene, or a part thereof which may comprise the modification, as a marker for identifying a plant showing a compact growth phenotype.

The 'use for identifying' or a 'method for identifying' as used in the current application may comprise the use of the described (causal) SNP in the Cullin1 gene as a marker. The invention also relates to other markers that can be developed based on a modification, including the causal SNP, in the Cullin1 gene, as well as to other markers that can be developed based on the wildtype sequence of the Cullin1 gene.

The invention further relates to the use of any of the sequences of SEQ ID NOs. 35-51, or a part thereof, as a marker for identifying a plant showing a compact growth phenotype, i.e. which may comprise a shorter internode length and/or a smaller leaf area. If a part of any of these sequences is used, the part must comprise the modification. For example, SEQ ID No. 35 or a part thereof may be used to identify a *Cucumis sativus* plant showing a shorter internode length and/or a smaller leaf area; SEQ ID No. 36 or a part thereof may be used to identify a *Cucumis melo* plant showing a shorter internode length and/or a smaller leaf area; SEQ ID No. 37 or a part thereof may be used to identify a *Cucurbita pepo* plant showing a shorter internode length and/or a smaller leaf area; SEQ ID No. 38 or a part thereof may be used to identify a *Citrullus lanatus* plant showing a shorter internode length and/or a smaller leaf area; SEQ ID No. 39 or a part thereof may be used to identify a *Solanum melongena* plant showing a shorter internode length and/or a smaller leaf area; SEQ ID No. 40 or a part thereof may be used to identify a *Solanum lycopersicum* plant showing a shorter internode length and/or a smaller leaf area; SEQ ID No. 41 or a part thereof may be used to identify a *Capsicum annuum* plant showing a shorter internode length and/or a smaller leaf area; SEQ ID No. 42 or a part thereof may be used to identify a *Brassica oleracea* plant showing a smaller leaf area; SEQ ID No. 43 or a part thereof may be used to identify a *Daucus carota* plant showing a shorter internode length and/or a smaller leaf area; SEQ ID No. 44 or a part thereof may be used to identify a *Apium graveolens* plant showing a shorter internode length and/or a smaller leaf area; SEQ ID No. 45 or a part thereof may be used to identify a *Cichorium intybus* plant showing a smaller leaf area; SEQ ID No. 46 or a part thereof may be used to identify a *Cichorium endivia* plant showing a smaller leaf area; SEQ ID No. 47 or a part thereof may be used to identify an *Allium ampeloprasum* plant showing a smaller leaf area; SEQ ID No. 48 or a part thereof may be used to identify a *Lactuca sativa* plant showing a smaller leaf area; SEQ ID No. 49 or a part thereof may be used to identify a *Raphanus sativus* plant showing a shorter internode length and/or a smaller leaf area; SEQ ID No. 50 or a part thereof may be used to identify a *Spinacia oleracea* plant showing a smaller leaf area; SEQ ID No. 51 or a part thereof may be used to identify a *Beta vulgaris* plant showing a shorter internode length and/or a smaller leaf area. The invention also relates to the use of any markers that are derived from SEQ ID Nos. 1-17 or SEQ ID NOs. 36-51 for identifying a plant showing a compact growth phenotype. Any such derived marker must comprise the modification that leads to the phenotype of the invention.

In general, to identify a plant showing a compact growth phenotype, it is thus determined in the Cullin1 gene whether there is an A, C, or T (SEQ ID Nos. 1-17) or a G (SEQ ID Nos. 35-51) on position 147, or a position corresponding thereto.

The invention further relates to a method for obtaining a plant which shows a compact growth phenotype which may comprise;
a) crossing a plant which may comprise the modified Cullin1 gene of the current invention with a plant not comprising the modified Cullin1 gene, to obtain an F1 population;
b) optionally performing one or more rounds of selfing and/or crossing a plant from the F1 to obtain a further generation population; and
c) selecting a plant that has a compact growth phenotype and the modified Cullin1 gene of the invention.

The invention also relates to a method for obtaining a plant which shows a compact growth phenotype which may comprise;
a) crossing a plant which may comprise the modified Cullin1 gene of the current invention with another plant which may comprise the modified Cullin1 gene, to obtain an F1 population;
b) optionally performing one or more rounds of selfing and/or crossing a plant from the F1 to obtain a further generation population; and
c) selecting a plant that has a compact growth phenotype and the modified Cullin1 gene of the invention.

The invention further relates to a marker for identifying a plant showing a compact growth phenotype, which may comprise the modified Cullin1, or a part thereof that may comprise the modification. Preferably, the modification is a nucleotide substitution on or around position 147 of SEQ ID No:1 of cucumber, or, in case of a crop other than cucumber, on or around a position corresponding to position 147 of SEQ ID No:1 of cucumber, which modification leads to an amino acid substitution in the Cullin1 protein.

The invention also relates to a method for selecting a plant showing a compact growth phenotype from a population of plants, which may comprise detecting the presence or absence of a guanine on position 147 of the cucumber nucleotide sequence of SEQ ID NO:1, or, for a crop other than cucumber, on a position corresponding to position 147 of the cucumber nucleotide sequence of SEQ ID No: 1, in the genome of a plant of a population of plants, and selecting a plant which may comprise a guanine on position 147 of SEQ ID NO:1, as shown in SEQ ID NO. 35, or, for a crop other than cucumber, on a position corresponding to position 147 of the cucumber nucleotide sequence of SEQ ID No: 1, as shown in any of SEQ ID Nos. 36-51.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1. Identification of the Cullin1 Gene Modification in *Cucumis sativus*

A F2 crossing population made from a commercially available "high wire" cucumber variety, "Hi Lisa", was used to create a new genetic map. In total, 375 markers and 398 F2 lines are used. A QTL analysis performed on these crossing populations revealed a major QTL on chromosome 6 that causes a smaller internode length and a smaller leaf surface. Sequencing of the peak marker of the QTL revealed a SNP present in the marker sequence. The particular sequence was polymorphic in the crossing population. The nucleotide sequence of the major QTL on chromosome 6 was identified by means of BLAST. The best BLAST hits for the sequence all resembled the sequence of the Cullin1 gene.

Example 2. Validation of the Effect of SNP in the Cullin1 Gene on Internode Length and Plant Leaf Area Different populations of *Cucumis sativus* plants, each made with different commercially available 'high wire' varieties, having the phenotype of shorter internodes, and smaller leaves, were phenotypically and genetically analysed. See Table 1 for the phenotypic and genetic data.

Plants were measured 3 weeks after sowing. For estimating the leaf area, from the second leaf on (not the cotyledons) all leafs present were measured, and the width and the length of a leaf were measured and multiplied with each other to obtain a (roughly estimation) score for leaf area. In the third column of Table 1, the different haplotypes for the Cullin1 gene SNP are given. The score A means that the SNP marker scored homozygous wildtype Cullin1 gene, B means homozygous modified Cullin1 gene.

In the first population, plants that are homozygous for the modified Cullin1 gene (B), show an internode length that is on average 63% of the length of the plants that score homozygous for the wild type Cullin1 gene (A). The B plants (homozygous for the modified Cullin1 gene) show a leaf area that is on average 38% of the length of the A plants (homozygous for the wild type Cullin1 gene).

In the second population, B plants show on average an internode length that is 78% and a leaf area that is 39% of the A plants of the same population.

In the third population, the B plants show on average an internode length of 66% and a leaf area of 47%, compared to the average of the A plants.

Table 1. Results of phenotypic and genotypic analyses of 3 different cucumber lines derived from commercially available high wire varieties. The internode length is defined as the length of the main stem divided by the number of internodes. The leaf area is roughly estimated by measuring from all leafs present on a plant starting with the second leaf (not the cotyledons) the length and the width, multiplying length and width, and computing the average per plant. For the scores of the Cullin1 SNP, score A means that the marker scored A homozygous (wildtype), B means homozygous (modified).

TABLE 1

Results of phenotypic and genotypic analyses of 3 different cucumbers lines derived from commercially available high wire varieties. The internodes length is defined as the length of the main stem divided by the number of internodes. The leaf area is roughly estimated by measuring from all leafs present on a plant starting with the second leaf (not the cotyledons) the length and width, multiplying length and width, and computing the average per plant. For the scores of the Cullin1 SNP, score A means that the marker scored A homozygous (wildtype), B means homozygous (modified).

| Plant material | Cullin1 haplotype | Internode length (H/I) | Leaf area (J × K) |
|---|---|---|---|
| BPQ-3 | B | 6 | 210 |
| BPQ-8 | B | 4.7 | 210 |
| BPQ-10 | B | 5.8 | 289 |
| BPQ-12 | B | 4.8 | 210 |
| BPQ-5 | A | 6.6 | 462 |
| BPQ-6 | A | 9.3 | 550 |
| BPQ-4 | A | 7.6 | 575 |
| BPQ-7 | A | 8.4 | 650 |
| BPQ-1 | A | 8.3 | 725 |
| BPQ-11 | A | 8.5 | 676 |
| BPQ-9 | A | 10.3 | 650 |
| 13L.3402-2 pl-1 | B | 4.3 | 208 |
| 13L.3402-2 pl-15 | B | 5.7 | 285 |
| 13L.3402-2 pl-7 | B | 5.8 | 238 |
| 13L.3402-2 pl-9 | B | 6.1 | 216 |
| 13L.3402-2 pl-17 | B | 6.6 | 238 |
| 13L.3402-2 pl-6 | A | 6.7 | 550 |
| 13L.3402-2 pl-3 | A | 6.8 | 616 |
| 13L.3402-2 pl-10 | A | 6.8 | 567 |
| 13L.3402-2 pl-13 | A | 7.2 | 675 |
| 13L.3402-2 pl-5 | A | 8 | 690 |
| 13L.3402-2 pl-8 | A | 8.6 | 546 |
| 12L.1480-2 pl-4 | B | 3.9 | 156 |
| 12L.1480-2 pl-8 | B | 4.1 | 195 |
| 12L.1480-2 pl-6 | B | 4.3 | 238 |
| 12L.1480-2 pl-2 | B | 4.4 | 195 |
| 12L.1480-2 pl-11 | B | 4.8 | 208 |
| 12L.1480-2 pl-5 | B | 4.9 | 224 |
| 12L.1480-2 pl-9 | A | 5.1 | 336 |
| 12L.1480-2 pl-10 | A | 7 | 480 |
| 12L.1480-2 pl-14 | A | 7.3 | 437 |
| 12L.1480-2 pl-12 | A | 7.4 | 483 |

Example 3. Creation of a Melon Plant with a Cullin1 Gene Mutation; Genetic Modification of Plants by Ethyl Methane Sulfonate (Ems) and Identification of Plants which have the Mutated Cullin1 Gene Melon seeds were treated with EMS by submergence of approximately 5000 seeds into an aerated solution of 0.07% (w/v) EMS during 24 hours at room temperature. The treated seeds were germinated on paper in a small plastic container and the resulting plants were grown and self-pollinated in a greenhouse to produce seeds. After maturation, these seeds were harvested and bulked in one pool. The resulting pool of seeds was used as starting material to identify the individual plants that show smaller internode length and/or smaller leaf area.

The Cullin1 mutants which were obtained were grown in a greenhouse in order to produce lines by self-fertilisation. Melon plant lines were analysed to confirm the smaller internode length and smaller leaf area. When a line was segregating for smaller internode length and/or smaller leaf area, plants were selected and after an additional cycle of inbreeding Cullin1 lines were selected. Cullin1 mutants were identified by their shorter internodes and/or smaller leaf area in comparison with control lines.

Example 4. Identification of Crops Comprising the Cullin1 Gene

A Basic Local Alignment Search Tool (BLAST) program was used to compare the Cullin1 gene as identified in SEQ ID NO:1 and the protein sequence as identified in SEQ ID NO:18 against the nucleotide coding sequences and protein sequences of other crop plants. This resulted in the identification of candidate Cullin1 orthologous genes in other plants. The multiple sequence alignment of the Cullin1 coding sequence confirmed that these were orthologous Cullin1 genes, see FIG. 69. Multiple sequence alignment of the protein sequences confirmed that these were orthologous Cullin1 proteins, see FIG. 70.

The invention is further described by the following numbered paragraphs:

1. Modified Cullin1 gene comprising a modification in the wild type Cullin1 nucleotide sequence of SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID NO: 13, SEQ ID NO: 14, SEQ ID NO: 15, SEQ ID NO: 16, SEQ ID NO: 17 which leads to a change in the wild type Cullin1 amino acid sequence of SEQ ID No: 18, SEQ ID No: 19, SEQ ID No: 20, SEQ ID No: 21, SEQ ID No: 22, SEQ ID No: 23, SEQ ID No: 24, SEQ ID No: 25, SEQ ID No: 26, SEQ ID No: 27, SEQ ID No: 28, SEQ ID NO: 29, SEQ ID NO: 30, SEQ ID NO: 31, SEQ ID NO:32, SEQ ID NO. 33, SEQ ID NO: 34 respectively.

2. Modified Cullin1 gene of paragraph 1, wherein the modification of the nucleotide sequence is a SNP on a position that leads to a change in the amino acid sequence of the Cullin1 protein.

3. Modified Cullin1 gene of paragraph 1 or 2, wherein the change in the amino acid sequence is a substitution.

4. Modified Cullin1 gene of any one of the paragraphs 1-3, wherein the change in the amino acid sequence is found in the part of the Cullin1 protein between the amino acids on positions 30-60, preferably in the part between the amino acids on positions 40-55 of the cucumber amino acid sequence of SEQ ID No: 18, or, on a position corresponding thereto, for other crops.

5. Modified Cullin1 gene of any one of the paragraphs 1-4, wherein the modification in the amino acid sequence is found in the part of the Cullin1 protein that binds SKP1 and/or ETA-2.

6. Modified Cullin1 gene of any of the paragraphs 1-5, wherein the modification of the nucleotide sequence is a SNP on position 147 of the cucumber nucleotide sequence of SEQ ID No: 1, or, for a crop other than cucumber, on a position corresponding to position 147 of the cucumber nucleotide sequence of SEQ ID No: 1, leading to an amino acid change on position 49 of the cucumber amino acid sequence of SEQ ID No: 18, or, for a crop other than cucumber, on a position corresponding to position 49 of the cucumber amino acid sequence of SEQ ID No: 18.

7. Modified Cullin1 gene of paragraph 6, wherein the SNP comprises a change from Adenine, Cytosine or Thymine to Guanine.

8. Modified Cullin1 gene of any of the paragraphs 1-7, wherein in cucumber the SNP comprises a change from Adenine, Cytosine or Thymine to Guanine and the amino acid substitution comprises a change from Isoleucine to Methionine.

9. Plant, comprising the modified Cullin1 gene of any one of the paragraphs 1-8.

10. Plant of paragraph 9, wherein the plant belongs to a species selected from the group consisting of *Cucumis sativus, Cucumis melo, Curcurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

11. Plant of paragraph 9 or 10, wherein the modified Cullin1 gene results in the plant showing a compact growth phenotype as compared to an isogenic plant of the same species not comprising the modification of the Cullin 1 gene.

12. Plant seed, comprising the modified Cullin1 gene of any of the paragraphs 1-8.

13. Plant seed of paragraph 12, wherein the plant seed belongs to a species selected from the group consisting of *Cucumis sativus, Cucumis melo, Curcurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

14. Propagation material capable of developing into and/or being derived from a plant of any of the paragraphs 9-11, wherein the propagation material comprises the modified Cullin1 gene of any of the paragraphs 1-8 and wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, or cell, or tissue culture thereof.

15. Use of the modified Cullin1 gene of any of the paragraphs 1-8 for the development of a plant showing a compact growth phenotype as compared to an isogenic plant not comprising the modified Cullin1 gene.

16. Use of the modified Cullin1 gene of any of the paragraphs 1-8 or a part thereof for identifying a plant showing a compact growth phenotype as compared to an isogenic plant not comprising the modified Cullin1 gene.

17. Use of any of the sequences of SEQ ID No: 1-SEQ ID No: 17 and/or SEQ ID No: 35-SEQ ID No: 51 or a part thereof, or a marker derived thereof, as a marker for identifying a plant showing a compact growth phenotype as compared to an isogenic plant not comprising the modified Cullin1 gene.

18. Use of any of the paragraphs 15-17, wherein the plant belongs to a species selected from the group consisting of *Cucumis sativus, Cucumis melo, Cucurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

19. Method for obtaining a plant which shows a compact growth phenotype comprising;

a) crossing a plant comprising the modified Cullin1 gene of any one of the paragraphs 1-8 with a plant not comprising the modified Cullin1 gene, to obtain an F1 population;

b) optionally performing one or more rounds of selfing and/or crossing a plant from the F1 to obtain a further generation population;

c) selecting a plant that has a compact growth phenotype and the modified Cullin1 gene of the invention.

20. Method for obtaining a plant which shows a compact growth phenotype comprising;

a) crossing a plant comprising the modified Cullin1 gene of the current invention with another plant comprising the modified Cullin1 gene, to obtain an F1 population;

b) optionally performing one or more rounds of selfing and/or crossing a plant from the F1 to obtain a further generation population; and c) selecting a plant that has a compact growth phenotype and the modified Cullin1 gene of the invention.

21. Method of paragraph 19 or 20, wherein the plant belongs to a species selected from the group consisting of *Cucumis sativus, Cucumis melo, Curcurbita pepo, Citrullus lanatus, Solanum melongena, Solanum lycopersicum, Capsicum annuum, Brassica oleracea, Daucus carota, Apium graveolens, Cichorium intybus, Cichorium endivia, Allium ampeloprasum, Lactuca sativa, Raphanus sativus, Spinacia oleracea*, and *Beta vulgaris*.

22. Marker for identifying a plant showing a compact growth phenotype, comprising the modified Cullin1 gene of any one of the paragraphs 1-8 or a part thereof that comprises the modification.

23. Marker of paragraph 22, wherein the modification is a nucleotide substitution on or around position 147 of SEQ ID No:1 of cucumber, or, in case of a crop other than cucumber, on or around a position corresponding to position 147 of SEQ ID No:1 of cucumber, which modification leads to an amino acid substitution in the Cullin1 protein.

24. Method for selecting a plant showing a compact growth phenotype from a population of plants, comprising detecting the presence or absence of a guanine on position 147 of the cucumber nucleotide sequence of SEQ ID NO:1, or, for a crop other than cucumber, on a position corresponding to position 147 of the cucumber nucleotide sequence of SEQ ID No: 1, in the genome of a plant of a population of plants, and selecting a plant comprising a guanine on position 147 of SEQ ID NO:1, or, for a crop other than cucumber, on a position corresponding to position 147 of the cucumber nucleotide sequence of SEQ ID No: 1.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method for selecting a *Cucumis sativus* plant, a *Cucumis melo* plant, a *Cucurbita pepo* plant, or a *Citrullus lanatus* plant comprising a modified Cullin1 gene and expressing a modified Cullin1 protein comprising a single non-silent amino acid substitution, wherein the *Cucumis sativus* plant, a *Cucumis melo* plant, a *Cucurbita pepo* plant, or a *Citrullus lanatus* plant expressing the modified Cullin1 protein exhibits a compact growth phenotype as compared to an isogenic line not comprising the modified Cullin 1 protein wherein the method comprises;

a) testing the plant for presence of the modified Cullin1 gene, or for the presence of the modified Cullin 1 protein, wherein:

when the plant is a Cucumis sativus plant, the testing comprises detecting modification of the nucleotide sequence of SEQ ID NO: 1 leading to change of the amino acid sequence of SEQ ID NO: 18, or detecting modification of the amino acid sequence of SEQ ID NO: 18 in the region that binds SKP1 and/or ETA2, wherein the modification of the nucleotide sequence of SEQ ID NO: 1 confers a substitution in the Cullin1polypeptide sequence of SEQ ID NO: 18 between positions 30 to 60 of SEQ ID NO: 18, wherein the modification of the nucleotide sequence excludes the substitution of A to G at position 147 of SEQ ID NO: 1;

when the plant is a Cucumis melo plant, the testing comprises detecting modification of the nucleotide sequence of SEQ ID NO: 2 leading to change of the amino acid sequence of SEQ ID NO: 19, or detecting modification of the amino acid sequence of SEQ ID NO: 19 in the region that binds SKP1 and/or ETA2 wherein the modification of the nucleotide sequence of SEQ ID NO: 2 confers a substitution in the Cullin1polypeptide sequence of SEQ ID NO: 19 between positions 30 to 60 of SEQ ID NO: 19;

when the plant is a *Cucurbita pepo* plant, the testing comprises detecting modification of the nucleotide sequence of SEQ ID NO: 3 leading to change of the amino acid sequence of SEQ ID NO: 20, or detecting modification of the amino acid sequence of SEQ ID NO: 20 in the region that binds SKP1 and/or ETA2 wherein the modification of the nucleotide sequence of SEQ ID NO: 3 confers a substitution in the Cullin 1polypeptide sequence of SEQ ID NO: 20 between positions 30 to 60 of SEQ ID NO: 20;

when the plant is a *Citrullus lanatus* plant, the testing comprises detecting modification of the nucleotide sequence of SEQ ID NO: 4 leading to change of the amino acid sequence of SEQ ID NO: 21, or detecting modification of the amino acid sequence of SEQ ID NO: 21 in the region that binds SKP1 and/or ETA2 wherein the modification of the nucleotide sequence of SEQ ID NO: 4 confers a substitution in the Cullin 1polypeptide sequence of SEQ ID NO: 21 between positions 30 to 60 of SEQ ID NO: 21;

b) selecting the *Cucumis sativus* plant, *Cucumis melo* plant, *Cucurbita pepo* plant, or *Citrullus lanatus* plant having the modified Cullin1 gene or the modified Cullin 1 protein; and c.) growing the *Cucumis sativus* plant, *Cucumis melo* plant, *Cucurbita pepo* plant, or *Citrullus lanatus* plant exhibiting a compact growth phenotype compared to an isogenic line not comprising the modified Cullin1 gene.

2. The method of claim 1, wherein the plant of step a) is a *Cucumis melo* plant, and the testing comprises detecting modification of the nucleotide sequence of SEQ ID NO: 2, wherein the modification of the nucleotide sequence of SEQ ID NO: 2 confers a substitution in the Cullin1 polypeptide sequence of SEQ ID NO: 19between positions 30 to 60 of SEQ ID NO: 19.

3. The method of claim 1, wherein the plant of step a) is a Cucurbita pepo plant, and the testing comprises detecting modification of the nucleotide sequence of SEQ ID NO: 3 wherein the modification of the nucleotide sequence of SEQ ID NO: 3 confers a substitution in the Cullin1 polypeptide sequence of SEQ ID NO: 20 between positions 30 to 60 of SEQ ID NO: 20.

4. The method of claim 1, wherein the plant of step a) is a Citrullus lanatus plant, the testing comprises detecting modification of the nucleotide sequence of SEQ ID NO: 4 wherein the modification of the nucleotide sequence of SEQ ID NO: 4 confers a substitution in the Cullin1 polypeptide sequence of SEQ ID NO: 21 between positions 30 to 60 of SEQ ID NO: 21.

5. A *Cucumis sativus* plant, a *Cucumis melo* plant, a *Cucurbita pepo* plant, or a *Citrullus lanatus* plant selected by the method of claim 1.

6. A plant seed from, or capable of developing into, the plant of claim 5, and comprising the Cullin1 gene comprising modified Cullin1 gene.

7. A propagation material from or capable of developing into the plant of claim 5, and comprising the modified Cullin1 gene.

8. A *Cucumis melo*, a *Cucurbita pepo* plant, or a *Citrullus lanatus* plant selected by the method of claim 1.

9. A *Cucumis melo* plant or a *Cucumis sativus* plant selected by the method of claim 1.

10. The propagation material of claim 7, wherein the propagation material comprises a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof.

11. The plant of claim 5 wherein the modified Cullin1 gene is introgressed into the plant.

12. The plant of claim 9 wherein the modified Cullin1 gene is introgressed into the plant.

13. A propagation material from or capable of developing into the plant of claim 11, and comprising the modified Cullin1 gene.

14. The propagation material of claim 13, wherein the propagation material comprises a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof.

15. A mutant *Cucumis* plant comprising a modified Cullin1 gene comprising a SNP in the wild type nucleotide sequence of SEQ ID NO: 1 which leads to a non-silent amino acid substitution change in the wild type Cullin1 amino acid sequence of SEQ ID NO: 18, excluding a *Cucumis sativus* plant with SEQ ID NO: 35 as the nucleotide sequence of the modified Cullin1 gene, wherein the modification of the nucleotide sequence of SEQ ID NO: 1 confers a substitution in the Cullin1 polypeptide sequence of SEQ ID NO: 18 between positions 30 to 60 of SEQ ID NO: 18, wherein the modification of the nucleotide sequence excludes the substitution of A to G at position 147 of SEQ ID NO: 1, and wherein the plant shows a compact growth phenotype as compared to an isogenic plant of the same species not comprising the modified Cullin1 gene.

16. The plant as claimed in claim 15, wherein the plant belongs to a species selected from the group consisting of *Cucumis sativus* and *Cucumis melo*.

17. A mutant *Cucumis* plant seed from, or capable of developing into, the plant of claim 15, and comprising the modified Cullin1 gene.

18. A mutant *Cucumis* plant seed from, or capable of developing into, the plant of claim 16, and comprising the modified Cullin1 gene.

19. A propagation material from, or capable of developing into, the plant as claimed in claim 15, wherein the propagation material comprises the modified Cullin1 gene.

20. The propagation material of claim 15, wherein the propagation material comprises a microspore, pollen, ovary, ovule, embryo, embryo sac, egg cell, cutting, root, hypocotyl, cotyledon, stem, leaf, flower, anther, seed, meristematic cell, protoplast, cell, or tissue culture thereof.

21. The plant of claim 15, wherein the modified Cullin1 gene is introgressed into the plant.

* * * * *

SEQUENCE LISTING

```
<160> NUMBER OF SEQ ID NOS: 69

<210> SEQ ID NO 1
<211> LENGTH: 2235
<212> TYPE: DNA
<213> ORGANISM: Cucumis sativus
<220> FEATURE:
<221> NAME/KEY: source
<222> LOCATION: 1..2235
<223> OTHER INFORMATION: /organism="Cucumis sativus"
```

/mol_type="unassigned DNA"

<400> SEQUENCE: 1

| | | | | | |
|---|---|---|---|---|---|
| atgacaatgg | gcgagcggaa | gactattgac | ttggagcagg | gatgggagtt | tatgcagaag | 60 |
| ggtatcacaa | agttgaagaa | cattctcgag | ggcttgcctg | agcctcagtt | cagctccgag | 120 |
| gactacatga | tgctttacac | taccatatat | aacatgtgca | cccaaaagcc | gccgcatgat | 180 |
| tactcccagc | agctgtatga | taaatatcgt | gaatcttttg | aagagtacat | cacttctatg | 240 |
| gtcttaccat | ccttgaggga | gaagcacgat | gagttcatgt | tgagagaact | agtaaaaagg | 300 |
| tggacaaacc | ataaagtcat | ggtgaggtgg | ctttctcgct | tcttccacta | tcttgatcgg | 360 |
| tacttcatcg | ctcgaaggtc | acttccacct | ctaaatgaag | ttggcctcac | atgcttccgc | 420 |
| gaattggtgt | acaaagagct | aaatagtaaa | gtgagggatg | cagtaatttc | attgattgat | 480 |
| caagaacgtg | aaggagaaca | gattgacaga | gctctactga | agaatgtact | agatatattt | 540 |
| gtggaaattg | gtatggggca | aatggattac | tatgaaaatg | actttgaagc | tgccatgctt | 600 |
| aaagatactg | ctgcttatta | ctctaggaag | gcttccaatt | ggatcctaga | agattcttgt | 660 |
| cccgattata | tgcttaaagc | agaggagtgc | ttgaaacgag | aaaaggatag | ggtttcccac | 720 |
| tatttgcact | ctagtagcga | gccaaagttg | ttggagaaag | ttcaacatga | actattatct | 780 |
| gtttatgcta | ctcaactgct | ggaaaaagag | cattcaggat | gccatgcatt | gcttagagat | 840 |
| gacaaggtgg | aagatttgtc | aaggatgttc | cgtctattct | ccaaaatacc | gaagggactg | 900 |
| gatccagttt | ccaacatatt | taagcagcat | gtaactgctg | aaggaacagc | actggtcaaa | 960 |
| caggcagaag | atgctgcaag | taacaagaag | gctgagaaaa | aggacatagt | tggtctgcag | 1020 |
| gaacaggttt | ttgtaagaaa | agtgattgag | cttcacgaca | agtacttggc | ttatgtgaat | 1080 |
| gattgtttcc | aaaaccacac | acttttccat | aaggctctca | aggaagcttt | tgaagtattt | 1140 |
| tgcaataagg | gtgttgctgg | aagttctagt | gcagaattgc | ttgctacctt | ttgtgataac | 1200 |
| atccttaaga | aggtgggag | tgagaagttg | agtgatgaag | caatcgagga | gacacttgag | 1260 |
| aaggttgtga | agttgttggc | atacatttgc | gacaaagatc | tgtttgctga | attctataga | 1320 |
| aaaaaacttg | cccgaaggct | tctctttgac | aagagcgcga | acgatgacca | cgagagaagt | 1380 |
| atattgacca | aattgaagca | acaatgtggt | ggtcagttca | cttctaagat | ggagggaatg | 1440 |
| gttactgatt | tgactttggc | aagggagaac | caaactagtt | ttgaggagta | tctgagcaat | 1500 |
| aatccacaag | cgagtcctgg | catcgacctg | actgttactg | ttttaactac | tggattttgg | 1560 |
| ccaagctaca | agtcttttga | cctcaacctg | ccggcagaga | tggtaaagtg | tgttgaagtt | 1620 |
| ttcagagagt | tttatcaaac | aaaaaccaag | catcgaaaac | ttacatggat | ttactcattg | 1680 |
| ggtacttgta | acatcagtgg | aaaatttgaa | ccgaaaacga | tggagctgat | tgtgacaact | 1740 |
| tatcaggctt | ctgccctgtt | gctattcaat | tcttcggata | gactaagtta | ctcggaaatc | 1800 |
| atgacacaat | taaatttgag | tgacgatgat | gtagttagac | tactccactc | gttgtcatgt | 1860 |
| gccaagtata | aaattcttaa | taaggaacca | aatacgaaaa | ccatctctcc | gaacgatcat | 1920 |
| tttgagttca | atgcaaaatt | ctccgacaaa | atgaggagaa | taaagatccc | tcttccgcct | 1980 |
| gtggatgaga | aaagaaagt | cattgaagat | gttgacaagg | atcgaaggta | tgctattgac | 2040 |
| gcctcaatcg | tgcgtatcat | gaagagtcgg | aaagttcttg | gtcatcagca | actagtgatg | 2100 |
| gagtgcgtcg | agcaattggg | ccgtatgttc | aagcccgatt | tcaaggcgat | aaagaagaga | 2160 |
| attgaagacc | tgatcactcg | ggattatcta | gagagagaca | aagacaaccc | ccacttgttt | 2220 |
| aggtacttgg | cttga | | | | | 2235 |

<210> SEQ ID NO 2
<211> LENGTH: 2235
<212> TYPE: DNA
<213> ORGANISM: Cucumis melo
<220> FEATURE:
<221> NAME/KEY: source
<222> LOCATION: 1..2235
<223> OTHER INFORMATION: /organism="Cucumis melo"
/mol_type="unassigned DNA"

<400> SEQUENCE: 2

| | | | | | | |
|---|---|---|---|---|---|---|
| atgacaatgg | gcgagcggaa | gactattgac | ttggaacagg | gatgggagtt | tatgcagaag | 60 |
| ggtatcacaa | agttgaagaa | cattcttgag | ggcttgcctg | agcccagtt | cagctccgag | 120 |
| gactacatga | tgcttacac | taccatatat | aacatgtgca | cccaaaagcc | gccgcatgat | 180 |
| tactcccagc | agctgtatga | taaatatcgt | gaatcttttg | aagagtacat | cacttctatg | 240 |
| gtcttaccat | ccttgaggga | gaagcatgac | gagttcatgt | tgagagaact | agtcaaaagg | 300 |
| tggacaaacc | ataaagtcat | ggtgaggtgg | ctttctcgct | tcttccacta | tcttgatcgg | 360 |
| tacttcatcg | ctcgaaggtc | acttccacct | ctaaatgaag | ttggcctcac | atgcttccgc | 420 |
| gaattggtgt | acaaagagct | aaacagtaaa | gtgagggatg | cagtaatctc | attgattgat | 480 |
| caagaacgtg | aaggagaaca | gattgacaga | gctctactga | agaatgtatt | agatatattt | 540 |
| gtggaaattg | gtatggggca | aatggattac | tatgaaaatg | actttgaagc | tgccatgctt | 600 |
| aaagatactg | ctgcttatta | ctctaggaag | gcttccaatt | ggatcctaga | agattcttgt | 660 |
| cccgattata | tgctaaaagc | agaggagtgc | ttgaagcgag | aaaaggatag | ggtttcccac | 720 |
| tatttgcact | ctagtagcga | gccaagttg | ttggagaaag | ttcaacacga | actgttatct | 780 |
| gtgtatgcta | ctcaactgct | ggaaaaagag | cattcaggat | gccatgcatt | gcttagagat | 840 |
| gacaaggtgg | aagatttgtc | aaggatgttc | cgtctcttct | ccaaaatacc | gaagggattg | 900 |
| gacccagttt | ccaacatatt | taagcagcat | gtaactgctg | aaggaacagc | actggtcaaa | 960 |
| caggcagaag | atgctgcaag | taacaagaag | gccgagaaaa | aggacatagt | tggtctgcag | 1020 |
| gaacaggttt | ttgtaagaaa | agtgattgag | cttcacgaca | agtacttggc | ttatgtgaat | 1080 |
| gattgtttcc | aaaaccacac | actttttccat | aaggctctca | aggaagcttt | tgaagtcttt | 1140 |
| tgcaataagg | gtgttgctgg | aagttctagt | gcagaattgc | ttgctacctt | ctgcgataac | 1200 |
| atccttaaga | aaggtgggag | tgagaagttg | agtgatgaag | caatcgaaga | gacacttgag | 1260 |
| aaggttgtga | agttgttggc | atacatctgc | gacaaagatc | tgtttgctga | attctataga | 1320 |
| aaaaaacttg | cccgaaggct | tctctttgat | aagagcgcca | acgatgacca | cgagagaagt | 1380 |
| atattgacca | aattgaagca | acaatgtggt | ggtcagttca | cttctaagat | ggagggaatg | 1440 |
| gttactgatt | tgactttggc | aagggagaac | caaactagtt | tcgaagagta | tctgagcaat | 1500 |
| aatccacaag | ctagtcctgg | aatcgaccta | actgttactg | ttttgactac | tggattttgg | 1560 |
| ccaagctaca | agtcttttga | cctcaacctg | ccggcggaga | tggtaaagtg | tgttgaagtt | 1620 |
| ttcagagagt | tttatcaaac | aaaaaccaag | catagaaaac | ttacatggat | ttactcattg | 1680 |
| ggtacttgta | acatcagtgg | aaaatttgaa | ccgaagacga | tggagctgat | tgtgacaaca | 1740 |
| tatcaggctt | ctgccctgtt | gctattcaat | tcttcggaca | gactaagtta | ctccgaaatc | 1800 |
| atgacacaat | taaatttgag | tgatgatgat | gttgttagac | tgctccactc | attgtcgtgt | 1860 |
| gccaagtata | aaattcttaa | taaggagcca | aatacgaaaa | ccatctcacc | gaacgatcat | 1920 |
| tttgagttca | atgcaaaatt | ctccgacaaa | atgaggagaa | taaagatccc | tcttccgcct | 1980 |

| | |
|---|---|
| gtggatgaga aaaagaaagt cattgaagat gttgacaagg atcgaaggta tgctattgac | 2040 |
| gcctcaatcg tgcgtatcat gaagagtcga aaagttcttg gtcatcagca actagtgatg | 2100 |
| gagtgcgtcg agcaattggg tcgtatgttc aagcccgatt tcaaggcgat aaagaagaga | 2160 |
| attgaagacc tgatcactcg ggactatcta gagagagaca agacaacccc ccacttgttt | 2220 |
| aggtacttgg cttga | 2235 |

<210> SEQ ID NO 3
<211> LENGTH: 2235
<212> TYPE: DNA
<213> ORGANISM: Cucurbita pepo
<220> FEATURE:
<221> NAME/KEY: source
<222> LOCATION: 1..2235
<223> OTHER INFORMATION: /organism="Cucurbita pepo"
　　　　/mol_type="unassigned DNA"

<400> SEQUENCE: 3

| | |
|---|---|
| atgacaatgg gtgagcggaa gactattgac ttggagcaag gatgggagtt tatgcagaag | 60 |
| ggaatcacaa aattgaagaa cattctggaa ggattgcctg agccacagtt cagctccgag | 120 |
| gactacatga tgctttacac tacaatatat aacatgtgta cccagaagcc accgcatgat | 180 |
| tactcccagc agctgtatga taaataccgc gaatcgtttg aggagtacat cagttctatg | 240 |
| gttttaccat ccttgaggga aagcatgac gaatttatgt tgagagaact ggtcaaaagg | 300 |
| tggaccaacc ataaagtcat ggtgaggtgg ctttctcgct tcttccacta tcttgatcga | 360 |
| tacttcattg ctcgaaggtc acttccacct ctcaatgaag ttggcctcac ttgcttccgt | 420 |
| gaattggtgt acaaagagct aaacagtaaa gtgagggatg cagtaatttc attgatcgat | 480 |
| caagaacgtg aaggagagca gattgacaga gctctgttga agaacgtgtt ggatatattt | 540 |
| gtggagattg ggatggggca atggattat tatgaaaatg actttgaagc tgccatgctt | 600 |
| aaagatactg ctgcttacta ctctaggaag gcatcaaatt ggatcttaga agattcttgt | 660 |
| cctgattata tgctaaaagc agaggagtgc ttgagacgag aaaaggaccg agtttctcac | 720 |
| tatctgcact ctagtagcga gccaaagtta ttggagaaag ttcaacatga actattgtct | 780 |
| gtttatgcta ctcaactgct ggagaaagag cattcaggat gccatgcatt gcttagagat | 840 |
| gacaaggtgg aagatttgtc aaggatgttc cgtctcttct ccaaaatacc caagggattg | 900 |
| gacccagttt ccaacatatt taagcagcat gtcactgctg aaggaacagc attagtcaaa | 960 |
| caggcagaag acgctgcaag taacaagaag gccgagaaaa aggacatcgt tggtctgcaa | 1020 |
| gaacaggttt tgttagaaa agtgattgag cttcacgaca agtacttggc atatgtgaat | 1080 |
| gattgtttcc aaaccacac acttttttcac aaggctctca aggaagcttt tgaagtcttt | 1140 |
| tgcaataagg gtgttgctgg aagttctagt gcagaattac ttgctaccttt tgtgataac | 1200 |
| atccttaaga aggtgggag tgagaagttg agtgatgaag caattgagga aacactcgag | 1260 |
| aaggtcgtga aattgctggc gtatatctgc gacaaagatc tgtttgctga attctataga | 1320 |
| aaaaaactcg cccgaaggct tctcttcgac aagagtgcga atgatgacca cgagagaagt | 1380 |
| atactgacga aattgaagca acaatgtggt ggtcagttta cctctaagat ggagggaatg | 1440 |
| gtcacggatt tgacactggc aagggagaac caaactagtt tgaggaata tctgagcaat | 1500 |
| aatccacaag ctagtcctgg aatcgacttg accgttaccg ttttgaccac tggttttggg | 1560 |
| ccaagctaca agtctttga cctcaacctg ccggcggaga tggtaaagtg tgttgaagtt | 1620 |
| ttcagggaat tttatcaaac aaaaaccaag cacagaaaac ttacgtggat ttactcgttg | 1680 |

```
ggtacctgta acatcagcgg aaaattcgaa ccgaaaacga tggagctgat cgtgacaacc    1740
tatcaggctt ctgccctgct gcttttcaat tcctcggata aactaagtta ctccgagatc    1800
atgactcaat taaacttgag tgacgatgat gttgttagac tgctccactc gttgtcgtgt    1860
gcgaagtata aaattcttaa caaggagcca aatacgaaaa ccatctctcc gaacgatcat    1920
tttgagttca acgcaaaatt ctccgacaaa atgaggagaa taaagatccc tcttccgcct    1980
gtggatgaga aaagaaagt aatagaagat gttgacaagg atcgaagata tgctatcgat    2040
gcctcgatcg tgcgtatcat gaagagtagg aaagttctgg gtcaccagca gttagtgatg    2100
gagtgcgtcg agcaactggg tcgtatgttc aagcctgatt tcaaggcgat aaagaagaga    2160
atcgaagatc tgatcactcg tgactattta gagagagaca agacaacccc ccacttgttt    2220
aggtacttgg cttga                                                    2235
```

<210> SEQ ID NO 4
<211> LENGTH: 2235
<212> TYPE: DNA
<213> ORGANISM: citrillus lanatus
<220> FEATURE:
<221> NAME/KEY: source
<222> LOCATION: 1..2235
<223> OTHER INFORMATION: /organism="citrillus lanatus"
     /mol_type="unassigned DNA"

<400> SEQUENCE: 4

```
atgacaatgg gcgagcggaa gactattgac ttggaacaag gatgggagtt tatgcagaag     60
ggaatcacaa agttgaagaa cattcttgag ggcttgcctg agcctcagtt cagctccgag    120
gactacatga tgctttatac caccatatac aacatgtgca cacaaaagcc gccacatgat    180
tactcccagc agctatacga taaataccgt gaatcttttg aggagtatat cacttctatg    240
gtcttaccat ccttgaggga gaagcatgac gagttcatgt tgagagaact ggtcaaaagg    300
tggacgaacc ataaagtcat ggtgaggtgg cttctctcgct tcttccacta tcttgaccga    360
tacttcattg ctcgaagatc acttccacct ctcaacgaag ttggcctcac atgcttccgt    420
gaattggtgt acaaagagct aaacagtaaa gtgagggatg cagtaatttc attgattgat    480
caagaacgtg aaggagagca gattgacaga gctctactga agaatgtatt agatatattt    540
gtggaaattg ggatggggca aatggattac tatgaaaatg actttgaagc tgccatgctt    600
aaagatactg ctgcttatta ctctaggaag gcttccaatt ggatcctaga agattcttgt    660
cccgattata tgctaaaagc agaggagtgc ttgaaacgag aaaaggatag agtttctcac    720
tatttgcact ctagtagcga gccaaagtta ttagagaaag ttcaacatga actgttatct    780
gtgtatgcta ctcaactgct ggaaaaagag cattcaggat gccatgcatt gcttagagat    840
gacaaggtgg aagatttgtc aaggatgttc cgcctcttct ccaaaatacc caagggattg    900
gacccagttt ccaacatatt taagcagcat gtcactgctg aaggaacagc attggtcaaa    960
caggcagaag atgctgcaag taacaagaag gccgagaaaa aggacatagt tggtctgcag   1020
gaacaggttt ttgtaagaaa agtgattgag cttcacgaca agtacttggc ttacgtgaat   1080
gattgtttcc aaaaccacac acttttttcac aaggctctca aggaagcttt tgaagtcttt   1140
tgcaataagg gtgttgctgg aagttctagt gcagaattac ttgctaccct ttgtgataac   1200
atccttaaga aggtgggag cgagaagttg agtgatgaag caattgagga gacacttgag   1260
aaggtcgtga agttgctggc atacatctgc gacaaagatc tgtttgctga attctataga   1320
aaaaaacttg cccgaaggct tctctttgac aagagtgcca acgatgacca tgagagaagt   1380
```

| | | | | |
|---|---|---|---|---|
| atattgacca | aattgaagca | acaatgtggt | ggccagttca | cctctaagat | ggaggggatg | 1440 |
| gtcactgatt | tgactttggc | aagggagaac | caaactagtt | tcgaggagta | tctgagcaat | 1500 |
| aatccacaag | ctagtcctgg | aatcgacttg | actgtcactg | ttttgactac | tggcttttgg | 1560 |
| ccaagctaca | agtcttttga | cctcaacctg | ccggcagaga | tggtaaagtg | tgttgaagtt | 1620 |
| ttcagagagt | tctatcaaac | aaaaacaaag | catagaaaac | ttacatggat | ttactcattg | 1680 |
| ggtacctgta | acatcagcgg | aaaatttgaa | ccgaaaacga | tggagctgat | tgtaacaact | 1740 |
| tatcaggctt | ctgccctgct | gctattcaat | cctcagata | gattaagtta | ttccgagatc | 1800 |
| atgacacaat | taaatttgag | tgacgatgat | gttgttagac | tgctccactc | attgtcatgt | 1860 |
| gccaagtata | aaattcttaa | taaggagccg | aacacgaaaa | ccatctctcc | gaatgatcat | 1920 |
| tttgagttca | atgcaaaatt | ctccgacaaa | atgaggagaa | taaagatccc | tcttccgcct | 1980 |
| gtggatgaga | aaagaaagt | cattgaagat | gttgacaagg | atcgaaggta | tgctattgat | 2040 |
| gcctcaatcg | tgcgtatcat | gaagagtcgg | aaagttctgg | gtcatcagca | gctagtgatg | 2100 |
| gagtgcgtcg | agcaattggg | tcgtatgttc | aagcccgact | tcaaagcgat | aaagaagaga | 2160 |
| atcgaagatc | tgatcactcg | ggactattta | gagagagaca | aagacaaccc | ccacttgttt | 2220 |
| aggtacttgg | cttga | | | | | 2235 |

<210> SEQ ID NO 5
<211> LENGTH: 2229
<212> TYPE: DNA
<213> ORGANISM: Solanum melongena
<220> FEATURE:
<221> NAME/KEY: source
<222> LOCATION: 1..2229
<223> OTHER INFORMATION: /organism="Solanum melongena"
     /mol_type="unassigned DNA"

<400> SEQUENCE: 5

| | | | | |
|---|---|---|---|---|
| atgaaccaac | gcagcacaat | cgatctggaa | catggatggg | atttcatgca | aaagggcatc | 60 |
| acaaagctga | agaacattct | agaagggctg | cctgagcctc | agttcagctc | agaggactat | 120 |
| atgatgctgt | atacgacaat | ttacaacatg | tgtactcaga | agcccccaca | tgattattct | 180 |
| caacagctgt | atgacaaata | tcgtgaagct | tttgaagaat | atatcacaac | gacggtatta | 240 |
| ccttcttttga | gagaaaaaca | tgacgagttc | atgttgcgag | agttggtaaa | aggtggtca | 300 |
| aaccataagg | tcatggttag | atggttatcg | cgattcttcc | attatcttga | ccgttatttc | 360 |
| attgctcgga | gatcactgcc | agggcttaat | gaagttggac | taacttgctt | ccgcgatctg | 420 |
| gtctaccaag | agttgaatgg | aaaagtcagg | gatgctgtta | tatctctgat | tgatcaagag | 480 |
| cgtgagggag | agcaaattga | cagagctcta | ctgaagaatg | tgctagatat | atttgttgaa | 540 |
| attggaatgg | ggtcaatgga | ttattatgag | aatgattttg | aagctgcaat | gctcaaggac | 600 |
| actgcggctt | attattctcg | caaagcttct | aactggatcc | tcgaagattc | atgtccagat | 660 |
| tatatgctga | aagctgagga | gtgcttgaaa | cgggagaagg | atagggtctc | ccattatctc | 720 |
| cattctagca | gtgagacaaa | gttgcttgag | aaagtgcaac | atgagttgtt | atctgtgtat | 780 |
| gccaatcaac | ttcttgagaa | ggagcactct | ggatgccatg | cattacttag | agatgataag | 840 |
| gtcgatgatt | tatcaaggat | gtatagactc | ttttctaaga | ttcctcgagg | cttagagcct | 900 |
| gtggctaata | tatttaagca | gcatgttact | gctgaaggta | cagctttggt | gaaacaggct | 960 |
| gaagatgctg | ctagcaacaa | aaaggcagag | aagagagatg | tggttggttt | gcaggaacag | 1020 |
| gttttttgttc | ggaaagtgat | tgagcttcat | gataaatatt | tggcgtatgt | gaataactgt | 1080 |

-continued

| | |
|---|---|
| ttccaaaacc acacactttt tcacaaggca cttaaagaag ctttcgaact tttctgcaac | 1140 |
| aagggtgttg ctggtagctc aaatgctgaa cttcttgcca cattctgcga caacattctc | 1200 |
| aaaaaaggcg ggagtgaaaa attgagtgat gaagccattg aagagacgct ggagaaggtg | 1260 |
| gtaaagctgc tggcttatat tagtgataag gacttgtttg cagaattcta taggaaaaag | 1320 |
| ctcgcccggc ggttgttatt tgataagagt gccaatgatg aacatgagag aagtatccta | 1380 |
| acaaagttga agcagcagtg tggaggtcag ttcacatcaa agatggaggg aatggtcaca | 1440 |
| gatttgacat tggcaaggga aaatcaagcc agctttgagg agtatttgag caataatcca | 1500 |
| acagcaaatc caggaattga cttgacggtg actgtcttga ctactggctt ctggcctagc | 1560 |
| tacaagtctt ttgatctcaa cctcccagca gaaatggtta ggtgtgttga agtattcaag | 1620 |
| gagttttatc aaacaaaaac gaagcacagg aaacttacat ggatatactc tttgggaact | 1680 |
| tgcaacataa atggaaaatt tgaggcaaag actattgagc tcgttgtcac tacttatcag | 1740 |
| gcttctgctc tgcttctctt taatgcatca gatagattga gttatcagga aatcatgacg | 1800 |
| caattaaacc tatcagatga tgatgttgtt cggcttcttc attccctttc atgtgcgaaa | 1860 |
| tacaagattc tcaacaagga gccaagcacc aaaacaattt ctccgactga tgtctttgag | 1920 |
| ttcaactcaa agttcactga caaatgagg aggatcaaga tacctctccc accagttgat | 1980 |
| gaaaagaaaa aggtaattga agacgttgac aaggataggc ggtatgctat agatgcctca | 2040 |
| attgtgcgta ttatgaagag tcgtaaagta ttgggctacc agcaactggt catggagtgc | 2100 |
| gttgagcagt tgggacgcat gttcaagcct gatgtcaaag ctatcaagaa gagaattgaa | 2160 |
| gatctgataa ctagagatta cctagagagg gacaaagata acccaaactt gttcaagtac | 2220 |
| ttggcatga | 2229 |

<210> SEQ ID NO 6
<211> LENGTH: 2229
<212> TYPE: DNA
<213> ORGANISM: Solanum lycopersicum
<220> FEATURE:
<221> NAME/KEY: source
<222> LOCATION: 1..2229
<223> OTHER INFORMATION: /organism="Solanum lycopersicum"
    /mol_type="unassigned DNA"

<400> SEQUENCE: 6

| | |
|---|---|
| atgaaccaac gaagcacaat cgatctggaa catggatggg acttcatgca aaggggcatt | 60 |
| acaaagctga gaacattct agaagggctg cctgagcctc aattcagctc agaggactat | 120 |
| atgatgctat atacgacaat ttacaacatg tgtactcaaa agcccccaca tgattattct | 180 |
| caacagctgt atgacaaata tcgtgaagct tttgaagaat atatcacaac aacggtattg | 240 |
| ccttctttga gagaaaaaca tgacgagttt atgttgcgag agttggtaaa aaggtggtca | 300 |
| aatcataaag tcatggtcag atggttgtca agattcttcc attaccttga ccggtatttc | 360 |
| attgcccgga gatctctgcc ggggcttaat gaagttggac taacttgctt ccgcgatcag | 420 |
| gtctaccaag agttgaatgg aaaagtcagg gatgctgtta tatctctgat tgatcaagag | 480 |
| cgtgagggag agcaaattga cagagctcta cttaagaatg tgcttgatat atttgtcgaa | 540 |
| attggaatgg ggttaatgga ttattatgag aatgattttg aagctgcaat gctcaaggac | 600 |
| acagcggctt attattctcg caaagcttct aattggatcc tcgaagattc atgtccggat | 660 |
| tatatgctga aagccgagga gtgcttgaaa cgggagaagg atagggtctc tcattatctc | 720 |
| cattcaagca gcgagacgaa gttgcttgag aaagtgcaac atgagttgtt gtctgtgtat | 780 |

```
gccactcaac ttcttgagaa ggagcactct ggatgccatg cgttactgag agatgataag      840
gttgaagatt tatcaaggat gtataggctc ttttctaaga tttctcgagg cttagaccct      900
gtggccaata ttttaagca gcatgttact gctgaaggta cagctttggt aaaacaggct       960
gaagatgctg ctagcaataa aaaggcagag aagagagatg tggttggttt gcaggaacag     1020 gttttttgttc ggaaagtgat tgaacttcat gataaatatt tggcttatgt gaataactgt    1080
ttccaaaacc acacactttt tcacaaggcg cttaaagaag cttttgagct tttctgcaac     1140
aagggtgttg ctggtagctc aagcgctgaa cttcttgcca ccttctgtga caacattctc     1200
aaaaaaggcg ggagtgagaa attgagtgat gaagctattg aagaaacgtt ggaaaaggtg     1260
gtaaagctac tagcttatat tagtgataag gacttgtttg cagaattcta taggaaaaag     1320
ctagcccggc ggttgttatt tgataagagt gccaatgatg aacatgaaag aagtatccta     1380
acaaagttga agcagcagtg tgggggggcag ttcacatcaa agatggaggg aatggtcaca     1440
gatttgacat tggcaaggga aaatcaagcc agcttcgagg agtatttgag caataatcca     1500
atagcaaatc caggaattga cttgacggtg actgtcttga ctactggctt ctggcctagc     1560
tacaagtctt ttgatctcaa cctcccagca gaaatggtta ggtgcgttga agtatttaag     1620
gagttctatc aaacaaaaac aaagcacagg aaacttacgt ggatatactc tttgggaact     1680
tgcaacataa atgaaaatt tgagccaaaa actattgagc tcgttgtcac tacttatcag     1740
gcttctgctc tgctgctctt taatgcatca gatagattga gttatcagga aatcatgacg     1800 caattaaaacc tatcagatga tgatgttgtt cggcttcttc attcccttc atgtgcgaag     1860 tacaagatac tcaacaagga gccaagcacc aaaacaattt ctccgactga tgtctttgag     1920
ttcaactcaa agttcactga caaaatgagg aggatcaaga tacctctccc tcctgttgat     1980
gagaagaaaa aggtaattga agacgttgac aaggataggc ggtatgctat agatgcttca     2040
attgtgcgta ttatgaagag ccgtaaagta ttgggctacc agcaactagt catggagtgc     2100
gttgagcagt tggggcgcat gttcaagcct gatgtcaaag ctatcaagaa gagaatcgaa     2160
gatttgataa ctagagatta cctagagagg gacaaagata atccaaacct gttcaagtac     2220
ttggcatga                                                              2229
```

<210> SEQ ID NO 7
<211> LENGTH: 2229
<212> TYPE: DNA
<213> ORGANISM: Capsicum annuum
<220> FEATURE:
<221> NAME/KEY: source
<222> LOCATION: 1..2229
<223> OTHER INFORMATION: /organism="Capsicum annuum"
    /mol_type="unassigned DNA"

<400> SEQUENCE: 7

```
atgaaccagc gttccacaat caatctagaa catggatggg acttcatgca aggggcatt       60 acaaagctga agaacattct agaagggctg cccgagcctc agttcagctc agaggactat     120
atgatgctgt atacgacaat ttacaacatg tgtactcaga agccccccaca tgattattct    180 caacagctgt atgacaaata tcgtgaagct tttgaagaat atatcacaac aacggtattg     240
ccttctttga gagaaaaaca tgacgagttc atgttgcgag agctggtaaa aaggtggtca     300
aaccataagg tcatggtcag atggttatcg cgattcttcc attatcttga tcgctatttc     360
attgcccgga gatctctacc gggcttaat gaagttggac taacttgctt ccagagatctg     420 gtctaccaag agttgaatgg aaaagtcagg gatgctgtta tatctctgat tgatcaagag      480
```

```
cgtgagggag agcaaattga cagagctcta ctgaagaatg tgctagatat atttgttgaa      540
attggaatgg ggtcgatgga ttattatgag aatgattttg aagctgcaat gctcaaggac      600
accgcagctt attattctcg caaagcttct aactggatac ttgaagattc atgtccagat      660
tatatgctga aagccgagga gtgcttgaaa cgggagaaaa atagggtctc tcactatctt      720
catttaagca gtgagacaaa gttgcttgag aaagtgcaac atgagttgtt gtctgtgtat      780
gccactcaac ttcttgagaa ggagcactct gggtgccatg cgttactaag agatgataag      840
gttgaagatt tatcaaggat gtataggctc ttttctaaga ttcctcgagg cttagaccct      900
gtggctaata tatttaagca gcatgttact gctgaaggta cagctttggt caaacaggct      960
gaagatgctg ctagcaacaa aaaggcagag aaaagagatg tggttggttt gcaggaacag     1020 attttgttc ggaaagtgat tgagcttcat gataagtata tggcatatgt gaataactgt      1080
ttccaaaacc acacactttt tcacaaggcg cttaagaag ctttcgaact tttctgcaac      1140
aagggtgttg ctggtagctc aagtgctgaa cttcttgcca cattctgcga caatattctc     1200
aagaaaggcg ggagtgagaa attgagtgat gaagccattg aagagacgct ggagaaggtt     1260
gtaaagctgc tagcatatat tagtgacaag gacttgtttg cagaattcta taggaaaaag     1320
ctagcccggc ggttgttatt tgataagagt gccaatgatg aacacgagag aagtatcctt     1380
acaaagttga agcagcagtg tgggggccag ttcacatcaa agatggaggg aatggtgaca     1440
gatttgacat tggcaaggga aaatcaagcc agctttgagg agtatttgag caacaatcca     1500
gcagcaaatc caggaattga cttgacggtg actgtcttga ctactggctt ctggcctagc     1560
tacaagtctt ttgatctcaa cctcccagca gaaatggtta ggtgcgttga agtattcaag     1620
gagttttatc aaacaaaaac gaagcacagg aaacttacgt ggatatactc tttgggaact     1680
tgcaatataa atggaaaatt tgagccaaag actattgagc tcgttgtcac tacttatcag     1740
gcttctgctc tgctgctctt taatgcatcg gatagattga gttatcagga aatcatgacg     1800
caactaaacc tatcagatga tgatgttgtt cggcttcttc attcccttc atgtgcgaag     1860 tacaagattc tcaacaagga gccaagcacc aaaacaattt ctccgactga tgtctttgag     1920 ttcaattta agttcactga caaatgagg aggatcaaga tacctctccc tcctgttgat      1980
gagaagaaaa aggtaattga agatgttgac aaagataggc ggtacgctat agatgcttca     2040
attgtgcgta ttatgaagag tcgtaaagta ttgggctacc agcaactggt catggagtgt     2100
gttgagcagt tgggacgtat gttcaagcct gatgtcaaag ctatcaagaa gagaattgaa     2160
gatttgataa ctagagatta cctagagagg gacaaagata tccgaacttt gttcaagtac     2220
ttggcatga                                                             2229
```

<210> SEQ ID NO 8
<211> LENGTH: 2217
<212> TYPE: DNA
<213> ORGANISM: Brassica oleracea
<220> FEATURE:
<221> NAME/KEY: source
<222> LOCATION: 1..2217
<223> OTHER INFORMATION: /organism="Brassica oleracea"
      /mol_type="unassigned DNA"

<400> SEQUENCE: 8

```
atggagcgca agacgattga cttggaccaa ggatgggact atatgcagac tggtatcact       60
aagctgaaac ggattcttga ggggctgcct gagccgcagt ttgactctga gcaatacatg      120
atgctctata cgactatcta caacatgtgc actcagaaac ctcctcatga ttactcacag      180
```

```
cagctttatg acaagtatcg tgaagcattt gaggagtata ttcactcaac tgttttgcct      240
gctctaaggg agaagcatga tgagtacatg ctgagggagc tggttaagag atggtctaac      300
cataaagtta tggttcgatg gctatcccgc ttcttctact atcttgaccg ttacttcatt      360
gctcggaggt cacttccacc cctgaatgaa gttggcctga cttgcttccg tgacctggtt      420
tataacgagt tgcattccaa ggtcaaagat gctgtaatag cacttgttga taaagaacgg      480
gagggtgagc agattgacag ggctctattg aaaaacgtat tagacattta tgtagagatt      540
ggaatgggac agatggaaag atacgaggag gattttgaaa gcttcatgct tttagattca      600
gcatcttact attctcgcaa ggcgtcaagc tggatccaag aagattcttg ccctgattac      660
atgctgaagt ctgaagaatg tcttaagaag agagggaga gagtggctca ctaccttcac      720
tcaagcagcg agccaaagct ggttgagaaa gtacaacatg agctgttggt agtgtatgca      780
aatcagcttc tagaaaaaga gcattcaggg tgccgtgcat tgctgagaga tgacaaggtt      840
gatgacctct ccaggatgta caggctttat cataaaattg tgaaaggttt ggaacctgtt      900
gcaaacatat ttaagcagca tgtcacagca gagggtaacg cacttgtcca acaggccgaa      960
gacacggcca ctaatcatgc tgcaaatact gctagcgtgc aggaacaggt tcttatcaga     1020
aaagtgattg aactacatga taaatacatg gtctatgttg ttgagtgttt ccagaaccac     1080
accctcttcc acaaggcatt gaaagaggca tttgagatat tctgtaacaa aacagtcgct     1140
ggaagttcta gtgctgaatt gcttgcaaca ttttgcgaca atattctcaa gaagggggga     1200
agtgaaaagc tgagcgatga agctattgaa gataccttg agaaggtggt caaattgctt     1260
gcttatataa gtgacaagga tcttttcgcc gagttctaca ggaagaagct ggcccgtagg     1320
ctcttatttg atcgcagtgc taatgatgat catgagagaa gtatcctgac aaagctcaag     1380
caacaatgtg gtgggcagtt tacttcgaag atggagggca tggtgactga tttgacattg     1440
gcaagggaaa accaaaacag cttcgaggag tatcttggca ataacccgc tgcaaaccca     1500 gggattgatt tgaccgtaac tgttcttacc actggttttt ggccaagtta caaatcattt     1560
gacataaatc tacccgctga aatggtcaag tgtgttgaag ttttcaaagg gttttatgaa     1620
acaaagacaa aacataggaa acttacctgg atctactcac taggaacttg ccacctcaat     1680
gggaagtttg atgtcaagcc cattgagtta gttgtgtcta cataccaggc tgctgtgctt     1740
ctgctgttca acacaacaga caaattgagc tacactgata tcctaactca gctgaacctg     1800
agccacgaag atctagtgag gttgcttcat tccttgtcat gtgctagata caagattctt     1860
ctcaaggagc caagcacaaa gactgtttcc cagtctgatt cttttgaatt caactccaaa     1920
ttcaccgaca gaatgcggag aataaagatc cctctcccac ctgttgatga gaggaagaaa     1980
gttgtggaag acgtggacaa agacagacgc tatgcgattg atgctgccat tgtgaggatc     2040
atgaagagca ggaaagtatt gggacatcaa caacttgttt ctgagtgcgt tgagcaactt     2100
agccgaatgt tcaagcctga tatcaaggca atcaagaagc gcatggagga tttgataacg     2160
agagattatc tggagaggga caaggagaac gctaacatgt ttaggtactt ggcttag        2217
```

<210> SEQ ID NO 9
<211> LENGTH: 2232
<212> TYPE: DNA
<213> ORGANISM: Daucus carota
<220> FEATURE:
<221> NAME/KEY: source
<222> LOCATION: 1..2232
<223> OTHER INFORMATION: /organism="Daucus carota"
    /mol_type="unassigned DNA"

<400> SEQUENCE: 9

```
atgatgattg agcggaaaac tatagacctg gagcagggat gggactttat gcaaaaggga      60
atcacaaagc taaagaatat tttagaaggc tttccggagc cgcaattcag ctcggaggat     120
tatatgatgc tttatacaac tatctataac atgtgtacac agaaacctcc acatgattac     180
tctcagcagc tgtatgaaaa gtatcgtgaa gctattgagg agtacattac ttctacagta     240
ttgccttcat tgagagagaa gcatgatgaa ttcatgctta gagaacttgt gaagagatgg     300
tctaatcata aggtcatggt caggtggctt tctcgattct ttcactatct tgatcgctat     360
tttattgctc ggaggtcact tccaccactt catgaagttg gactcacttg ctttcgggac     420
ctggtttacc aggagataaa tgggaaagta agggatgctg taatatcatt gattaatcaa     480
gagcgcgagg gagagcaaat tgaccgagct tgttgaaga atgttctaga tatatttgtt      540
gaagttggaa tgagtcaaat ggattattat gagaatgact ttgaagcaga catgctcaaa     600
gatacagcag catactattc tcgaaaggct ccaactgga tcttagaaga ttcttgtcca      660
gattatatgc tcaaagcgga agagtgtttg agacgggaaa aggacagggt ctctaactac     720
cttcattcta gtagtgaacc caagttgctt gagaaagttc aacatgagtt actatcacac     780
tatgcaactc agctgcttga gaaagaacac tctgggtgtc atgcattgct tagggatgac     840
aaggtggcag atttatcaag gatgtatagg ctcttctcta aaatacctcg aggcctagat     900
cccgtgtcta atattttcaa gcagcatgtt actgctgaag gtacagcttt ggtcaaacaa     960
gcagaagatg cagctagcaa caagaaggca gagaagagag atgtagtagg tttacaagaa    1020
caggttttg tgaggaaaat aattgaattg catgacaaat accttacata cgtaaatgac     1080
tgttttacaa accacactct cttccataag gcgcttaagg aggcttttga aatcttctgc    1140
aataagggtg tctctggaag ctctagtgca gaattacttg ccacattctg tgataatatt    1200
ctcaagaaag gtggaagcga gaagttaagt gatgaagcca ttgaggaaac acttgagaag    1260
gttgtaaggt tgcttgctta taagtgac aaagactat ttgctgaatt ttataggaaa       1320
aagcttgcac ggcgtctctt attcgacaag agtgccaatg atgagcatga gagaagtata    1380
ttgactaagc tgaagcaaca atgtgggggt caatttacat caaagatgga aggaatggtc    1440
actgacttga cgttggcaaa ggaaaatcag tccaacttcg aggagtacct caataataat    1500
tcaaacgtaa atcctggaat tgacttgaca gttactgttc taaccactgg gttttggcca    1560
agttacaaat ctttcgatct caacctccca gcagagatgg tcaaatgtgt tgaagttttt    1620
agagaattct accaaacaaa aacaaagcac agaaaactga catggatata ctctttgggt    1680
acttgtaaca tcattggaaa atttgatcca aaaaccatgg agcttattgt gacaacatac    1740
caggcctctg ctctgctgct atttaactct tctgatagac ttagttataa tgaaataatg    1800
actcagttga acttgtcgga tgatgatgtt gtcagactac ttcattctct ttcgtgtgca    1860
aagtacaaga ttctatctaa agagccgaac accaaaacta tatctccaac tgattgcttt    1920
cagttcaatt ccaaatttac tgataaaatg aggaggatta agattccact tccccagtg     1980
gatgagaaga aaaaggtaat tgaagatgtt gataaagaca ggcgatatgc tatagatgct    2040
tcaattgtcc gtatcatgaa gagccgcaaa gttttgggtt atcagcagct agtaatggag    2100
tgcgttgaac aattgggtcg catgtttaag cctgatgtca aagcaatcaa gaagagaatc    2160
gaagatttaa taactcggga ttatctggaa agagacaagg acaatgccaa cttgttcagg    2220
tatctggcat ga                                                        2232
```

<210> SEQ ID NO 10
<211> LENGTH: 2229
<212> TYPE: DNA
<213> ORGANISM: Apium graveolens
<220> FEATURE:
<221> NAME/KEY: source
<222> LOCATION: 1..2229
<223> OTHER INFORMATION: /organism="Apium graveolens"
      /mol_type="unassigned DNA"

<400> SEQUENCE: 10

```
atgaacgagc ggaagactat cgatttggat aatggatggg aatttatgca gaaagggatc      60
actaagttga agaagattct cgaaggtcaa cctgagcctc agtttagctc cgaggactat     120
atgatgcttt acacaactat ctataatatg tgtacgcaga agcctccaca tgattattct     180
caacagctgt atgacaagta ccgtgaggcc tttgaggagt acataacttc aactgtcctg     240
ccttctttac gagagaagca tgatgagttt atgttgagag agctcgtgaa tagatggaca     300
aaccataaag tcatggtcag gtggctttct cgattctttc actatcttga tcggtacttc     360
attgcgagga ggtcacttcc tgcacttcat gaagttggac tcacgtgctt ccgggatctg     420
gtctatcagg agctgaaagt taaagtgagg atgctgtaa tatctctgat cgatcaagag      480
cgtgaggggg aacagattga ccgagcttta ttaaagaacg tgttagatat atttgttgaa     540
atcggaatga gtcaaatgga tcaatatgag aatgactttg aagaagccat gctcactgat     600
actgctgctt actattctcg aaaagcttca aactggatcc ttgaagattc ttgtcctgat     660
tatatgttaa aggcagaaga atgtttgcga cgagagaagg acagggtttc ccactaccta     720
cattttagta gcgagccaaa gttgcttgag aaagtgcaac atgagctgct atctgtgtat     780
gcaacccaat tactcgagaa ggaacattct ggttgtcatg cattgcttag ggatgacaag     840
gtggatgatt tgtctaggat gtacagactc ttctcgaaaa tacctaaagg cctggatcca     900
gtttcttata tttttaagca gcatgttaca aatgaaggga tggcattggt taaacaagca     960
gaagatgcag caagcaacaa gaaggcagaa agagagacg tggttagttt acaggagcag    1020
gttttttgtta gaaaaattat tgaattacat gacaaatacc tcgcctatgt gaatgactgc    1080
tttacaaacc atactctttt ccataaggct ctcaaggagg cttttgaaat cttttgcaac    1140
aagggtgttg ctggaagctc taatgctgaa ctacttgcta cttttctgtga taacatcctc    1200
aaaaagggtg ggagtgagaa attaagtgat gaggctattg aagaaacact tgagaaggta    1260
gtaaaattgt tagcttacat tagcgataaa gacttgttcg ctgaatttta cagaaaaaag    1320
cttgcacgga gacttctctt tgataagagt gcaaatgacg agcatgaacg aagtattttg    1380
actaaactaa agcaacagtg cggtggtcag ttcacatcga aaatggaggg gatggtcaca    1440
gatttgactt tggctaaaga aaatcaatcc agctttgagg agtatctggg aaataatgcc    1500
aatgtgaatc ctggcattga cttgacggtt actgttctga ccactggctt ctggcctagt    1560
tataaatcct ttgatctcaa ccttcctgct gagatggtca agtgcgttga agtatttaga    1620
gaattttatc aaacaaaaac gaagcataga aagctcacat ggatatattc tctgggtact    1680
tgtaatatca atggaaaatt tgaacccaaa accattgagc tgattgtgac aacctaccag    1740
gcctctgctc tcctgttatt taatacttct gataggttga gttatcaaga aatcatgact    1800
cagttaaatt tgtcggatga tgatgttgtt cgcctgcttc attccctttc atgtgccaag    1860
tataaaattc ttactaaaga gccgaacaac aaaacaattt cccctacgga ttactttgag    1920
ttcaactcca agttcactga caaatgaggg agaattaaga ttccactacc tccagttgat    1980
```

-continued

| | | |
|---|---|---|
| gagaagaaaa aggtaattga agatgttgac aaggaccggc gatatgccat tgatgcatct | 2040 |
| attgtccgca ttatgaagag ccgtaaagtt ttgggctacc aacaattggt tatggaatgt | 2100 |
| gttgagcaat tgggacgcat gtttaagcct gatgtcaaag caattaagaa gagaatcgaa | 2160 |
| gatttaataa cgcgtgatta tctggaaaga gacaaggata atgccaacct tttcagatat | 2220 |
| ttggcatga | 2229 |

<210> SEQ ID NO 11
<211> LENGTH: 2229
<212> TYPE: DNA
<213> ORGANISM: Cichorium intybus
<220> FEATURE:
<221> NAME/KEY: source
<222> LOCATION: 1..2229
<223> OTHER INFORMATION: /organism="Cichorium intybus"
/mol_type="unassigned DNA"

<400> SEQUENCE: 11

| | | |
|---|---|---|
| atgaatgaaa gaaaaacaat agacttagaa caaggatggg acttcatgca gaaaggcata | 60 |
| acaaagttga gaacattct agaaggtctt cccgagccac aattcagctc ggaagattac | 120 |
| atgatgctct acacaaccat ctacaatatg tgcacacaaa aaccgccaca tgattactct | 180 |
| caacaattgt atgacaaata ccgcgagtct tttgaagagt acattacttc aacggtgtta | 240 |
| ccttctttaa gagaagaagca tgatgagttt atgcttagag agcttgttag aagatggtca | 300 |
| aatcataaag tgatggttag gtggctttct agattcttcc attatcttga tcgatacttc | 360 |
| attgcccgaa gatctcttcc accattaaat gaagttggac ttgcgtgttt tcgtgatctg | 420 |
| gtataccaag aggtgaatgg gaaagtgaga gatgctgtaa tatctttgat tgatcaagag | 480 |
| cgtgaaggcg agcaaattga ccgagcatta ctcaagaatg ttctagatat atttgttgaa | 540 |
| ataggaatgg gacaaatgga atattatgag aatgattttg aagcatccat gcttaatgat | 600 |
| acagcagcat attattcacg caaagcttcc aattggattc tagaagattc ttgtccagat | 660 |
| tatatgctca agctgagga gtgcttaaaa agagaaaagg acagagtttc tcattatctt | 720 |
| cattccagca gtgaaccaaa gcttcttgag aaagttcaaa cagagttatt atctgtttat | 780 |
| gcaactcaat tgcttgaaaa ggagcactcc ggttgtcatg cattacttag ggatgacaag | 840 |
| gttgatgatt tatcaagaat gtacagactc ttttcaaaga tacaaaaagg gctggatcct | 900 |
| gtttctagta tgtttaagca gcatgtcact gctgaaggca caacattggt taaacaggca | 960 |
| gaagatgcag caagtactaa gaaggctgaa aagagagacg tggttggctt acaagaacag | 1020 |
| gttttgtta gaaaagttat cgagcttcat gacaagtacc ttgcatatgt aaatgactgt | 1080 |
| tttatgaatc ataccctgtt tcacaaggct cttaagaggg catttgaaat attctgcaac | 1140 |
| aagggcgttg ctggaagttc aagtgcagaa ttacttgcta cattttgtga taatattctt | 1200 |
| aaaaaaggtg gaagtgaaaa attgagtgat gaagccattg aggacacact tgagaaggtg | 1260 |
| gtaaagttgc ttgcttacat cagcgataaa gatctatttg cagagtttta taggaaaaaa | 1320 |
| ctggctagac ggcttttatt tgacaaaagt gcaaatgatg agcacgaaag aagtattttg | 1380 |
| acaaaattga aacaacaatg tggcggtcaa tttacatcaa aaatggaagg aatggttaca | 1440 |
| gatttgacat tggcaaaaga aaatcaatca cattttgagg agtatttgaa taataatccc | 1500 |
| aatgttagcc ctggcattga cttgaccgtg actgtgttga ccactggttt ttggcctagt | 1560 |
| tacaaatctt ttgaccctaaa tctccctgca gaaatggtca aatgcgttga agttttcaga | 1620 |
| gaattttatc aaacaaaaac aaaacacaga aaactcacat ggatatattc attgggcacc | 1680 |

| | |
|---|---|
| tgcaatataa acggaaaatt cgaaccaaaa accatggagc taatcgttac aacttaccag | 1740 |
| gcatctgctt tattactgtt caactcatca gatcgattga gttatcaaga aatcatgact | 1800 |
| caattaaact tatcagatga tgatgttgtt agactactcc attcattatc atgtgcaaaa | 1860 |
| tataaaattt tattaaaaga accaaataca aaaacaatct ctccaactga tttctttgaa | 1920 |
| ttcaactcaa agtttacaga taaaatgaga aggatcaaga ttcctctacc tcctgttgat | 1980 |
| gaaaagaaaa agtaattga agatgttgac aaagaccgac gttatgcaat tgatgcttca | 2040 |
| attgtacgga taatgaaaag cagaaaagtt cttggatacc aacaattggt catggaatgt | 2100 |
| gttgaacaat taggccgtat gtttaagcct gatgtaaaag caatcaagaa acgtattgaa | 2160 |
| gatctcataa ctcgtgatta tcttgaaaga gacaagaaa atccaaattt gtttcggtac | 2220 |
| ttggcatga | 2229 |

<210> SEQ ID NO 12
<211> LENGTH: 2229
<212> TYPE: DNA
<213> ORGANISM: Cichorium endivia
<220> FEATURE:
<221> NAME/KEY: source
<222> LOCATION: 1..2229
<223> OTHER INFORMATION: /organism="Cichorium endivia"
      /mol_type="unassigned DNA"

<400> SEQUENCE: 12

| | |
|---|---|
| atgaatgaaa gaaaaacaat agacttagaa caaggatggg acttcatgca aaaaggcata | 60 |
| acaaagttga gaacattct agaaggtctt cccgagccac aattcagctc agaggattac | 120 |
| atgatgctct acacaaccat ctacaatatg tgcacacaaa aaccgccaca tgattactct | 180 |
| caacaattat atgacaaata ccgcgagtct tttgaagagt acataacttc aacggtgtta | 240 |
| ccttctttaa gagagaagca tgatgagttt atgcttagag agcttgttag aaggtggtca | 300 |
| aatcataaag tgatggttag gtggcttttct agattcttcc attatcttga tcgatacttt | 360 |
| attgcaagaa gatctcttcc accattaaat gaagttggac ttgcgtgttt tcgtgatctg | 420 |
| gtataccaag aggtgaatgg aaaagtgaga gatgctgtaa tatctttgat tgatcaagag | 480 |
| cgtgaaggcg agcaaattga ccgagcatta ctgaagaatg ttctagatat atttgttgaa | 540 |
| ataggaatgg gacaaatgga atattatgag aatgattttg aagcatctat gcttaatgat | 600 |
| acagcagcat attattcacg caaagcttcc aactggattc tagaagattc ttgtccagat | 660 |
| tatatgctca agctgagga gtgcttaaaa agagaaaagg acagagtttc tcattatctt | 720 |
| cattcaagta gtgaaccaaa gcttcttgag aaagttcaaa cagagttatt atctgtttat | 780 |
| gcaactcaat tgctcgaaaa ggaacactca ggttgtcatg cattacttag agatgacaag | 840 |
| gttgatgatt tatcaagaat gtacagactc ttttcaaaga tacaaaaagg actggatcct | 900 |
| gtttccagta tgtttaagca gcatgtcact gctgaaggca caacattagt aaaacaagca | 960 |
| gaagatgcag caagtactaa gaaggctgaa agagagacg tggttggctt acaggaacag | 1020 |
| gttttttgtta gaaaagtaat cgagcttcat gacaagtacc tcgcatatgt aaacgactgt | 1080 |
| tttatgaatc acacattgtt ccacaaggct cttaaagagg catttgaaat attctgcaac | 1140 |
| aagggcgttg ctggaagttc aagtgcagaa ttacttgcca cattttgtga taatattctt | 1200 |
| aaaaaggtg gaagtgaaaa attgagtgat gaagccattg aagacacact tgagaaggta | 1260 |
| gtaaagttgc ttgcttacat cagcgataaa gatctatttg cagagtttta taggaaaaaa | 1320 |
| ctggctagaa ggcttttatt tgacaaaagt gcaaatgatg agcatgaaag aagtatttta | 1380 |

-continued

```
acaaagttga agcaacaatg tggtggtcag tttacatcaa agatggaagg aatggttaca    1440
gatttaacac tggcaaaaga aaatcaatca cattttgagg agtatttgaa aataatccc     1500 aatgttagcc ctggcattga cttgaccgtg actgtgttga ccacgggatt ttggcctagt    1560
tacaaatctt ttgacctaaa tcttcctgca gaaatggtca aatgcgttga agttttcaga    1620
gaattttatc aaacaaaaac aaaacacaga aaactcacat ggatttattc attgggcacc    1680
tgcaatatta acgaaaaatt cgaaccaaaa accatggagc taatcgttac aacttaccag    1740
gcatctgctt tattgttatt caactcatca gatcgattaa gttatcaaga aatcatgact    1800
caattaaatt tatcagatga tgatgttgtt agactactac attcattatc atgtgcaaaa    1860
tataaaattt tattaaaaga accaaatacc aaaacaatat ctccaaccga tttctttgaa    1920
ttcaactcaa agtttacaga taaaatgaga aggatcaaga ttcctctacc tcctgttgat    1980
gaaaagaaaa agtaattga agatgttgac aaagatagaa ggtatgcaat tgatgcttca     2040
attgtacgaa taatgaaaag cagaaaagtt cttggatacc aacaattggt tatgagtgt     2100 gttgaacaat taggccgtat gtttaagcct gatgtaaaag caatcaagaa gcgtattgaa    2160
gatttgataa cgcgtgatta tcttgaaaga gacaagaaaa atccaaattt gtttcggtac    2220
ttggcatga                                                            2229
```

<210> SEQ ID NO 13
<211> LENGTH: 2235
<212> TYPE: DNA
<213> ORGANISM: Allium ampeloprasum
<220> FEATURE:
<221> NAME/KEY: source
<222> LOCATION: 1..2235
<223> OTHER INFORMATION: /organism="Allium ampeloprasum"
    /mol_type="unassigned DNA"

<400> SEQUENCE: 13

```
atgtcgttgc acgaaaggaa aaccattgat ttggagcagg gatgggcttt tatgcagaaa     60
gggatcacca aactgaagaa tattcttgat gagttgaatg aacctcagtt cagctcagag    120
gattacatga tgctctatac gactatctat aatatgtgta ctcagaagcc gccacatgat    180
tattctcagg agttgtatga taagtaccga gagtcctttg aagagtatat cactaccact    240
gtgcttcctt cattgagaga aaagcatgat gaatacatgt taaggagct cgtgagaagg    300 tggtcaaatc ataaaataat ggttagatgg ctttcacgct tttccatta tcttgatcgc    360 tactttatag cacgaagatc attgcctgct cttaatgaag tcggtctcac ttgtttccgt    420
gatctggtgt acaacgaagt ccatgggaaa gttaaagatg ccgtgatctc attgattgac    480
caagagaggg aaggggagca aattgacaga gctttattaa agaatgtttt gggtatttt     540 gtagagattg gtttgggaag catggaatgt tatgagaatg attttgaaac atcaatgctt    600
aatgctacag cagcctatta ttcacgaaaa gcttcaaatt ggattctaga agattcatgt    660
ccagattata tgctaaaagc cgaggagtgc ttaaaacatg agaaagatag agttgctcat    720
tatttgcatt caagcagtga acagaagctg ttagagaaag tgcaacatga gttactttc     780 gtatatgcaa gtcaacttct cgagaaagaa cattccggat gtcatgcatt gcttcgcgat    840
gacaaggtgg gagatctttc acgcatgtat cggctgttct gtagaattac acgtggtttg    900
gaccctgtgt ctcaaatatt taagcagcat gtgactgcag aaggtactgc tttggtcaaa    960
catgccgaag atgctgcaag taacaagaag gccgagaaaa aagacattgt tggtttgcaa    1020
gagcaggtct tcgttaggaa agtaattgag ctgcatgata aatacttggc ctatgtgact    1080
```

-continued

```
gactgctttc aaaatcactc tctatttcac aaggcactta agaggcatt cgaggtattc       1140 tgcaataaag gtgttgcagg tagctcaagc gctgaacttc tggctgcttt ttgtgacaat       1200
atattgaaga agggtggaag cgagaaacta agcgatgagg ccatagagga tactcttgag       1260
aaggttgtaa aactattggc atatattagc gataaagatc tgtttgctga attttacagg       1320
aagaagcttg cacgaagatt actctttgac aaaagtgcta atgatgacca tgagaggagc       1380
atccttacaa agctgaaaca gcaatgtgga gggcagttca cctctaaaat ggaaggcatg       1440
gtaaccgatc tgacacttgc acgagaaaat caatcaagtt ttgacgatta ccttagcagc       1500
aatcctaaag caaattctgg aattgacttg actgttacag tcttaacaac tggcttctgg       1560
cccagttaca agtcttttga tctcaatctt cctgatgaga tggtaaaatg cgttgaaatt       1620
tttaaagagt tttacgagac aaaaaccaaa cacagaaaac ttacatggat ttattcgttg       1680
ggcacttgca acatcaatgg caagttcgaa accaagacaa tagagttggt tgttacaacc       1740
tatcaggctg cagtgttgct tctattcaac tctgcagata aattaagtta ttctgagatt       1800
gtgcagcagc taaacttatc tgatgatgat gtaatcagat tacttcactc tctttcatgc       1860
gctaaataca aaattctcaa taaagaaccc gctaccaaga ctattacccc gaatgatcat       1920
tttgagttca attctaaatt cactgataga atgagaagga tcaagattcc cctgcctcct       1980
gtggatgaga agaaaaaagt aattgaagat gttgacaaag acagaagata tgcaattgac       2040
gcatccatag ttcgaataat gaaaagtaga aaagttcttg gtcatcagca gcttgttttg       2100
gaatgtgttg agcaattagg ccgcatgttt aagcctgact taaggccat caagaaaagg       2160 attgaagatc tgatcgctag agattatttg gagagggaca aggacaatcc aaacctcttt       2220
aaatatttgg cctaa                                                       2235
```

<210> SEQ ID NO 14
<211> LENGTH: 2229
<212> TYPE: DNA
<213> ORGANISM: Lactuca sativa
<220> FEATURE:
<221> NAME/KEY: source
<222> LOCATION: 1..2229
<223> OTHER INFORMATION: /organism="Lactuca sativa"
      /mol_type="unassigned DNA"

<400> SEQUENCE: 14

```
atgaacgaaa gaaaaacaat agacttagag caaggatggg acttcatgca gaaaggaata        60
acaaagttga agaatattct agaaggtctt cccgagccac aattcagctc ggaggattac       120
atgatgctct acacaaccat ctacaacatg tgtacacaga aaccaccaca tgattactcc       180
caacagttgt atgacaaata tcgtgagtct tttgaagagt atattacttc aactgtgtta       240
ccttctttaa gagagaagca tgatgagttc atgctgagag agcttgttag aaggtggtca       300
aatcataaag tcatggtgcg gtggctttct agattcttcc attatcttga ccgatatttc       360
attgcccgaa gatctcttcc gccactaaat gaagttggac ttgcctgttt tcgtgatctg       420
gtataccaag aggtgaatgg taaagtgaga gatgctgtaa tatctttgat tgatcaagag       480
cgtgaagggg agcagattga tcgagcttta ctgaagaatg ttctagatat atttgttgag       540
ataggaatgg gacaaatgga gtattatgag aatgattttg aagcatccat gcttaatgat       600
acagcagcat attattcacg caaggcttcc aactggattc tagaagattc ttgtccagat       660
tatatgctca aagcagagga gtgcttaaaa agagaaaagg acagagtgtc tcattatctt       720
cattccagca gtgagccaaa gcttcttgag aaagttcaaa atgagttatt gtctgtttat       780
```

| | |
|---|---|
| gcaactcaat tgcttgagaa agagcactca ggttgtcatg cattgctcag ggatgacaag | 840 |
| gttgatgatt tatcaagaat gtacagactc ttttcaaaga taccaaaagg attggatcct | 900 |
| gtttctagta tgtttaagca gcatgtcact gctgaaggca acacattggt taaacaagca | 960 |
| gaagatgcag caagtaccaa gaaggctgaa aagagagatg tggttgggtt gcaggaacag | 1020 |
| gtttttgtta gaaaagttat tgagctccat gacaagtacc tggcatatgt aaatgactgt | 1080 |
| ttcatgaacc atactctttt ccacaaggct cttaaagagg catttgaaat attctgcaac | 1140 |
| aagggtgttg ctggaagttc aagtgcagag ttacttgcca cattttgtga taatattctt | 1200 |
| aaaaaaggtg gaagtgagaa actgagcgat gaagccattg aggacaccct tgagaaggta | 1260 |
| gtaaagttgc ttgcctacat cagtgataaa gatctatttg ctgaatttta caggaaaaaa | 1320 |
| cttgctagga ggcttttgtt tgacaagagt gcaaacgatg agcatgagag aagtattctc | 1380 |
| acaaagctga agcaacagtg tggtggtcag ttcacatcaa agatggaagg gatggttaca | 1440 |
| gatttgacat tggcaaagga aaaccaatcc cattttgaag agtatttgaa caataatccc | 1500 |
| aatgtcagcc ctggaattga cttgactgtc actgtgttga ctaccggctt ctggcccagc | 1560 |
| tacaaatctt ttgacctaaa tctccctgcc gaaatggtta aatgcgttga agttttcaga | 1620 |
| gaattttatc aaacaaaaac aaagcacagg aagcttacat ggatatattc attgggtacc | 1680 |
| tgcaatataa acgggaaatt tgaacccaaa acaatggagc tcatagtcac aacctaccag | 1740 |
| gcatctgctt tattactgtt caacttatcg gatcgattga gttatcaaga aatcatgact | 1800 |
| cagttgaact tgtcagatga tgatgttgtt aggctgctcc attctttgtc atgtgcaaaa | 1860 |
| tacaaaattc ttttaaagga gcctaatacc aaaacaatct ctccaaccga ttacttcgaa | 1920 |
| ttcaactcca agtttacaga taaaatgagg aggatcaaga ttcctctacc tcctgtggat | 1980 |
| gagaagaaaa aggtgattga ggatgttgac aaagacagac gttatgccat tgatgcttcc | 2040 |
| attgtaagga taatgaagag cagaaaggtg cttggatacc agcagttggt tatggagtgt | 2100 |
| gttgaacagt tgggacgcat gtttaagcct gatgtaaaag caatcaagaa gcggattgaa | 2160 |
| gatctgataa ctcgtgatta tcttgaaaga gacaaagaga accccaactt gttccgatac | 2220 |
| ttggcatga | 2229 |

<210> SEQ ID NO 15
<211> LENGTH: 2217
<212> TYPE: DNA
<213> ORGANISM: Raphanus sativus
<220> FEATURE:
<221> NAME/KEY: source
<222> LOCATION: 1..2217
<223> OTHER INFORMATION: /organism="Raphanus sativus"
    /mol_type="unassigned DNA"

<400> SEQUENCE: 15

| | |
|---|---|
| atggagcgga agacgattga tctggaacaa ggatgggact atatgcagac tgggatcact | 60 |
| aagctgaaac ggattcttga aggattgcct gagccgcaat tcgactctga gcagtacatg | 120 |
| atgctttata cgactatcta acacatgtgc acccagaaac ctcctcatga ttactctcag | 180 |
| cagctttatg acaagtatcg cgaagctttt gaggagtaca ttgactctac tgttttgcct | 240 |
| gctttgaagg agaagcatga tgaatacatg ctacgggagc tggttaagag atggtctaac | 300 |
| cataaagtta tggttagatg gctatcccga ttcttctact atcttgaccg ttacttcatt | 360 |
| gctcggagat cgctgccacc gcttaatgaa gttgggctca catgcttccg tgaccgggtg | 420 |
| tataaggagt tgcattccaa ggtcaaagat gctgtaaatag cacttgttga taagaacgg | 480 |

-continued

| | |
|---|---|
| gaaggcgagc agattgacag ggctcttctg aaaaacgtat tagatatcta tgtagagatt | 540 |
| ggaatgggac agatggaaag atacgaagtg gattttgaaa gcttcatgct tttggattca | 600 |
| gcatcttact attctcgcaa agcatcaaac tggatccagg aagattcttg ccctgattac | 660 |
| atgctgaagt ctgaagaatg ccttaagaag gagagggaga gggttgctca ctaccttcat | 720 |
| tcaagcagcg agccaaagct ggttgagaaa gtacaacatg agctgttggt tgtctatgca | 780 |
| aatcagcttc ttgaaaagga gcactcaggg tgccgtgcat tgctgagaga cgacaaggtt | 840 |
| gacgatctct ccaggatgta caggctctat cataaaattg ctaaaggttt agaacctgtt | 900 |
| gcaaacatat ttaagcagca tgtcacagcc gagggtaacg cacttgtcca acaggccgaa | 960 |
| gacacagcca ctaatcaggc tgcaaatact gctagcgtgc aggaacaggt tctcatcaga | 1020 |
| aaagtgattg agctacatga taagtacatg gtctatgtcg tggagtgctt ccagaaccac | 1080 |
| accctcttcc acaaggctct gaaagaggca tttgagatat tctgtaacaa aacagtcgct | 1140 |
| ggaagttcaa gtgcagaact gcttgcaaca ttctgcgaca acatcctcaa gaagggggt | 1200 |
| agtgagaagc tgagtgacga agctattgaa gatacgcttg agaaggttgt caaattgctt | 1260 |
| gcttatataa gcgacaagga tcttttcgcc gagttctaca ggaagaagct ggcacgtagg | 1320 |
| ctcttatttg atcgcagtgc gaatgatgat catgagagaa gcatcctac aaagctcaag | 1380 |
| caacaatgtg gtgggcagtt cacttctaag atggagggca tggtaacgga cttgacattg | 1440 |
| gcaagagaga accaaaccag tttcgaggag tatctaggca taaccccgc tgcaaaccca | 1500 |
| gggattgatt tgaccgtcac tgttcttacc actggtttct ggccaagtta caatcattc | 1560 |
| gacataaatc taccaagtga aatggtcaag tgtgttgaag ttttcaaagg gttttatgag | 1620 |
| acgaaaacta acataggaa acttacatgg atctactcac taggaacttg tcacctcaac | 1680 |
| ggaaagtttg atcacaagcc cattgagtta gttgtgtcta cttaccaggc tgctgtgctt | 1740 |
| ctgctgttca acacaacaga caaattgagc tacaacgata tcctaactca actgaaccta | 1800 |
| agccacgaag atttagtgag gttgcttcat tccctgtcat gtgctaggta caagatcctt | 1860 |
| ctcaaggagc caagcacgaa gactgttaca cagactgatt catttgaatt caatgccaaa | 1920 |
| ttcacggaca gaatgcgcag aatcaagatc cctctccctc ctgttgatga aggaagaag | 1980 |
| gttgtggaag atgtggacaa agacagacgc tatgcgattg atgctgccat tgttaggatc | 2040 |
| atgaagagca ggaaagtgtt gggacatcaa caactcgtct ctgagtgcgt tgagcaactt | 2100 |
| agccgaatgt tcaagcctga tatcaaagcg atcaagaagc gtatggagga tctaattacg | 2160 |
| agggattatt tggagaggga caaggagaac cctaacatgt ttaggtactt ggcttag | 2217 |

<210> SEQ ID NO 16
<211> LENGTH: 2223
<212> TYPE: DNA
<213> ORGANISM: Spinacia oleracea
<220> FEATURE:
<221> NAME/KEY: source
<222> LOCATION: 1..2223
<223> OTHER INFORMATION: /organism="Spinacia oleracea"
    /mol_type="unassigned DNA"

<400> SEQUENCE: 16

| | |
|---|---|
| atgaacgatc gtaaagttat cgaactagag caaggatggg agttcatggg gaagggatt | 60 |
| acgaagttga aaaggatttt ggaaggatta ccagagccgc ttttaattc ggaagactac | 120 |
| atgatgctgt acacgacaat atacaacatg tgtacacaga aaccccctca tgattactct | 180 |
| caacaactct atgacaatta caagaggca tttgtggatt acatacattc aacggtttta | 240 |

```
ccttctttgg gggacaaaca tgatgagttt atgctgagag agcttgtgaa gagatggtca    300
aatcataaag taatggtgag gtggttgtct cgcttcttcc attatctgga tcggtacttc    360
atcgctcgga gatcgcttcc ttctttgaat gatgttggat tgacgtgctt ccgtgatctg    420
gtttatcaag aaatatctgg caaagccaag gatgctgtta ttgctctgat tgatgaagaa    480
agagagggtg ggcaaattga cagagcctta ttgaagaatg tacttgatat atacgttgaa    540
attggaatga cacaaatgga ttactacgaa aaggactttg aagctcatat gctggatgat    600
actgctgctt attactcacg caaggcctca agctggattc tggaggactc atgtccggaa    660
tacatgttga gtcggagga gtgtttgaag aaagagaaag atagagtggc tcattatcta    720
cattccagca gtgagccaaa gcttctggag aaagtacaaa atgagttgct actggtttac    780
gaaaatcagt tgcttgagaa ggagaattct ggatgtcgtg cattgttgaa agatgacaag    840
gtggaagatc tttccaggat gtacaggctt tatagcaagg ttaccaaagg gttggaaccc    900
attggcagta tcttcaaaca gcatataacc gatgaaggaa cagccctggt gcagcaggcc    960
gaagacgctg caattagcaa ggctgaaaat gctggcggtg gttcacatga gcaggtcttc   1020
gtcaggaaag tgattgagtt gcatgacaaa tttatgacct atgttacaga ttgcttcaac   1080
agccatacca tctttcacaa ggctctcaag gaagcttttg aggtattctt aaacaagggt   1140
gttgctggta gttcaagtgc tgaacttcta gcttcatttt gtgataatat tctcaagaaa   1200
ggtggtagtg aaaaattaag tgatgaggct attgaggatt cactggagaa ggtggtgaag   1260
cttctcgcat atgtcagtga taaagacctg tttgctgaat tttacagaaa gaagctctct   1320
cgccggctac tctttgacaa aagtgctaat gatgatcatg agaggagtat tttaacaaaa   1380
ttgaagcagc agtgtggggg acagttcaca tcaaagatgg aggggatggt gacagacttg   1440
acattggcga gggagaatca aactaatttt gaggaatatc ttggacaaaa tacagatgcc   1500
agtcctggtc ttgatttgac tgtgacagtt ttgaccactg ggttctggcc aagttacaaa   1560
tcttctgatc ttaaccttcc tgctgagatg gtgaggtgtg ttgaagtttt taagcaattt   1620
tatcaaacaa agacaaaaca caggaagctc acctgggtat attcgttggg aagttgtaac   1680
attaatggca gtttggtcc gaaaacaatt gaattggttg ttggaactta tcaggctgct   1740
gcgctgatgc tctttaacac atcagatcga ctgagttatt cagaaataac gacccaacta   1800
aatctagctg acgaagactt ggttagagtg cttcaatctc tatcttgcgc aaagtataag   1860
attcttctaa aagagccaag cacaagaaac gtgatctcaa ctgattgttt ttcattcaac   1920
tctaattttta ctgacagaat gaggaggatt aggattcctc ttcctccaat ggatgagagg   1980
aaaaaggttg ttgaagatgt tgacaaagat agaagatatg ctattgatgc ctcaattgta   2040
cgcataatga aaagtaggaa ggctttggga tatcaacaat taatcacgga gtgtgtggag   2100
cagctaagcc gcatgttcaa gcctgatttc aaagcaatta agaagaggat cgaggacttg   2160
ataaccagag attatattga aagagacaag gaaaaccctc agctattccg gtacttggct   2220
tga                                                                  2223
```

<210> SEQ ID NO 17
<211> LENGTH: 2220
<212> TYPE: DNA
<213> ORGANISM: Beta vulgaris
<220> FEATURE:
<221> NAME/KEY: source
<222> LOCATION: 1..2220
<223> OTHER INFORMATION: /organism="Beta vulgaris"
      /mol_type="unassigned DNA"

<400> SEQUENCE: 17

```
atgaatgatc gtaaagttat tgaactagag caaggatggg agttcatggg gaaggggatt      60
acaaagttga agaggattct ggaaggattg ccagagccac catttaattc tgaagactac     120
atgatgttgt acacgacgat atacaatatg tgtactcaga accccccaca tgattactct     180
caacagctct atgacaatta caaacaggct tttgtggatt acatcaactc gacggtttta     240
ccttctttgc gggagaagca tgatgagttt atgttaagag aacttgtgaa agatgggca      300
aatcataaag taatggtcag gtggttgtct cgtttcttcc attatctgga ccggtatttc     360
attgctcgga ggtcgcttcc ttctttgaat gaagttggac tgacttgttt ccgtgatctg     420
gtttatcaag aaatatctgg caaagccaag gatgctgtta tagccctgat tgatatagaa     480
agagaaggtg gcagattga cagatcatta ttgaaaaatg tacttgatat atatgttgaa     540
attggaatgg gacaaatgga tcactatgaa aaagactttg aagctcatat gctggatgat     600
actgctgctt actactcgcg caaagcgtct agctggattc ttgaggactc ttgtccggaa     660
tacatgttaa agtctgagga gtgtttgaag aaggagaaag agagagtggc taattattta     720
cattccagca gtgagccaaa gcttctggag aaagtgcaaa acgagttgct attggtttat     780
gaaagccaat gcttgagaa ggagaattcg ggatgtcgtg cattactgaa agatgacaag     840
gtggatgatc tttccaggat gtacaggctt tacagtaagg ttaccaaagg attggaaccc     900
attggcagta tcttcaaaca gcatataact gatgaaggaa cagccttagt gcagcaggcc     960
gaagatgctg ctatcagcaa ggctgaaaat actggtggtt cacatgagca ggtcttcgtc    1020
aggaaagtaa tagagttgca tgacaaattc atgacttatg tcaccgattg cttcaacagc    1080
cataccatat ttcacaaggc tcttaaggag gcttttgagg tatttttgaa caagggtgtt    1140
gctggtagct caagtgctga gttgctagct acattctgtg ataacattct caagaaaggt    1200
gggagcgaaa aactaagcga tgaggctatt gaggattcac ttgagaaggt ggtgaagctt    1260
ctggcctatg tcagtgataa agacctgttt gctgaatttt acagaaagaa gctctctcgc    1320
cggctactct ttgacaagag tgctaatgat gatcatgaaa gaagtatttt aaccaaattg    1380
aagcagcagt gtggcggaca attcacatca aagatggagg ggatggtgac agacttgacc    1440
ttggcgaggg agaatcaaac taattttgag gaatatctta gtcagaatcc agatgccagt    1500
cctggtcttg atttgactgt gactgttctg acaactgggt tctggccaag ttacaaatct    1560
tccgatctta accttcccgc tgagatggtg aggtgtgttg aagtttttaa gcagttctat    1620
tcaactaaaa caaagcacag gaagctgacc tgggtttact cattgggaag ctgtaatatt    1680
aatggcaagt tggtccaaa aactattgaa ttggttgtcg gaacttatca ggctgctgct    1740
ttgatgctct ttaacacatc agaccgactg agttattcag agatagcaac tcaactaaat    1800
ttagctgatg aagatctggt tagagtgctt caatctttat cctgcgcaaa gtataagatt    1860
cttttaaagg agccaaacac gaaaaccgtg tccccgactg attgtttttc atttaactct    1920
agtttcactg acaggatgag gaggataaga attcctcttc ctccgatgga tgagaggaaa    1980
aaggttgttg aggatgttga caaagataga agatatgcta ttgatgcctc aattgtacgc    2040
ataatgaaaa gtaggaaggt tttggggtac cagcaattaa tcacagagtg tgtggagcag    2100
ctaagccgca tgttcaagcc tgatttcaag gcaattaaga agaggatcga ggacttaata    2160
acccgagatt atattgaaag agacaaggag aacccgcagc tattccgata cttggcttga    2220
```

<210> SEQ ID NO 18
<211> LENGTH: 744

<212> TYPE: PRT
<213> ORGANISM: Cucumis sativus

<400> SEQUENCE: 18

```
Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
        35                  40                  45

Ile Tyr Asn Met Cys Thr Gln Lys Pro Pro His Asp Tyr Ser Gln Gln
    50                  55                  60

Leu Tyr Asp Lys Tyr Arg Glu Ser Phe Glu Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400
```

```
Ile Leu Lys Lys Gly Gly Ser Glu Lys Leu Ser Asp Glu Ala Ile Glu
            405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Leu Ala Arg Arg Leu Leu
        435                 440                 445

Phe Asp Lys Ser Ala Asn Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
                500                 505                 510

Thr Val Leu Thr Thr Gly Phe Trp Pro Ser Tyr Lys Ser Phe Asp Leu
            515                 520                 525

Asn Leu Pro Ala Glu Met Val Lys Cys Val Glu Val Phe Arg Glu Phe
        530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Phe Asn Ser Ser
                580                 585                 590

Asp Arg Leu Ser Tyr Ser Glu Ile Met Thr Gln Leu Asn Leu Ser Asp
            595                 600                 605

Asp Asp Val Val Arg Leu Leu His Ser Leu Ser Cys Ala Lys Tyr Lys
610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Val Ile Glu Asp Val Asp
            660                 665                 670

Lys Asp Arg Arg Tyr Ala Ile Asp Ala Ser Ile Val Arg Ile Met Lys
            675                 680                 685

Ser Arg Lys Val Leu Gly His Gln Gln Leu Val Met Glu Cys Val Glu
690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740

<210> SEQ ID NO 19
<211> LENGTH: 744
<212> TYPE: PRT
<213> ORGANISM: Cucumis melo

<400> SEQUENCE: 19

Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
```

-continued

```
                20                  25                  30
Pro Glu Pro Gln Phe Ser Ser Glu Asp Tyr Met Met Leu Tyr Thr Thr
                35                  40                  45
Ile Tyr Asn Met Cys Thr Gln Lys Pro Pro His Asp Tyr Ser Gln Gln
                50                  55                  60
Leu Tyr Asp Lys Tyr Arg Glu Ser Phe Glu Tyr Ile Thr Ser Met
65                  70                  75                  80
Val Leu Pro Ser Leu Arg Glu Lys His Asp Glu Phe Met Leu Arg Glu
                85                  90                  95
Leu Val Lys Arg Trp Thr Asn His Lys Val Met Val Arg Trp Leu Ser
                100                 105                 110
Arg Phe Phe His Tyr Leu Asp Arg Tyr Phe Ile Ala Arg Arg Ser Leu
                115                 120                 125
Pro Pro Leu Asn Glu Val Gly Leu Thr Cys Phe Arg Glu Leu Val Tyr
                130                 135                 140
Lys Glu Leu Asn Ser Lys Val Arg Asp Ala Val Ile Ser Leu Ile Asp
145                 150                 155                 160
Gln Glu Arg Glu Gly Glu Gln Ile Asp Arg Ala Leu Leu Lys Asn Val
                165                 170                 175
Leu Asp Ile Phe Val Glu Ile Gly Met Gly Gln Met Asp Tyr Tyr Glu
                180                 185                 190
Asn Asp Phe Glu Ala Ala Met Leu Lys Asp Thr Ala Ala Tyr Tyr Ser
                195                 200                 205
Arg Lys Ala Ser Asn Trp Ile Leu Glu Asp Ser Cys Pro Asp Tyr Met
                210                 215                 220
Leu Lys Ala Glu Glu Cys Leu Lys Arg Glu Lys Asp Arg Val Ser His
225                 230                 235                 240
Tyr Leu His Ser Ser Ser Glu Pro Lys Leu Leu Glu Lys Val Gln His
                245                 250                 255
Glu Leu Leu Ser Val Tyr Ala Thr Gln Leu Leu Glu Lys Glu His Ser
                260                 265                 270
Gly Cys His Ala Leu Leu Arg Asp Asp Lys Val Glu Asp Leu Ser Arg
                275                 280                 285
Met Phe Arg Leu Phe Ser Lys Ile Pro Lys Gly Leu Asp Pro Val Ser
                290                 295                 300
Asn Ile Phe Lys Gln His Val Thr Ala Glu Gly Thr Ala Leu Val Lys
305                 310                 315                 320
Gln Ala Glu Asp Ala Ala Ser Asn Lys Lys Ala Glu Lys Lys Asp Ile
                325                 330                 335
Val Gly Leu Gln Glu Gln Val Phe Val Arg Lys Val Ile Glu Leu His
                340                 345                 350
Asp Lys Tyr Leu Ala Tyr Val Asn Asp Cys Phe Gln Asn His Thr Leu
                355                 360                 365
Phe His Lys Ala Leu Lys Glu Ala Phe Glu Val Phe Cys Asn Lys Gly
                370                 375                 380
Val Ala Gly Ser Ser Ser Ala Glu Leu Leu Ala Thr Phe Cys Asp Asn
385                 390                 395                 400
Ile Leu Lys Lys Gly Gly Ser Glu Lys Leu Ser Asp Glu Ala Ile Glu
                405                 410                 415
Glu Thr Leu Glu Lys Val Val Lys Leu Leu Ala Tyr Ile Cys Asp Lys
                420                 425                 430
Asp Leu Phe Ala Glu Phe Tyr Arg Lys Lys Leu Ala Arg Arg Leu Leu
                435                 440                 445
```

Phe Asp Lys Ser Ala Asn Asp His Glu Arg Ser Ile Leu Thr Lys
            450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
            500                 505                 510

Thr Val Leu Thr Thr Gly Phe Trp Pro Ser Tyr Lys Ser Phe Asp Leu
            515                 520                 525

Asn Leu Pro Ala Glu Met Val Lys Cys Val Glu Val Phe Arg Glu Phe
530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Phe Asn Ser Ser
                580                 585                 590

Asp Arg Leu Ser Tyr Ser Glu Ile Met Thr Gln Leu Asn Leu Ser Asp
            595                 600                 605

Asp Asp Val Val Arg Leu Leu His Ser Leu Ser Cys Ala Lys Tyr Lys
610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Val Ile Glu Asp Val Asp
            660                 665                 670

Lys Asp Arg Arg Tyr Ala Ile Asp Ala Ser Ile Val Arg Ile Met Lys
            675                 680                 685

Ser Arg Lys Val Leu Gly His Gln Gln Leu Val Met Glu Cys Val Glu
690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740

<210> SEQ ID NO 20
<211> LENGTH: 744
<212> TYPE: PRT
<213> ORGANISM: Cucurbita pepo

<400> SEQUENCE: 20

Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
                20                  25                  30

Pro Glu Pro Gln Phe Ser Ser Asp Tyr Met Met Leu Tyr Thr Thr
            35                  40                  45

Ile Tyr Asn Met Cys Thr Gln Lys Pro Pro His Asp Tyr Ser Gln Gln
50                  55                  60

Leu Tyr Asp Lys Tyr Arg Glu Ser Phe Glu Glu Tyr Ile Ser Ser Met

```
              65                  70                  75                  80
Val Leu Pro Ser Leu Arg Glu Lys His Asp Glu Phe Met Leu Arg Glu
                    85                  90                  95

Leu Val Lys Arg Trp Thr Asn His Lys Val Met Val Arg Trp Leu Ser
               100                 105                 110

Arg Phe Phe His Tyr Leu Asp Arg Tyr Phe Ile Ala Arg Ser Leu
           115                 120                 125

Pro Pro Leu Asn Glu Val Gly Leu Thr Cys Phe Arg Glu Leu Val Tyr
       130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
               165                 170                 175

Leu Asp Ile Phe Val Glu Ile Gly Met Gly Gln Met Asp Tyr Tyr Glu
           180                 185                 190

Asn Asp Phe Glu Ala Ala Met Leu Lys Asp Thr Ala Ala Tyr Tyr Ser
       195                 200                 205

Arg Lys Ala Ser Asn Trp Ile Leu Glu Asp Ser Cys Pro Asp Tyr Met
210                 215                 220

Leu Lys Ala Glu Glu Cys Leu Arg Arg Glu Lys Asp Arg Val Ser His
225                 230                 235                 240

Tyr Leu His Ser Ser Glu Pro Lys Leu Leu Glu Lys Val Gln His
               245                 250                 255

Glu Leu Leu Ser Val Tyr Ala Thr Gln Leu Leu Glu Lys Glu His Ser
           260                 265                 270

Gly Cys His Ala Leu Leu Arg Asp Asp Lys Val Glu Asp Leu Ser Arg
       275                 280                 285

Met Phe Arg Leu Phe Ser Lys Ile Pro Lys Gly Leu Asp Pro Val Ser
       290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
               325                 330                 335

Val Gly Leu Gln Glu Gln Val Phe Val Arg Lys Val Ile Glu Leu His
           340                 345                 350

Asp Lys Tyr Leu Ala Tyr Val Asn Asp Cys Phe Gln Asn His Thr Leu
       355                 360                 365

Phe His Lys Ala Leu Lys Glu Ala Phe Glu Val Phe Cys Asn Lys Gly
       370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
               405                 410                 415

Glu Thr Leu Glu Lys Val Val Lys Leu Leu Ala Tyr Ile Cys Asp Lys
           420                 425                 430

Asp Leu Phe Ala Glu Phe Tyr Arg Lys Lys Leu Ala Arg Arg Leu Leu
       435                 440                 445

Phe Asp Lys Ser Ala Asn Asp His Glu Arg Ser Ile Leu Thr Lys
       450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
               485                 490                 495
```

```
Tyr Leu Ser Asn Asn Pro Gln Ala Ser Pro Gly Ile Asp Leu Thr Val
                500                 505                 510

Thr Val Leu Thr Thr Gly Phe Trp Pro Ser Tyr Lys Ser Phe Asp Leu
            515                 520                 525

Asn Leu Pro Ala Glu Met Val Lys Cys Val Glu Val Phe Arg Glu Phe
        530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Lys Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740

<210> SEQ ID NO 21
<211> LENGTH: 744
<212> TYPE: PRT
<213> ORGANISM: citrillus lanatus

<400> SEQUENCE: 21

Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
        35                  40                  45

Ile Tyr Asn Met Cys Thr Gln Lys Pro His Asp Tyr Ser Gln Gln
    50                  55                  60

Leu Tyr Asp Lys Tyr Arg Glu Ser Phe Glu Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
```

-continued

```
            115                 120                 125
Pro Pro Leu Asn Glu Val Gly Leu Thr Cys Phe Arg Glu Leu Val Tyr
130                 135                 140
Lys Glu Leu Asn Ser Lys Val Arg Asp Ala Val Ile Ser Leu Ile Asp
145                 150                 155                 160
Gln Glu Arg Glu Gly Glu Gln Ile Asp Arg Ala Leu Leu Lys Asn Val
                165                 170                 175
Leu Asp Ile Phe Val Glu Ile Gly Met Gly Gln Met Asp Tyr Tyr Glu
            180                 185                 190
Asn Asp Phe Glu Ala Ala Met Leu Lys Asp Thr Ala Ala Tyr Tyr Ser
        195                 200                 205
Arg Lys Ala Ser Asn Trp Ile Leu Glu Asp Ser Cys Pro Asp Tyr Met
210                 215                 220
Leu Lys Ala Glu Glu Cys Leu Lys Arg Glu Lys Asp Arg Val Ser His
225                 230                 235                 240
Tyr Leu His Ser Ser Glu Pro Lys Leu Leu Glu Lys Val Gln His
                245                 250                 255
Glu Leu Leu Ser Val Tyr Ala Thr Gln Leu Leu Glu Lys Glu His Ser
            260                 265                 270
Gly Cys His Ala Leu Leu Arg Asp Asp Lys Val Glu Asp Leu Ser Arg
        275                 280                 285
Met Phe Arg Leu Phe Ser Lys Ile Pro Lys Gly Leu Asp Pro Val Ser
290                 295                 300
Asn Ile Phe Lys Gln His Val Thr Ala Glu Gly Thr Ala Leu Val Lys
305                 310                 315                 320
Gln Ala Glu Asp Ala Ala Ser Asn Lys Lys Ala Glu Lys Lys Asp Ile
                325                 330                 335
Val Gly Leu Gln Glu Gln Val Phe Val Arg Lys Val Ile Glu Leu His
            340                 345                 350
Asp Lys Tyr Leu Ala Tyr Val Asn Asp Cys Phe Gln Asn His Thr Leu
        355                 360                 365
Phe His Lys Ala Leu Lys Glu Ala Phe Glu Val Phe Cys Asn Lys Gly
370                 375                 380
Val Ala Gly Ser Ser Ala Glu Leu Leu Ala Thr Phe Cys Asp Asn
385                 390                 395                 400
Ile Leu Lys Lys Gly Gly Ser Lys Leu Ser Asp Glu Ala Ile Glu
                405                 410                 415
Glu Thr Leu Glu Lys Val Val Lys Leu Leu Ala Tyr Ile Cys Asp Lys
            420                 425                 430
Asp Leu Phe Ala Glu Phe Tyr Arg Lys Lys Leu Ala Arg Arg Leu Leu
        435                 440                 445
Phe Asp Lys Ser Ala Asn Asp His Glu Arg Ser Ile Leu Thr Lys
450                 455                 460
Leu Lys Gln Gln Cys Gly Gly Gln Phe Thr Ser Lys Met Glu Gly Met
465                 470                 475                 480
Val Thr Asp Leu Thr Leu Ala Arg Glu Asn Gln Thr Ser Phe Glu Glu
                485                 490                 495
Tyr Leu Ser Asn Asn Pro Gln Ala Ser Pro Gly Ile Asp Leu Thr Val
            500                 505                 510
Thr Val Leu Thr Thr Gly Phe Trp Pro Ser Tyr Lys Ser Phe Asp Leu
        515                 520                 525
Asn Leu Pro Ala Glu Met Val Lys Cys Val Glu Val Phe Arg Glu Phe
530                 535                 540
```

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
            565                 570                 575

Ile Val Thr Thr Tyr Gln Ala Ser Ala Leu Leu Leu Phe Asn Ser Ser
            580                 585                 590

Asp Arg Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740

<210> SEQ ID NO 22
<211> LENGTH: 742
<212> TYPE: PRT
<213> ORGANISM: Solanum melongena

<400> SEQUENCE: 22

Met Asn Gln Arg Ser Thr Ile Asp Leu Glu His Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Leu Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp

```
                165                 170                 175
Ile Phe Val Glu Ile Gly Met Gly Ser Met Asp Tyr Tyr Glu Asn Asp
            180                 185                 190
Phe Glu Ala Ala Met Leu Lys Asp Thr Ala Ala Tyr Tyr Ser Arg Lys
            195                 200                 205
Ala Ser Asn Trp Ile Leu Glu Asp Ser Cys Pro Asp Tyr Met Leu Lys
            210                 215                 220
Ala Glu Glu Cys Leu Lys Arg Glu Lys Asp Arg Val Ser His Tyr Leu
225                 230                 235                 240
His Ser Ser Ser Glu Thr Lys Leu Leu Glu Lys Val Gln His Glu Leu
            245                 250                 255
Leu Ser Val Tyr Ala Asn Gln Leu Leu Glu Lys Glu His Ser Gly Cys
            260                 265                 270
His Ala Leu Leu Arg Asp Asp Lys Val Asp Asp Leu Ser Arg Met Tyr
            275                 280                 285
Arg Leu Phe Ser Lys Ile Pro Arg Gly Leu Glu Pro Val Ala Asn Ile
            290                 295                 300
Phe Lys Gln His Val Thr Ala Glu Gly Thr Ala Leu Val Lys Gln Ala
305                 310                 315                 320
Glu Asp Ala Ala Ser Asn Lys Lys Ala Glu Lys Arg Asp Val Val Gly
            325                 330                 335
Leu Gln Glu Gln Val Phe Val Arg Lys Val Ile Glu Leu His Asp Lys
            340                 345                 350
Tyr Leu Ala Tyr Val Asn Asn Cys Phe Gln Asn His Thr Leu Phe His
            355                 360                 365
Lys Ala Leu Lys Glu Ala Phe Glu Leu Phe Cys Asn Lys Gly Val Ala
            370                 375                 380
Gly Ser Ser Asn Ala Glu Leu Leu Ala Thr Phe Cys Asp Asn Ile Leu
385                 390                 395                 400
Lys Lys Gly Gly Ser Glu Lys Leu Ser Asp Glu Ala Ile Glu Glu Thr
            405                 410                 415
Leu Glu Lys Val Val Lys Leu Leu Ala Tyr Ile Ser Asp Lys Asp Leu
            420                 425                 430
Phe Ala Glu Phe Tyr Arg Lys Lys Leu Ala Arg Arg Leu Leu Phe Asp
            435                 440                 445
Lys Ser Ala Asn Asp Glu His Glu Arg Ser Ile Leu Thr Lys Leu Lys
            450                 455                 460
Gln Gln Cys Gly Gly Gln Phe Thr Ser Lys Met Glu Gly Met Val Thr
465                 470                 475                 480
Asp Leu Thr Leu Ala Arg Glu Asn Gln Ala Ser Phe Glu Glu Tyr Leu
            485                 490                 495
Ser Asn Asn Pro Thr Ala Asn Pro Gly Ile Asp Leu Thr Val Thr Val
            500                 505                 510
Leu Thr Thr Gly Phe Trp Pro Ser Tyr Lys Ser Phe Asp Leu Asn Leu
            515                 520                 525
Pro Ala Glu Met Val Arg Cys Val Glu Val Phe Lys Glu Phe Tyr Gln
            530                 535                 540
Thr Lys Thr Lys His Arg Lys Leu Thr Trp Ile Tyr Ser Leu Gly Thr
545                 550                 555                 560
Cys Asn Ile Asn Gly Lys Phe Glu Ala Lys Thr Ile Glu Leu Val Val
            565                 570                 575
Thr Thr Tyr Gln Ala Ser Ala Leu Leu Leu Phe Asn Ala Ser Asp Arg
            580                 585                 590
```

```
Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
610                 615                 620

Asn Lys Glu Pro Ser Thr Lys Thr Ile Ser Pro Thr Asp Val Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
                675                 680                 685

Lys Val Leu Gly Tyr Gln Gln Leu Val Met Glu Cys Val Glu Gln Leu
            690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740

<210> SEQ ID NO 23
<211> LENGTH: 742
<212> TYPE: PRT
<213> ORGANISM: Solanum lycopersicum

<400> SEQUENCE: 23

Met Asn Gln Arg Ser Thr Ile Asp Leu Glu His Gly Trp Asp Phe Met
1               5                   10                  15

Gln Arg Gly Ile Thr Lys Leu Lys Asn Ile Leu Glu Gly Leu Pro Glu
                20                  25                  30

Pro Gln Phe Ser Ser Glu Asp Tyr Met Met Leu Tyr Thr Thr Ile Tyr
            35                  40                  45

Asn Met Cys Thr Gln Lys Pro Pro His Asp Tyr Ser Gln Gln Leu Tyr
50                  55                  60

Asp Lys Tyr Arg Glu Ala Phe Glu Glu Tyr Ile Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Gln Val Tyr Gln Glu
130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Leu Met Asp Tyr Tyr Glu Asn Asp
            180                 185                 190

Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
```

```
            210                 215                 220
Ala Glu Glu Cys Leu Lys Arg Glu Lys Asp Arg Val Ser His Tyr Leu
225                 230                 235                 240

His Ser Ser Ser Glu Thr Lys Leu Leu Glu Lys Val Gln His Glu Leu
                245                 250                 255

Leu Ser Val Tyr Ala Thr Gln Leu Leu Glu Lys Glu His Ser Gly Cys
                260                 265                 270

His Ala Leu Leu Arg Asp Asp Lys Val Glu Asp Leu Ser Arg Met Tyr
            275                 280                 285

Arg Leu Phe Ser Lys Ile Ser Arg Gly Leu Asp Pro Val Ala Asn Ile
        290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Val Phe Val Arg Lys Val Ile Glu Leu His Asp Lys
                340                 345                 350

Tyr Leu Ala Tyr Val Asn Asn Cys Phe Gln Asn His Thr Leu Phe His
            355                 360                 365

Lys Ala Leu Lys Glu Ala Phe Glu Leu Phe Cys Asn Lys Gly Val Ala
370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
                420                 425                 430

Phe Ala Glu Phe Tyr Arg Lys Lys Leu Ala Arg Arg Leu Leu Phe Asp
            435                 440                 445

Lys Ser Ala Asn Asp Glu His Glu Arg Ser Ile Leu Thr Lys Leu Lys
        450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Ile Ala Asn Pro Gly Ile Asp Leu Thr Val Thr Val
                500                 505                 510

Leu Thr Thr Gly Phe Trp Pro Ser Tyr Lys Ser Phe Asp Leu Asn Leu
            515                 520                 525

Pro Ala Glu Met Val Arg Cys Val Glu Val Phe Lys Glu Phe Tyr Gln
        530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
                565                 570                 575

Thr Thr Tyr Gln Ala Ser Ala Leu Leu Leu Phe Asn Ala Ser Asp Arg
                580                 585                 590

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
        610                 615                 620

Asn Lys Glu Pro Ser Thr Lys Thr Ile Ser Pro Thr Asp Val Phe Glu
625                 630                 635                 640
```

```
Phe Asn Ser Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740
```

<210> SEQ ID NO 24
<211> LENGTH: 742
<212> TYPE: PRT
<213> ORGANISM: Capsicum annuum

<400> SEQUENCE: 24

```
Met Asn Gln Arg Ser Thr Ile Asn Leu Glu His Gly Trp Asp Phe Met
1               5                   10                  15

Gln Arg Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Leu Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Ser Met Asp Tyr Tyr Glu Asn Asp
            180                 185                 190

Phe Glu Ala Ala Met Leu Lys Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Leu Ser Ser Glu Thr Lys Leu Leu Glu Lys Val Gln His Glu Leu
                245                 250                 255

Leu Ser Val Tyr Ala Thr Gln Leu Leu Glu Lys Glu His Ser Gly Cys
```

```
                260                 265                 270
His Ala Leu Leu Arg Asp Asp Lys Val Glu Asp Leu Ser Arg Met Tyr
            275                 280                 285

Arg Leu Phe Ser Lys Ile Pro Arg Gly Leu Asp Pro Val Ala Asn Ile
        290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Ile Phe Val Arg Lys Val Ile Glu Leu His Asp Lys
            340                 345                 350

Tyr Met Ala Tyr Val Asn Asn Cys Phe Gln Asn His Thr Leu Phe His
        355                 360                 365

Lys Ala Leu Lys Glu Ala Phe Glu Leu Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Ala Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
        515                 520                 525

Pro Ala Glu Met Val Arg Cys Val Glu Val Phe Lys Glu Phe Tyr Gln
    530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
                565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
        595                 600                 605

Val Val Arg Leu Leu His Ser Leu Ser Cys Ala Lys Tyr Lys Ile Leu
    610                 615                 620

Asn Lys Glu Pro Ser Thr Lys Thr Ile Ser Pro Thr Asp Val Phe Glu
625                 630                 635                 640

Phe Asn Phe Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685
```

Lys Val Leu Gly Tyr Gln Gln Leu Val Met Glu Cys Val Glu Gln Leu
            690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740

<210> SEQ ID NO 25
<211> LENGTH: 738
<212> TYPE: PRT
<213> ORGANISM: Brassica oleracea

<400> SEQUENCE: 25

Met Glu Arg Lys Thr Ile Asp Leu Asp Gln Gly Trp Asp Tyr Met Gln
1               5                   10                  15

Thr Gly Ile Thr Lys Leu Lys Arg Ile Leu Glu Gly Leu Pro Glu Pro
            20                  25                  30

Gln Phe Asp Ser Glu Gln Tyr Met Met Leu Tyr Thr Thr Ile Tyr Asn
        35                  40                  45

Met Cys Thr Gln Lys Pro Pro His Asp Tyr Ser Gln Leu Tyr Asp
50                  55                  60

Lys Tyr Arg Glu Ala Phe Glu Glu Tyr Ile His Ser Thr Val Leu Pro
65                  70                  75                  80

Ala Leu Arg Glu Lys His Asp Glu Tyr Met Leu Arg Glu Leu Val Lys
                85                  90                  95

Arg Trp Ser Asn His Lys Val Met Val Arg Trp Leu Ser Arg Phe Phe
            100                 105                 110

Tyr Tyr Leu Asp Arg Tyr Phe Ile Ala Arg Arg Ser Leu Pro Pro Leu
        115                 120                 125

Asn Glu Val Gly Leu Thr Cys Phe Arg Asp Leu Val Tyr Asn Glu Leu
130                 135                 140

His Ser Lys Val Lys Asp Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Glu Asp Phe
            180                 185                 190

Glu Ser Phe Met Leu Leu Asp Ser Ala Ser Tyr Tyr Ser Arg Lys Ala
        195                 200                 205

Ser Ser Trp Ile Gln Glu Asp Ser Cys Pro Asp Tyr Met Leu Lys Ser
210                 215                 220

Glu Glu Cys Leu Lys Lys Glu Arg Glu Arg Val Ala His Tyr Leu His
225                 230                 235                 240

Ser Ser Ser Glu Pro Lys Leu Val Glu Lys Val Gln His Glu Leu Leu
                245                 250                 255

Val Val Tyr Ala Asn Gln Leu Leu Glu Lys Glu His Ser Gly Cys Arg
            260                 265                 270

Ala Leu Leu Arg Asp Asp Lys Val Asp Asp Leu Ser Arg Met Tyr Arg
        275                 280                 285

Leu Tyr His Lys Ile Val Lys Gly Leu Glu Pro Val Ala Asn Ile Phe
290                 295                 300

Lys Gln His Val Thr Ala Glu Gly Asn Ala Leu Val Gln Gln Ala Glu

-continued

```
                305                 310                 315                 320
Asp Thr Ala Thr Asn His Ala Ala Asn Thr Ala Ser Val Gln Glu Gln
                    325                 330                 335
Val Leu Ile Arg Lys Val Ile Glu Leu His Asp Lys Tyr Met Val Tyr
                340                 345                 350
Val Val Glu Cys Phe Gln Asn His Thr Leu Phe His Lys Ala Leu Lys
                355                 360                 365
Glu Ala Phe Glu Ile Phe Cys Asn Lys Thr Val Ala Gly Ser Ser Ser
            370                 375                 380
Ala Glu Leu Leu Ala Thr Phe Cys Asp Asn Ile Leu Lys Lys Gly Gly
385                 390                 395                 400
Ser Glu Lys Leu Ser Asp Glu Ala Ile Glu Asp Thr Leu Glu Lys Val
                405                 410                 415
Val Lys Leu Leu Ala Tyr Ile Ser Asp Lys Asp Leu Phe Ala Glu Phe
            420                 425                 430
Tyr Arg Lys Lys Leu Ala Arg Arg Leu Leu Phe Asp Arg Ser Ala Asn
        435                 440                 445
Asp Asp His Glu Arg Ser Ile Leu Thr Lys Leu Lys Gln Gln Cys Gly
    450                 455                 460
Gly Gln Phe Thr Ser Lys Met Glu Gly Met Val Thr Asp Leu Thr Leu
465                 470                 475                 480
Ala Arg Glu Asn Gln Asn Ser Phe Glu Glu Tyr Leu Gly Asn Asn Pro
                485                 490                 495
Ala Ala Asn Pro Gly Ile Asp Leu Thr Val Thr Val Leu Thr Thr Gly
            500                 505                 510
Phe Trp Pro Ser Tyr Lys Ser Phe Asp Ile Asn Leu Pro Ala Glu Met
        515                 520                 525
Val Lys Cys Val Glu Val Phe Lys Gly Phe Tyr Glu Thr Lys Thr Lys
    530                 535                 540
His Arg Lys Leu Thr Trp Ile Tyr Ser Leu Gly Thr Cys His Leu Asn
545                 550                 555                 560
Gly Lys Phe Asp Val Lys Pro Ile Glu Leu Val Val Ser Thr Tyr Gln
                565                 570                 575
Ala Ala Val Leu Leu Leu Phe Asn Thr Thr Asp Lys Leu Ser Tyr Thr
            580                 585                 590
Asp Ile Leu Thr Gln Leu Asn Leu Ser His Glu Asp Leu Val Arg Leu
        595                 600                 605
Leu His Ser Leu Ser Cys Ala Arg Tyr Lys Ile Leu Leu Lys Glu Pro
    610                 615                 620
Ser Thr Lys Thr Val Ser Gln Ser Asp Ser Phe Glu Phe Asn Ser Lys
625                 630                 635                 640
Phe Thr Asp Arg Met Arg Arg Ile Lys Ile Pro Leu Pro Pro Val Asp
                645                 650                 655
Glu Arg Lys Lys Val Val Glu Asp Val Asp Lys Asp Arg Arg Tyr Ala
                660                 665                 670
Ile Asp Ala Ala Ile Val Arg Ile Met Lys Ser Arg Lys Val Leu Gly
            675                 680                 685
His Gln Gln Leu Val Ser Glu Cys Val Glu Gln Leu Ser Arg Met Phe
        690                 695                 700
Lys Pro Asp Ile Lys Ala Ile Lys Lys Arg Met Glu Asp Leu Ile Thr
705                 710                 715                 720
Arg Asp Tyr Leu Glu Arg Asp Lys Glu Asn Ala Asn Met Phe Arg Tyr
                725                 730                 735
```

Leu Ala

<210> SEQ ID NO 26
<211> LENGTH: 743
<212> TYPE: PRT
<213> ORGANISM: Daucus carota

<400> SEQUENCE: 26

Met Met Ile Glu Arg Lys Thr Ile Asp Leu Glu Gln Gly Trp Asp Phe
1               5                   10                  15

Met Gln Lys Gly Ile Thr Lys Leu Lys Asn Ile Leu Glu Gly Phe Pro
            20                  25                  30

Glu Pro Gln Phe Ser Ser Glu Asp Tyr Met Met Leu Tyr Thr Thr Ile
        35                  40                  45

Tyr Asn Met Cys Thr Gln Lys Pro Pro His Asp Tyr Ser Gln Gln Leu
50                  55                  60

Tyr Glu Lys Tyr Arg Glu Ala Ile Glu Glu Tyr Ile Thr Ser Thr Val
65                  70                  75                  80

Leu Pro Ser Leu Arg Glu Lys His Asp Glu Phe Met Leu Arg Glu Leu
                85                  90                  95

Val Lys Arg Trp Ser Asn His Lys Val Met Val Arg Trp Leu Ser Arg
            100                 105                 110

Phe Phe His Tyr Leu Asp Arg Tyr Phe Ile Ala Arg Arg Ser Leu Pro
        115                 120                 125

Pro Leu His Glu Val Gly Leu Thr Cys Phe Arg Asp Leu Val Tyr Gln
    130                 135                 140

Glu Ile Asn Gly Lys Val Arg Asp Ala Val Ile Ser Leu Ile Asn Gln
145                 150                 155                 160

Glu Arg Glu Gly Glu Gln Ile Asp Arg Ala Leu Leu Lys Asn Val Leu
                165                 170                 175

Asp Ile Phe Val Glu Val Gly Met Ser Gln Met Asp Tyr Tyr Glu Asn
            180                 185                 190

Asp Phe Glu Ala Asp Met Leu Lys Asp Thr Ala Ala Tyr Tyr Ser Arg
        195                 200                 205

Lys Ala Ser Asn Trp Ile Leu Glu Asp Ser Cys Pro Asp Tyr Met Leu
210                 215                 220

Lys Ala Glu Glu Cys Leu Arg Arg Glu Lys Asp Arg Val Ser Asn Tyr
225                 230                 235                 240

Leu His Ser Ser Ser Glu Pro Lys Leu Leu Glu Lys Val Gln His Glu
                245                 250                 255

Leu Leu Ser His Tyr Ala Thr Gln Leu Leu Glu Lys Glu His Ser Gly
            260                 265                 270

Cys His Ala Leu Leu Arg Asp Asp Lys Val Ala Asp Leu Ser Arg Met
        275                 280                 285

Tyr Arg Leu Phe Ser Lys Ile Pro Arg Gly Leu Asp Pro Val Ser Asn
    290                 295                 300

Ile Phe Lys Gln His Val Thr Ala Glu Gly Thr Ala Leu Val Lys Gln
305                 310                 315                 320

Ala Glu Asp Ala Ala Ser Asn Lys Lys Ala Lys Arg Asp Val Val
                325                 330                 335

Gly Leu Gln Glu Gln Val Phe Val Arg Lys Ile Ile Glu Leu His Asp
            340                 345                 350

Lys Tyr Leu Thr Tyr Val Asn Asp Cys Phe Thr Asn His Thr Leu Phe
        355                 360                 365

His Lys Ala Leu Lys Glu Ala Phe Glu Ile Phe Cys Asn Lys Gly Val
    370                 375                 380

Ser Gly Ser Ser Ser Ala Glu Leu Leu Ala Thr Phe Cys Asp Asn Ile
385                 390                 395                 400

Leu Lys Lys Gly Gly Ser Glu Lys Leu Ser Asp Glu Ala Ile Glu Glu
                405                 410                 415

Thr Leu Glu Lys Val Val Arg Leu Leu Ala Tyr Ile Ser Asp Lys Asp
            420                 425                 430

Leu Phe Ala Glu Phe Tyr Arg Lys Lys Leu Ala Arg Arg Leu Leu Phe
        435                 440                 445

Asp Lys Ser Ala Asn Asp Glu His Glu Arg Ser Ile Leu Thr Lys Leu
    450                 455                 460

Lys Gln Gln Cys Gly Gly Gln Phe Thr Ser Lys Met Glu Gly Met Val
465                 470                 475                 480

Thr Asp Leu Thr Leu Ala Lys Glu Asn Gln Ser Asn Phe Glu Glu Tyr
                485                 490                 495

Leu Asn Asn Asn Ser Asn Val Asn Pro Gly Ile Asp Leu Thr Val Thr
            500                 505                 510

Val Leu Thr Thr Gly Phe Trp Pro Ser Tyr Lys Ser Phe Asp Leu Asn
        515                 520                 525

Leu Pro Ala Glu Met Val Lys Cys Val Glu Val Phe Arg Glu Phe Tyr
    530                 535                 540

Gln Thr Lys Thr Lys His Arg Lys Leu Thr Trp Ile Tyr Ser Leu Gly
545                 550                 555                 560

Thr Cys Asn Ile Ile Gly Lys Phe Asp Pro Lys Thr Met Glu Leu Ile
                565                 570                 575

Val Thr Thr Tyr Gln Ala Ser Ala Leu Leu Leu Phe Asn Ser Ser Asp
            580                 585                 590

Arg Leu Ser Tyr Asn Glu Ile Met Thr Gln Leu Asn Leu Ser Asp Asp
        595                 600                 605

Asp Val Val Arg Leu Leu His Ser Leu Ser Cys Ala Lys Tyr Lys Ile
    610                 615                 620

Leu Ser Lys Glu Pro Asn Thr Lys Thr Ile Ser Pro Thr Asp Cys Phe
625                 630                 635                 640

Gln Phe Asn Ser Lys Phe Thr Asp Lys Met Arg Arg Ile Lys Ile Pro
                645                 650                 655

Leu Pro Pro Val Asp Glu Lys Lys Val Ile Glu Asp Val Asp Lys
            660                 665                 670

Asp Arg Arg Tyr Ala Ile Asp Ala Ser Ile Val Arg Ile Met Lys Ser
        675                 680                 685

Arg Lys Val Leu Gly Tyr Gln Gln Leu Val Met Glu Cys Val Glu Gln
    690                 695                 700

Leu Gly Arg Met Phe Lys Pro Asp Val Lys Ala Ile Lys Lys Arg Ile
705                 710                 715                 720

Glu Asp Leu Ile Thr Arg Asp Tyr Leu Glu Arg Asp Lys Asp Asn Ala
                725                 730                 735

Asn Leu Phe Arg Tyr Leu Ala
            740

<210> SEQ ID NO 27
<211> LENGTH: 742
<212> TYPE: PRT
<213> ORGANISM: Apium graveolens

```
<400> SEQUENCE: 27

Met Asn Glu Arg Lys Thr Ile Asp Leu Asp Asn Gly Trp Glu Phe Met
1               5                   10                  15

Gln Lys Gly Ile Thr Lys Leu Lys Lys Ile Leu Glu Gly Gln Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Asn Arg Trp Thr Asn His Lys Val Met Val Arg Trp Leu Ser Arg Phe
            100                 105                 110

Phe His Tyr Leu Asp Arg Tyr Phe Ile Ala Arg Arg Ser Leu Pro Ala
        115                 120                 125

Leu His Glu Val Gly Leu Thr Cys Phe Arg Asp Leu Val Tyr Gln Glu
    130                 135                 140

Leu Lys Val Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Ser Gln Met Asp Gln Tyr Glu Asn Asp
            180                 185                 190

Phe Glu Glu Ala Met Leu Thr Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Arg Arg Glu Lys Asp Arg Val Ser His Tyr Leu
225                 230                 235                 240

His Phe Ser Ser Glu Pro Lys Leu Leu Glu Lys Val Gln His Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Lys Gly Leu Asp Pro Val Ser Tyr Ile
    290                 295                 300

Phe Lys Gln His Val Thr Asn Glu Gly Met Ala Leu Val Lys Gln Ala
305                 310                 315                 320

Glu Asp Ala Ala Ser Asn Lys Lys Ala Glu Lys Arg Asp Val Val Ser
                325                 330                 335

Leu Gln Glu Gln Val Phe Val Arg Lys Ile Ile Glu Leu His Asp Lys
            340                 345                 350

Tyr Leu Ala Tyr Val Asn Asp Cys Phe Thr Asn His Thr Leu Phe His
        355                 360                 365

Lys Ala Leu Lys Glu Ala Phe Glu Ile Phe Cys Asn Lys Gly Val Ala
    370                 375                 380

Gly Ser Ser Asn Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415
```

```
Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
            435                 440                 445

Lys Ser Ala Asn Asp Glu His Glu Arg Ser Ile Leu Thr Lys Leu Lys
            450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser Ser Phe Glu Glu Tyr Leu
                485                 490                 495

Gly Asn Asn Ala Asn Val Asn Pro Gly Ile Asp Leu Thr Val Thr Val
            500                 505                 510

Leu Thr Thr Gly Phe Trp Pro Ser Tyr Lys Ser Phe Asp Leu Asn Leu
            515                 520                 525

Pro Ala Glu Met Val Lys Cys Val Glu Val Phe Arg Glu Phe Tyr Gln
            530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Ile Val
                565                 570                 575

Thr Thr Tyr Gln Ala Ser Ala Leu Leu Leu Phe Asn Thr Ser Asp Arg
            580                 585                 590

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
            610                 615                 620

Thr Lys Glu Pro Asn Asn Lys Thr Ile Ser Pro Thr Asp Tyr Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
            675                 680                 685

Lys Val Leu Gly Tyr Gln Gln Leu Val Met Glu Cys Val Glu Gln Leu
690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Ala Asn
                725                 730                 735

Leu Phe Arg Tyr Leu Ala
            740

<210> SEQ ID NO 28
<211> LENGTH: 742
<212> TYPE: PRT
<213> ORGANISM: Cichorium intybus

<400> SEQUENCE: 28

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
```

```
                    35                  40                  45
Asn Met Cys Thr Gln Lys Pro Pro His Asp Tyr Ser Gln Gln Leu Tyr
 50                  55                  60
Asp Lys Tyr Arg Glu Ser Phe Glu Glu Tyr Ile Thr Ser Thr Val Leu
 65                      70                  75                  80
Pro Ser Leu Arg Glu Lys His Asp Glu Phe Met Leu Arg Glu Leu Val
                     85                  90                  95
Arg Arg Trp Ser Asn His Lys Val Met Val Arg Trp Leu Ser Arg Phe
                100                 105                 110
Phe His Tyr Leu Asp Arg Tyr Phe Ile Ala Arg Arg Ser Leu Pro Pro
                115                 120                 125
Leu Asn Glu Val Gly Leu Ala Cys Phe Arg Asp Leu Val Tyr Gln Glu
130                 135                 140
Val Asn Gly Lys Val Arg Asp Ala Val Ile Ser Leu Ile Asp Gln Glu
145                 150                 155                 160
Arg Glu Gly Glu Gln Ile Asp Arg Ala Leu Leu Lys Asn Val Leu Asp
                165                 170                 175
Ile Phe Val Glu Ile Gly Met Gly Gln Met Glu Tyr Tyr Glu Asn Asp
                180                 185                 190
Phe Glu Ala Ser Met Leu Asn Asp Thr Ala Ala Tyr Tyr Ser Arg Lys
                195                 200                 205
Ala Ser Asn Trp Ile Leu Glu Asp Ser Cys Pro Asp Tyr Met Leu Lys
210                 215                 220
Ala Glu Glu Cys Leu Lys Arg Glu Lys Asp Arg Val Ser His Tyr Leu
225                 230                 235                 240
His Ser Ser Ser Glu Pro Lys Leu Leu Glu Lys Val Gln Thr Glu Leu
                245                 250                 255
Leu Ser Val Tyr Ala Thr Gln Leu Leu Glu Lys Glu His Ser Gly Cys
                260                 265                 270
His Ala Leu Leu Arg Asp Asp Lys Val Asp Asp Leu Ser Arg Met Tyr
                275                 280                 285
Arg Leu Phe Ser Lys Ile Gln Lys Gly Leu Asp Pro Val Ser Ser Met
290                 295                 300
Phe Lys Gln His Val Thr Ala Glu Gly Thr Thr Leu Val Lys Gln Ala
305                 310                 315                 320
Glu Asp Ala Ala Ser Thr Lys Lys Ala Glu Lys Arg Asp Val Val Gly
                325                 330                 335
Leu Gln Glu Gln Val Phe Val Arg Lys Val Ile Glu Leu His Asp Lys
                340                 345                 350
Tyr Leu Ala Tyr Val Asn Asp Cys Phe Met Asn His Thr Leu Phe His
                355                 360                 365
Lys Ala Leu Lys Glu Ala Phe Glu Ile Phe Cys Asn Lys Gly Val Ala
                370                 375                 380
Gly Ser Ser Ser Ala Glu Leu Leu Ala Thr Phe Cys Asp Asn Ile Leu
385                 390                 395                 400
Lys Lys Gly Gly Ser Glu Lys Leu Ser Asp Glu Ala Ile Glu Asp Thr
                405                 410                 415
Leu Glu Lys Val Val Lys Leu Leu Ala Tyr Ile Ser Asp Lys Asp Leu
                420                 425                 430
Phe Ala Glu Phe Tyr Arg Lys Lys Leu Ala Arg Arg Leu Leu Phe Asp
                435                 440                 445
Lys Ser Ala Asn Asp Glu His Glu Arg Ser Ile Leu Thr Lys Leu Lys
450                 455                 460
```

```
Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
            515                 520                 525

Pro Ala Glu Met Val Lys Cys Val Glu Val Phe Arg Glu Phe Tyr Gln
530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Ser Ser Asp Arg
            580                 585                 590

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
            675                 680                 685

Lys Val Leu Gly Tyr Gln Gln Leu Val Met Glu Cys Val Glu Gln Leu
690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740

<210> SEQ ID NO 29
<211> LENGTH: 742
<212> TYPE: PRT
<213> ORGANISM: Cichorium endivia

<400> SEQUENCE: 29

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
                20                  25                  30

Pro Gln Phe Ser Ser Glu Asp Tyr Met Met Leu Tyr Thr Thr Ile Tyr
            35                  40                  45

Asn Met Cys Thr Gln Lys Pro Pro His Asp Tyr Ser Gln Gln Leu Tyr
        50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
```

```
                    85                  90                  95
Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
            115                 120                 125

Leu Asn Glu Val Gly Leu Ala Cys Phe Arg Asp Leu Val Tyr Gln Glu
            130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
            195                 200                 205

Ala Ser Asn Trp Ile Leu Glu Asp Ser Cys Pro Asp Tyr Met Leu Lys
            210                 215                 220

Ala Glu Glu Cys Leu Lys Arg Glu Lys Asp Arg Val Ser His Tyr Leu
225                 230                 235                 240

His Ser Ser Glu Pro Lys Leu Leu Glu Lys Val Gln Thr Glu Leu
                245                 250                 255

Leu Ser Val Tyr Ala Thr Gln Leu Leu Glu Lys Glu His Ser Gly Cys
                260                 265                 270

His Ala Leu Leu Arg Asp Asp Lys Val Asp Asp Leu Ser Arg Met Tyr
                275                 280                 285

Arg Leu Phe Ser Lys Ile Gln Lys Gly Leu Asp Pro Val Ser Ser Met
            290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
                340                 345                 350

Tyr Leu Ala Tyr Val Asn Asp Cys Phe Met Asn His Thr Leu Phe His
            355                 360                 365

Lys Ala Leu Lys Glu Ala Phe Glu Ile Phe Cys Asn Lys Gly Val Ala
            370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
                420                 425                 430

Phe Ala Glu Phe Tyr Arg Lys Lys Leu Ala Arg Arg Leu Leu Phe Asp
            435                 440                 445

Lys Ser Ala Asn Asp Glu His Glu Arg Ser Ile Leu Thr Lys Leu Lys
            450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
                500                 505                 510
```

Leu Thr Thr Gly Phe Trp Pro Ser Tyr Lys Ser Phe Asp Leu Asn Leu
            515                 520                 525

Pro Ala Glu Met Val Lys Cys Val Glu Val Phe Arg Glu Phe Tyr Gln
530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
            565                 570                 575

Thr Thr Tyr Gln Ala Ser Ala Leu Leu Leu Phe Asn Ser Ser Asp Arg
            580                 585                 590

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
            610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Ile Lys Ile Pro Leu
            645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
            675                 680                 685

Lys Val Leu Gly Tyr Gln Gln Leu Val Met Glu Cys Val Glu Gln Leu
            690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
            725                 730                 735

Leu Phe Arg Tyr Leu Ala
            740

<210> SEQ ID NO 30
<211> LENGTH: 744
<212> TYPE: PRT
<213> ORGANISM: Allium ampeloprasum

<400> SEQUENCE: 30

Met Ser Leu His Glu Arg Lys Thr Ile Asp Leu Glu Gln Gly Trp Ala
1               5                   10                  15

Phe Met Gln Lys Gly Ile Thr Lys Leu Lys Asn Ile Leu Asp Glu Leu
            20                  25                  30

Asn Glu Pro Gln Phe Ser Ser Glu Asp Tyr Met Met Leu Tyr Thr Thr
            35                  40                  45

Ile Tyr Asn Met Cys Thr Gln Lys Pro Pro His Asp Tyr Ser Gln Glu
        50                  55                  60

Leu Tyr Asp Lys Tyr Arg Glu Ser Phe Glu Tyr Ile Thr Thr Thr
65                  70                  75                  80

Val Leu Pro Ser Leu Arg Glu Lys His Asp Glu Tyr Met Leu Arg Glu
                85                  90                  95

Leu Val Arg Arg Trp Ser Asn His Lys Ile Met Val Arg Trp Leu Ser
            100                 105                 110

Arg Phe Phe His Tyr Leu Asp Arg Tyr Phe Ile Ala Arg Arg Ser Leu
            115                 120                 125

Pro Ala Leu Asn Glu Val Gly Leu Thr Cys Phe Arg Asp Leu Val Tyr

-continued

```
                130                 135                 140
Asn Glu Val His Gly Lys Val Lys Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Gly Ile Phe Val Glu Ile Gly Leu Gly Ser Met Glu Cys Tyr Glu
                180                 185                 190

Asn Asp Phe Glu Thr Ser Met Leu Asn Ala Thr Ala Ala Tyr Tyr Ser
                195                 200                 205

Arg Lys Ala Ser Asn Trp Ile Leu Glu Asp Ser Cys Pro Asp Tyr Met
                210                 215                 220

Leu Lys Ala Glu Glu Cys Leu Lys His Glu Lys Asp Arg Val Ala His
225                 230                 235                 240

Tyr Leu His Ser Ser Ser Glu Gln Lys Leu Leu Glu Lys Val Gln His
                245                 250                 255

Glu Leu Leu Phe Val Tyr Ala Ser Gln Leu Leu Glu Lys Glu His Ser
                260                 265                 270

Gly Cys His Ala Leu Leu Arg Asp Asp Lys Val Gly Asp Leu Ser Arg
                275                 280                 285

Met Tyr Arg Leu Phe Cys Arg Ile Thr Arg Gly Leu Asp Pro Val Ser
                290                 295                 300

Gln Ile Phe Lys Gln His Val Thr Ala Glu Gly Thr Ala Leu Val Lys
305                 310                 315                 320

His Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
                340                 345                 350

Asp Lys Tyr Leu Ala Tyr Val Thr Asp Cys Phe Gln Asn His Ser Leu
                355                 360                 365

Phe His Lys Ala Leu Lys Glu Ala Phe Glu Val Phe Cys Asn Lys Gly
                370                 375                 380

Val Ala Gly Ser Ser Ser Ala Glu Leu Leu Ala Ala Phe Cys Asp Asn
385                 390                 395                 400

Ile Leu Lys Lys Gly Gly Ser Glu Lys Leu Ser Asp Glu Ala Ile Glu
                405                 410                 415

Asp Thr Leu Glu Lys Val Val Lys Leu Leu Ala Tyr Ile Ser Asp Lys
                420                 425                 430

Asp Leu Phe Ala Glu Phe Tyr Arg Lys Lys Leu Ala Arg Arg Leu Leu
                435                 440                 445

Phe Asp Lys Ser Ala Asn Asp His Glu Arg Ser Ile Leu Thr Lys
                450                 455                 460

Leu Lys Gln Gln Cys Gly Gly Gln Phe Thr Lys Met Glu Gly Met
465                 470                 475                 480

Val Thr Asp Leu Thr Leu Ala Arg Glu Asn Gln Ser Ser Phe Asp Asp
                485                 490                 495

Tyr Leu Ser Ser Asn Pro Lys Ala Asn Ser Gly Ile Asp Leu Thr Val
                500                 505                 510

Thr Val Leu Thr Thr Gly Phe Trp Pro Ser Tyr Lys Ser Phe Asp Leu
                515                 520                 525

Asn Leu Pro Asp Glu Met Val Lys Cys Val Glu Ile Phe Lys Glu Phe
                530                 535                 540

Tyr Glu Thr Lys Thr Lys His Arg Lys Leu Thr Trp Ile Tyr Ser Leu
545                 550                 555                 560
```

```
Gly Thr Cys Asn Ile Asn Gly Lys Phe Glu Thr Lys Thr Ile Glu Leu
                565                 570                 575

Val Val Thr Thr Tyr Gln Ala Ala Val Leu Leu Phe Asn Ser Ala
            580                 585                 590

Asp Lys Leu Ser Tyr Ser Glu Ile Val Gln Gln Leu Asn Leu Ser Asp
            595                 600                 605

Asp Asp Val Ile Arg Leu Leu His Ser Leu Ser Cys Ala Lys Tyr Lys
610                 615                 620

Ile Leu Asn Lys Glu Pro Ala Thr Lys Thr Ile Thr Pro Asn Asp His
625                 630                 635                 640

Phe Glu Phe Asn Ser Lys Phe Thr Asp Arg Met Arg Arg Ile Lys Ile
                645                 650                 655

Pro Leu Pro Pro Val Asp Glu Lys Lys Val Ile Glu Asp Val Asp
            660                 665                 670

Lys Asp Arg Arg Tyr Ala Ile Asp Ala Ser Ile Val Arg Ile Met Lys
            675                 680                 685

Ser Arg Lys Val Leu Gly His Gln Gln Leu Val Leu Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Ala Arg Asp Tyr Leu Glu Arg Asp Lys Asp Asn
                725                 730                 735

Pro Asn Leu Phe Lys Tyr Leu Ala
                740

<210> SEQ ID NO 31
<211> LENGTH: 742
<212> TYPE: PRT
<213> ORGANISM: Lactuca sativa

<400> SEQUENCE: 31

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
    50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
```

-continued

```
                180                 185                 190
Phe Glu Ala Ser Met Leu Asn Asp Thr Ala Tyr Tyr Ser Arg Lys
            195                 200                 205
Ala Ser Asn Trp Ile Leu Glu Asp Ser Cys Pro Asp Tyr Met Leu Lys
210                 215                 220
Ala Glu Glu Cys Leu Lys Arg Glu Lys Asp Arg Val Ser His Tyr Leu
225                 230                 235                 240
His Ser Ser Ser Glu Pro Lys Leu Leu Glu Lys Val Gln Asn Glu Leu
                245                 250                 255
Leu Ser Val Tyr Ala Thr Gln Leu Leu Glu Lys Glu His Ser Gly Cys
            260                 265                 270
His Ala Leu Leu Arg Asp Asp Lys Val Asp Asp Leu Ser Arg Met Tyr
        275                 280                 285
Arg Leu Phe Ser Lys Ile Pro Lys Gly Leu Asp Pro Val Ser Ser Met
    290                 295                 300
Phe Lys Gln His Val Thr Ala Glu Gly Thr Thr Leu Val Lys Gln Ala
305                 310                 315                 320
Glu Asp Ala Ala Ser Thr Lys Lys Ala Glu Lys Arg Asp Val Val Gly
                325                 330                 335
Leu Gln Glu Gln Val Phe Val Arg Lys Val Ile Glu Leu His Asp Lys
            340                 345                 350
Tyr Leu Ala Tyr Val Asn Asp Cys Phe Met Asn His Thr Leu Phe His
        355                 360                 365
Lys Ala Leu Lys Glu Ala Phe Glu Ile Phe Cys Asn Lys Gly Val Ala
    370                 375                 380
Gly Ser Ser Ser Ala Glu Leu Leu Ala Thr Phe Cys Asp Asn Ile Leu
385                 390                 395                 400
Lys Lys Gly Gly Ser Glu Lys Leu Ser Asp Glu Ala Ile Glu Asp Thr
                405                 410                 415
Leu Glu Lys Val Val Lys Leu Leu Ala Tyr Ile Ser Asp Lys Asp Leu
            420                 425                 430
Phe Ala Glu Phe Tyr Arg Lys Lys Leu Ala Arg Arg Leu Leu Phe Asp
        435                 440                 445
Lys Ser Ala Asn Asp Glu His Glu Arg Ser Ile Leu Thr Lys Leu Lys
    450                 455                 460
Gln Gln Cys Gly Gly Gln Phe Thr Ser Lys Met Glu Gly Met Val Thr
465                 470                 475                 480
Asp Leu Thr Leu Ala Lys Glu Asn Gln Ser His Phe Glu Glu Tyr Leu
                485                 490                 495
Asn Asn Asn Pro Asn Val Ser Pro Gly Ile Asp Leu Thr Val Thr Val
            500                 505                 510
Leu Thr Thr Gly Phe Trp Pro Ser Tyr Lys Ser Phe Asp Leu Asn Leu
        515                 520                 525
Pro Ala Glu Met Val Lys Cys Val Glu Val Phe Arg Glu Phe Tyr Gln
    530                 535                 540
Thr Lys Thr Lys His Arg Lys Leu Thr Trp Ile Tyr Ser Leu Gly Thr
545                 550                 555                 560
Cys Asn Ile Asn Gly Lys Phe Glu Pro Lys Thr Met Glu Leu Ile Val
                565                 570                 575
Thr Thr Tyr Gln Ala Ser Ala Leu Leu Leu Phe Asn Leu Ser Asp Arg
            580                 585                 590
Leu Ser Tyr Gln Glu Ile Met Thr Gln Leu Asn Leu Ser Asp Asp Asp
        595                 600                 605
```

```
Val Val Arg Leu Leu His Ser Leu Ser Cys Ala Lys Tyr Lys Ile Leu
    610                 615                 620

Leu Lys Glu Pro Asn Thr Lys Thr Ile Ser Pro Thr Asp Tyr Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
    690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740

<210> SEQ ID NO 32
<211> LENGTH: 738
<212> TYPE: PRT
<213> ORGANISM: Raphanus sativus

<400> SEQUENCE: 32

Met Glu Arg Lys Thr Ile Asp Leu Glu Gln Gly Trp Asp Tyr Met Gln
1               5                   10                  15

Thr Gly Ile Thr Lys Leu Lys Arg Ile Leu Glu Gly Leu Pro Glu Pro
                20                  25                  30

Gln Phe Asp Ser Glu Gln Tyr Met Met Leu Tyr Thr Thr Ile Tyr Asn
            35                  40                  45

Met Cys Thr Gln Lys Pro Pro His Asp Tyr Ser Gln Gln Leu Tyr Asp
50                  55                  60

Lys Tyr Arg Glu Ala Phe Glu Glu Tyr Ile Asp Ser Thr Val Leu Pro
65                  70                  75                  80

Ala Leu Lys Glu Lys His Asp Glu Tyr Met Leu Arg Glu Leu Val Lys
                85                  90                  95

Arg Trp Ser Asn His Lys Val Met Val Arg Trp Leu Ser Arg Phe Phe
            100                 105                 110

Tyr Tyr Leu Asp Arg Tyr Phe Ile Ala Arg Arg Ser Leu Pro Pro Leu
        115                 120                 125

Asn Glu Val Gly Leu Thr Cys Phe Arg Asp Arg Val Tyr Lys Glu Leu
    130                 135                 140

His Ser Lys Val Lys Asp Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Val Asp Phe
            180                 185                 190

Glu Ser Phe Met Leu Leu Asp Ser Ala Ser Tyr Tyr Ser Arg Lys Ala
        195                 200                 205

Ser Asn Trp Ile Gln Glu Asp Ser Cys Pro Asp Tyr Met Leu Lys Ser
    210                 215                 220

Glu Glu Cys Leu Lys Lys Glu Arg Glu Arg Val Ala His Tyr Leu His
```

```
                225                 230                 235                 240
        Ser Ser Ser Glu Pro Lys Leu Val Glu Lys Val Gln His Glu Leu Leu
                        245                 250                 255

Val Val Tyr Ala Asn Gln Leu Leu Glu Lys Glu His Ser Gly Cys Arg
                        260                 265                 270

Ala Leu Leu Arg Asp Asp Lys Val Asp Asp Leu Ser Arg Met Tyr Arg
                        275                 280                 285

Leu Tyr His Lys Ile Ala Lys Gly Leu Glu Pro Val Ala Asn Ile Phe
                290                 295                 300

Lys Gln His Val Thr Ala Glu Gly Asn Ala Leu Val Gln Gln Ala Glu
        305                 310                 315                 320

Asp Thr Ala Thr Asn Gln Ala Ala Asn Thr Ala Ser Val Gln Glu Gln
                        325                 330                 335

Val Leu Ile Arg Lys Val Ile Glu Leu His Asp Lys Tyr Met Val Tyr
                        340                 345                 350

Val Val Glu Cys Phe Gln Asn His Thr Leu Phe His Lys Ala Leu Lys
                        355                 360                 365

Glu Ala Phe Glu Ile Phe Cys Asn Lys Thr Val Ala Gly Ser Ser Ser
        370                 375                 380

Ala Glu Leu Leu Ala Thr Phe Cys Asp Asn Ile Leu Lys Lys Gly Gly
        385                 390                 395                 400

Ser Glu Lys Leu Ser Asp Glu Ala Ile Glu Asp Thr Leu Glu Lys Val
                        405                 410                 415

Val Lys Leu Leu Ala Tyr Ile Ser Asp Lys Asp Leu Phe Ala Glu Phe
                        420                 425                 430

Tyr Arg Lys Lys Leu Ala Arg Arg Leu Leu Phe Asp Arg Ser Ala Asn
                        435                 440                 445

Asp Asp His Glu Arg Ser Ile Leu Thr Lys Leu Lys Gln Gln Cys Gly
                450                 455                 460

Gly Gln Phe Thr Ser Lys Met Glu Gly Met Val Thr Asp Leu Thr Leu
        465                 470                 475                 480

Ala Arg Glu Asn Gln Thr Ser Phe Glu Glu Tyr Leu Gly Asn Asn Pro
                        485                 490                 495

Ala Ala Asn Pro Gly Ile Asp Leu Thr Val Thr Val Leu Thr Thr Gly
                        500                 505                 510

Phe Trp Pro Ser Tyr Lys Ser Phe Asp Ile Asn Leu Pro Ser Glu Met
                        515                 520                 525

Val Lys Cys Val Glu Val Phe Lys Gly Phe Tyr Glu Thr Lys Thr Lys
                        530                 535                 540

His Arg Lys Leu Thr Trp Ile Tyr Ser Leu Gly Thr Cys His Leu Asn
        545                 550                 555                 560

Gly Lys Phe Asp His Lys Pro Ile Glu Leu Val Val Ser Thr Tyr Gln
                        565                 570                 575

Ala Ala Val Leu Leu Leu Phe Asn Thr Thr Asp Lys Leu Ser Tyr Asn
                        580                 585                 590

Asp Ile Leu Thr Gln Leu Asn Leu Ser His Glu Asp Leu Val Arg Leu
                595                 600                 605

Leu His Ser Leu Ser Cys Ala Arg Tyr Lys Ile Leu Lys Glu Pro
                610                 615                 620

Ser Thr Lys Thr Val Thr Gln Thr Asp Ser Phe Glu Phe Asn Ala Lys
        625                 630                 635                 640

Phe Thr Asp Arg Met Arg Arg Ile Lys Ile Pro Leu Pro Pro Val Asp
                        645                 650                 655
```

```
Glu Arg Lys Lys Val Glu Asp Val Asp Lys Asp Arg Arg Tyr Ala
            660             665             670
Ile Asp Ala Ala Ile Val Arg Ile Met Lys Ser Arg Lys Val Leu Gly
            675             680             685
His Gln Gln Leu Val Ser Glu Cys Val Glu Gln Leu Ser Arg Met Phe
        690             695             700
Lys Pro Asp Ile Lys Ala Ile Lys Lys Arg Met Glu Asp Leu Ile Thr
705             710             715             720
Arg Asp Tyr Leu Glu Arg Asp Lys Glu Asn Pro Asn Met Phe Arg Tyr
                725             730             735
Leu Ala

<210> SEQ ID NO 33
<211> LENGTH: 740
<212> TYPE: PRT
<213> ORGANISM: Spinacia oleracea

<400> SEQUENCE: 33

Met Asn Asp Arg Lys Val Ile Glu Leu Glu Gln Gly Trp Glu Phe Met
1               5                   10                  15
Gly Lys Gly Ile Thr Lys Leu Lys Arg Ile Leu Glu Gly Leu Pro Glu
            20                  25                  30
Pro Pro Phe Asn Ser Glu Asp Tyr Met Met Leu Tyr Thr Thr Ile Tyr
        35                  40                  45
Asn Met Cys Thr Gln Lys Pro Pro His Asp Tyr Ser Gln Gln Leu Tyr
    50                  55                  60
Asp Asn Tyr Lys Glu Ala Phe Val Asp Tyr Ile His Ser Thr Val Leu
65                  70                  75                  80
Pro Ser Leu Gly Asp Lys His Asp Glu Phe Met Leu Arg Glu Leu Val
                85                  90                  95
Lys Arg Trp Ser Asn His Lys Val Met Val Arg Trp Leu Ser Arg Phe
            100                 105                 110
Phe His Tyr Leu Asp Arg Tyr Phe Ile Ala Arg Arg Ser Leu Pro Ser
        115                 120                 125
Leu Asn Asp Val Gly Leu Thr Cys Phe Arg Asp Leu Val Tyr Gln Glu
    130                 135                 140
Ile Ser Gly Lys Ala Lys Asp Ala Val Ile Ala Leu Ile Asp Glu Glu
145                 150                 155                 160
Arg Glu Gly Gly Gln Ile Asp Arg Ala Leu Leu Lys Asn Val Leu Asp
                165                 170                 175
Ile Tyr Val Glu Ile Gly Met Thr Gln Met Asp Tyr Tyr Glu Lys Asp
            180                 185                 190
Phe Glu Ala His Met Leu Asp Asp Thr Ala Ala Tyr Tyr Ser Arg Lys
        195                 200                 205
Ala Ser Ser Trp Ile Leu Glu Asp Ser Cys Pro Glu Tyr Met Leu Lys
    210                 215                 220
Ser Glu Glu Cys Leu Lys Lys Glu Lys Asp Arg Val Ala His Tyr Leu
225                 230                 235                 240
His Ser Ser Ser Glu Pro Lys Leu Leu Glu Lys Val Gln Asn Glu Leu
                245                 250                 255
Leu Leu Val Tyr Glu Asn Gln Leu Leu Glu Lys Glu Asn Ser Gly Cys
            260                 265                 270
Arg Ala Leu Leu Lys Asp Asp Lys Val Glu Asp Leu Ser Arg Met Tyr
        275                 280                 285
```

-continued

Arg Leu Tyr Ser Lys Val Thr Lys Gly Leu Glu Pro Ile Gly Ser Ile
290                 295                 300

Phe Lys Gln His Ile Thr Asp Glu Gly Thr Ala Leu Val Gln Gln Ala
305                 310                 315                 320

Glu Asp Ala Ala Ile Ser Lys Ala Glu Asn Ala Gly Gly Gly Ser His
                325                 330                 335

Glu Gln Val Phe Val Arg Lys Val Ile Glu Leu His Asp Lys Phe Met
            340                 345                 350

Thr Tyr Val Thr Asp Cys Phe Asn Ser His Thr Ile Phe His Lys Ala
        355                 360                 365

Leu Lys Glu Ala Phe Glu Val Phe Leu Asn Lys Gly Val Ala Gly Ser
370                 375                 380

Ser Ser Ala Glu Leu Leu Ala Ser Phe Cys Asp Asn Ile Leu Lys Lys
385                 390                 395                 400

Gly Gly Ser Glu Lys Leu Ser Asp Glu Ala Ile Glu Asp Ser Leu Glu
                405                 410                 415

Lys Val Val Lys Leu Leu Ala Tyr Val Ser Asp Lys Asp Leu Phe Ala
            420                 425                 430

Glu Phe Tyr Arg Lys Lys Leu Ser Arg Arg Leu Leu Phe Asp Lys Ser
        435                 440                 445

Ala Asn Asp Asp His Glu Arg Ser Ile Leu Thr Lys Leu Lys Gln Gln
450                 455                 460

Cys Gly Gly Gln Phe Thr Ser Lys Met Glu Gly Met Val Thr Asp Leu
465                 470                 475                 480

Thr Leu Ala Arg Glu Asn Gln Thr Asn Phe Glu Glu Tyr Leu Gly Gln
                485                 490                 495

Asn Thr Asp Ala Ser Pro Gly Leu Asp Leu Thr Val Thr Val Leu Thr
            500                 505                 510

Thr Gly Phe Trp Pro Ser Tyr Lys Ser Ser Asp Leu Asn Leu Pro Ala
        515                 520                 525

Glu Met Val Arg Cys Val Glu Val Phe Lys Gln Phe Tyr Gln Thr Lys
530                 535                 540

Thr Lys His Arg Lys Leu Thr Trp Val Tyr Ser Leu Gly Ser Cys Asn
545                 550                 555                 560

Ile Asn Gly Lys Phe Gly Pro Lys Thr Ile Glu Leu Val Val Gly Thr
                565                 570                 575

Tyr Gln Ala Ala Ala Leu Met Leu Phe Asn Thr Ser Asp Arg Leu Ser
            580                 585                 590

Tyr Ser Glu Ile Thr Thr Gln Leu Asn Leu Ala Asp Glu Asp Leu Val
        595                 600                 605

Arg Val Leu Gln Ser Leu Ser Cys Ala Lys Tyr Lys Ile Leu Leu Lys
610                 615                 620

Glu Pro Ser Thr Arg Asn Val Ile Ser Thr Asp Cys Phe Ser Phe Asn
625                 630                 635                 640

Ser Asn Phe Thr Asp Arg Met Arg Arg Ile Arg Ile Pro Leu Pro Pro
                645                 650                 655

Met Asp Glu Arg Lys Lys Val Val Glu Asp Val Asp Lys Asp Arg Arg
            660                 665                 670

Tyr Ala Ile Asp Ala Ser Ile Val Arg Ile Met Lys Ser Arg Lys Ala
        675                 680                 685

Leu Gly Tyr Gln Gln Leu Ile Thr Glu Cys Val Glu Gln Leu Ser Arg
690                 695                 700

```
Met Phe Lys Pro Asp Phe Lys Ala Ile Lys Arg Ile Glu Asp Leu
705                 710                 715                 720

Ile Thr Arg Asp Tyr Ile Glu Arg Asp Lys Glu Asn Pro Gln Leu Phe
                725                 730                 735

Arg Tyr Leu Ala
            740

<210> SEQ ID NO 34
<211> LENGTH: 739
<212> TYPE: PRT
<213> ORGANISM: Beta vulgaris

<400> SEQUENCE: 34

Met Asn Asp Arg Lys Val Ile Glu Leu Glu Gln Gly Trp Glu Phe Met
1               5                   10                  15

Gly Lys Gly Ile Thr Lys Leu Lys Arg Ile Leu Glu Gly Leu Pro Glu
            20                  25                  30

Pro Pro Phe Asn Ser Glu Asp Tyr Met Met Leu Tyr Thr Thr Ile Tyr
        35                  40                  45

Asn Met Cys Thr Gln Lys Pro Pro His Asp Tyr Ser Gln Gln Leu Tyr
50                  55                  60

Asp Asn Tyr Lys Gln Ala Phe Val Asp Tyr Ile Asn Ser Thr Val Leu
65                  70                  75                  80

Pro Ser Leu Arg Glu Lys His Asp Glu Phe Met Leu Arg Glu Leu Val
                85                  90                  95

Lys Arg Trp Ala Asn His Lys Val Met Val Arg Trp Leu Ser Arg Phe
            100                 105                 110

Phe His Tyr Leu Asp Arg Tyr Phe Ile Ala Arg Arg Ser Leu Pro Ser
        115                 120                 125

Leu Asn Glu Val Gly Leu Thr Cys Phe Arg Asp Leu Val Tyr Gln Glu
    130                 135                 140

Ile Ser Gly Lys Ala Lys Asp Ala Val Ile Ala Leu Ile Asp Ile Glu
145                 150                 155                 160

Arg Glu Gly Gly Gln Ile Asp Arg Ser Leu Leu Lys Asn Val Leu Asp
                165                 170                 175

Ile Tyr Val Glu Ile Gly Met Gly Gln Met Asp His Tyr Glu Lys Asp
            180                 185                 190

Phe Glu Ala His Met Leu Asp Asp Thr Ala Ala Tyr Tyr Ser Arg Lys
        195                 200                 205

Ala Ser Ser Trp Ile Leu Glu Asp Ser Cys Pro Glu Tyr Met Leu Lys
    210                 215                 220

Ser Glu Glu Cys Leu Lys Lys Glu Lys Glu Arg Val Ala Asn Tyr Leu
225                 230                 235                 240

His Ser Ser Ser Glu Pro Lys Leu Leu Glu Lys Val Gln Asn Glu Leu
                245                 250                 255

Leu Leu Val Tyr Glu Ser Gln Leu Leu Glu Lys Glu Asn Ser Gly Cys
            260                 265                 270

Arg Ala Leu Leu Lys Asp Asp Lys Val Asp Asp Leu Ser Arg Met Tyr
        275                 280                 285

Arg Leu Tyr Ser Lys Val Thr Lys Gly Leu Glu Pro Ile Gly Ser Ile
    290                 295                 300

Phe Lys Gln His Ile Thr Asp Glu Gly Thr Ala Leu Val Gln Gln Ala
305                 310                 315                 320

Glu Asp Ala Ala Ile Ser Lys Ala Glu Asn Thr Gly Gly Ser His Glu
                325                 330                 335
```

```
Gln Val Phe Val Arg Lys Val Ile Glu Leu His Asp Lys Phe Met Thr
            340                 345                 350
Tyr Val Thr Asp Cys Phe Asn Ser His Thr Ile Phe His Lys Ala Leu
        355                 360                 365
Lys Glu Ala Phe Glu Val Phe Leu Asn Lys Gly Val Ala Gly Ser Ser
370                 375                 380
Ser Ala Glu Leu Leu Ala Thr Phe Cys Asp Asn Ile Leu Lys Lys Gly
385                 390                 395                 400
Gly Ser Glu Lys Leu Ser Asp Glu Ala Ile Glu Asp Ser Leu Glu Lys
                405                 410                 415
Val Val Lys Leu Leu Ala Tyr Val Ser Asp Lys Asp Leu Phe Ala Glu
            420                 425                 430
Phe Tyr Arg Lys Lys Leu Ser Arg Arg Leu Leu Phe Asp Lys Ser Ala
        435                 440                 445
Asn Asp Asp His Glu Arg Ser Ile Leu Thr Lys Leu Lys Gln Gln Cys
    450                 455                 460
Gly Gly Gln Phe Thr Ser Lys Met Glu Gly Met Val Thr Asp Leu Thr
465                 470                 475                 480
Leu Ala Arg Glu Asn Gln Thr Asn Phe Glu Glu Tyr Leu Ser Gln Asn
                485                 490                 495
Pro Asp Ala Ser Pro Gly Leu Asp Leu Thr Val Thr Val Leu Thr Thr
            500                 505                 510
Gly Phe Trp Pro Ser Tyr Lys Ser Ser Asp Leu Asn Leu Pro Ala Glu
        515                 520                 525
Met Val Arg Cys Val Glu Val Phe Lys Gln Phe Tyr Ser Thr Lys Thr
    530                 535                 540
Lys His Arg Lys Leu Thr Trp Val Tyr Ser Leu Gly Ser Cys Asn Ile
545                 550                 555                 560
Asn Gly Lys Phe Gly Pro Lys Thr Ile Glu Leu Val Val Gly Thr Tyr
                565                 570                 575
Gln Ala Ala Ala Leu Met Leu Phe Asn Thr Ser Asp Arg Leu Ser Tyr
            580                 585                 590
Ser Glu Ile Ala Thr Gln Leu Asn Leu Ala Asp Glu Asp Leu Val Arg
        595                 600                 605
Val Leu Gln Ser Leu Ser Cys Ala Lys Tyr Lys Ile Leu Leu Lys Glu
    610                 615                 620
Pro Asn Thr Lys Thr Val Ser Pro Thr Asp Cys Phe Ser Phe Asn Ser
625                 630                 635                 640
Ser Phe Thr Asp Arg Met Arg Ile Arg Ile Pro Leu Pro Pro Met
                645                 650                 655
Asp Glu Arg Lys Lys Val Val Glu Asp Val Asp Lys Ser Arg Arg Tyr
            660                 665                 670
Ala Ile Asp Ala Ser Ile Val Arg Ile Met Lys Ser Arg Lys Val Leu
        675                 680                 685
Gly Tyr Gln Gln Leu Ile Thr Glu Cys Val Glu Gln Leu Ser Arg Met
    690                 695                 700
Phe Lys Pro Asp Phe Lys Ala Ile Lys Lys Arg Ile Glu Asp Leu Ile
705                 710                 715                 720
Thr Arg Asp Tyr Ile Glu Arg Asp Lys Glu Asn Pro Gln Leu Phe Arg
                725                 730                 735
Tyr Leu Ala
```

-continued

```
<210> SEQ ID NO 35
<211> LENGTH: 2235
<212> TYPE: DNA
<213> ORGANISM: Cucumis sativus
<220> FEATURE:
<221> NAME/KEY: source
<222> LOCATION: 1..2235
<223> OTHER INFORMATION: /organism="Cucumis sativus"
      /mol_type="unassigned DNA"

<400> SEQUENCE: 35
atgacaatgg gcgagcggaa gactattgac ttggagcagg gatgggagtt tatgcagaag      60
ggtatcacaa agttgaagaa cattctcgag ggcttgcctg agcctcagtt cagctccgag     120
gactacatga tgctttacac taccatgtat aacatgtgca cccaaaagcc gccgcatgat     180
tactcccagc agctgtatga taaatatcgt gaatcttttg aagagtacat cacttctatg     240
gtcttaccat ccttgaggga gaagcacgat gagttcatgt tgagagaact agtaaaaagg     300
tggacaaacc ataaagtcat ggtgaggtgg ctttctcgct tcttccacta tcttgatcgg     360
tacttcatcg ctcgaaggtc acttccacct ctaaatgaag ttggcctcac atgcttccgc     420
gaattggtgt acaaagagct aaatagtaaa gtgagggatg cagtaatttc attgattgat     480
caagaacgtg aaggagaaca gattgacaga gctctactga agaatgtact agatatattt     540
gtggaaattg gtatggggca aatggattac tatgaaaatg actttgaagc tgccatgctt     600
aaagatactg ctgcttatta ctctaggaag gcttccaatt ggatcctaga agattcttgt     660
cccgattata tgcttaaagc agaggagtgc ttgaaacgag aaaaggatag gtttcccac     720 tatttgcact ctagtagcga gccaaagttg ttggagaaag ttcaacatga actattatct     780
gtttatgcta ctcaactgct ggaaaaagag cattcaggat gccatgcatt gcttagagat     840
gacaaggtgg aagatttgtc aaggatgttc cgtctattct ccaaaatacc gaagggactg     900
gatccagttt ccaacatatt taagcagcat gtaactgctg aaggaacagc actggtcaaa     960
caggcagaag atgctgcaag taacaagaag gctgagaaaa aggacatagt tggtctgcag    1020
gaacaggttt ttgtaagaaa agtgattgag cttcacgaca agtacttggc ttatgtgaat    1080
gattgtttcc aaaaccacac acttttccat aaggctctca aggaagcttt tgaagtattt    1140
tgcaataagg gtgttgctgg aagttctagt gcagaattgc ttgctacctt tgtgataac    1200 atccttaaga aggtgggag tgagaagttg agtgatgaag caatcgagga gacacttgag    1260
aaggttgtga agttgttggc atacatttgc gacaaagatc tgtttgctga attctataga    1320
aaaaaacttg cccgaaggct tctctttgac aagagcgcga acgatgacca cgagagaagt    1380
atattgacca aattgaagca acaatgtggt ggtcagttca cttctaagat ggagggaatg    1440
gttactgatt tgactttggc aagggagaac caaactagtt ttgaggagta tctgagcaat    1500
aatccacaag cgagtcctgg catcgacctg actgttactg ttttaactac tggattttgg    1560
ccaagctaca agtcttttga cctcaacctg ccggcagaga tggtaaagtg tgttgaagtt    1620
ttcagagagt tttatcaaac aaaaaccaag catcgaaaac ttacatggat ttactcattg    1680
ggtacttgta acatcagtgg aaaatttgaa ccgaaaacga tggagctgat tgtgacaact    1740
tatcaggctt ctgccctgtt gctattcaat tcttcggata gactaagtta tcggaaatc    1800 atgacacaat taaatttgag tgacgatgat gtagttagac tactccactc gttgtcatgt    1860
gccaagtata aaattcttaa taaggaacca aatacgaaaa ccatctctcc gaacgatcat    1920
tttgagttca atgcaaaatt ctccgacaaa atgaggagaa taaagatccc tcttccgcct    1980
gtggatgaga aaaagaaagt cattgaagat gttgacaagg atcgaaggta tgctattgac    2040
```

-continued

```
gcctcaatcg tgcgtatcat gaagagtcgg aaagttcttg gtcatcagca actagtgatg    2100
gagtgcgtcg agcaattggg ccgtatgttc aagcccgatt tcaaggcgat aaagaagaga    2160
attgaagacc tgatcactcg ggattatcta gagagagaca agacaacccc ccacttgttt    2220
aggtacttgg cttga                                                     2235
```

<210> SEQ ID NO 36
<211> LENGTH: 2235
<212> TYPE: DNA
<213> ORGANISM: Cucumis melo
<220> FEATURE:
<221> NAME/KEY: source
<222> LOCATION: 1..2235
<223> OTHER INFORMATION: /organism="Cucumis melo"
 /mol_type="unassigned DNA"

<400> SEQUENCE: 36

```
atgacaatgg gcgagcggaa gactattgac ttggaacagg gatgggagtt tatgcagaag      60
ggtatcacaa agttgaagaa cattcttgag ggcttgcctg agccccagtt cagctccgag     120
gactacatga tgctttacac taccatgtat aacatgtgca cccaaaagcc gccgcatgat     180
tactcccagc agctgtatga taaatatcgt gaatcttttg aagagtacat cacttctatg     240
gtcttaccat ccttgaggga gaagcatgac gagttcatgt tgagagaact agtcaaaagg     300
tggacaaacc ataaagtcat ggtgaggtgg ctttctcgct tcttccacta tcttgatcgg     360
tacttcatcg ctcgaaggtc acttccacct ctaaatgaag ttggcctcac atgcttccgc     420
gaattggtgt acaagagct aaacagtaaa gtgagggatg cagtaatctc attgattgat      480
caagaacgtg aaggagaaca gattgacaga gctctactga agaatgtatt agatatattt     540
gtggaaattg gtatggggca atggattac tatgaaaatg actttgaagc tgccatgctt      600
aaagatactg ctgcttatta ctctaggaag gcttccaatt ggatcctaga agattcttgt     660
cccgattata tgctaaaagc agaggagtgc ttgaagcgag aaaaggatag ggtttcccac     720
tatttgcact ctagtagcga gccaaagttg ttggagaaag ttcaacacga actgttatct     780
gtgtatgcta ctcaactgct ggaaaaagag cattcaggat gccatgcatt gcttagagat     840
gacaaggtgg aagatttgtc aaggatgttc cgtctcttct ccaaaatacc gaagggattg     900
gacccagttt ccaacatatt taagcagcat gtaactgctg aaggaacagc actggtcaaa     960
caggcagaag atgctgcaag taacaagaag gccgagaaaa aggacatagt tggtctgcag    1020
gaacaggttt ttgtaagaaa agtgattgag cttcacgaca agtacttggc ttatgtgaat    1080
gattgtttcc aaaaccacac acttttccat aaggctctca aggaagcttt tgaagtcttt    1140
tgcaataagg gtgttgctgg aagttctagt gcagaattgc ttgctacctt ctgcgataac    1200
atccttaaga aggtgggag tgagaagttg agtgatgaag caatcgaaga gacacttgag    1260
aaggttgtga agttgttggc atacatctgc gacaaagatc tgtttgctga attctataga    1320
aaaaaacttg cccgaaggct tctctttgat aagagcgcca acgatgacca cgagagaagt    1380
atattgacca aattgaagca acaatgtggt ggtcagttca cttctaagat ggagggaatg    1440
gttactgatt tgactttggc aagggagaac caaactagtt tcgaagagta tctgagcaat    1500
aatccacaag ctagtcctgg aatcgaccta actgttactg ttttgactac tggattttgg    1560
ccaagctaca agtcttttga cctcaacctg ccggcggaga tggtaaagtg tgttgaagtt    1620
ttcagagagt tttatcaaac aaaaaccaag catagaaaac ttacatggat ttactcattg    1680
ggtacttgta acatcagtgg aaaatttgaa ccgaagacga tggagctgat tgtgacaaca    1740
```

```
tatcaggctt ctgccctgtt gctattcaat tcttcggaca gactaagtta ctccgaaatc    1800
atgacacaat taaatttgag tgatgatgat gttgttagac tgctccactc attgtcgtgt    1860
gccaagtata aaattcttaa taaggagcca aatacgaaaa ccatctcacc gaacgatcat    1920
tttgagttca atgcaaaatt ctccgacaaa atgaggagaa taaagatccc tcttccgcct    1980
gtggatgaga aaagaaagt cattgaagat gttgacaagg atcgaaggta tgctattgac    2040
gcctcaatcg tgcgtatcat gaagagtcga aaagttcttg gtcatcagca actagtgatg    2100
gagtgcgtcg agcaattggg tcgtatgttc aagcccgatt tcaaggcgat aaagaagaga    2160
attgaagacc tgatcactcg ggactatcta gagagagaca agacaaccc ccacttgttt    2220 aggtacttgg cttga                                                     2235
```

<210> SEQ ID NO 37
<211> LENGTH: 2235
<212> TYPE: DNA
<213> ORGANISM: Cucurbita pepo
<220> FEATURE:
<221> NAME/KEY: source
<222> LOCATION: 1..2235
<223> OTHER INFORMATION: /organism="Cucurbita pepo"
    /mol_type="unassigned DNA"

<400> SEQUENCE: 37

```
atgacaatgg gtgagcggaa gactattgac ttggagcaag gatgggagtt tatgcagaag      60
ggaatcacaa aattgaagaa cattctggaa ggattgcctg agccacagtt cagctccgag     120
gactacatga tgctttacac tacaatgtat aacatgtgta cccagaagcc accgcatgat     180
tactcccagc agctgtatga taaataccgc gaatcgtttg aggagtacat cagttctatg     240
gttttaccat ccttgaggga gaagcatgac gaatttatgt tgagagaact ggtcaaaagg     300
tggaccaacc ataaagtcat ggtgaggtgg cttttctcgct tcttccacta tcttgatcga     360
tacttcattg ctcgaaggtc acttccacct ctcaatgaag ttggcctcac ttgcttccgt      420
gaattggtgt acaaagagct aaacagtaaa gtgagggatg cagtaatttc attgatcgat     480
caagaacgtg aaggagagca gattgacaga gctctgttga agaacgtgtt ggatatattt     540
gtggagattg ggatggggca aatggattat tatgaaaatg actttgaagc tgccatgctt     600
aaagatactg ctgcttacta ctctaggaag gcatcaaatt ggatcttaga agattcttgt     660
cctgattata tgctaaaagc agaggagtgc ttgagacgag aaaaggaccg agtttctcac     720
tatctgcact ctagtagcga gccaaagtta ttggagaaag ttcaacatga actattgtct     780
gtttatgcta ctcaactgct ggagaaagag cattcaggat gccatgcatt gcttagagat     840
gacaaggtgg aagatttgtc aaggatgttc cgtctcttct ccaaaatacc caagggattg     900
gacccagttt ccaacatatt taagcagcat gtcactgctg aaggaacagc attagtcaaa     960
caggcagaag acgctgcaag taacaagaag gccgagaaaa aggacatcgt tggtctgcaa    1020
gaacaggttt ttgttagaaa agtgattgag cttcacgaca gtacttggc atatgtgaat    1080 gattgtttcc aaaaccacac acttttttcac aaggctctca aggaagcttt tgaagtcttt    1140
tgcaataagg gtgttgctgg aagttctagt gcagaattac ttgctacctt ttgtgataac    1200
atccttaaga aggtgggag tgagaagttg agtgatgaag caattgagga aacactcgag    1260
aaggtcgtga aattgctggc gtatatctgc gacaaagatc tgtttgctga attctataga    1320
aaaaaactcg cccgaaggct tctccttgac aagagtgcga atgatgacca cgagagaagt    1380
atactgacga aattgaagca acaatgtggt ggtcagttta cctctaagat ggagggaatg    1440
```

```
gtcacggatt tgacactggc aagggagaac caaactagtt ttgaggaata tctgagcaat    1500
aatccacaag ctagtcctgg aatcgacttg accgttaccg ttttgaccac tggttttgg     1560 ccaagctaca agtctttga cctcaacctg ccggcggaga tggtaaagtg tgttgaagtt    1620
ttcagggaat tttatcaaac aaaaaccaag cacagaaaac ttacgtggat ttactcgttg    1680
ggtacctgta acatcagcgg aaaattcgaa ccgaaaacga tggagctgat cgtgacaacc    1740
tatcaggctt ctgccctgct gcttttcaat tcctcggata aactaagtta ctccgagatc    1800
atgactcaat taaacttgag tgacgatgat gttgttagac tgctccactc gttgtcgtgt    1860
gcgaagtata aaattcttaa caaggagcca aatacgaaaa ccatctctcc gaacgatcat    1920
tttgagttca acgcaaaatt ctccgacaaa atgaggagaa taaagatccc tcttccgcct    1980
gtggatgaga aaagaaagt aatagaagat gttgacaagg atcgaagata tgctatcgat    2040
gcctcgatcg tgcgtatcat gaagagtagg aaagttctgg gtcaccagca gttagtgatg    2100
gagtgcgtcg agcaactggg tcgtatgttc aagcctgatt tcaaggcgat aaagaagaga    2160
atcgaagatc tgatcactcg tgactattta gagagagaca agacaacccc ccacttgttt    2220
aggtacttgg cttga                                                    2235

<210> SEQ ID NO 38
<211> LENGTH: 2235
<212> TYPE: DNA
<213> ORGANISM: citrillus lanatus
<220> FEATURE:
<221> NAME/KEY: source
<222> LOCATION: 1..2235
<223> OTHER INFORMATION: /organism="citrillus lanatus"
      /mol_type="unassigned DNA"

<400> SEQUENCE: 38
atgacaatgg gcgagcggaa gactattgac ttggaacaag gatgggagtt tatgcagaag      60
ggaatcacaa agttgaagaa cattcttgag ggcttgcctg agcctcagtt cagctccgag     120
gactacatga tgctttatac caccatgtac aacatgtgca cacaaaagcc gccacatgat     180
tactcccagc agctatacga taaataccgt gaatcttttg aggagtatat cacttctatg     240
gtcttaccat ccttgaggga gaagcatgac gagttcatgt tgagagaact ggtcaaaagg     300
tggacgaacc ataaagtcat ggtgaggtgg ctttctcgct tcttccacta tcttgaccga     360
tacttcattg ctcgaagatc acttccacct ctcaacgaag ttggcctcac atgcttccgt     420
gaattggtgt acaagagct aaacagtaaa gtgagggatg cagtaatttc attgattgat     480
caagaacgtg aaggagagca gattgacaga gctctactga agaatgtatt agatatattt     540
gtggaaattg ggatgggca aatggattac tatgaaaatg actttgaagc tgccatgctt     600
aaagatactg ctgcttatta ctctaggaag gcttccaatt ggatcctaga agattcttgt     660
cccgattata tgctaaaagc agaggagtgc ttgaaacgag aaaaggatag agtttctcac     720
tatttgcact ctagtagcga gccaaagtta ttagagaaag ttcaacatga actgttatct     780
gtgtatgcta ctcaactgct ggaaaaagag cattcaggat gccatgcatt gcttagagat    840
gacaaggtgg aagatttgtc aaggatgttc cgcctcttct ccaaaatacc caagggattg    900
gacccagttt ccaacatatt taagcagcat gtcactgctg aaggaacagc attggtcaaa    960
caggcagaag atgctgcaag taacaagaag gccgagaaaa aggacatagt tggtctgcag   1020
gaacaggttt ttgtaagaaa agtgattgag cttcacgaca gtacttggc ttacgtgaat    1080 gattgtttcc aaaaccacac actttttcac aaggctctca aggaagcttt tgaagtcttt   1140
```

```
tgcaataagg gtgttgctgg aagttctagt gcagaattac ttgctacctt ttgtgataac    1200
atccttaaga aaggtgggag cgagaagttg agtgatgaag caattgagga gacacttgag    1260
aaggtcgtga agttgctggc atacatctgc gacaaagatc tgtttgctga attctataga    1320
aaaaaacttg cccgaaggct tctctttgac aagagtgcca acgatgacca tgagagaagt    1380
atattgacca aattgaagca acaatgtggt ggccagttca cctctaagat ggaggggatg    1440
gtcactgatt tgactttggc aagggagaac caaactagtt tcgaggagta tctgagcaat    1500
aatccacaag ctagtcctgg aatcgacttg actgtcactg ttttgactac tggcttttgg    1560
ccaagctaca agtcttttga cctcaacctg ccggcagaga tggtaaagtg tgttgaagtt    1620
ttcagagagt tctatcaaac aaaaacaaag catagaaaac ttacatggat ttactcattg    1680
ggtacctgta acatcagcgg aaaatttgaa ccgaaaacga tggagctgat tgtaacaact    1740
tatcaggctt ctgccctgct gctattcaat tcctcagata gattaagtta ttccgagatc    1800 atgcacacaat taaatttgag tgacgatgat gttgttagac tgctccactc attgtcatgt    1860
gccaagtata aaattcttaa taaggagccg aacacgaaaa ccatctctcc gaatgatcat    1920
tttgagttca atgcaaaatt ctccgacaaa atgaggagaa taaagatccc tcttccgcct    1980
gtggatgaga aaagaaagt cattgaagat gttgacaagg atcgaaggta tgctattgat    2040
gcctcaatcg tgcgtatcat gaagagtcgg aaagttctgg gtcatcagca gctagtgatg    2100
gagtgcgtcg agcaattggg tcgtatgttc aagcccgact tcaaagcgat aaagaagaga    2160
atcgaagatc tgatcactcg ggactattta gagagagaca agacaacccc ccacttgttt    2220
aggtacttgg cttga                                                    2235

<210> SEQ ID NO 39
<211> LENGTH: 2229
<212> TYPE: DNA
<213> ORGANISM: Solanum melongena
<220> FEATURE:
<221> NAME/KEY: source
<222> LOCATION: 1..2229
<223> OTHER INFORMATION: /organism="Solanum melongena"
      /mol_type="unassigned DNA"

<400> SEQUENCE: 39
atgaaccaac gcagcacaat cgatctggaa catggatggg atttcatgca aaagggcatc      60
acaaagctga agaacattct agaagggctg cctgagcctc agttcagctc agaggactat     120
atgatgctgt atacgacaat gtacaacatg tgtactcaga agccccccaca tgattattct    180 caacagctgt atgacaaata tcgtgaagct tttgaagaat atatcacaac gacggtatta    240
ccttctttga gagaaaaaca tgacgagttc atgttgcgag agttggtaaa aggtggtca    300 aaccataagg tcatggttag atggttatcg cgattcttcc attatcttga ccgttatttc    360
attgctcgga gatcactgcc agggcttaat gaagttggac taacttgctt ccgcgatctg    420
gtctaccaag agttgaatgg aaaagtcagg gatgctgtta tatctctgat tgatcaagag    480
cgtgagggag agcaaattga cagagctcta ctgaagaatg tgctagatat atttgttgaa    540
attggaatgg ggtcaatgga ttattatgag aatgattttg aagctgcaat gctcaaggac    600
actgcggctt attattctcg caaagcttct aactggatcc tcgaagattc atgtccagat    660
tatatgctga agctgaggga gtgcttgaaa cgggagaagg ataggtctc ccattatctc    720 cattctagca gtgagacaaa gttgcttgag aaagtgcaac atgagttgtt atctgtgtat    780
gccaatcaac ttcttgagaa ggagcactct ggatgccatg cattacttag agatgataag    840
```

```
gtcgatgatt tatcaaggat gtatagactc ttttctaaga ttcctcgagg cttagagcct    900
gtggctaata tatttaagca gcatgttact gctgaaggta cagctttggt gaaacaggct    960
gaagatgctg ctagcaacaa aaaggcagag aagagagatg tggttggttt gcaggaacag   1020
gttttgttc ggaaagtgat tgagcttcat gataaatatt tggcgtatgt gaataactgt   1080
ttccaaaacc acacactttt tcacaaggca cttaagaag ctttcgaact tttctgcaac   1140
aagggtgttg ctggtagctc aaatgctgaa cttcttgcca cattctgcga caacattctc   1200
aaaaaaggcg ggagtgaaaa attgagtgat gaagccattg aagagacgct ggagaaggtg   1260
gtaaagctgc tggcttatat tagtgataag gacttgtttg cagaattcta taggaaaaag   1320
ctcgcccggc ggttgttatt tgataagagt gccaatgatg aacatgagag aagtatccta   1380
acaaagttga gcagcagtg tggaggtcag ttcacatcaa agatggaggg aatggtcaca   1440
gatttgacat tggcaaggga aaatcaagcc agctttgagg agtatttgag caataatcca   1500
acagcaaatc caggaattga cttgacggtg actgtcttga ctactggctt ctggcctagc   1560
tacaagtctt ttgatctcaa cctcccagca gaaatggtta ggtgtgttga agtattcaag   1620
gagttttatc aaacaaaaac gaagcacagg aaacttacat ggatatactc tttgggaact   1680
tgcaacataa atggaaaatt tgaggcaaag actattgagc tcgttgtcac tacttatcag   1740
gcttctgctc tgcttctctt taatgcatca gatagattga gttatcagga aatcatgacg   1800
caattaaaacc tatcagatga tgatgttgtt cggcttcttc attccctttc atgtgcgaaa   1860
tacaagattc tcaacaagga gccaagcacc aaaacaattt ctccgactga tgtctttgag   1920
ttcaactcaa agttcactga caaatgaggg aggatcaaga tacctctccc accagttgat   1980
gaaaagaaaa aggtaattga agacgttgac aaggataggc ggtatgctat agatgcctca   2040
attgtgcgta ttatgaagag tcgtaaagta ttgggctacc agcaactggt catggagtgc   2100
gttgagcagt tgggacgcat gttcaagcct gatgtcaaag ctatcaagaa gagaattgaa   2160
gatctgataa ctagagatta cctagagagg gacaaagata acccaaactt gttcaagtac   2220
ttggcatga                                                           2229
```

<210> SEQ ID NO 40
<211> LENGTH: 2229
<212> TYPE: DNA
<213> ORGANISM: Solanum lycopersicum
<220> FEATURE:
<221> NAME/KEY: source
<222> LOCATION: 1..2229
<223> OTHER INFORMATION: /organism="Solanum lycopersicum"
    /mol_type="unassigned DNA"

<400> SEQUENCE: 40

```
atgaaccaac gaagcacaat cgatctggaa catggatggg acttcatgca aagggggcatt    60
acaaagctga gaacattct agaagggctg cctgagcctc aattcagctc agaggactat   120
atgatgctat atacgacaat gtacaacatg tgtactcaaa agcccccaca tgattattct   180
caacagctgt atgacaaata tcgtgaagct tttgaagaat atatcacaac aacggtattg   240
ccttctttga gagaaaaaca tgacgagttt atgttgcgag agttggtaaa aggtggtca   300
aatcataaag tcatggtcag atggttgtca agattcttcc attaccttga ccggtatttc   360
attgcccgga gatctctgcc ggggcttaat gaagttggac taacttgctt ccgcgatcag   420
gtctaccaag agttgaatgg aaaagtcagg gatgctgtta tatctctgat tgatcaagag   480
cgtgagggag agcaaattga cagagctcta cttaagaatg tgcttgatat atttgtcgaa   540
```

```
attggaatgg ggttaatgga ttattatgag aatgattttg aagctgcaat gctcaaggac      600
acagcggctt attattctcg caaagcttct aattggatcc tcgaagattc atgtccggat      660
tatatgctga agccgagga gtgcttgaaa cgggagaagg atagggtctc tcattatctc       720
cattcaagca gcgagacgaa gttgcttgag aaagtgcaac atgagttgtt gtctgtgtat      780
gccactcaac ttcttgagaa ggagcactct ggatgccatg cgttactgag agatgataag      840
gttgaagatt tatcaaggat gtataggctc ttttctaaga tttctcgagg cttagaccct      900
gtggccaata tttttaagca gcatgttact gctgaaggta cagctttggt aaaacaggct      960
gaagatgctg ctagcaataa aaaggcagag aagagagatg tggttggttt gcaggaacag     1020
gtttttgttc ggaaagtgat tgaacttcat gataaatatt tggcttatgt gaataactgt     1080
ttccaaaacc acacactttt tcacaaggcg cttaaagaag cttttgagct tttctgcaac     1140
aagggtgttg ctggtagctc aagcgctgaa cttcttgcca ccttctgtga caacattctc     1200
aaaaaaggcg ggagtgagaa attgagtgat gaagctattg aagaaacgtt ggaaaaggtg     1260
gtaaagctac tagcttatat tagtgataag gacttgtttg cagaattcta taggaaaaag     1320
ctagcccggc ggttgttatt tgataagagt gccaatgatg aacatgaaag aagtatcccta    1380 acaaagttga agcagcagtg tggggggcag ttcacatcaa agatggaggg aatggtcaca     1440
gatttgacat tggcaaggga aaatcaagcc agcttcgagg agtatttgag caataatcca     1500
atagcaaatc caggaattga cttgacggtg actgtcttga ctactggctt ctggcctagc     1560
tacaagtctt ttgatctcaa cctcccagca gaaatggtta ggtgcgttga agtatttaag     1620
gagttctatc aaacaaaaac aaagcacagg aaacttacgt ggatatactc tttgggaact     1680
tgcaacataa atgaaaatt tgagccaaaa actattgagc tcgttgtcac tacttatcag     1740
gcttctgctc tgctgctctt taatgcatca gatagattga gttatcagga aatcatgacg     1800
caattaaacc tatcagatga tgatgttgtt cggcttcttc attcccttc atgtgcgaag      1860 tacaagatac tcaacaagga gccaagcacc aaaacaattt ctccgactga tgtctttgag     1920
ttcaactcaa agttcactga caaaatgagg aggatcaaga tacctctccc tcctgttgat     1980
gagaagaaaa aggtaattga agacgttgac aaggataggc ggtatgctat agatgcttca    2040
attgtgcgta ttatgaagag ccgtaaagta ttgggctacc agcaactagt catggagtgc    2100
gttgagcagt tggggcgcat gttcaagcct gatgtcaaag ctatcaagaa agaaatcgaa    2160
gatttgataa ctagagatta cctagagagg gacaaagata tccaaacct gttcaagtac     2220 ttggcatga                                                             2229
```

<210> SEQ ID NO 41  
<211> LENGTH: 2229  
<212> TYPE: DNA  
<213> ORGANISM: Capsicum annuum  
<220> FEATURE:  
<221> NAME/KEY: source  
<222> LOCATION: 1..2229  
<223> OTHER INFORMATION: /organism="Capsicum annuum"  
      /mol_type="unassigned DNA"

<400> SEQUENCE: 41

```
atgaaccagc gttccacaat caatctagaa catggatggg acttcatgca aggggcatt       60 acaaagctga agaacattct agaagggctg cccgagcctc agttcagctc agaggactat     120
atgatgctgt atacgacaat gtacaacatg tgtactcaga agcccccaca tgattattct     180
caacagctgt atgacaaata tcgtgaagct tttgaagaat atatcacaac aacggtattg     240
```

```
ccttctttga gagaaaaaca tgacgagttc atgttgcgag agctggtaaa aaggtggtca    300
aaccataagg tcatggtcag atggttatcg cgattcttcc attatcttga tcgctatttc    360
attgcccgga gatctctacc ggggcttaat gaagttggac taacttgctt ccgagatctg    420
gtctaccaag agttgaatgg aaaagtcagg gatgctgtta tatctctgat tgatcaagag    480
cgtgagggag agcaaattga cagagctcta ctgaagaatg tgctagatat atttgttgaa    540
attggaatgg ggtcgatgga ttattatgag aatgattttg aagctgcaat gctcaaggac    600
accgcagctt attattctcg caaagcttct aactggatac ttgaagattc atgtccagat    660
tatatgctga aagccgagga gtgcttgaaa cgggagaaag atagggtctc tcactatctt    720
catttaagca gtgagacaaa gttgcttgag aaagtgcaac atgagttgtt gtctgtgtat    780
gccactcaac ttcttgagaa ggagcactct gggtgccatg cgttactaag agatgataag    840
gttgaagatt tatcaaggat gtataggctc ttttctaaga ttcctcgagg cttagaccct    900
gtggctaata tatttaagca gcatgttact gctgaaggta cagctttggt caaacaggct    960
gaagatgctg ctagcaacaa aaaggcagag aaaagagatg tggttggttt gcaggaacag    1020 attttttgttc ggaaagtgat tgagcttcat gataagtata tggcatatgt gaataactgt    1080
ttccaaaacc acacactttt tcacaaggcg cttaagaag ctttcgaact tttctgcaac    1140
aagggtgttg ctggtagctc aagtgctgaa cttcttgcca cattctgcga caatattctc    1200
aagaaaggcg ggagtgagaa attgagtgat gaagccattg aagagacgct ggagaaggtt    1260
gtaaagctgc tagcatatat tagtgacaag gacttgtttg cagaattcta taggaaaaag    1320
ctagcccggc ggttgttatt tgataagagt gccaatgatg aacacgagag aagtatcctt    1380
acaaagttga agcagcagtg tgggggccag ttcacatcaa agatggaggg aatggtgaca    1440
gatttgacat tggcaaggga aaatcaagcc agctttgagg agtatttgag caacaatcca    1500
gcagcaaatc caggaattga cttgacggtg actgtcttga ctactggctt ctggcctagc    1560
tacaagtctt ttgatctcaa cctcccagca gaaatggtta ggtgcgttga agtattcaag    1620 gagtttttatc aaacaaaaac gaagcacagg aaacttacgt ggatatactc tttgggaact    1680
tgcaatataa atgaaaaatt tgagccaaag actattgagc tcgttgtcac tacttatcag    1740
gcttctgctc tgctgctctt taatgcatcg gatagattga gttatcagga aatcatgacg    1800
caactaaacc tatcagatga tgatgttgtt cggcttcttc attcccttcc atgtgcgaag    1860
tacaagattc tcaacaagga gccaagcacc aaaacaattt ctccgactga tgtctttgag    1920 ttcaattta gttcactga caaaatgagg aggatcaaga tacctctccc tcctgttgat    1980
gagaagaaaa aggtaattga agatgttgac aaagataggc ggtacgctat agatgcttca    2040
attgtgcgta ttatgaagag tcgtaaagta ttgggctacc agcaactggt catggagtgt    2100
gttgagcagt tgggacgtat gttcaagcct gatgtcaaag ctatcaagaa gagaattgaa    2160
gatttgataa ctagagatta cctagagagg gacaaagata atccgaactt gttcaagtac    2220
ttggcatga                                                            2229
```

<210> SEQ ID NO 42
<211> LENGTH: 2217
<212> TYPE: DNA
<213> ORGANISM: Brassica oleracea
<220> FEATURE:
<221> NAME/KEY: source
<222> LOCATION: 1..2217
<223> OTHER INFORMATION: /organism="Brassica oleracea"
    /mol_type="unassigned DNA"

<400> SEQUENCE: 42

```
atggagcgca agacgattga cttggaccaa ggatgggact atatgcagac tggtatcact        60
aagctgaaac ggattcttga ggggctgcct gagccgcagt ttgactctga gcaatacatg       120
atgctctata cgactatgta caacatgtgc actcagaaac ctcctcatga ttactcacag       180
cagctttatg acaagtatcg tgaagcattt gaggagtata ttcactcaac tgttttgcct       240
gctctaaggg agaagcatga tgagtacatg ctgagggagc tggttaagag atggtctaac       300
cataaagtta tggttcgatg ctatcccgc ttcttctact atcttgaccg ttacttcatt        360
gctcggaggt cacttccacc cctgaatgaa gttggcctga cttgcttccg tgacctggtt       420
tataacgagt tgcattccaa ggtcaaagat gctgtaatag cacttgttga taagaacgg        480
gagggtgagc agattgacag ggctctattg aaaaacgtat tagacattta tgtagagatt       540
ggaatgggac agatggaaag atacgaggag gattttgaaa gcttcatgct tttagattca       600
gcatcttact attctcgcaa ggcgtcaagc tggatccaag aagattcttg ccctgattac       660
atgctgaagt ctgaagaatg tcttaagaag gagagggaga gagtggctca ctaccttcac       720
tcaagcagcg agccaaagct ggttgagaaa gtacaacatg agctgttggt agtgtatgca       780
aatcagcttc tagaaaaaga gcattcaggg tgccgtgcat tgctgagaga tgacaaggtt       840
gatgacctct ccaggatgta caggctttat cataaaattg tgaaaggttt ggaacctgtt       900
gcaaacatat ttaagcagca tgtcacagca gagggtaacg cacttgtcca acaggccgaa       960
gacacggcca ctaatcatgc tgcaaatact gctagcgtgc aggaacaggt tcttatcaga      1020
aaagtgattg aactacatga taaatacatg gtctatgttg ttgagtgttt ccagaaccac      1080
accctcttcc acaaggcatt gaagaggca tttgagatat tctgtaacaa aacagtcgct       1140
ggaagttcta gtgctgaatt gcttgcaaca ttttgcgaca atattctcaa gaagggggga      1200
agtgaaaagc tgagcgatga agctattgaa gataccttg agaaggtggt caaattgctt       1260
gcttatataa gtgacaagga tcttttcgcc gagttctaca ggaagaagct ggcccgtagg      1320
ctcttatttg atcgcagtgc taatgatgat catgagagaa gtatcctgac aaagctcaag      1380
caacaatgtg gtgggcagtt tacttcgaag atggagggca tggtgactga tttgacattg      1440
gcaagggaaa accaaaacag cttcgaggag tatcttggca ataaccccgc tgcaaaccca      1500
gggattgatt tgaccgtaac tgttcttacc actggttttt ggccaagtta caatcatttt      1560
gacataaatc tacccgctga aatggtcaag tgtgttgaag ttttcaaagg gtttatgaa       1620
acaaagacaa aacataggaa acttacctgg atctactcac taggaacttg ccacctcaat      1680
gggaagtttg atgtcaagcc cattgagtta gttgtgtcta cataccaggc tgctgtgctt      1740
ctgctgttca acacaacaga caattgagc tacactgata tcctaactca gctgaacctg       1800
agccacgaag atctagtgag gttgcttcat tccttgtcat gtgctagata caagattctt      1860
ctcaaggagc caagcacaaa gactgtttcc cagtctgatt cttttgaatt caactccaaa      1920
ttcaccgaca gaatgcggag aataaagatc cctctcccac ctgttgatga gaggaagaaa      1980
gttgtggaag acgtggacaa agacagacgc tatgcgattg atgctgccat tgtgaggatc      2040
atgaagagca ggaaagtatt gggacatcaa caacttgttt ctgagtgcgt tgagcaactt      2100
agccgaatgt tcaagcctga tatcaaggca atcaagaagc gcatggagga tttgataacg      2160
agagattatc tggagaggga caaggagaac gctaacatgt ttaggtactt ggcttag         2217
```

<210> SEQ ID NO 43

<211> LENGTH: 2232
<212> TYPE: DNA
<213> ORGANISM: Daucus carota
<220> FEATURE:
<221> NAME/KEY: source
<222> LOCATION: 1..2232
<223> OTHER INFORMATION: /organism="Daucus carota"
    /mol_type="unassigned DNA"

<400> SEQUENCE: 43

| | | | | | |
|---|---|---|---|---|---|
| atgatgattg | agcggaaaac | tatagacctg | gagcagggat | gggactttat | gcaaaaggga | 60 |
| atcacaaagc | taaagaatat | tttagaaggc | tttccggagc | cgcaattcag | ctcggaggat | 120 |
| tatatgatgc | tttatacaac | tatgtataac | atgtgtacac | agaaacctcc | acatgattac | 180 |
| tctcagcagc | tgtatgaaaa | gtatcgtgaa | gctattgagg | agtacattac | ttctacagta | 240 |
| ttgccttcat | tgagagagaa | gcatgatgaa | ttcatgctta | gagaacttgt | gaagagatgg | 300 |
| tctaatcata | aggtcatggt | caggtggctt | tctcgattct | ttcactatct | tgatcgctat | 360 |
| tttattgctc | ggaggtcact | tccaccactt | catgaagttg | gactcacttg | ctttcgggac | 420 |
| ctggtttacc | aggagataaa | tgggaaagta | agggatgctg | taatatcatt | gattaatcaa | 480 |
| gagcgcgagg | gagagcaaat | tgaccgagct | tgttgaaga | atgttctaga | tatatttgtt | 540 |
| gaagttggaa | tgagtcaaat | ggattattat | gagaatgact | ttgaagcaga | catgctcaaa | 600 |
| gatacagcag | catactattc | tcgaaaggct | tccaactgga | tcttagaaga | ttcttgtcca | 660 |
| gattatatgc | tcaaagcgga | agagtgtttg | agacgggaaa | aggacagggt | ctctaactac | 720 |
| cttcattcta | gtagtgaacc | caagttgctt | gagaaagttc | aacatgagtt | actatcacac | 780 |
| tatgcaactc | agctgcttga | gaaagaacac | tctgggtgtc | atgcattgct | tagggatgac | 840 |
| aaggtggcag | atttatcaag | gatgtatagg | ctcttctcta | aaatacctcg | aggcctagat | 900 |
| cccgtgtcta | atattttcaa | gcagcatgtt | actgctgaag | gtacagcttt | ggtcaaacaa | 960 |
| gcagaagatg | cagctagcaa | caagaaggca | gagaagagag | atgtagtagg | tttacaagaa | 1020 |
| caggttttg | tgaggaaaat | aattgaattg | catgacaaat | accttacata | cgtaaatgac | 1080 |
| tgttttacaa | accacactct | cttccataag | gcgcttaagg | aggcttttga | aatcttctgc | 1140 |
| aataagggtg | tctctggaag | ctctagtgca | gaattacttg | ccacattctg | tgataatatt | 1200 |
| ctcaagaaag | gtggaagcga | gaagttaagt | gatgaagcca | ttgaggaaac | acttgagaag | 1260 |
| gttgtaaggt | tgcttgctta | tataagtgac | aaagactat | ttgctgaatt | ttataggaaa | 1320 |
| aagcttgcac | ggcgtctctt | attcgacaag | agtgccaatg | atgagcatga | gagaagtata | 1380 |
| ttgactaagc | tgaagcaaca | atgtgggggt | caatttacat | caaagatgga | aggaatggtc | 1440 |
| actgacttga | cgttggcaaa | ggaaaatcag | tccaacttcg | aggagtacct | caataataat | 1500 |
| tcaaacgtaa | atcctggaat | tgacttgaca | gttactgttc | taaccactgg | gttttggcca | 1560 |
| agttacaaat | ctttcgatct | caacctccca | gcagagatgg | tcaaatgtgt | tgaagttttt | 1620 |
| agagaattct | accaaacaaa | aacaaagcac | agaaaactga | catggatata | ctctttgggt | 1680 |
| acttgtaaca | tcattggaaa | atttgatcca | aaaaccatgg | agcttattgt | gacaacatac | 1740 |
| caggcctctg | ctctgctgct | atttaactct | tctgatagac | ttagttataa | tgaaataatg | 1800 |
| actcagttga | acttgtcgga | tgatgatgtt | gtcagactac | ttcattctct | ttcgtgtgca | 1860 |
| aagtacaaga | ttctatctaa | agagccgaac | accaaaacta | tatctccaac | tgattgcttt | 1920 |
| cagttcaatt | ccaaatttac | tgataaaatg | aggaggatta | agattccact | tccccagtg | 1980 |
| gatgagaaga | aaaaggtaat | tgaagatgtt | gataaagaca | ggcgatatgc | tatagatgct | 2040 |

-continued

```
tcaattgtcc gtatcatgaa gagccgcaaa gttttgggtt atcagcagct agtaatggag    2100
tgcgttgaac aattgggtcg catgtttaag cctgatgtca aagcaatcaa gaagagaatc    2160
gaagatttaa taactcggga ttatctggaa agagacaagg acaatgccaa cttgttcagg    2220
tatctggcat ga                                                        2232
```

<210> SEQ ID NO 44
<211> LENGTH: 2229
<212> TYPE: DNA
<213> ORGANISM: Apium graveolens
<220> FEATURE:
<221> NAME/KEY: source
<222> LOCATION: 1..2229
<223> OTHER INFORMATION: /organism="Apium graveolens"
    /mol_type="unassigned DNA"

<400> SEQUENCE: 44

```
atgaacgagc ggaagactat cgatttggat aatggatggg aatttatgca gaaagggatc     60
actaagttga gaagattct cgaaggtcaa cctgagcctc agtttagctc cgaggactat    120
atgatgcttt acacaactat gtataatatg tgtacgcaga agcctccaca tgattattct    180
caacagctgt atgacaagta ccgtgaggcc tttgaggagt acataacttc aactgtcctg    240
ccttctttac gagagaagca tgatgagttt atgttgagag agctcgtgaa tagatggaca    300
aaccataaag tcatggtcag gtggctttct cgattctttc actatcttga tcggtacttc    360
attgcgagga ggtcacttcc tgcacttcat gaagttggac tcacgtgctt ccgggatctg    420
gtctatcagg agctgaaagt taaagtgagg gatgctgtaa tatctctgat cgatcaagag    480
cgtgaggggg aacagattga ccgagcttta ttaaagaacg tgttagatat atttgttgaa    540
atcggaatga gtcaaatgga tcaatatgag aatgactttg aagaagccat gctcactgat    600
actgctgctt actattctcg aaaagcttca aactggatcc ttgaagattc ttgtcctgat    660
tatatgttaa aggcagaaga atgtttgcga cgagagaagg acagggtttc ccactaccta    720
cattttagta gcgagccaaa gttgcttgag aaagtgcaac atgagctgct atctgtgtat    780
gcaacccaat tactcgagaa ggaacattct ggttgtcatg cattgcttag ggatgacaag    840
gtggatgatt tgtctaggat gtacagactc ttctcgaaaa tacctaaagg cctggatcca    900
gtttcttata tttttaagca gcatgttaca aatgaaggga tggcattggt taaacaagca    960
gaagatgcag caagcaacaa gaaggcagaa agagagacac tggttagttt acaggagcag   1020 gttttttgtta gaaaaattat tgaattacat gacaaatacc tcgcctatgt gaatgactgc   1080
tttacaaacc atactctttt ccataaggct ctcaaggagg cttttgaaat cttttgcaac   1140
aagggtgttg ctggaagctc taatgctgaa ctacttgcta cttctgtga taacatcctc   1200 aaaaagggtg ggagtgagaa attaagtgat gaggctattg aagaaacact tgagaaggta   1260
gtaaaattgt tagcttacat tagcgataaa gacttgttcg ctgaattta cagaaaaaag   1320 cttgcacgga gacttctctt tgataagagt gcaaatgacg agcatgaacg aagtattttg   1380
actaaactaa agcaacagtg cggtggtcag ttcacatcga aaatggaggg gatggtcaca   1440
gatttgactt tggctaaaga aaatcaatcc agctttgagg agtatctggg aaataatgcc   1500
aatgtgaatc ctggcattga cttgacggtt actgttctga ccactggctt ctggcctagt   1560
tataaatcct ttgatctcaa ccttcctgct gagatggtca agtgcgttga agtatttaga   1620
gaattttatc aaacaaaaac gaagcataga agctcacat ggatatattc tctgggtact   1680
tgtaatatca atggaaaatt tgaacccaaa accattgagc tgattgtgac aacctaccag   1740
```

```
gcctctgctc tcctgttatt taatacttct gataggttga gttatcaaga aatcatgact      1800
cagttaaatt tgtcggatga tgatgttgtt cgcctgcttc attccctttc atgtgccaag      1860
tataaaattc ttactaaaga gccgaacaac aaaacaattt cccctacgga ttactttgag      1920
ttcaactcca agttcactga caaaatgagg agaattaaga ttccactacc tccagttgat      1980
gagaagaaaa aggtaattga agatgttgac aaggaccggc gatatgccat tgatgcatct      2040
attgtccgca ttatgaagag ccgtaaagtt tgggctacc aacaattggt tatgaatgt       2100 gttgagcaat tgggacgcat gtttaagcct gatgtcaaag caattaagaa gagaatcgaa      2160
gatttaataa cgcgtgatta tctggaaaga gacaaggata atgccaacct tttcagatat      2220
ttggcatga                                                              2229
```

<210> SEQ ID NO 45
<211> LENGTH: 2229
<212> TYPE: DNA
<213> ORGANISM: Cichorium intybus
<220> FEATURE:
<221> NAME/KEY: source
<222> LOCATION: 1..2229
<223> OTHER INFORMATION: /organism="Cichorium intybus"
    /mol_type="unassigned DNA"

<400> SEQUENCE: 45

```
atgaatgaaa gaaaaacaat agacttagaa caaggatggg acttcatgca gaaaggcata       60
acaaagttga gaacattct agaaggtctt cccgagccac aattcagctc ggaagattac       120
atgatgctct acacaaccat gtacaatatg tgcacacaaa accgccaca tgattactct       180 caacaattgt atgacaaata ccgcgagtct tttgaagagt acattacttc aacggtgtta       240
ccttctttaa gagagaagca tgatgagttt atgcttagag agcttgttag aagatggtca       300
aatcataaag tgatggttag gtggctttct agattcttcc attatcttga tcgatacttc       360
attgcccgaa gatctcttcc accattaaat gaagttggac ttgcgtgttt tcgtgatctg       420
gtataccaag aggtgaatgg gaaagtgaga gatgctgtaa tatctttgat tgatcaagag       480
cgtgaaggcg agcaaattga ccgagcatta ctcaagaatg ttctagatat atttgttgaa       540
ataggaatgg gacaaatgga atattatgag aatgattttg aagcatccat gcttaatgat       600
acagcagcat attattcacg caaagcttcc aattggattc tagaagattc ttgtccagat       660
tatatgctca agctgagga gtgcttaaaa agagaaaagg acagagtttc tcattatctt       720
cattccagca gtgaaccaaa gcttcttgag aaagttcaaa cagagttatt atctgtttat       780
gcaactcaat tgcttgaaaa ggagcactcc ggttgtcatg cattacttag ggatgacaag      840
gttgatgatt tatcaagaat gtacagactc ttttcaaaga tacaaaaagg gctggatcct       900
gtttctagta tgtttaagca gcatgtcact gctgaaggca aacattggt taaacaggca       960 gaagatgcag caagtactaa gaaggctgaa agagagacg tggttggctt acaagaacag      1020 gttttttgtta gaaaagttat cgagcttcat gacaagtacc ttgcatatgt aaatgactgt      1080
tttatgaatc ataccctgtt tcacaaggct cttaaagagg catttgaaat attctgcaac      1140
aagggcgttg ctggaagttc aagtgcagaa ttacttgcta catttttgtga taatattctt      1200 aaaaaaggtg gaagtgaaaa attgagtgat gaagccattg aggacacact tgagaaggtg      1260
gtaaagttgc ttgcttacat cagcgataaa gatctatttg cagagttta taggaaaaaa       1320 ctggctagac ggcttttatt tgacaaaagt gcaaatgatg agcacgaaag aagtattttg      1380
acaaaattga acaacaatg tggcggtcaa tttacatcaa aaatggaagg aatggttaca      1440
```

```
gatttgacat tggcaaaaga aaatcaatca cattttgagg agtatttgaa taataatccc    1500
aatgttagcc ctggcattga cttgaccgtg actgtgttga ccactggttt ttggcctagt    1560
tacaaatctt ttgacctaaa tctccctgca gaaatggtca aatgcgttga agttttcaga    1620
gaattttatc aaacaaaaac aaaacacaga aaactcacat ggatatattc attgggcacc    1680
tgcaatataa acggaaaatt cgaaccaaaa accatggagc taatcgttac aacttaccag    1740
gcatctgctt tattactgtt caactcatca gatcgattga gttatcaaga aatcatgact    1800
caattaaact tatcagatga tgatgttgtt agactactcc attcattatc atgtgcaaaa    1860
tataaaattt tattaaaaga accaaataca aaaacaatct ctccaactga tttctttgaa    1920
ttcaactcaa agtttacaga taaaatgaga aggatcaaga ttcctctacc tcctgttgat    1980
gaaaagaaaa aagtaattga agatgttgac aaagaccgac gttatgcaat tgatgcttca    2040
attgtacgga taatgaaaag cagaaaagtt cttggatacc aacaattggt catggaatgt    2100
gttgaacaat taggccgtat gtttaagcct gatgtaaaag caatcaagaa acgtattgaa    2160
gatctcataa ctcgtgatta tcttgaaaga gacaagaaaa atccaaattt gtttcggtac    2220
ttggcatga                                                           2229
```

<210> SEQ ID NO 46
<211> LENGTH: 2229
<212> TYPE: DNA
<213> ORGANISM: Cichorium endivia
<220> FEATURE:
<221> NAME/KEY: source
<222> LOCATION: 1..2229
<223> OTHER INFORMATION: /organism="Cichorium endivia"
    /mol_type="unassigned DNA"

<400> SEQUENCE: 46

```
atgaatgaaa gaaaaacaat agacttagaa caaggatggg acttcatgca aaaaggcata     60
acaaagttga gaacattct agaaggtctt cccgagccac aattcagctc agaggattac    120
atgatgctct acacaaccat gtacaatatg tgcacacaaa aaccgccaca tgattactct    180
caacaattat atgacaaata ccgcgagtct tttgaagagt acataacttc aacggtgtta    240
ccttctttaa gagagaagca tgatgagttt atgcttagag agcttgttag aaggtggtca    300
aatcataaag tgatggttag gtggcttcct agattcttcc attatcttga tcgatacttt    360
attgcaagaa gatctcttcc accattaaat gaagttggac ttgcgtgttt cgtgatctg     420 gtataccaag aggtgaatgg aaaagtgaga gatgctgtaa tatctttgat tgatcaagag    480
cgtgaaggcg agcaaattga ccgagcatta ctgaagaatg ttctagatat atttgttgaa    540
ataggaatgg gacaaatgga atattatgag aatgattttg aagcatctat gcttaatgat    600
acagcagcat attattcacg caaagcttcc aactggattc tagaagattc ttgtccagat    660
tatatgctca agctgagga gtgcttaaaa agagaaaagg acagagtttc tcattatctt    720
cattcaagta gtgaaccaaa gcttcttgag aaagttcaaa cagagttatt atctgtttat    780
gcaactcaat tgctcgaaaa ggaacactca ggttgtcatg cattacttag agatgacaag    840
gttgatgatt tatcaagaat gtacagactc ttttcaaaga tacaaaaagg actggatcct    900
gtttccagta tgtttaagca gcatgtcact gctgaaggca aacattagt aaaacaagca    960 gaagatgcag caagtactaa gaaggctgaa agagagacg tggttggctt acaggaacag   1020 gttttttgtta gaaagtaat cgagcttcat gacaagtacc tcgcatatgt aaacgactgt   1080
tttatgaatc acacattgtt ccacaaggct cttaagagg catttgaaat attctgcaac   1140
```

```
aagggcgttg ctggaagttc aagtgcagaa ttacttgcca cattttgtga taatattctt    1200
aaaaaaggtg gaagtgaaaa attgagtgat gaagccattg aagacacact tgagaaggta    1260
gtaaagttgc ttgcttacat cagcgataaa gatctatttg cagagtttta taggaaaaaa    1320
ctggctagaa ggcttttatt tgacaaaagt gcaaatgatg agcatgaaag aagtattta    1380 acaaagttga agcaacaatg tggtggtcag tttacatcaa agatggaagg aatggttaca    1440
gatttaacac tggcaaaaga aaatcaatca cattttgagg agtatttgaa taataatccc    1500
aatgttagcc ctggcattga cttgaccgtg actgtgttga ccacgggatt ttggcctagt    1560
tacaaatctt ttgacctaaa tcttcctgca gaaatggtca aatgcgttga agttttcaga    1620
gaattttatc aaacaaaaac aaaacacaga aaactcacat ggatttattc attgggcacc    1680
tgcaatatta acgaaaaatt cgaaccaaaa accatggagc taatcgttac aacttaccag    1740
gcatctgctt tattgttatt caactcatca gatcgattaa gttatcaaga aatcatgact    1800
caattaaatt tatcagatga tgatgttgtt agactactac attcattatc atgtgcaaaa    1860
tataaaattt tattaaaaga accaaatacc aaaacaatat ctccaaccga tttctttgaa    1920
ttcaactcaa agtttacaga taaaatgaga aggatcaaga ttcctctacc tcctgttgat    1980
gaaaagaaaa agtaattga agatgttgac aaagatagaa ggtatgcaat tgatgcttca    2040
attgtacgaa taatgaaaag cagaaaagtt cttggatacc aacaattggt tatgagtgt    2100 gttgaacaat taggccgtat gtttaagcct gatgtaaaag caatcaagaa gcgtattgaa    2160
gatttgataa cgcgtgatta tcttgaaaga gacaaagaaa atccaaattt gtttcggtac    2220
ttggcatga                                                            2229

<210> SEQ ID NO 47
<211> LENGTH: 2235
<212> TYPE: DNA
<213> ORGANISM: Allium ampeloprasum
<220> FEATURE:
<221> NAME/KEY: source
<222> LOCATION: 1..2235
<223> OTHER INFORMATION: /organism="Allium ampeloprasum"
      /mol_type="unassigned DNA"

<400> SEQUENCE: 47
atgtcgttgc acgaaaggaa aaccattgat ttggagcagg gatgggcttt tatgcagaaa      60
gggatcacca aactgaagaa tattcttgat gagttgaatg aacctcagtt cagctcagag    120
gattacatga tgctctatac gactatgtat aatatgtgta ctcagaagcc gccacatgat    180
tattctcagg agttgtatga taagtaccga gagtcctttg aagagtatat cactaccact    240
gtgcttcctt cattgagaga aaagcatgat gaatacatgt taagggagct cgtgagaagg    300
tggtcaaatc ataaaataat ggttagatgg ctttcacgct ttttccatta tcttgatcgc    360
tactttatag cacgaagatc attgcctgct cttaatgaag tcggtctcac ttgtttccgt    420
gatctggtgt acaacgaagt ccatgggaaa gttaaagatg ccgtgatctc attgattgac    480
caagagaggg aaggggagca aattgacaga gctttattaa agaatgtttt gggtattttt    540
gtagagattg gtttgggaag catggaatgt tatgagaatg atttttgaaac atcaatgctt    600 aatgctacag cagcctatta ttcacgaaaa gcttcaaatt ggattctaga agattcatgt    660
ccagattata tgctaaaagc cgaggagtgc ttaaaacatg agaaagatag agttgctcat    720
tatttgcatt caagcagtga acagaagctg ttagagaaag tgcaacatga gttacttttc    780
gtatatgcaa gtcaacttct cgagaaagaa cattccggat gtcatgcatt gcttcgcgat    840
```

```
gacaaggtgg gagatctttc acgcatgtat cggctgttct gtagaattac acgtggtttg      900
gaccctgtgt ctcaaatatt taagcagcat gtgactgcag aaggtactgc tttggtcaaa      960
catgccgaag atgctgcaag taacaagaag gccgagaaaa aagacattgt tggtttgcaa     1020
gagcaggtct tcgttaggaa agtaattgag ctgcatgata aatacttggc ctatgtgact     1080
gactgctttc aaaatcactc tctatttcac aaggcactta agaggcatt cgaggtattc      1140 tgcaataaag gtgttgcagg tagctcaagc gctgaacttc tggctgcttt ttgtgacaat     1200
atattgaaga agggtggaag cgagaaacta agcgatgagg ccatagagga tactcttgag     1260
aaggttgtaa aactattggc atatattagc gataaagatc tgtttgctga atttttacagg    1320 aagaagcttg cacgaagatt actctttgac aaaagtgcta atgatgacca tgagaggagc     1380
atccttacaa agctgaaaca gcaatgtgga gggcagttca cctctaaaat ggaaggcatg     1440
gtaaccgatc tgacacttgc acgagaaaat caatcaagtt ttgacgatta ccttagcagc     1500
aatcctaaag caaattctgg aattgacttg actgttacag tcttaacaac tggcttctgg     1560
cccagttaca agtcttttga tctcaatctt cctgatgaga tggtaaaatg cgttgaaatt     1620
tttaaagagt tttacgagac aaaaaccaaa cacagaaaac ttacatggat ttattcgttg     1680
ggcacttgca acatcaatgg caagttcgaa accaagacaa tagagttggt tgttacaacc     1740
tatcaggctg cagtgttgct tctattcaac tctgcagata aattaagtta ttctgagatt     1800
gtgcagcagc taaacttatc tgatgatgat gtaatcagat tacttcactc tctttcatgc     1860
gctaaataca aaattctcaa taaagaaccc gctaccaaga ctattacccc gaatgatcat     1920
tttgagttca attctaaatt cactgataga atgagaagga tcaagattcc cctgcctcct     1980
gtggatgaga agaaaaaagt aattgaagat gttgacaaag acagaagata tgcaattgac     2040
gcatccatag ttcgaataat gaaagtagaa aagttcttg gtcatcagca gcttgttttg      2100
gaatgtgttg agcaattagg ccgcatgttt aagcctgact ttaaggccat caagaaaagg     2160
attgaagatc tgatcgctag agattatttg gagagggaca aggacaatcc aaacctcttt     2220
aaatatttgg cctaa                                                      2235
```

<210> SEQ ID NO 48
<211> LENGTH: 2229
<212> TYPE: DNA
<213> ORGANISM: Lactuca sativa
<220> FEATURE:
<221> NAME/KEY: source
<222> LOCATION: 1..2229
<223> OTHER INFORMATION: /organism="Lactuca sativa"
    /mol_type="unassigned DNA"

<400> SEQUENCE: 48

```
atgaacgaaa gaaaaacaat agacttagag caaggatggg acttcatgca gaaaggaata       60
acaaagttga gaatattct agaaggtctt cccgagccac aattcagctc ggaggattac       120
atgatgctct acacaaccat gtacaacatg tgtacacaga aaccaccaca tgattactcc      180
caacagttgt atgacaaata tcgtgagtct tttgaagagt atattacttc aactgtgtta      240
ccttctttaa gagagaagca tgatgagttc atgctgagag agcttgttag aaggtggtca      300
aatcataaag tcatggtgcg gtggctttct agattcttcc attatcttga ccgatatttc      360
attgcccgaa gatctcttcc gccactaaat gaagttggac ttgcctgttt tcgtgatctg      420
gtataccaag aggtgaatgg taaagtgaga gatgctgtaa tatctttgat tgatcaagag     480
cgtgaagggg agcagattga tcgagcttta ctgaagaatg ttctagatat atttgttgag      540
```

| | |
|---|---|
| ataggaatgg gacaaatgga gtattatgag aatgattttg aagcatccat gcttaatgat | 600 |
| acagcagcat attattcacg caaggcttcc aactggattc tagaagattc ttgtccagat | 660 |
| tatatgctca aagcagagga gtgcttaaaa agagaaaagg acagagtgtc tcattatctt | 720 |
| cattccagca gtgagccaaa gcttcttgag aaagttcaaa atgagttatt gtctgtttat | 780 |
| gcaactcaat tgcttgagaa agagcactca ggttgtcatg cattgctcag ggatgacaag | 840 |
| gttgatgatt tatcaagaat gtacagactc ttttcaaaga taccaaaagg attggatcct | 900 |
| gtttctagta tgtttaagca gcatgtcact gctgaaggca acacattggt taaacaagca | 960 |
| gaagatgcag caagtaccaa gaaggctgaa aagagagatg tggttgggtt gcaggaacag | 1020 |
| gttttttgtta gaaaagttat tgagctccat gacaagtacc tggcatatgt aaatgactgt | 1080 |
| ttcatgaacc atactctttt ccacaaggct cttaaagagg catttgaaat attctgcaac | 1140 |
| aagggtgttg ctggaagttc aagtgcagag ttacttgcca cattttgtga taatattctt | 1200 |
| aaaaaggtg gaagtgagaa actgagcgat gaagccattg aggacaccct tgagaaggta | 1260 |
| gtaaagttgc ttgcctacat cagtgataaa gatctatttg ctgaattta caggaaaaaa | 1320 |
| cttgctagga ggcttttgtt tgacaagagt gcaaacgatg agcatgagag aagtattctc | 1380 |
| acaaagctga agcaacagtg tggtggtcag ttcacatcaa agatggaagg gatggttaca | 1440 |
| gatttgacat tggcaaagga aaaccaatcc cattttgaag agtatttgaa caataatccc | 1500 |
| aatgtcagcc ctggaattga cttgactgtc actgtgttga ctaccggctt ctggcccagc | 1560 |
| tacaaatctt tgacctaaa tctccctgcc gaaatggtta aatgcgttga agttttcaga | 1620 |
| gaattttatc aaacaaaaac aaagcacagg aagcttacat ggatatattc attgggtacc | 1680 |
| tgcaatataa acgggaaatt tgaacccaaa acaatggagc tcatagtcac aacctaccag | 1740 |
| gcatctgctt tattactgtt caacttatcg gatcgattga gttatcaaga aatcatgact | 1800 |
| cagttgaact tgtcagatga tgatgttgtt aggctgctcc attctttgtc atgtgcaaaa | 1860 |
| tacaaaattc ttttaaagga gcctaatacc aaaacaatct ctccaaccga ttacttcgaa | 1920 |
| ttcaactcca gtttacaga taaaatgagg aggatcaaga ttcctctacc tcctgtggat | 1980 |
| gagaagaaaa aggtgattga ggatgttgac aaagacagac gttatgccat tgatgcttcc | 2040 |
| attgtaagga taatgaagag cagaaaggtg cttggatacc agcagttggt tatggagtgt | 2100 |
| gttgaacagt tgggacgcat gtttaagcct gatgtaaaag caatcaagaa gcggattgaa | 2160 |
| gatctgataa ctcgtgatta tcttgaaaga gacaaagaga accccaactt gttccgatac | 2220 |
| ttggcatga | 2229 |

<210> SEQ ID NO 49
<211> LENGTH: 2217
<212> TYPE: DNA
<213> ORGANISM: Raphanus sativus
<220> FEATURE:
<221> NAME/KEY: source
<222> LOCATION: 1..2217
<223> OTHER INFORMATION: /organism="Raphanus sativus"
    /mol_type="unassigned DNA"

<400> SEQUENCE: 49

| | |
|---|---|
| atggagcgga agacgattga tctggaacaa ggatgggact atatgcagac tgggatcact | 60 |
| aagctgaaac ggattcttga aggattgcct gagccgcaat tcgactctga gcagtacatg | 120 |
| atgctttata cgactatgta caacatgtgc acccagaaac ctcctcatga ttactctcag | 180 |
| cagctttatg acaagtatcg cgaagctttt gaggagtaca ttgactctac tgttttgcct | 240 |

```
gctttgaagg agaagcatga tgaatacatg ctacgggagc tggttaagag atggtctaac      300
cataaagtta tggttagatg ctatcccga ttcttctact atcttgaccg ttacttcatt       360
gctcggagat cgctgccacc gcttaatgaa gttgggctca catgcttccg tgaccgggtg      420
tataaggagt tgcattccaa ggtcaaagat gctgtaatag cacttgttga taaagaacgg      480
gaaggcgagc agattgacag ggctcttctg aaaaacgtat tagatatcta tgtagagatt      540
ggaatgggac agatggaaag atacgaagtg gattttgaaa gcttcatgct tttggattca      600
gcatcttact attctcgcaa agcatcaaac tggatccagg aagattcttg ccctgattac      660
atgctgaagt ctgaagaatg ccttaagaag gagagggaga gggttgctca ctaccttcat      720
tcaagcagcg agccaaagct ggttgagaaa gtacaacatg agctgttggt tgtctatgca      780
aatcagcttc ttgaaaagga gcactcaggg tgccgtgcat tgctgagaga cgacaaggtt      840
gacgatctct ccaggatgta caggctctat cataaaattg ctaaaggttt agaacctgtt      900
gcaaacatat ttaagcagca tgtcacagcc gagggtaacg cacttgtcca acaggccgaa      960
gacacagcca ctaatcaggc tgcaaatact gctagcgtgc aggaacaggt tctcatcaga     1020
aaagtgattg agctacatga taagtacatg gtctatgtcg tggagtgctt ccagaaccac     1080
accctcttcc acaaggctct gaaagaggca tttgagatat tctgtaacaa aacagtcgct     1140
ggaagttcaa gtgcagaact gcttgcaaca ttctgcgaca acatcctcaa gaagggggt      1200 agtgagaagc tgagtgacga agctattgaa gatacgcttg agaaggttgt caaattgctt     1260
gcttatataa gcgacaagga tcttttcgcc gagttctaca ggaagaagct ggcacgtagg     1320
ctcttatttg atcgcagtgc gaatgatgat catgagagaa gcatccttac aaagctcaag     1380
caacaatgtg gtgggcagtt cacttctaag atggagggca tggtaacgga cttgacattg     1440
gcaagagaga accaaaccag tttcgaggag tatctaggca ataaccccgc tgcaaaccca     1500
gggattgatt tgaccgtcac tgttcttacc actggtttct ggccaagtta caaatcattc     1560
gacataaatc taccaagtga aatggtcaag tgtgttgaag ttttcaaagg gttttatgag     1620
acgaaaacta aacataggaa acttacatgg atctactcac taggaacttg tcacctcaac     1680
ggaaagtttg atcacaagcc cattgagtta gttgtgtcta cttaccaggc tgctgtgctt     1740
ctgctgttca acacaacaga caaattgagc tacaacgata tcctaactca actgaaccta     1800
agccacgaag atttagtgag gttgcttcat tccctgtcat gtgctaggta caagatcctt     1860
ctcaaggagc caagcacgaa gactgttaca cagactgatt catttgaatt caatgccaaa     1920
ttcacggaca gaatgcgcag aatcaagatc cctctccctc ctgttgatga aaggaagaag     1980
gttgtggaag atgtggacaa agacagacgc tatgcgattg atgctgccat tgttaggatc     2040
atgaagagca ggaaagtgtt gggacatcaa caactcgtct ctgagtgcgt tgagcaactt     2100
agccgaatgt tcaagcctga tatcaaagcg atcaagaagc gtatggagga tctaattacg     2160
agggattatt tggagaggga caaggagaac cctaacatgt ttaggtactt ggcttag        2217
```

<210> SEQ ID NO 50
<211> LENGTH: 2223
<212> TYPE: DNA
<213> ORGANISM: Spinacia oleracea
<220> FEATURE:
<221> NAME/KEY: source
<222> LOCATION: 1..2223
<223> OTHER INFORMATION: /organism="Spinacia oleracea"
      /mol_type="unassigned DNA"

<400> SEQUENCE: 50

```
atgaacgatc gtaaagttat cgaactagag caaggatggg agttcatggg gaaggggatt    60
acgaagttga aaaggatttt ggaaggatta ccagagccgc cttttaattc ggaagactac   120
atgatgctgt acacgacaat gtacaacatg tgtacacaga aaccccctca tgattactct   180
caacaactct atgacaatta caaagaggca tttgtggatt acatacattc aacggttta    240
ccttctttgg gggacaaaca tgatgagttt atgctgagag agcttgtgaa agatggtca    300
aatcataaag taatggtgag gtggttgtct cgcttcttcc attatctgga tcggtacttc   360
atcgctcgga gatcgcttcc ttctttgaat gatgttggat tgacgtgctt ccgtgatctg   420
gtttatcaag aaatatctgg caaagccaag gatgctgtta ttgctctgat tgatgaagaa   480
agagagggtg ggcaaattga cagagcctta ttgaagaatg tacttgatat atacgttgaa   540
attggaatga cacaaatgga ttactacgaa aaggactttg aagctcatat gctggatgat   600
actgctgctt attactcacg caaggcctca agctggattc tggaggactc atgtccggaa   660
tacatgttga gtcggagga gtgtttgaag aaagagaaag atagagtggc tcattatcta   720
cattccagca gtgagccaaa gcttctggag aaagtacaaa atgagttgct actggtttac   780
gaaaatcagt tgcttgagaa ggagaattct ggatgtcgtg cattgttgaa agatgacaag   840
gtggaagatc tttccaggat gtacaggctt atagcaagg ttaccaaagg gttggaaccc    900
attggcagta tcttcaaaca gcatataacc gatgaaggaa cagccctggt gcagcaggcc   960
gaagacgctg caattagcaa ggctgaaaat gctggcggtg ttcacatga gcaggtcttc   1020
gtcaggaaag tgattgagtt gcatgacaaa tttatgacct atgttacaga ttgcttcaac  1080
agccatacca tctttcacaa ggctctcaag gaagcttttg aggtattctt aaacaagggt  1140
gttgctggta gttcaagtgc tgaacttcta gcttcatttt gtgataatat tctcaagaaa  1200
ggtggtagta aaaaattaag tgatgaggct attgaggatt cactggagaa ggtggtgaag  1260
cttctcgcat atgtcagtga taaagacctg tttgctgaat tttacagaaa gaagctctct  1320
cgccggctac tctttgacaa aagtgctaat gatgatcatg agaggagtat tttaacaaaa  1380
ttgaagcagc agtgtggggg acagttcaca tcaaagatgg aggggatggt gacagacttg  1440
acattggcga gggagaatca aactaatttt gaggaatatc ttggacaaaa tacagatgcc  1500
agtcctggtc ttgatttgac tgtgacagtt ttgaccactg ggttctggcc aagttacaaa  1560
tcttctgatc ttaaccttcc tgctgagatg gtgaggtgtg ttgaagtttt taagcaattt  1620
tatcaaacaa agacaaaaca caggaagctc acctgggtat attcgttggg aagttgtaac  1680
attaatggca gtttggtcc gaaaacaatt gaattggttg ttggaactta tcaggctgct  1740
gcgctgatgc tctttaacac atcagatcga ctgagttatt cagaaataac gacccaacta  1800
aatctagctg acgaagactt ggttagagtg cttcaatctc tatcttgcgc aaagtataag  1860
attcttctaa aagagccaag cacaagaaac gtgatctcaa ctgattgttt ttcattcaac  1920
tctaattttta ctgacagaat gaggaggatt aggattcctc ttcctccaat ggatgagagg  1980
aaaaaggttg ttgaagatgt tgacaaagat agaagatatg ctattgatgc ctcaattgta  2040
cgcataatga aaagtaggaa ggctttggga tatcaacaat taatcacgga gtgtgtggag  2100
cagctaagcc gcatgttcaa gcctgatttc aaagcaatta agaagaggat cgaggacttg  2160
ataaccagag attatattga agagacaag gaaaaccctc agctattccg gtacttggct  2220
tga                                                                2223

<210> SEQ ID NO 51
<211> LENGTH: 2220
```

```
<212> TYPE: DNA
<213> ORGANISM: Beta vulgaris
<220> FEATURE:
<221> NAME/KEY: source
<222> LOCATION: 1..2220
<223> OTHER INFORMATION: /organism="Beta vulgaris"
      /mol_type="unassigned DNA"

<400> SEQUENCE: 51
atgaatgatc gtaaagttat tgaactagag caaggatggg agttcatggg gaagggatt      60 acaaagttga agaggattct ggaaggattg ccagagccac catttaattc tgaagactac    120
atgatgttgt acacgacgat gtacaatatg tgtactcaga acccccaca tgattactct    180 caacagctct atgacaatta caaacaggct tttgtggatt acatcaactc gacggtttta    240
ccttctttgc gggagaagca tgatgagttt atgttaagag aacttgtgaa agatgggca    300 aatcataaag taatggtcag gtggttgtct cgtttcttcc attatctgga ccggtatttc    360
attgctcgga ggtcgcttcc ttctttgaat gaagttggac tgacttgttt ccgtgatctg    420
gtttatcaag aaatatctgg caaagccaag gatgctgtta tagccctgat tgatatagaa    480
agagaaggtg ggcagattga cagatcatta ttgaaaaatg tacttgatat atatgttgaa    540
attggaatgg gacaaatgga tcactatgaa aaagactttg aagctcatat gctggatgat    600
actgctgctt actactcgcg caaagcgtct agctggattc ttgaggactc ttgtccggaa    660
tacatgttaa gtctgagga gtgtttgaag aaggagaaag agagagtggc taattattta    720
cattccagca gtgagccaaa gcttctggag aaagtgcaaa acgagttgct attggtttat    780
gaaagccaat tgcttgagaa ggagaattcg ggatgtcgtg cattactgaa agatgacaag    840
gtggatgatc tttccaggat gtacaggctt tacagtaagg ttaccaaagg attggaaccc    900
attggcagta tcttcaaaca gcatataact gatgaaggaa cagccttagt gcagcaggcc    960
gaagatgctg ctatcagcaa ggctgaaaat actggtggtt cacatgagca ggtcttcgtc   1020
aggaaagtaa tagagttgca tgacaaattc atgacttatg tcaccgattg cttcaacagc   1080
cataccatat ttcacaaggc tcttaaggag gcttttgagg tattttttgaa caagggtgtt   1140 gctggtagct caagtgctga gttgctagct acattctgtg ataacattct caagaaaggt   1200
gggagcgaaa aactaagcga tgaggctatt gaggattcac ttgagaaggt ggtgaagctt   1260
ctggcctatg tcagtgataa agacctgttt gctgaatttt acagaaagaa gctctctcgc   1320
cggctactct ttgacaagag tgctaatgat gatcatgaaa gaagtatttt aaccaaattg   1380
aagcagcagt gtggcggaca attcacatca aagatggagg ggatggtgac agacttgacc   1440
ttggcgaggg agaatcaaac taattttgag gaatatctta gtcagaatcc agatgccagt   1500
cctggtcttg atttgactgt gactgttctg acaactgggt tctggccaag ttacaaatct   1560
tccgatctta accttcccgc tgagatggtg aggtgtgttg aagttttttaa gcagttctat   1620 tcaactaaaa caaagcacag gaagctgacc tgggtttact cattgggaag ctgtaatatt   1680
aatggcaagt ttggtccaaa aactattgaa ttggttgtcg gaacttatca ggctgctgct   1740
ttgatgctct ttaacacatc agaccgactg agttattcag agatagcaac tcaactaaat   1800
ttagctgatg aagatctggt tagagtgctt caatctttat cctgcgcaaa gtataagatt   1860
cttttaaagg agccaaacac gaaaaccgtg tccccgactg attgtttttc atttaactct   1920
agtttcactg acaggatgag gaggataaga attcctcttc ctccgatgga tgagaggaaa   1980
aaggttgttg aggatgttga caaagataga agatatgcta ttgatgcctc aattgtacgc   2040
ataatgaaaa gtaggaaggt tttggggtac cagcaattaa tcacagagtg tgtggagcag   2100
```

```
ctaagccgca tgttcaagcc tgatttcaag gcaattaaga agaggatcga ggacttaata      2160
acccgagatt atattgaaag agacaaggag aacccgcagc tattccgata cttggcttga      2220
```

<210> SEQ ID NO 52
<211> LENGTH: 744
<212> TYPE: PRT
<213> ORGANISM: Cucumis sativus

<400> SEQUENCE: 52

```
Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
                20                  25                  30

Pro Glu Pro Gln Phe Ser Ser Glu Asp Tyr Met Met Leu Tyr Thr Thr
            35                  40                  45

Met Tyr Asn Met Cys Thr Gln Lys Pro Pro His Asp Tyr Ser Gln Gln
        50                  55                  60

Leu Tyr Asp Lys Tyr Arg Glu Ser Phe Glu Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350
```

```
Asp Lys Tyr Leu Ala Tyr Val Asn Asp Cys Phe Gln Asn His Thr Leu
            355                 360                 365
Phe His Lys Ala Leu Lys Glu Ala Phe Glu Val Phe Cys Asn Lys Gly
        370                 375                 380
Val Ala Gly Ser Ser Ala Glu Leu Leu Ala Thr Phe Cys Asp Asn
385                 390                 395                 400
Ile Leu Lys Lys Gly Ser Glu Lys Leu Ser Asp Glu Ala Ile Glu
                405                 410                 415
Glu Thr Leu Glu Lys Val Val Lys Leu Leu Ala Tyr Ile Cys Asp Lys
                    420                 425                 430
Asp Leu Phe Ala Glu Phe Tyr Arg Lys Leu Ala Arg Arg Leu Leu
            435                 440                 445
Phe Asp Lys Ser Ala Asn Asp Asp His Glu Arg Ser Ile Leu Thr Lys
        450                 455                 460
Leu Lys Gln Gln Cys Gly Gly Gln Phe Thr Ser Lys Met Glu Gly Met
465                 470                 475                 480
Val Thr Asp Leu Thr Leu Ala Arg Glu Asn Gln Thr Ser Phe Glu Glu
                485                 490                 495
Tyr Leu Ser Asn Asn Pro Gln Ala Ser Pro Gly Ile Asp Leu Thr Val
            500                 505                 510
Thr Val Leu Thr Thr Gly Phe Trp Pro Ser Tyr Lys Ser Phe Asp Leu
        515                 520                 525
Asn Leu Pro Ala Glu Met Val Lys Cys Val Glu Val Phe Arg Glu Phe
        530                 535                 540
Tyr Gln Thr Lys Thr Lys His Arg Lys Leu Thr Trp Ile Tyr Ser Leu
545                 550                 555                 560
Gly Thr Cys Asn Ile Ser Gly Lys Phe Glu Pro Lys Thr Met Glu Leu
                565                 570                 575
Ile Val Thr Thr Tyr Gln Ala Ser Ala Leu Leu Phe Asn Ser Ser
            580                 585                 590
Asp Arg Leu Ser Tyr Ser Glu Ile Met Thr Gln Leu Asn Leu Ser Asp
            595                 600                 605
Asp Asp Val Val Arg Leu Leu His Ser Leu Ser Cys Ala Lys Tyr Lys
    610                 615                 620
Ile Leu Asn Lys Glu Pro Asn Thr Lys Thr Ile Ser Pro Asn Asp His
625                 630                 635                 640
Phe Glu Phe Asn Ala Lys Phe Ser Asp Lys Met Arg Arg Ile Lys Ile
                645                 650                 655
Pro Leu Pro Pro Val Asp Glu Lys Lys Lys Val Ile Glu Asp Val Asp
            660                 665                 670
Lys Asp Arg Arg Tyr Ala Ile Asp Ala Ser Ile Val Arg Ile Met Lys
    675                 680                 685
Ser Arg Lys Val Leu Gly His Gln Gln Leu Val Met Glu Cys Val Glu
    690                 695                 700
Gln Leu Gly Arg Met Phe Lys Pro Asp Phe Lys Ala Ile Lys Lys Arg
705                 710                 715                 720
Ile Glu Asp Leu Ile Thr Arg Asp Tyr Leu Glu Arg Asp Lys Asp Asn
                725                 730                 735
Pro His Leu Phe Arg Tyr Leu Ala
            740

<210> SEQ ID NO 53
<211> LENGTH: 744
<212> TYPE: PRT
```

<213> ORGANISM: Cucumis melo

<400> SEQUENCE: 53

```
Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
            20                  25                  30

Pro Glu Pro Gln Phe Ser Ser Glu Asp Tyr Met Met Leu Tyr Thr Thr
        35                  40                  45

Met Tyr Asn Met Cys Thr Gln Lys Pro Pro His Asp Tyr Ser Gln Gln
50                  55                  60

Leu Tyr Asp Lys Tyr Arg Glu Ser Phe Glu Tyr Ile Thr Ser Met
65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
210                 215                 220

Leu Lys Ala Glu Glu Cys Leu Lys Arg Glu Lys Asp Arg Val Ser His
225                 230                 235                 240

Tyr Leu His Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
370                 375                 380

Val Ala Gly Ser Ser Ala Glu Leu Leu Ala Thr Phe Cys Asp Asn
385                 390                 395                 400
```

```
Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Leu Ala Arg Arg Leu Leu
        435                 440                 445

Phe Asp Lys Ser Ala Asn Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495

Tyr Leu Ser Asn Asn Pro Gln Ala Ser Pro Gly Ile Asp Leu Thr Val
                500                 505                 510

Thr Val Leu Thr Thr Gly Phe Trp Pro Ser Tyr Lys Ser Phe Asp Leu
            515                 520                 525

Asn Leu Pro Ala Glu Met Val Lys Cys Val Glu Val Phe Arg Glu Phe
        530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
                580                 585                 590

Asp Arg Leu Ser Tyr Ser Glu Ile Met Thr Gln Leu Asn Leu Ser Asp
            595                 600                 605

Asp Asp Val Val Arg Leu Leu His Ser Leu Ser Cys Ala Lys Tyr Lys
        610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Val Ile Glu Asp Val Asp
                660                 665                 670

Lys Asp Arg Arg Tyr Ala Ile Asp Ala Ser Ile Val Arg Ile Met Lys
            675                 680                 685

Ser Arg Lys Val Leu Gly His Gln Gln Leu Val Met Glu Cys Val Glu
        690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
                740

<210> SEQ ID NO 54
<211> LENGTH: 744
<212> TYPE: PRT
<213> ORGANISM: Cucurbita pepo

<400> SEQUENCE: 54

Met Thr Met Gly Glu Arg Lys Thr Ile Asp Leu Glu Gln Gly Trp Glu
1               5                   10                  15

Phe Met Gln Lys Gly Ile Thr Lys Leu Lys Asn Ile Leu Glu Gly Leu
                20                  25                  30
```

```
Pro Glu Pro Gln Phe Ser Ser Glu Asp Tyr Met Met Leu Tyr Thr Thr
            35                  40                  45

Met Tyr Asn Met Cys Thr Gln Lys Pro Pro His Asp Tyr Ser Gln Gln
     50                  55                  60

Leu Tyr Asp Lys Tyr Arg Glu Ser Phe Glu Tyr Ile Ser Ser Met
 65                  70                  75                  80

Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
                100                 105                 110

Arg Phe Phe His Tyr Leu Asp Arg Tyr Phe Ile Ala Arg Arg Ser Leu
             115                 120                 125

Pro Pro Leu Asn Glu Val Gly Leu Thr Cys Phe Arg Glu Leu Val Tyr
         130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
             180                 185                 190

Asn Asp Phe Glu Ala Ala Met Leu Lys Asp Thr Ala Ala Tyr Tyr Ser
         195                 200                 205

Arg Lys Ala Ser Asn Trp Ile Leu Glu Asp Ser Cys Pro Asp Tyr Met
     210                 215                 220

Leu Lys Ala Glu Glu Cys Leu Arg Arg Glu Lys Asp Arg Val Ser His
225                 230                 235                 240

Tyr Leu His Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
             260                 265                 270

Gly Cys His Ala Leu Leu Arg Asp Asp Lys Val Glu Asp Leu Ser Arg
         275                 280                 285

Met Phe Arg Leu Phe Ser Lys Ile Pro Lys Gly Leu Asp Pro Val Ser
     290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
             340                 345                 350

Asp Lys Tyr Leu Ala Tyr Val Asn Asp Cys Phe Gln Asn His Thr Leu
         355                 360                 365

Phe His Lys Ala Leu Lys Glu Ala Phe Glu Val Phe Cys Asn Lys Gly
     370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
             420                 425                 430

Asp Leu Phe Ala Glu Phe Tyr Arg Lys Lys Leu Ala Arg Arg Leu Leu
         435                 440                 445
```

-continued

```
Phe Asp Lys Ser Ala Asn Asp His Glu Arg Ser Ile Leu Thr Lys
    450                 455                 460
Leu Lys Gln Gln Cys Gly Gly Gln Phe Thr Ser Lys Met Glu Gly Met
465                 470                 475                 480
Val Thr Asp Leu Thr Leu Ala Arg Glu Asn Gln Thr Ser Phe Glu Glu
                485                 490                 495
Tyr Leu Ser Asn Asn Pro Gln Ala Ser Pro Gly Ile Asp Leu Thr Val
            500                 505                 510
Thr Val Leu Thr Thr Gly Phe Trp Pro Ser Tyr Lys Ser Phe Asp Leu
            515                 520                 525
Asn Leu Pro Ala Glu Met Val Lys Cys Val Glu Val Phe Arg Glu Phe
530                 535                 540
Tyr Gln Thr Lys Thr Lys His Arg Lys Leu Thr Trp Ile Tyr Ser Leu
545                 550                 555                 560
Gly Thr Cys Asn Ile Ser Gly Lys Phe Glu Pro Lys Thr Met Glu Leu
                565                 570                 575
Ile Val Thr Thr Tyr Gln Ala Ser Ala Leu Leu Leu Phe Asn Ser Ser
            580                 585                 590
Asp Lys Leu Ser Tyr Ser Glu Ile Met Thr Gln Leu Asn Leu Ser Asp
            595                 600                 605
Asp Asp Val Val Arg Leu Leu His Ser Leu Ser Cys Ala Lys Tyr Lys
610                 615                 620
Ile Leu Asn Lys Glu Pro Asn Thr Lys Thr Ile Ser Pro Asn Asp His
625                 630                 635                 640
Phe Glu Phe Asn Ala Lys Phe Ser Asp Lys Met Arg Arg Ile Lys Ile
                645                 650                 655
Pro Leu Pro Pro Val Asp Glu Lys Lys Val Ile Glu Asp Val Asp
            660                 665                 670
Lys Asp Arg Arg Tyr Ala Ile Asp Ala Ser Ile Val Arg Ile Met Lys
            675                 680                 685
Ser Arg Lys Val Leu Gly His Gln Gln Leu Val Met Glu Cys Val Glu
            690                 695                 700
Gln Leu Gly Arg Met Phe Lys Pro Asp Phe Lys Ala Ile Lys Lys Arg
705                 710                 715                 720
Ile Glu Asp Leu Ile Thr Arg Asp Tyr Leu Glu Arg Asp Lys Asp Asn
                725                 730                 735
Pro His Leu Phe Arg Tyr Leu Ala
            740
```

<210> SEQ ID NO 55
<211> LENGTH: 744
<212> TYPE: PRT
<213> ORGANISM: citrillus lanatus

<400> SEQUENCE: 55

```
Met Thr Met Gly Glu Arg Lys Thr Ile Asp Leu Glu Gln Gly Trp Glu
1               5                   10                  15
Phe Met Gln Lys Gly Ile Thr Lys Leu Lys Asn Ile Leu Glu Gly Leu
                20                  25                  30
Pro Glu Pro Gln Phe Ser Ser Glu Asp Tyr Met Met Leu Tyr Thr Thr
            35                  40                  45
Met Tyr Asn Met Cys Thr Gln Lys Pro Pro His Asp Tyr Ser Gln Gln
        50                  55                  60
Leu Tyr Asp Lys Tyr Arg Glu Ser Phe Glu Glu Tyr Ile Thr Ser Met
65                  70                  75                  80
```

```
Val Leu Pro Ser Leu Arg Glu Lys His Asp Glu Phe Met Leu Arg Glu
                85                  90                  95

Leu Val Lys Arg Trp Thr Asn His Lys Val Met Val Arg Trp Leu Ser
            100                 105                 110

Arg Phe Phe His Tyr Leu Asp Arg Tyr Phe Ile Ala Arg Arg Ser Leu
        115                 120                 125

Pro Pro Leu Asn Glu Val Gly Leu Thr Cys Phe Arg Glu Leu Val Tyr
    130                 135                 140

Lys Glu Leu Asn Ser Lys Val Arg Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Asp Ile Phe Val Glu Ile Gly Met Gly Gln Met Asp Tyr Tyr Glu
            180                 185                 190

Asn Asp Phe Glu Ala Ala Met Leu Lys Asp Thr Ala Ala Tyr Tyr Ser
        195                 200                 205

Arg Lys Ala Ser Asn Trp Ile Leu Glu Asp Ser Cys Pro Asp Tyr Met
    210                 215                 220

Leu Lys Ala Glu Glu Cys Leu Lys Arg Glu Lys Asp Arg Val Ser His
225                 230                 235                 240

Tyr Leu His Ser Ser Glu Pro Lys Leu Leu Glu Lys Val Gln His
                245                 250                 255

Glu Leu Leu Ser Val Tyr Ala Thr Gln Leu Leu Glu Lys Glu His Ser
            260                 265                 270

Gly Cys His Ala Leu Leu Arg Asp Asp Lys Val Glu Asp Leu Ser Arg
        275                 280                 285

Met Phe Arg Leu Phe Ser Lys Ile Pro Lys Gly Leu Asp Pro Val Ser
    290                 295                 300

Asn Ile Phe Lys Gln His Val Thr Ala Glu Gly Thr Ala Leu Val Lys
305                 310                 315                 320

Gln Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Asn Asp Cys Phe Gln Asn His Thr Leu
        355                 360                 365

Phe His Lys Ala Leu Lys Glu Ala Phe Glu Val Phe Cys Asn Lys Gly
    370                 375                 380

Val Ala Gly Ser Ser Ser Ala Glu Leu Leu Ala Thr Phe Cys Asp Asn
385                 390                 395                 400

Ile Leu Lys Lys Gly Gly Ser Glu Lys Leu Ser Asp Glu Ala Ile Glu
                405                 410                 415

Glu Thr Leu Glu Lys Val Val Lys Leu Leu Ala Tyr Ile Cys Asp Lys
            420                 425                 430

Asp Leu Phe Ala Glu Phe Tyr Arg Lys Lys Leu Ala Arg Arg Leu Leu
        435                 440                 445

Phe Asp Lys Ser Ala Asn Asp Asp His Glu Arg Ser Ile Leu Thr Lys
    450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Thr Ser Phe Glu Glu
                485                 490                 495
```

Tyr Leu Ser Asn Asn Pro Gln Ala Ser Pro Gly Ile Asp Leu Thr Val
            500                 505                 510

Thr Val Leu Thr Thr Gly Phe Trp Pro Ser Tyr Lys Ser Phe Asp Leu
        515                 520                 525

Asn Leu Pro Ala Glu Met Val Lys Cys Val Glu Val Phe Arg Glu Phe
    530                 535                 540

Tyr Gln Thr Lys Thr Lys His Arg Lys Leu Thr Trp Ile Tyr Ser Leu
545                 550                 555                 560

Gly Thr Cys Asn Ile Ser Gly Lys Phe Glu Pro Lys Thr Met Glu Leu
                565                 570                 575

Ile Val Thr Thr Tyr Gln Ala Ser Ala Leu Leu Leu Phe Asn Ser Ser
            580                 585                 590

Asp Arg Leu Ser Tyr Ser Glu Ile Met Thr Gln Leu Asn Leu Ser Asp
        595                 600                 605

Asp Asp Val Val Arg Leu Leu His Ser Leu Ser Cys Ala Lys Tyr Lys
    610                 615                 620

Ile Leu Asn Lys Glu Pro Asn Thr Lys Thr Ile Ser Pro Asn Asp His
625                 630                 635                 640

Phe Glu Phe Asn Ala Lys Phe Ser Asp Lys Met Arg Arg Ile Lys Ile
                645                 650                 655

Pro Leu Pro Pro Val Asp Glu Lys Lys Val Ile Glu Asp Val Asp
            660                 665                 670

Lys Asp Arg Arg Tyr Ala Ile Asp Ala Ser Ile Val Arg Ile Met Lys
        675                 680                 685

Ser Arg Lys Val Leu Gly His Gln Gln Leu Val Met Glu Cys Val Glu
    690                 695                 700

Gln Leu Gly Arg Met Phe Lys Pro Asp Phe Lys Ala Ile Lys Lys Arg
705                 710                 715                 720

Ile Glu Asp Leu Ile Thr Arg Asp Tyr Leu Glu Arg Asp Lys Asp Asn
                725                 730                 735

Pro His Leu Phe Arg Tyr Leu Ala
            740

<210> SEQ ID NO 56
<211> LENGTH: 742
<212> TYPE: PRT
<213> ORGANISM: Solanum melongena

<400> SEQUENCE: 56

Met Asn Gln Arg Ser Thr Ile Asp Leu Glu His Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Met Thr Tyr
        35                  40                  45

Asn Met Cys Thr Gln Lys Pro Pro His Asp Tyr Ser Gln Gln Leu Tyr
    50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

```
Leu Asn Glu Val Gly Leu Thr Cys Phe Arg Asp Leu Val Tyr Gln Glu
        130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Ser Met Asp Tyr Tyr Glu Asn Asp
                180                 185                 190

Phe Glu Ala Ala Met Leu Lys Asp Thr Ala Ala Tyr Tyr Ser Arg Lys
            195                 200                 205

Ala Ser Asn Trp Ile Leu Glu Asp Ser Cys Pro Asp Tyr Met Leu Lys
210                 215                 220

Ala Glu Glu Cys Leu Lys Arg Glu Lys Asp Arg Val Ser His Tyr Leu
225                 230                 235                 240

His Ser Ser Ser Glu Thr Lys Leu Leu Glu Lys Val Gln His Glu Leu
                245                 250                 255

Leu Ser Val Tyr Ala Asn Gln Leu Leu Glu Lys His Ser Gly Cys
                260                 265                 270

His Ala Leu Leu Arg Asp Asp Lys Val Asp Asp Leu Ser Arg Met Tyr
            275                 280                 285

Arg Leu Phe Ser Lys Ile Pro Arg Gly Leu Glu Pro Val Ala Asn Ile
290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asn Cys Phe Gln Asn His Thr Leu Phe His
            355                 360                 365

Lys Ala Leu Lys Glu Ala Phe Glu Leu Phe Cys Asn Lys Gly Val Ala
            370                 375                 380

Gly Ser Ser Asn Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
            435                 440                 445

Lys Ser Ala Asn Asp Glu His Glu Arg Ser Ile Leu Thr Lys Leu Lys
450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Thr Ala Asn Pro Gly Ile Asp Leu Thr Val Thr Val
                500                 505                 510

Leu Thr Thr Gly Phe Trp Pro Ser Tyr Lys Ser Phe Asp Leu Asn Leu
            515                 520                 525

Pro Ala Glu Met Val Arg Cys Val Glu Val Phe Lys Glu Phe Tyr Gln
530                 535                 540
```

```
Thr Lys Thr Lys His Arg Lys Leu Thr Trp Ile Tyr Ser Leu Gly Thr
545                 550                 555                 560

Cys Asn Ile Asn Gly Lys Phe Glu Ala Lys Thr Ile Glu Leu Val Val
            565                 570                 575

Thr Thr Tyr Gln Ala Ser Ala Leu Leu Leu Phe Asn Ala Ser Asp Arg
        580                 585                 590

Leu Ser Tyr Gln Glu Ile Met Thr Gln Leu Asn Leu Ser Asp Asp Asp
    595                 600                 605

Val Val Arg Leu Leu His Ser Leu Ser Cys Ala Lys Tyr Lys Ile Leu
610                 615                 620

Asn Lys Glu Pro Ser Thr Lys Thr Ile Ser Pro Thr Asp Val Phe Glu
625                 630                 635                 640

Phe Asn Ser Lys Phe Thr Asp Lys Met Arg Arg Ile Lys Ile Pro Leu
            645                 650                 655

Pro Pro Val Asp Glu Lys Lys Val Ile Glu Val Asp Lys Asp
        660                 665                 670

Arg Arg Tyr Ala Ile Asp Ala Ser Ile Val Arg Ile Met Lys Ser Arg
        675                 680                 685

Lys Val Leu Gly Tyr Gln Gln Leu Val Met Glu Cys Val Glu Gln Leu
690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
            725                 730                 735

Leu Phe Lys Tyr Leu Ala
            740

<210> SEQ ID NO 57
<211> LENGTH: 742
<212> TYPE: PRT
<213> ORGANISM: Solanum lycopersicum

<400> SEQUENCE: 57

Met Asn Gln Arg Ser Thr Ile Asp Leu Glu His Gly Trp Asp Phe Met
1               5                   10                  15

Gln Arg Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Gly
        115                 120                 125

Leu Asn Glu Val Gly Leu Thr Cys Phe Arg Asp Gln Val Tyr Gln Glu
    130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175
```

```
Ile Phe Val Glu Ile Gly Met Gly Leu Met Asp Tyr Glu Asn Asp
                180                 185                 190

Phe Glu Ala Ala Met Leu Lys Asp Thr Ala Ala Tyr Tyr Ser Arg Lys
                195                 200                 205

Ala Ser Asn Trp Ile Leu Glu Asp Ser Cys Pro Asp Tyr Met Leu Lys
                210                 215                 220

Ala Glu Glu Cys Leu Lys Arg Glu Lys Asp Arg Val Ser His Tyr Leu
225                 230                 235                 240

His Ser Ser Ser Glu Thr Lys Leu Leu Glu Lys Val Gln His Glu Leu
                245                 250                 255

Leu Ser Val Tyr Ala Thr Gln Leu Leu Glu Lys Glu His Ser Gly Cys
                260                 265                 270

His Ala Leu Leu Arg Asp Asp Lys Val Glu Asp Leu Ser Arg Met Tyr
                275                 280                 285

Arg Leu Phe Ser Lys Ile Ser Arg Gly Leu Asp Pro Val Ala Asn Ile
                290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
                325                 330                 335

Leu Gln Glu Gln Val Phe Val Arg Lys Val Ile Glu Leu His Asp Lys
                340                 345                 350

Tyr Leu Ala Tyr Val Asn Asn Cys Phe Gln Asn His Thr Leu Phe His
                355                 360                 365

Lys Ala Leu Lys Glu Ala Phe Glu Leu Phe Cys Asn Lys Gly Val Ala
                370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
                405                 410                 415

Leu Glu Lys Val Val Lys Leu Leu Ala Tyr Ile Ser Asp Lys Asp Leu
                420                 425                 430

Phe Ala Glu Phe Tyr Arg Lys Lys Leu Ala Arg Arg Leu Leu Phe Asp
                435                 440                 445

Lys Ser Ala Asn Asp Glu His Glu Arg Ser Ile Leu Thr Lys Leu Lys
                450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
                485                 490                 495

Ser Asn Asn Pro Ile Ala Asn Pro Gly Ile Asp Leu Thr Val Thr Val
                500                 505                 510

Leu Thr Thr Gly Phe Trp Pro Ser Tyr Lys Ser Phe Asp Leu Asn Leu
                515                 520                 525

Pro Ala Glu Met Val Arg Cys Val Glu Val Phe Lys Glu Phe Tyr Gln
                530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
                565                 570                 575

Thr Thr Tyr Gln Ala Ser Ala Leu Leu Leu Phe Asn Ala Ser Asp Arg
                580                 585                 590
```

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
610                 615                 620

Asn Lys Glu Pro Ser Thr Lys Thr Ile Ser Pro Thr Asp Val Phe Glu
625                 630                 635                 640

Phe Asn Ser Lys Phe Thr Asp Lys Met Arg Arg Ile Lys Ile Pro Leu
            645                 650                 655

Pro Pro Val Asp Glu Lys Lys Val Ile Glu Asp Val Asp Lys Asp
                660                 665                 670

Arg Arg Tyr Ala Ile Asp Ala Ser Ile Val Arg Ile Met Lys Ser Arg
            675                 680                 685

Lys Val Leu Gly Tyr Gln Gln Leu Val Met Glu Cys Val Glu Gln Leu
            690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
            725                 730                 735

Leu Phe Lys Tyr Leu Ala
            740

<210> SEQ ID NO 58
<211> LENGTH: 742
<212> TYPE: PRT
<213> ORGANISM: Capsicum annuum

<400> SEQUENCE: 58

Met Asn Gln Arg Ser Thr Ile Asn Leu Glu His Gly Trp Asp Phe Met
1               5                   10                  15

Gln Arg Gly Ile Thr Lys Leu Lys Asn Ile Leu Glu Gly Leu Pro Glu
                20                  25                  30

Pro Gln Phe Ser Ser Glu Asp Tyr Met Met Leu Tyr Thr Thr Met Tyr
            35                  40                  45

Asn Met Cys Thr Gln Lys Pro Pro His Asp Tyr Ser Gln Gln Leu Tyr
50                  55                  60

Asp Lys Tyr Arg Glu Ala Phe Glu Glu Tyr Ile Thr Thr Thr Val Leu
65                  70                  75                  80

Pro Ser Leu Arg Glu Lys His Asp Glu Phe Met Leu Arg Glu Leu Val
                85                  90                  95

Lys Arg Trp Ser Asn His Lys Val Met Val Arg Trp Leu Ser Arg Phe
                100                 105                 110

Phe His Tyr Leu Asp Arg Tyr Phe Ile Ala Arg Arg Ser Leu Pro Gly
            115                 120                 125

Leu Asn Glu Val Gly Leu Thr Cys Phe Arg Asp Leu Val Tyr Gln Glu
130                 135                 140

Leu Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Ser Met Asp Tyr Tyr Glu Asn Asp
            180                 185                 190

Phe Glu Ala Ala Met Leu Lys Asp Thr Ala Ala Tyr Tyr Ser Arg Lys
            195                 200                 205

Ala Ser Asn Trp Ile Leu Glu Asp Ser Cys Pro Asp Tyr Met Leu Lys
210                 215                 220

```
Ala Glu Glu Cys Leu Lys Arg Glu Lys Asp Arg Val Ser His Tyr Leu
225                 230                 235                 240

His Leu Ser Ser Glu Thr Lys Leu Leu Glu Lys Val Gln His Glu Leu
            245                 250                 255

Leu Ser Val Tyr Ala Thr Gln Leu Leu Glu Lys Glu His Ser Gly Cys
            260                 265                 270

His Ala Leu Leu Arg Asp Asp Lys Val Glu Asp Leu Ser Arg Met Tyr
            275                 280                 285

Arg Leu Phe Ser Lys Ile Pro Arg Gly Leu Asp Pro Val Ala Asn Ile
            290                 295                 300

Phe Lys Gln His Val Thr Ala Glu Gly Thr Ala Leu Val Lys Gln Ala
305                 310                 315                 320

Glu Asp Ala Ala Ser Asn Lys Lys Ala Glu Lys Arg Asp Val Val Gly
            325                 330                 335

Leu Gln Glu Gln Ile Phe Val Arg Lys Val Ile Glu Leu His Asp Lys
            340                 345                 350

Tyr Met Ala Tyr Val Asn Asn Cys Phe Gln Asn His Thr Leu Phe His
            355                 360                 365

Lys Ala Leu Lys Glu Ala Phe Glu Leu Phe Cys Asn Lys Gly Val Ala
370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Glu Thr
            405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
            435                 440                 445

Lys Ser Ala Asn Asp Glu His Glu Arg Ser Ile Leu Thr Lys Leu Lys
            450                 455                 460

Gln Gln Cys Gly Gly Gln Phe Thr Ser Lys Met Glu Gly Met Val Thr
465                 470                 475                 480

Asp Leu Thr Leu Ala Arg Glu Asn Gln Ala Ser Phe Glu Glu Tyr Leu
            485                 490                 495

Ser Asn Asn Pro Ala Ala Asn Pro Gly Ile Asp Leu Thr Val Thr Val
            500                 505                 510

Leu Thr Thr Gly Phe Trp Pro Ser Tyr Lys Ser Phe Asp Leu Asn Leu
            515                 520                 525

Pro Ala Glu Met Val Arg Cys Val Glu Val Phe Lys Glu Phe Tyr Gln
            530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Ile Glu Leu Val Val
            565                 570                 575

Thr Thr Tyr Gln Ala Ser Ala Leu Leu Leu Phe Asn Ala Ser Asp Arg
            580                 585                 590

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
            610                 615                 620

Asn Lys Glu Pro Ser Thr Lys Thr Ile Ser Pro Thr Asp Val Phe Glu
625                 630                 635                 640
```

Phe Asn Phe Lys Phe Thr Asp Lys Met Arg Arg Ile Lys Ile Pro Leu
                    645                 650                 655

Pro Pro Val Asp Glu Lys Lys Val Ile Glu Asp Val Asp Lys Asp
                660                 665                 670

Arg Arg Tyr Ala Ile Asp Ala Ser Ile Val Arg Ile Met Lys Ser Arg
                675                 680                 685

Lys Val Leu Gly Tyr Gln Gln Leu Val Met Glu Cys Val Glu Gln Leu
            690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Asp Asn Pro Asn
                725                 730                 735

Leu Phe Lys Tyr Leu Ala
            740

<210> SEQ ID NO 59
<211> LENGTH: 738
<212> TYPE: PRT
<213> ORGANISM: Brassica oleracea

<400> SEQUENCE: 59

Met Glu Arg Lys Thr Ile Asp Leu Asp Gln Gly Trp Asp Tyr Met Gln
1               5                   10                  15

Thr Gly Ile Thr Lys Leu Lys Arg Ile Leu Glu Gly Leu Pro Glu Pro
                20                  25                  30

Gln Phe Asp Ser Glu Gln Tyr Met Met Leu Tyr Thr Thr Met Tyr Asn
            35                  40                  45

Met Cys Thr Gln Lys Pro Pro His Asp Tyr Ser Gln Leu Tyr Asp
50                  55                  60

Lys Tyr Arg Glu Ala Phe Glu Glu Tyr Ile His Ser Thr Val Leu Pro
65                  70                  75                  80

Ala Leu Arg Glu Lys His Asp Glu Tyr Met Leu Arg Glu Leu Val Lys
                85                  90                  95

Arg Trp Ser Asn His Lys Val Met Val Arg Trp Leu Ser Arg Phe Phe
                100                 105                 110

Tyr Tyr Leu Asp Arg Tyr Phe Ile Ala Arg Arg Ser Leu Pro Pro Leu
            115                 120                 125

Asn Glu Val Gly Leu Thr Cys Phe Arg Asp Leu Val Tyr Asn Glu Leu
        130                 135                 140

His Ser Lys Val Lys Asp Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Glu Asp Phe
            180                 185                 190

Glu Ser Phe Met Leu Leu Asp Ser Ala Ser Tyr Tyr Ser Arg Lys Ala
        195                 200                 205

Ser Ser Trp Ile Gln Glu Asp Ser Cys Pro Asp Tyr Met Leu Lys Ser
    210                 215                 220

Glu Glu Cys Leu Lys Lys Glu Arg Glu Val Ala His Tyr Leu His
225                 230                 235                 240

Ser Ser Ser Glu Pro Lys Leu Val Glu Lys Val Gln His Glu Leu Leu
                245                 250                 255

Val Val Tyr Ala Asn Gln Leu Leu Glu Lys Glu His Ser Gly Cys Arg
            260                 265                 270

```
Ala Leu Leu Arg Asp Asp Lys Val Asp Leu Ser Arg Met Tyr Arg
            275                 280                 285

Leu Tyr His Lys Ile Val Lys Gly Leu Glu Pro Val Ala Asn Ile Phe
        290                 295                 300

Lys Gln His Val Thr Ala Glu Gly Asn Ala Leu Val Gln Gln Ala Glu
305                 310                 315                 320

Asp Thr Ala Thr Asn His Ala Ala Asn Thr Ala Ser Val Gln Glu Gln
                325                 330                 335

Val Leu Ile Arg Lys Val Ile Glu Leu His Asp Lys Tyr Met Val Tyr
            340                 345                 350

Val Val Glu Cys Phe Gln Asn His Thr Leu Phe His Lys Ala Leu Lys
            355                 360                 365

Glu Ala Phe Glu Ile Phe Cys Asn Lys Thr Val Ala Gly Ser Ser Ser
        370                 375                 380

Ala Glu Leu Leu Ala Thr Phe Cys Asp Asn Ile Leu Lys Lys Gly Gly
385                 390                 395                 400

Ser Glu Lys Leu Ser Asp Glu Ala Ile Glu Asp Thr Leu Glu Lys Val
                405                 410                 415

Val Lys Leu Leu Ala Tyr Ile Ser Asp Lys Asp Leu Phe Ala Glu Phe
            420                 425                 430

Tyr Arg Lys Lys Leu Ala Arg Arg Leu Leu Phe Asp Arg Ser Ala Asn
        435                 440                 445

Asp His Glu Arg Ser Ile Leu Thr Lys Leu Lys Gln Gln Cys Gly
    450                 455                 460

Gly Gln Phe Thr Ser Lys Met Glu Gly Met Val Thr Asp Leu Thr Leu
465                 470                 475                 480

Ala Arg Glu Asn Gln Asn Ser Phe Glu Glu Tyr Leu Gly Asn Asn Pro
                485                 490                 495

Ala Ala Asn Pro Gly Ile Asp Leu Thr Val Thr Val Leu Thr Thr Gly
            500                 505                 510

Phe Trp Pro Ser Tyr Lys Ser Phe Asp Ile Asn Leu Pro Ala Glu Met
        515                 520                 525

Val Lys Cys Val Glu Val Phe Lys Gly Phe Tyr Glu Thr Lys Thr Lys
530                 535                 540

His Arg Lys Leu Thr Trp Ile Tyr Ser Leu Gly Thr Cys His Leu Asn
545                 550                 555                 560

Gly Lys Phe Asp Val Lys Pro Ile Glu Leu Val Val Ser Thr Tyr Gln
                565                 570                 575

Ala Ala Val Leu Leu Leu Phe Asn Thr Thr Asp Lys Leu Ser Tyr Thr
            580                 585                 590

Asp Ile Leu Thr Gln Leu Asn Leu Ser His Glu Asp Leu Val Arg Leu
        595                 600                 605

Leu His Ser Leu Ser Cys Ala Arg Tyr Lys Ile Leu Leu Lys Glu Pro
    610                 615                 620

Ser Thr Lys Thr Val Ser Gln Ser Asp Ser Phe Glu Phe Asn Ser Lys
625                 630                 635                 640

Phe Thr Asp Arg Met Arg Arg Ile Lys Ile Pro Leu Pro Pro Val Asp
                645                 650                 655

Glu Arg Lys Lys Val Val Glu Asp Val Asp Lys Asp Arg Arg Tyr Ala
            660                 665                 670

Ile Asp Ala Ala Ile Val Arg Ile Met Lys Ser Arg Lys Val Leu Gly
        675                 680                 685
```

```
His Gln Gln Leu Val Ser Glu Cys Val Glu Gln Leu Ser Arg Met Phe
    690                 695                 700
Lys Pro Asp Ile Lys Ala Ile Lys Lys Arg Met Glu Asp Leu Ile Thr
705                 710                 715                 720
Arg Asp Tyr Leu Glu Arg Asp Lys Glu Asn Ala Asn Met Phe Arg Tyr
                725                 730                 735
Leu Ala

<210> SEQ ID NO 60
<211> LENGTH: 743
<212> TYPE: PRT
<213> ORGANISM: Daucus carota

<400> SEQUENCE: 60

Met Met Ile Glu Arg Lys Thr Ile Asp Leu Glu Gln Gly Trp Asp Phe
1               5                   10                  15
Met Gln Lys Gly Ile Thr Lys Leu Lys Asn Ile Leu Glu Gly Phe Pro
                20                  25                  30
Glu Pro Gln Phe Ser Ser Glu Asp Tyr Met Met Leu Tyr Thr Thr Met
            35                  40                  45
Tyr Asn Met Cys Thr Gln Lys Pro Pro His Asp Tyr Ser Gln Gln Leu
50                  55                  60
Tyr Glu Lys Tyr Arg Glu Ala Ile Glu Tyr Ile Thr Ser Thr Val
65                  70                  75                  80
Leu Pro Ser Leu Arg Glu Lys His Asp Glu Phe Met Leu Arg Glu Leu
                85                  90                  95
Val Lys Arg Trp Ser Asn His Lys Val Met Val Arg Trp Leu Ser Arg
                100                 105                 110
Phe Phe His Tyr Leu Asp Arg Tyr Phe Ile Ala Arg Arg Ser Leu Pro
            115                 120                 125
Pro Leu His Glu Val Gly Leu Thr Cys Phe Arg Asp Leu Val Tyr Gln
130                 135                 140
Glu Ile Asn Gly Lys Val Arg Asp Ala Val Ile Ser Leu Ile Asn Gln
145                 150                 155                 160
Glu Arg Glu Gly Glu Gln Ile Asp Arg Ala Leu Leu Lys Asn Val Leu
                165                 170                 175
Asp Ile Phe Val Glu Val Gly Met Ser Gln Met Asp Tyr Tyr Glu Asn
            180                 185                 190
Asp Phe Glu Ala Asp Met Leu Lys Asp Thr Ala Ala Tyr Tyr Ser Arg
        195                 200                 205
Lys Ala Ser Asn Trp Ile Leu Glu Asp Ser Cys Pro Asp Tyr Met Leu
    210                 215                 220
Lys Ala Glu Glu Cys Leu Arg Arg Glu Lys Asp Arg Val Ser Asn Tyr
225                 230                 235                 240
Leu His Ser Ser Glu Pro Lys Leu Leu Glu Lys Val Gln His Glu
                245                 250                 255
Leu Leu Ser His Tyr Ala Thr Gln Leu Leu Glu Lys Glu His Ser Gly
            260                 265                 270
Cys His Ala Leu Leu Arg Asp Asp Lys Val Ala Asp Leu Ser Arg Met
        275                 280                 285
Tyr Arg Leu Phe Ser Lys Ile Pro Arg Gly Leu Asp Pro Val Ser Asn
    290                 295                 300
Ile Phe Lys Gln His Val Thr Ala Glu Gly Thr Ala Leu Val Lys Gln
305                 310                 315                 320
```

-continued

Ala Glu Asp Ala Ala Ser Asn Lys Lys Ala Glu Lys Arg Asp Val Val
                325                 330                 335

Gly Leu Gln Glu Gln Val Phe Val Arg Lys Ile Ile Glu Leu His Asp
            340                 345                 350

Lys Tyr Leu Thr Tyr Val Asn Asp Cys Phe Thr Asn His Thr Leu Phe
            355                 360                 365

His Lys Ala Leu Lys Glu Ala Phe Glu Ile Phe Cys Asn Lys Gly Val
        370                 375                 380

Ser Gly Ser Ser Ser Ala Glu Leu Leu Ala Thr Phe Cys Asp Asn Ile
385                 390                 395                 400

Leu Lys Lys Gly Gly Ser Glu Lys Leu Ser Asp Glu Ala Ile Glu Glu
                405                 410                 415

Thr Leu Glu Lys Val Val Arg Leu Leu Ala Tyr Ile Ser Asp Lys Asp
            420                 425                 430

Leu Phe Ala Glu Phe Tyr Arg Lys Lys Leu Ala Arg Arg Leu Leu Phe
        435                 440                 445

Asp Lys Ser Ala Asn Asp Glu His Glu Arg Ser Ile Leu Thr Lys Leu
    450                 455                 460

Lys Gln Gln Cys Gly Gly Gln Phe Thr Ser Lys Met Glu Gly Met Val
465                 470                 475                 480

Thr Asp Leu Thr Leu Ala Lys Glu Asn Gln Ser Asn Phe Glu Glu Tyr
            485                 490                 495

Leu Asn Asn Asn Ser Asn Val Asn Pro Gly Ile Asp Leu Thr Val Thr
                500                 505                 510

Val Leu Thr Thr Gly Phe Trp Pro Ser Tyr Lys Ser Phe Asp Leu Asn
        515                 520                 525

Leu Pro Ala Glu Met Val Lys Cys Val Glu Val Phe Arg Glu Phe Tyr
    530                 535                 540

Gln Thr Lys Thr Lys His Arg Lys Leu Thr Trp Ile Tyr Ser Leu Gly
545                 550                 555                 560

Thr Cys Asn Ile Ile Gly Lys Phe Asp Pro Lys Thr Met Glu Leu Ile
            565                 570                 575

Val Thr Thr Tyr Gln Ala Ser Ala Leu Leu Leu Phe Asn Ser Ser Asp
        580                 585                 590

Arg Leu Ser Tyr Asn Glu Ile Met Thr Gln Leu Asn Leu Ser Asp Asp
    595                 600                 605

Asp Val Val Arg Leu Leu His Ser Leu Ser Cys Ala Lys Tyr Lys Ile
    610                 615                 620

Leu Ser Lys Glu Pro Asn Thr Lys Thr Ile Ser Pro Thr Asp Cys Phe
625                 630                 635                 640

Gln Phe Asn Ser Lys Phe Thr Asp Lys Met Arg Arg Ile Lys Ile Pro
            645                 650                 655

Leu Pro Pro Val Asp Glu Lys Lys Val Ile Glu Asp Val Asp Lys
            660                 665                 670

Asp Arg Arg Tyr Ala Ile Asp Ala Ser Ile Val Arg Ile Met Lys Ser
            675                 680                 685

Arg Lys Val Leu Gly Tyr Gln Gln Leu Val Met Glu Cys Val Glu Gln
        690                 695                 700

Leu Gly Arg Met Phe Lys Pro Asp Val Lys Ala Ile Lys Lys Arg Ile
705                 710                 715                 720

Glu Asp Leu Ile Thr Arg Asp Tyr Leu Glu Arg Asp Lys Asp Asn Ala
                725                 730                 735

Asn Leu Phe Arg Tyr Leu Ala

-continued

740

<210> SEQ ID NO 61
<211> LENGTH: 742
<212> TYPE: PRT
<213> ORGANISM: Apium graveolens

<400> SEQUENCE: 61

```
Met Asn Glu Arg Lys Thr Ile Asp Leu Asp Asn Gly Trp Glu Phe Met
1               5                   10                  15

Gln Lys Gly Ile Thr Lys Leu Lys Lys Ile Leu Glu Gly Gln Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
50                  55                  60

Asp Lys Tyr Arg Glu Ala Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Asn Arg Trp Thr Asn His Lys Val Met Val Arg Trp Leu Ser Arg Phe
            100                 105                 110

Phe His Tyr Leu Asp Arg Tyr Phe Ile Ala Arg Arg Ser Leu Pro Ala
        115                 120                 125

Leu His Glu Val Gly Leu Thr Cys Phe Arg Asp Leu Val Tyr Gln Glu
    130                 135                 140

Leu Lys Val Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Ser Gln Met Asp Gln Tyr Glu Asn Asp
            180                 185                 190

Phe Glu Glu Ala Met Leu Thr Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Arg Arg Glu Lys Asp Arg Val Ser His Tyr Leu
225                 230                 235                 240

His Phe Ser Ser Glu Pro Lys Leu Leu Glu Lys Val Gln His Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Pro Lys Gly Leu Asp Pro Val Ser Tyr Ile
    290                 295                 300

Phe Lys Gln His Val Thr Asn Glu Gly Met Ala Leu Val Lys Gln Ala
305                 310                 315                 320

Glu Asp Ala Ala Ser Asn Lys Lys Ala Glu Lys Arg Asp Val Val Ser
                325                 330                 335

Leu Gln Glu Gln Val Phe Val Arg Lys Ile Ile Glu Leu His Asp Lys
            340                 345                 350

Tyr Leu Ala Tyr Val Asn Asp Cys Phe Thr Asn His Thr Leu Phe His
        355                 360                 365
```

```
Lys Ala Leu Lys Glu Ala Phe Glu Ile Phe Cys Asn Lys Gly Val Ala
        370                 375                 380
Gly Ser Ser Asn Ala Glu Leu Leu Ala Thr Phe Cys Asp Asn Ile Leu
385                 390                 395                 400
Lys Lys Gly Gly Ser Glu Lys Leu Ser Asp Glu Ala Ile Glu Thr
                    405                 410                 415
Leu Glu Lys Val Val Lys Leu Leu Ala Tyr Ile Ser Asp Lys Asp Leu
                420                 425                 430
Phe Ala Glu Phe Tyr Arg Lys Lys Leu Ala Arg Arg Leu Leu Phe Asp
            435                 440                 445
Lys Ser Ala Asn Asp Glu His Glu Arg Ser Ile Leu Thr Lys Leu Lys
450                 455                 460
Gln Gln Cys Gly Gly Gln Phe Thr Ser Lys Met Glu Gly Met Val Thr
465                 470                 475                 480
Asp Leu Thr Leu Ala Lys Glu Asn Gln Ser Ser Phe Glu Glu Tyr Leu
                485                 490                 495
Gly Asn Asn Ala Asn Val Asn Pro Gly Ile Asp Leu Thr Val Thr Val
                500                 505                 510
Leu Thr Thr Gly Phe Trp Pro Ser Tyr Lys Ser Phe Asp Leu Asn Leu
            515                 520                 525
Pro Ala Glu Met Val Lys Cys Val Glu Val Phe Arg Glu Phe Tyr Gln
530                 535                 540
Thr Lys Thr Lys His Arg Lys Leu Thr Trp Ile Tyr Ser Leu Gly Thr
545                 550                 555                 560
Cys Asn Ile Asn Gly Lys Phe Glu Pro Lys Thr Ile Glu Leu Ile Val
                565                 570                 575
Thr Thr Tyr Gln Ala Ser Ala Leu Leu Leu Phe Asn Thr Ser Asp Arg
                580                 585                 590
Leu Ser Tyr Gln Glu Ile Met Thr Gln Leu Asn Leu Ser Asp Asp Asp
            595                 600                 605
Val Val Arg Leu Leu His Ser Leu Ser Cys Ala Lys Tyr Lys Ile Leu
610                 615                 620
Thr Lys Glu Pro Asn Asn Lys Thr Ile Ser Pro Thr Asp Tyr Phe Glu
625                 630                 635                 640
Phe Asn Ser Lys Phe Thr Asp Lys Met Arg Arg Ile Lys Ile Pro Leu
                645                 650                 655
Pro Pro Val Asp Glu Lys Lys Val Ile Glu Asp Val Asp Lys Asp
                660                 665                 670
Arg Arg Tyr Ala Ile Asp Ala Ser Ile Val Arg Ile Met Lys Ser Arg
            675                 680                 685
Lys Val Leu Gly Tyr Gln Gln Leu Val Met Glu Cys Val Glu Gln Leu
690                 695                 700
Gly Arg Met Phe Lys Pro Asp Val Lys Ala Ile Lys Lys Arg Ile Glu
705                 710                 715                 720
Asp Leu Ile Thr Arg Asp Tyr Leu Glu Arg Asp Lys Asp Asn Ala Asn
                725                 730                 735
Leu Phe Arg Tyr Leu Ala
            740

<210> SEQ ID NO 62
<211> LENGTH: 742
<212> TYPE: PRT
<213> ORGANISM: Cichorium intybus

<400> SEQUENCE: 62
```

```
Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
                20                  25                  30

Pro Gln Phe Ser Ser Glu Asp Tyr Met Met Leu Tyr Thr Thr Met Tyr
            35                  40                  45

Asn Met Cys Thr Gln Lys Pro Pro His Asp Tyr Ser Gln Gln Leu Tyr
50                      55                  60

Asp Lys Tyr Arg Glu Ser Phe Glu Glu Tyr Ile Thr Ser Thr Val Leu
65              70                  75                      80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
                100                 105                 110

Phe His Tyr Leu Asp Arg Tyr Phe Ile Ala Arg Arg Ser Leu Pro Pro
            115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
            195                 200                 205

Ala Ser Asn Trp Ile Leu Glu Asp Ser Cys Pro Asp Tyr Met Leu Lys
210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Thr Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
            275                 280                 285

Arg Leu Phe Ser Lys Ile Gln Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
            355                 360                 365

Lys Ala Leu Lys Glu Ala Phe Glu Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Gly Lys Leu Ser Asp Glu Ala Ile Glu Asp Thr
                405                 410                 415
```

Leu Glu Lys Val Val Lys Leu Leu Ala Tyr Ile Ser Asp Lys Asp Leu
                420                 425                 430

Phe Ala Glu Phe Tyr Arg Lys Lys Leu Ala Arg Arg Leu Leu Phe Asp
            435                 440                 445

Lys Ser Ala Asn Asp Glu His Glu Arg Ser Ile Leu Thr Lys Leu Lys
450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
            515                 520                 525

Pro Ala Glu Met Val Lys Cys Val Glu Val Phe Arg Glu Phe Tyr Gln
            530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Ser Ser Asp Arg
            580                 585                 590

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
            610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
            660                 665                 670

Arg Arg Tyr Ala Ile Asp Ala Ser Ile Val Arg Ile Met Lys Ser Arg
            675                 680                 685

Lys Val Leu Gly Tyr Gln Gln Leu Val Met Glu Cys Val Glu Gln Leu
            690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740

<210> SEQ ID NO 63
<211> LENGTH: 742
<212> TYPE: PRT
<213> ORGANISM: Cichorium endivia

<400> SEQUENCE: 63

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Met Tyr
            35                  40                  45

```
Asn Met Cys Thr Gln Lys Pro Pro His Asp Tyr Ser Gln Gln Leu Tyr
    50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140

Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
        195                 200                 205

Ala Ser Asn Trp Ile Leu Glu Asp Ser Cys Pro Asp Tyr Met Leu Lys
    210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Thr Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
        275                 280                 285

Arg Leu Phe Ser Lys Ile Gln Lys Gly Leu Asp Pro Val Ser Ser Met
    290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
        355                 360                 365

Lys Ala Leu Lys Glu Ala Phe Gly Ile Phe Cys Asn Lys Gly Val Ala
    370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
        435                 440                 445

Lys Ser Ala Asn Asp Glu His Glu Arg Ser Ile Leu Thr Lys Leu Lys
    450                 455                 460
```

```
Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
                500                 505                 510

Leu Thr Thr Gly Phe Trp Pro Ser Tyr Lys Ser Phe Asp Leu Asn Leu
                515                 520                 525

Pro Ala Glu Met Val Lys Cys Val Glu Val Phe Arg Glu Phe Tyr Gln
                530                 535                 540

Thr Lys Thr Lys His Arg Lys Leu Thr Trp Ile Tyr Ser Leu Gly Thr
545                 550                 555                 560

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Ser Ser Asp Arg
                580                 585                 590

Leu Ser Tyr Gln Glu Ile Met Thr Gln Leu Asn Leu Ser Asp Asp Asp
                595                 600                 605

Val Val Arg Leu Leu His Ser Leu Ser Cys Ala Lys Tyr Lys Ile Leu
                610                 615                 620

Leu Lys Glu Pro Asn Thr Lys Thr Ile Ser Pro Thr Asp Phe Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Lys Val Ile Glu Asp Val Asp Lys Asp
                660                 665                 670

Arg Arg Tyr Ala Ile Asp Ala Ser Ile Val Arg Ile Met Lys Ser Arg
                675                 680                 685

Lys Val Leu Gly Tyr Gln Gln Leu Val Met Glu Cys Val Glu Gln Leu
                690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
                740

<210> SEQ ID NO 64
<211> LENGTH: 744
<212> TYPE: PRT
<213> ORGANISM: Allium ampeloprasum

<400> SEQUENCE: 64

Met Ser Leu His Glu Arg Lys Thr Ile Asp Leu Glu Gln Gly Trp Ala
1               5                   10                  15

Phe Met Gln Lys Gly Ile Thr Lys Leu Lys Asn Ile Leu Asp Glu Leu
                20                  25                  30

Asn Glu Pro Gln Phe Ser Ser Glu Asp Tyr Met Met Leu Tyr Thr Thr
                35                  40                  45

Met Tyr Asn Met Cys Thr Gln Lys Pro Pro His Asp Tyr Ser Gln Glu
                50                  55                  60

Leu Tyr Asp Lys Tyr Arg Glu Ser Phe Glu Glu Tyr Ile Thr Thr Thr
65                  70                  75                  80

Val Leu Pro Ser Leu Arg Glu Lys His Asp Glu Tyr Met Leu Arg Glu
                85                  90                  95
```

```
Leu Val Arg Arg Trp Ser Asn His Lys Ile Met Val Arg Trp Leu Ser
            100                 105                 110

Arg Phe Phe His Tyr Leu Asp Arg Tyr Phe Ile Ala Arg Ser Leu
            115                 120                 125

Pro Ala Leu Asn Glu Val Gly Leu Thr Cys Phe Arg Asp Leu Val Tyr
            130                 135                 140

Asn Glu Val His Gly Lys Val Lys Asp Ala Val Ile Ser Leu Ile Asp
145                 150                 155                 160

Gln Glu Arg Glu Gly Glu Gln Ile Asp Arg Ala Leu Leu Lys Asn Val
                165                 170                 175

Leu Gly Ile Phe Val Glu Ile Gly Leu Gly Ser Met Glu Cys Tyr Glu
            180                 185                 190

Asn Asp Phe Glu Thr Ser Met Leu Asn Ala Thr Ala Ala Tyr Tyr Ser
            195                 200                 205

Arg Lys Ala Ser Asn Trp Ile Leu Glu Asp Ser Cys Pro Asp Tyr Met
            210                 215                 220

Leu Lys Ala Glu Glu Cys Leu Lys His Glu Lys Asp Arg Val Ala His
225                 230                 235                 240

Tyr Leu His Ser Ser Glu Gln Lys Leu Leu Glu Lys Val Gln His
                245                 250                 255

Glu Leu Leu Phe Val Tyr Ala Ser Gln Leu Leu Glu Lys Glu His Ser
            260                 265                 270

Gly Cys His Ala Leu Leu Arg Asp Asp Lys Val Gly Asp Leu Ser Arg
            275                 280                 285

Met Tyr Arg Leu Phe Cys Arg Ile Thr Arg Gly Leu Asp Pro Val Ser
            290                 295                 300

Gln Ile Phe Lys Gln His Val Thr Ala Glu Gly Thr Ala Leu Val Lys
305                 310                 315                 320

His Ala Glu Asp Ala Ala Ser Asn Lys Lys Ala Glu Lys Lys Asp Ile
                325                 330                 335

Val Gly Leu Gln Glu Gln Val Phe Val Arg Lys Val Ile Glu Leu His
            340                 345                 350

Asp Lys Tyr Leu Ala Tyr Val Thr Asp Cys Phe Gln Asn His Ser Leu
            355                 360                 365

Phe His Lys Ala Leu Lys Glu Ala Phe Glu Val Phe Cys Asn Lys Gly
            370                 375                 380

Val Ala Gly Ser Ser Ser Ala Glu Leu Leu Ala Ala Phe Cys Asp Asn
385                 390                 395                 400

Ile Leu Lys Lys Gly Gly Ser Glu Lys Leu Ser Asp Glu Ala Ile Glu
                405                 410                 415

Asp Thr Leu Glu Lys Val Val Lys Leu Leu Ala Tyr Ile Ser Asp Lys
            420                 425                 430

Asp Leu Phe Ala Glu Phe Tyr Arg Lys Lys Leu Ala Arg Arg Leu Leu
            435                 440                 445

Phe Asp Lys Ser Ala Asn Asp His Glu Arg Ser Ile Leu Thr Lys
            450                 455                 460

Leu Lys Gln Gln Cys Gly Gly Gln Phe Thr Ser Lys Met Glu Gly Met
465                 470                 475                 480

Val Thr Asp Leu Thr Leu Ala Arg Glu Asn Gln Ser Ser Phe Asp Asp
                485                 490                 495

Tyr Leu Ser Ser Asn Pro Lys Ala Asn Ser Gly Ile Asp Leu Thr Val
            500                 505                 510
```

```
Thr Val Leu Thr Thr Gly Phe Trp Pro Ser Tyr Lys Ser Phe Asp Leu
            515                 520                 525

Asn Leu Pro Asp Glu Met Val Lys Cys Val Glu Ile Phe Lys Glu Phe
530                 535                 540

Tyr Glu Thr Lys Thr Lys His Arg Lys Leu Thr Trp Ile Tyr Ser Leu
545                 550                 555                 560

Gly Thr Cys Asn Ile Asn Gly Lys Phe Glu Thr Lys Thr Ile Glu Leu
                565                 570                 575

Val Val Thr Thr Tyr Gln Ala Ala Val Leu Leu Leu Phe Asn Ser Ala
            580                 585                 590

Asp Lys Leu Ser Tyr Ser Glu Ile Val Gln Gln Leu Asn Leu Ser Asp
            595                 600                 605

Asp Asp Val Ile Arg Leu Leu His Ser Leu Ser Cys Ala Lys Tyr Lys
610                 615                 620

Ile Leu Asn Lys Glu Pro Ala Thr Lys Thr Ile Thr Pro Asn Asp His
625                 630                 635                 640

Phe Glu Phe Asn Ser Lys Phe Thr Asp Arg Met Arg Arg Ile Lys Ile
                645                 650                 655

Pro Leu Pro Pro Val Asp Glu Lys Lys Val Ile Glu Asp Val Asp
                660                 665                 670

Lys Asp Arg Arg Tyr Ala Ile Asp Ala Ser Ile Val Arg Ile Met Lys
            675                 680                 685

Ser Arg Lys Val Leu Gly His Gln Gln Leu Val Leu Glu Cys Val Glu
            690                 695                 700

Gln Leu Gly Arg Met Phe Lys Pro Asp Phe Lys Ala Ile Lys Lys Arg
705                 710                 715                 720

Ile Glu Asp Leu Ile Ala Arg Asp Tyr Leu Glu Arg Asp Lys Asp Asn
                725                 730                 735

Pro Asn Leu Phe Lys Tyr Leu Ala
            740

<210> SEQ ID NO 65
<211> LENGTH: 742
<212> TYPE: PRT
<213> ORGANISM: Lactuca sativa

<400> SEQUENCE: 65

Met Asn Glu Arg Lys Thr Ile Asp Leu Glu Gln Gly Trp Asp Phe Met
1               5                   10                  15

Gln Lys Gly Ile Thr Lys Leu Lys Asn Ile Leu Glu Gly Leu Pro Glu
            20                  25                  30

Pro Gln Phe Ser Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
    50                  55                  60

Asp Lys Tyr Arg Glu Ser Phe Glu Glu Tyr Ile Thr Ser Thr Val Leu
65                  70                  75                  80

Pro Ser Leu Arg Glu Lys His Asp Glu Phe Met Leu Arg Glu Leu Val
                85                  90                  95

Arg Arg Trp Ser Asn His Lys Val Met Val Arg Trp Leu Ser Arg Phe
            100                 105                 110

Phe His Tyr Leu Asp Arg Tyr Phe Ile Ala Arg Arg Ser Leu Pro Pro
        115                 120                 125

Leu Asn Glu Val Gly Leu Ala Cys Phe Arg Asp Leu Val Tyr Gln Glu
    130                 135                 140
```

```
Val Asn Gly Lys Val Arg Asp Ala Val Ile Ser Leu Ile Asp Gln Glu
145                 150                 155                 160

Arg Glu Gly Glu Gln Ile Asp Arg Ala Leu Leu Lys Asn Val Leu Asp
                165                 170                 175

Ile Phe Val Glu Ile Gly Met Gly Gln Met Glu Tyr Tyr Glu Asn Asp
            180                 185                 190

Phe Glu Ala Ser Met Leu Asn Asp Thr Ala Ala Tyr Tyr Ser Arg Lys
            195                 200                 205

Ala Ser Asn Trp Ile Leu Glu Asp Ser Cys Pro Asp Tyr Met Leu Lys
210                 215                 220

Ala Glu Glu Cys Leu Lys Arg Glu Lys Asp Arg Val Ser His Tyr Leu
225                 230                 235                 240

His Ser Ser Ser Glu Pro Lys Leu Leu Glu Lys Val Gln Asn Glu Leu
                245                 250                 255

Leu Ser Val Tyr Ala Thr Gln Leu Leu Glu Lys Glu His Ser Gly Cys
            260                 265                 270

His Ala Leu Leu Arg Asp Asp Lys Val Asp Asp Leu Ser Arg Met Tyr
            275                 280                 285

Arg Leu Phe Ser Lys Ile Pro Lys Gly Leu Asp Pro Val Ser Ser Met
290                 295                 300

Phe Lys Gln His Val Thr Ala Glu Gly Thr Thr Leu Val Lys Gln Ala
305                 310                 315                 320

Glu Asp Ala Ala Ser Thr Lys Lys Ala Glu Lys Arg Asp Val Val Gly
                325                 330                 335

Leu Gln Glu Gln Val Phe Val Arg Lys Val Ile Glu Leu His Asp Lys
            340                 345                 350

Tyr Leu Ala Tyr Val Asn Asp Cys Phe Met Asn His Thr Leu Phe His
            355                 360                 365

Lys Ala Leu Lys Glu Ala Phe Glu Ile Phe Cys Asn Lys Gly Val Ala
            370                 375                 380

Gly Ser Ser Ser Ala Glu Leu Leu Ala Thr Phe Cys Asp Asn Ile Leu
385                 390                 395                 400

Lys Lys Gly Gly Ser Glu Lys Leu Ser Asp Glu Ala Ile Glu Asp Thr
                405                 410                 415

Leu Glu Lys Val Val Lys Leu Leu Ala Tyr Ile Ser Asp Lys Asp Leu
            420                 425                 430

Phe Ala Glu Phe Tyr Arg Lys Lys Leu Ala Arg Arg Leu Leu Phe Asp
            435                 440                 445

Lys Ser Ala Asn Asp Glu His Glu Arg Ser Ile Leu Thr Lys Leu Lys
450                 455                 460

Gln Gln Cys Gly Gly Gln Phe Thr Ser Lys Met Glu Gly Met Val Thr
465                 470                 475                 480

Asp Leu Thr Leu Ala Lys Glu Asn Gln Ser His Phe Glu Glu Tyr Leu
                485                 490                 495

Asn Asn Asn Pro Asn Val Ser Pro Gly Ile Asp Leu Thr Val Thr Val
            500                 505                 510

Leu Thr Thr Gly Phe Trp Pro Ser Tyr Lys Ser Phe Asp Leu Asn Leu
            515                 520                 525

Pro Ala Glu Met Val Lys Cys Val Glu Val Phe Arg Glu Phe Tyr Gln
530                 535                 540

Thr Lys Thr Lys His Arg Lys Leu Thr Trp Ile Tyr Ser Leu Gly Thr
545                 550                 555                 560
```

Cys Asn Ile Asn Gly Lys Phe Glu Pro Lys Thr Met Glu Leu Ile Val
                565                 570                 575

Thr Thr Tyr Gln Ala Ser Ala Leu Leu Leu Phe Asn Leu Ser Asp Arg
            580                 585                 590

Leu Ser Tyr Gln Glu Ile Met Thr Gln Leu Asn Leu Ser Asp Asp Asp
            595                 600                 605

Val Val Arg Leu Leu His Ser Leu Ser Cys Ala Lys Tyr Lys Ile Leu
610                 615                 620

Leu Lys Glu Pro Asn Thr Lys Thr Ile Ser Pro Thr Asp Tyr Phe Glu
625                 630                 635                 640

Phe Asn Ser Lys Phe Thr Asp Lys Met Arg Arg Ile Lys Ile Pro Leu
                645                 650                 655

Pro Pro Val Asp Glu Lys Lys Val Ile Glu Asp Val Asp Lys Asp
                660                 665                 670

Arg Arg Tyr Ala Ile Asp Ala Ser Ile Val Arg Ile Met Lys Ser Arg
            675                 680                 685

Lys Val Leu Gly Tyr Gln Gln Leu Val Met Glu Cys Val Glu Gln Leu
690                 695                 700

Gly Arg Met Phe Lys Pro Asp Val Lys Ala Ile Lys Lys Arg Ile Glu
705                 710                 715                 720

Asp Leu Ile Thr Arg Asp Tyr Leu Glu Arg Asp Lys Glu Asn Pro Asn
                725                 730                 735

Leu Phe Arg Tyr Leu Ala
            740

<210> SEQ ID NO 66
<211> LENGTH: 738
<212> TYPE: PRT
<213> ORGANISM: Raphanus sativus

<400> SEQUENCE: 66

Met Glu Arg Lys Thr Ile Asp Leu Glu Gln Gly Trp Asp Tyr Met Gln
1               5                   10                  15

Thr Gly Ile Thr Lys Leu Lys Arg Ile Leu Glu Gly Leu Pro Glu Pro
                20                  25                  30

Gln Phe Asp Ser Glu Gln Tyr Met Met Leu Tyr Thr Thr Met Tyr Asn
            35                  40                  45

Met Cys Thr Gln Lys Pro Pro His Asp Tyr Ser Gln Gln Leu Tyr Asp
        50                  55                  60

Lys Tyr Arg Glu Ala Phe Glu Glu Tyr Ile Asp Ser Thr Val Leu Pro
65                  70                  75                  80

Ala Leu Lys Glu Lys His Asp Glu Tyr Met Leu Arg Glu Leu Val Lys
                85                  90                  95

Arg Trp Ser Asn His Lys Val Met Val Arg Trp Leu Ser Arg Phe Phe
                100                 105                 110

Tyr Tyr Leu Asp Arg Tyr Phe Ile Ala Arg Arg Ser Leu Pro Pro Leu
            115                 120                 125

Asn Glu Val Gly Leu Thr Cys Phe Arg Asp Arg Val Tyr Lys Glu Leu
130                 135                 140

His Ser Lys Val Lys Asp Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Val Asp Phe
            180                 185                 190

```
Glu Ser Phe Met Leu Leu Asp Ser Ala Ser Tyr Tyr Ser Arg Lys Ala
            195                 200                 205

Ser Asn Trp Ile Gln Glu Asp Ser Cys Pro Asp Tyr Met Leu Lys Ser
    210                 215                 220

Glu Glu Cys Leu Lys Lys Glu Arg Glu Arg Val Ala His Tyr Leu His
225                 230                 235                 240

Ser Ser Ser Glu Pro Lys Leu Val Glu Lys Val Gln His Glu Leu Leu
                245                 250                 255

Val Val Tyr Ala Asn Gln Leu Leu Glu Lys Glu His Ser Gly Cys Arg
            260                 265                 270

Ala Leu Leu Arg Asp Asp Lys Val Asp Asp Leu Ser Arg Met Tyr Arg
                275                 280                 285

Leu Tyr His Lys Ile Ala Lys Gly Leu Glu Pro Val Ala Asn Ile Phe
            290                 295                 300

Lys Gln His Val Thr Ala Glu Gly Asn Ala Leu Val Gln Gln Ala Glu
305                 310                 315                 320

Asp Thr Ala Thr Asn Gln Ala Ala Asn Thr Ala Ser Val Gln Glu Gln
                325                 330                 335

Val Leu Ile Arg Lys Val Ile Glu Leu His Asp Lys Tyr Met Val Tyr
            340                 345                 350

Val Val Glu Cys Phe Gln Asn His Thr Leu Phe His Lys Ala Leu Lys
            355                 360                 365

Glu Ala Phe Glu Ile Phe Cys Asn Lys Thr Val Ala Gly Ser Ser Ser
    370                 375                 380

Ala Glu Leu Leu Ala Thr Phe Cys Asp Asn Ile Leu Lys Lys Gly Gly
385                 390                 395                 400

Ser Glu Lys Leu Ser Asp Glu Ala Ile Glu Asp Thr Leu Glu Lys Val
                405                 410                 415

Val Lys Leu Leu Ala Tyr Ile Ser Asp Lys Asp Leu Phe Ala Glu Phe
            420                 425                 430

Tyr Arg Lys Lys Leu Ala Arg Arg Leu Leu Phe Asp Arg Ser Ala Asn
        435                 440                 445

Asp Asp His Glu Arg Ser Ile Leu Thr Lys Leu Lys Gln Gln Cys Gly
    450                 455                 460

Gly Gln Phe Thr Ser Lys Met Glu Gly Met Val Thr Asp Leu Thr Leu
465                 470                 475                 480

Ala Arg Glu Asn Gln Thr Ser Phe Glu Glu Tyr Leu Gly Asn Asn Pro
                485                 490                 495

Ala Ala Asn Pro Gly Ile Asp Leu Thr Val Thr Val Leu Thr Thr Gly
            500                 505                 510

Phe Trp Pro Ser Tyr Lys Ser Phe Asp Ile Asn Leu Pro Ser Glu Met
            515                 520                 525

Val Lys Cys Val Glu Val Phe Lys Gly Phe Tyr Glu Thr Lys Thr Lys
530                 535                 540

His Arg Lys Leu Thr Trp Ile Tyr Ser Leu Gly Thr Cys His Leu Asn
545                 550                 555                 560

Gly Lys Phe Asp His Lys Pro Ile Glu Leu Val Val Ser Thr Tyr Gln
                565                 570                 575

Ala Ala Val Leu Leu Leu Phe Asn Thr Thr Asp Lys Leu Ser Tyr Asn
            580                 585                 590

Asp Ile Leu Thr Gln Leu Asn Leu Ser His Glu Asp Leu Val Arg Leu
            595                 600                 605
```

```
Leu His Ser Leu Ser Cys Ala Arg Tyr Lys Ile Leu Leu Lys Glu Pro
    610                 615                 620

Ser Thr Lys Thr Val Thr Gln Thr Asp Ser Phe Glu Phe Asn Ala Lys
625                 630                 635                 640

Phe Thr Asp Arg Met Arg Arg Ile Lys Ile Pro Leu Pro Pro Val Asp
                    645                 650                 655

Glu Arg Lys Lys Val Glu Asp Val Asp Lys Asp Arg Arg Tyr Ala
                660                 665                 670

Ile Asp Ala Ala Ile Val Arg Ile Met Lys Ser Arg Lys Val Leu Gly
                675                 680                 685

His Gln Gln Leu Val Ser Glu Cys Val Glu Gln Leu Ser Arg Met Phe
690                 695                 700

Lys Pro Asp Ile Lys Ala Ile Lys Lys Arg Met Glu Asp Leu Ile Thr
705                 710                 715                 720

Arg Asp Tyr Leu Glu Arg Asp Lys Glu Asn Pro Asn Met Phe Arg Tyr
                725                 730                 735

Leu Ala
```

<210> SEQ ID NO 67
<211> LENGTH: 740
<212> TYPE: PRT
<213> ORGANISM: Spinacia oleracea

<400> SEQUENCE: 67

```
Met Asn Asp Arg Lys Val Ile Glu Leu Glu Gln Gly Trp Glu Phe Met
1               5                   10                  15

Gly Lys Gly Ile Thr Lys Leu Lys Arg Ile Leu Glu Gly Leu Pro Glu
                20                  25                  30

Pro Pro Phe Asn Ser Glu Asp Tyr Met Met Leu Tyr Thr Thr Met Tyr
            35                  40                  45

Asn Met Cys Thr Gln Lys Pro Pro His Asp Tyr Ser Gln Gln Leu Tyr
50                  55                  60

Asp Asn Tyr Lys Glu Ala Phe Val Asp Tyr Ile His Ser Thr Val Leu
65                  70                  75                  80

Pro Ser Leu Gly Asp Lys His Asp Glu Phe Met Leu Arg Glu Leu Val
                85                  90                  95

Lys Arg Trp Ser Asn His Lys Val Met Val Arg Trp Leu Ser Arg Phe
                100                 105                 110

Phe His Tyr Leu Asp Arg Tyr Phe Ile Ala Arg Arg Ser Leu Pro Ser
            115                 120                 125

Leu Asn Asp Val Gly Leu Thr Cys Phe Arg Asp Leu Val Tyr Gln Glu
130                 135                 140

Ile Ser Gly Lys Ala Lys Asp Ala Val Ile Ala Leu Ile Asp Glu Glu
145                 150                 155                 160

Arg Glu Gly Gly Gln Ile Asp Arg Ala Leu Leu Lys Asn Val Leu Asp
                165                 170                 175

Ile Tyr Val Glu Ile Gly Met Thr Gln Met Asp Tyr Tyr Glu Lys Asp
            180                 185                 190

Phe Glu Ala His Met Leu Asp Asp Thr Ala Ala Tyr Tyr Ser Arg Lys
        195                 200                 205

Ala Ser Ser Trp Ile Leu Glu Asp Ser Cys Pro Glu Tyr Met Leu Lys
210                 215                 220

Ser Glu Glu Cys Leu Lys Lys Glu Lys Asp Arg Val Ala His Tyr Leu
225                 230                 235                 240
```

-continued

```
His Ser Ser Ser Glu Pro Lys Leu Leu Glu Lys Val Gln Asn Glu Leu
            245                 250                 255

Leu Leu Val Tyr Glu Asn Gln Leu Leu Glu Lys Glu Asn Ser Gly Cys
        260                 265                 270

Arg Ala Leu Leu Lys Asp Asp Lys Val Glu Asp Leu Ser Arg Met Tyr
            275                 280                 285

Arg Leu Tyr Ser Lys Val Thr Lys Gly Leu Glu Pro Ile Gly Ser Ile
        290                 295                 300

Phe Lys Gln His Ile Thr Asp Glu Gly Thr Ala Leu Val Gln Gln Ala
305                 310                 315                 320

Glu Asp Ala Ala Ile Ser Lys Ala Glu Asn Ala Gly Gly Gly Ser His
                325                 330                 335

Glu Gln Val Phe Val Arg Lys Val Ile Glu Leu His Asp Lys Phe Met
            340                 345                 350

Thr Tyr Val Thr Asp Cys Phe Asn Ser His Thr Ile Phe His Lys Ala
        355                 360                 365

Leu Lys Glu Ala Phe Glu Val Phe Leu Asn Lys Gly Val Ala Gly Ser
        370                 375                 380

Ser Ser Ala Glu Leu Leu Ala Ser Phe Cys Asp Asn Ile Leu Lys Lys
385                 390                 395                 400

Gly Gly Ser Glu Lys Leu Ser Asp Glu Ala Ile Glu Asp Ser Leu Glu
            405                 410                 415

Lys Val Val Lys Leu Leu Ala Tyr Val Ser Asp Lys Asp Leu Phe Ala
        420                 425                 430

Glu Phe Tyr Arg Lys Lys Leu Ser Arg Arg Leu Leu Phe Asp Lys Ser
        435                 440                 445

Ala Asn Asp Asp His Glu Arg Ser Ile Leu Thr Lys Leu Lys Gln Gln
450                 455                 460

Cys Gly Gly Gln Phe Thr Ser Lys Met Glu Gly Met Val Thr Asp Leu
465                 470                 475                 480

Thr Leu Ala Arg Glu Asn Gln Thr Asn Phe Glu Glu Tyr Leu Gly Gln
            485                 490                 495

Asn Thr Asp Ala Ser Pro Gly Leu Asp Leu Thr Val Thr Val Leu Thr
        500                 505                 510

Thr Gly Phe Trp Pro Ser Tyr Lys Ser Ser Asp Leu Asn Leu Pro Ala
        515                 520                 525

Glu Met Val Arg Cys Val Glu Val Phe Lys Gln Phe Tyr Gln Thr Lys
        530                 535                 540

Thr Lys His Arg Lys Leu Thr Trp Val Tyr Ser Leu Gly Ser Cys Asn
545                 550                 555                 560

Ile Asn Gly Lys Phe Gly Pro Lys Thr Ile Glu Leu Val Val Gly Thr
                565                 570                 575

Tyr Gln Ala Ala Ala Leu Met Leu Phe Asn Thr Ser Asp Arg Leu Ser
            580                 585                 590

Tyr Ser Glu Ile Thr Thr Gln Leu Asn Leu Ala Asp Glu Asp Leu Val
        595                 600                 605

Arg Val Leu Gln Ser Leu Ser Cys Ala Lys Tyr Lys Ile Leu Leu Lys
        610                 615                 620

Glu Pro Ser Thr Arg Asn Val Ile Ser Thr Asp Cys Phe Ser Phe Asn
625                 630                 635                 640

Ser Asn Phe Thr Asp Arg Met Arg Arg Ile Arg Ile Pro Leu Pro Pro
                645                 650                 655

Met Asp Glu Arg Lys Lys Val Val Glu Asp Val Asp Lys Asp Arg Arg
```

```
                       660                 665                 670
Tyr Ala Ile Asp Ala Ser Ile Val Arg Ile Met Lys Ser Arg Lys Ala
                675                 680                 685

Leu Gly Tyr Gln Gln Leu Ile Thr Glu Cys Val Glu Gln Leu Ser Arg
            690                 695                 700

Met Phe Lys Pro Asp Phe Lys Ala Ile Lys Lys Arg Ile Glu Asp Leu
705                 710                 715                 720

Ile Thr Arg Asp Tyr Ile Glu Arg Asp Lys Glu Asn Pro Gln Leu Phe
                725                 730                 735

Arg Tyr Leu Ala
            740

<210> SEQ ID NO 68
<211> LENGTH: 739
<212> TYPE: PRT
<213> ORGANISM: Beta vulgaris

<400> SEQUENCE: 68

Met Asn Asp Arg Lys Val Ile Glu Leu Glu Gln Gly Trp Glu Phe Met
1               5                   10                  15

Gly Lys Gly Ile Thr Lys Leu Lys Arg Ile Leu Glu Gly Leu Pro Glu
            20                  25                  30

Pro Pro Phe Asn Ser Glu Asp Tyr Met Met Leu Tyr Thr Thr Met Tyr
        35                  40                  45

Asn Met Cys Thr Gln Lys Pro Pro His Asp Tyr Ser Gln Gln Leu Tyr
50                  55                  60

Asp Asn Tyr Lys Gln Ala Phe Val Asp Tyr Ile Asn Ser Thr Val Leu
65                  70                  75                  80

Pro Ser Leu Arg Glu Lys His Asp Glu Phe Met Leu Arg Glu Leu Val
                85                  90                  95

Lys Arg Trp Ala Asn His Lys Val Met Val Arg Trp Leu Ser Arg Phe
            100                 105                 110

Phe His Tyr Leu Asp Arg Tyr Phe Ile Ala Arg Arg Ser Leu Pro Ser
        115                 120                 125

Leu Asn Glu Val Gly Leu Thr Cys Phe Arg Asp Leu Val Tyr Gln Glu
    130                 135                 140

Ile Ser Gly Lys Ala Lys Asp Ala Val Ile Ala Leu Ile Asp Ile Glu
145                 150                 155                 160

Arg Glu Gly Gly Gln Ile Asp Arg Ser Leu Leu Lys Asn Val Leu Asp
                165                 170                 175

Ile Tyr Val Glu Ile Gly Met Gly Gln Met Asp His Tyr Glu Lys Asp
            180                 185                 190

Phe Glu Ala His Met Leu Asp Asp Thr Ala Ala Tyr Tyr Ser Arg Lys
        195                 200                 205

Ala Ser Ser Trp Ile Leu Glu Asp Ser Cys Pro Glu Tyr Met Leu Lys
    210                 215                 220

Ser Glu Glu Cys Leu Lys Lys Glu Lys Glu Arg Val Ala Asn Tyr Leu
225                 230                 235                 240

His Ser Ser Ser Glu Pro Lys Leu Leu Glu Lys Val Gln Asn Glu Leu
                245                 250                 255

Leu Leu Val Tyr Glu Ser Gln Leu Leu Glu Lys Glu Asn Ser Gly Cys
            260                 265                 270

Arg Ala Leu Leu Lys Asp Asp Lys Val Asp Asp Leu Ser Arg Met Tyr
        275                 280                 285
```

-continued

Arg Leu Tyr Ser Lys Val Thr Lys Gly Leu Glu Pro Ile Gly Ser Ile
290                 295                 300

Phe Lys Gln His Ile Thr Asp Glu Gly Thr Ala Leu Val Gln Gln Ala
305                 310                 315                 320

Glu Asp Ala Ala Ile Ser Lys Ala Glu Asn Thr Gly Gly Ser His Glu
            325                 330                 335

Gln Val Phe Val Arg Lys Val Ile Glu Leu His Asp Lys Phe Met Thr
                340                 345                 350

Tyr Val Thr Asp Cys Phe Asn Ser His Thr Ile Phe His Lys Ala Leu
                355                 360                 365

Lys Glu Ala Phe Glu Val Phe Leu Asn Lys Gly Val Ala Gly Ser Ser
370                 375                 380

Ser Ala Glu Leu Leu Ala Thr Phe Cys Asp Asn Ile Leu Lys Lys Gly
385                 390                 395                 400

Gly Ser Glu Lys Leu Ser Asp Glu Ala Ile Glu Asp Ser Leu Glu Lys
            405                 410                 415

Val Val Lys Leu Leu Ala Tyr Val Ser Asp Lys Asp Leu Phe Ala Glu
                420                 425                 430

Phe Tyr Arg Lys Lys Leu Ser Arg Arg Leu Leu Phe Asp Lys Ser Ala
                435                 440                 445

Asn Asp Asp His Glu Arg Ser Ile Leu Thr Lys Leu Lys Gln Gln Cys
450                 455                 460

Gly Gly Gln Phe Thr Ser Lys Met Glu Gly Met Val Thr Asp Leu Thr
465                 470                 475                 480

Leu Ala Arg Glu Asn Gln Thr Asn Phe Glu Glu Tyr Leu Ser Gln Asn
            485                 490                 495

Pro Asp Ala Ser Pro Gly Leu Asp Leu Thr Val Thr Val Leu Thr Thr
                500                 505                 510

Gly Phe Trp Pro Ser Tyr Lys Ser Ser Asp Leu Asn Leu Pro Ala Glu
                515                 520                 525

Met Val Arg Cys Val Glu Val Phe Lys Gln Phe Tyr Ser Thr Lys Thr
530                 535                 540

Lys His Arg Lys Leu Thr Trp Val Tyr Ser Leu Gly Ser Cys Asn Ile
545                 550                 555                 560

Asn Gly Lys Phe Gly Pro Lys Thr Ile Glu Leu Val Val Gly Thr Tyr
            565                 570                 575

Gln Ala Ala Ala Leu Met Leu Phe Asn Thr Ser Asp Arg Leu Ser Tyr
                580                 585                 590

Ser Glu Ile Ala Thr Gln Leu Asn Leu Ala Asp Glu Asp Leu Val Arg
            595                 600                 605

Val Leu Gln Ser Leu Ser Cys Ala Lys Tyr Lys Ile Leu Leu Lys Glu
610                 615                 620

Pro Asn Thr Lys Thr Val Ser Pro Thr Asp Cys Phe Ser Phe Asn Ser
625                 630                 635                 640

Ser Phe Thr Asp Arg Met Arg Arg Ile Arg Ile Pro Leu Pro Pro Met
            645                 650                 655

Asp Glu Arg Lys Lys Val Val Glu Asp Val Asp Lys Asp Arg Arg Tyr
                660                 665                 670

Ala Ile Asp Ala Ser Ile Val Arg Ile Met Lys Ser Arg Lys Val Leu
                675                 680                 685

Gly Tyr Gln Gln Leu Ile Thr Glu Cys Val Glu Gln Leu Ser Arg Met
690                 695                 700

Phe Lys Pro Asp Phe Lys Ala Ile Lys Lys Arg Ile Glu Asp Leu Ile

```
                705                 710                 715                 720
Thr Arg Asp Tyr Ile Glu Arg Asp Lys Glu Asn Pro Gln Leu Phe Arg
                    725                 730                 735
Tyr Leu Ala

<210> SEQ ID NO 69
<211> LENGTH: 738
<212> TYPE: PRT
<213> ORGANISM: Arabidopsis

<400> SEQUENCE: 69

Met Glu Arg Lys Thr Ile Asp Leu Glu Gln Gly Trp Asp Tyr Met Gln
1               5                   10                  15

Thr Gly Ile Thr Lys Leu Lys Arg Ile Leu Glu Gly Leu Asn Glu Pro
                20                  25                  30

Ala Phe Asp Ser Glu Gln Tyr Met Met Leu Tyr Thr Thr Ile Tyr Asn
            35                  40                  45

Met Cys Thr Gln Lys Pro Pro His Asp Tyr Ser Gln Gln Leu Tyr Asp
    50                  55                  60

Lys Tyr Arg Glu Ala Phe Glu Glu Tyr Ile Asn Ser Thr Val Leu Pro
65                  70                  75                  80

Ala Leu Arg Glu Lys His Asp Glu Phe Met Leu Arg Glu Leu Phe Lys
                85                  90                  95

Arg Trp Ser Asn His Lys Val Met Val Arg Trp Leu Ser Arg Phe Phe
                100                 105                 110

Tyr Tyr Leu Asp Arg Tyr Phe Ile Ala Arg Arg Ser Leu Pro Pro Leu
            115                 120                 125

Asn Glu Val Gly Leu Thr Cys Phe Arg Asp Leu Val Tyr Asn Glu Leu
    130                 135                 140

His Ser Lys Val Lys Gln Ala Val Ile Ala Leu Val Asp Lys Glu Arg
145                 150                 155                 160

Glu Gly Glu Gln Ile Asp Arg Ala Leu Leu Lys Asn Val Leu Asp Ile
                165                 170                 175

Tyr Val Glu Ile Gly Met Gly Gln Met Glu Arg Tyr Glu Glu Asp Phe
            180                 185                 190

Glu Ser Phe Met Leu Gln Asp Thr Ser Ser Tyr Tyr Ser Arg Lys Ala
    195                 200                 205

Ser Ser Trp Ile Gln Glu Asp Ser Cys Pro Asp Tyr Met Leu Lys Ser
210                 215                 220

Glu Glu Cys Leu Lys Lys Glu Arg Glu Arg Val Ala His Tyr Leu His
225                 230                 235                 240

Ser Ser Ser Glu Pro Lys Leu Val Glu Lys Val Gln His Glu Leu Leu
                245                 250                 255

Val Val Phe Ala Ser Gln Leu Leu Glu Lys Glu His Ser Gly Cys Arg
            260                 265                 270

Ala Leu Leu Arg Asp Asp Lys Val Asp Asp Leu Ser Arg Met Tyr Arg
    275                 280                 285

Leu Tyr His Lys Ile Leu Arg Gly Leu Glu Pro Val Ala Asn Ile Phe
290                 295                 300

Lys Gln His Val Thr Ala Glu Gly Asn Ala Leu Val Gln Gln Ala Glu
305                 310                 315                 320

Asp Thr Ala Thr Asn Gln Val Ala Asn Thr Ala Ser Val Gln Glu Gln
                325                 330                 335

Val Leu Ile Arg Lys Val Ile Glu Leu His Asp Lys Tyr Met Val Tyr
```

```
                340             345             350
Val Thr Glu Cys Phe Gln Asn His Thr Leu Phe His Lys Ala Leu Lys
            355             360             365
Glu Ala Phe Glu Ile Phe Cys Asn Lys Thr Val Ala Gly Ser Ser Ser
        370             375             380
Ala Glu Leu Leu Ala Thr Phe Cys Asp Asn Ile Leu Lys Lys Gly Gly
385             390             395             400
Ser Glu Lys Leu Ser Asp Glu Ala Ile Glu Asp Thr Leu Glu Lys Val
            405             410             415
Val Lys Leu Leu Ala Tyr Ile Ser Asp Lys Asp Leu Phe Ala Glu Phe
        420             425             430
Tyr Arg Lys Lys Leu Ala Arg Arg Leu Leu Phe Asp Arg Ser Ala Asn
            435             440             445
Asp Asp His Glu Arg Ser Ile Leu Thr Lys Leu Lys Gln Gln Cys Gly
        450             455             460
Gly Gln Phe Thr Ser Lys Met Glu Gly Met Val Thr Asp Leu Thr Leu
465             470             475             480
Ala Arg Glu Asn Gln Asn Ser Phe Glu Asp Tyr Leu Gly Ser Asn Pro
            485             490             495
Ala Ala Asn Pro Gly Ile Asp Leu Thr Val Thr Val Leu Thr Thr Gly
        500             505             510
Phe Trp Pro Ser Tyr Lys Ser Phe Asp Ile Asn Leu Pro Ser Glu Met
        515             520             525
Ile Lys Cys Val Glu Val Phe Lys Gly Phe Tyr Glu Thr Lys Thr Lys
        530             535             540
His Arg Lys Leu Thr Trp Ile Tyr Ser Leu Gly Thr Cys His Ile Asn
545             550             555             560
Gly Lys Phe Asp Gln Lys Ala Ile Glu Leu Ile Val Ser Thr Tyr Gln
            565             570             575
Ala Ala Val Leu Leu Leu Phe Asn Thr Thr Asp Lys Leu Ser Tyr Thr
        580             585             590
Glu Ile Leu Ala Gln Leu Asn Leu Ser His Glu Asp Leu Val Arg Leu
        595             600             605
Leu His Ser Leu Ser Cys Ala Lys Tyr Lys Ile Leu Leu Lys Glu Pro
        610             615             620
Asn Thr Lys Thr Val Ser Gln Asn Asp Ala Phe Glu Phe Asn Ser Lys
625             630             635             640
Phe Thr Asp Arg Met Arg Arg Ile Lys Ile Pro Leu Pro Pro Val Asp
            645             650             655
Glu Arg Lys Lys Val Val Glu Asp Val Asp Lys Asp Arg Arg Tyr Ala
            660             665             670
Ile Asp Ala Ala Ile Val Arg Ile Met Lys Ser Arg Lys Val Leu Gly
        675             680             685
His Gln Gln Leu Val Ser Glu Cys Val Glu Gln Leu Ser Arg Met Phe
        690             695             700
Lys Pro Asp Ile Lys Ala Ile Lys Lys Arg Met Glu Asp Leu Ile Thr
705             710             715             720
Arg Asp Tyr Leu Glu Arg Asp Lys Glu Asn Pro Asn Met Phe Arg Tyr
            725             730             735
Leu Ala
```